United States Patent
Sim et al.

(10) Patent No.: US 11,917,909 B2
(45) Date of Patent: Feb. 27, 2024

(54) ORGANIC COMPOUND AND ORGANIC ELECTROLUMINESCENCE DEVICE USING THE SAME

(71) Applicant: Solus Advanced Materials Co., Ltd., Iksan (KR)

(72) Inventors: Jaeyi Sim, Yongin (KR); Hocheol Park, Yongin (KR); Minsik Eum, Yongin (KR); Youngmo Kim, Yongin (KR); Yonghwan Lee, Yongin (KR); Woojae Park, Yongin (KR)

(73) Assignee: SOLUS ADVANCED MATERIALS CO., LTD., Iksan (KR)

( * ) Notice: Subject to any disclaimer, the term of this patent is extended or adjusted under 35 U.S.C. 154(b) by 389 days.

(21) Appl. No.: 17/264,565

(22) PCT Filed: Jul. 25, 2019

(86) PCT No.: PCT/KR2019/009219
§ 371 (c)(1),
(2) Date: Jan. 29, 2021

(87) PCT Pub. No.: WO2020/159019
PCT Pub. Date: Aug. 6, 2020

(65) Prior Publication Data
US 2022/0115596 A1    Apr. 14, 2022

(30) Foreign Application Priority Data
Jan. 30, 2019 (KR) .................. 10-2019-0011770

(51) Int. Cl.
*H01L 51/00* (2006.01)
*C07D 311/96* (2006.01)
(Continued)

(52) U.S. Cl.
CPC ......... *H10K 85/636* (2023.02); *C07D 311/96* (2013.01); *C07D 335/04* (2013.01);
(Continued)

(58) Field of Classification Search
None
See application file for complete search history.

(56) References Cited

U.S. PATENT DOCUMENTS
2015/0333277 A1    11/2015    Kim

FOREIGN PATENT DOCUMENTS
CN    104781247 A    7/2015
CN    106946839 A    7/2017
(Continued)

OTHER PUBLICATIONS

Machine English translation of Gao et al. (CN 106946839 A). Mar. 21, 2023.*
EP Office Action dated Sep. 13, 2022.
International Search Report dated Nov. 15, 2019.
Office Action dated Feb. 10, 2022.
(Continued)

*Primary Examiner* — Jay Yang
(74) *Attorney, Agent, or Firm* — Harvest IP Law, LLP

(57) ABSTRACT

The present invention relates to novel organic light emitting compound and an organic electroluminescence device using the same, and more particularly, to a compound having excellent thermal stability, electrochemical stability, luminescence ability, and hole/electron transporting ability, and an organic electroluminescence device which includes the compound in at least one organic layer and thus has improved characteristics such as luminous efficiency, driving voltage, and lifespan.

11 Claims, 1 Drawing Sheet

(51) Int. Cl.
*C09K 11/06* (2006.01)
*C07D 407/12* (2006.01)
*C07D 409/12* (2006.01)
*C07D 405/12* (2006.01)
*C07D 409/14* (2006.01)
*C07D 335/04* (2006.01)
*H10K 85/60* (2023.01)
*H10K 50/15* (2023.01)

(52) U.S. Cl.
CPC ......... *C07D 405/12* (2013.01); *C07D 407/12* (2013.01); *C07D 409/12* (2013.01); *C07D 409/14* (2013.01); *C09K 11/06* (2013.01); *H10K 85/633* (2023.02); *C09K 2211/1018* (2013.01); *H10K 50/15* (2023.02); *H10K 85/615* (2023.02); *H10K 85/6572* (2023.02); *H10K 85/6574* (2023.02); *H10K 85/6576* (2023.02)

(56) References Cited

FOREIGN PATENT DOCUMENTS

| | | |
|---|---|---|
| JP | 2016505518 A | 2/2016 |
| KR | 10-2014-0135117 A | 11/2014 |
| KR | 1020140135117 A | 11/2014 |
| KR | 10-2015-0083917 A | 7/2015 |
| KR | 10-2017-0138799 A | 12/2017 |
| KR | 10-2018-0080603 A | 7/2018 |
| WO | 14072017 A1 | 5/2014 |
| WO | 2017-061832 A1 | 4/2017 |
| WO | 2017061832 A1 | 4/2017 |
| WO | 2018066830 A1 | 4/2018 |
| WO | 2018069167 A1 | 4/2018 |
| WO | 2018080066 A1 | 5/2018 |

OTHER PUBLICATIONS

CN Office Action dated Feb. 23, 2023.
European Search Report dated Jan. 16, 2023.

\* cited by examiner

[FIG. 1]
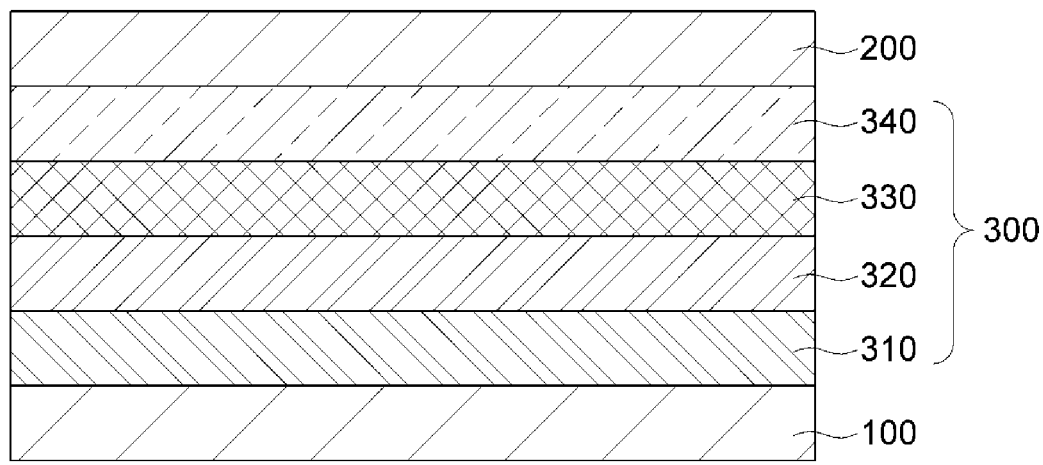
[FIG. 2]
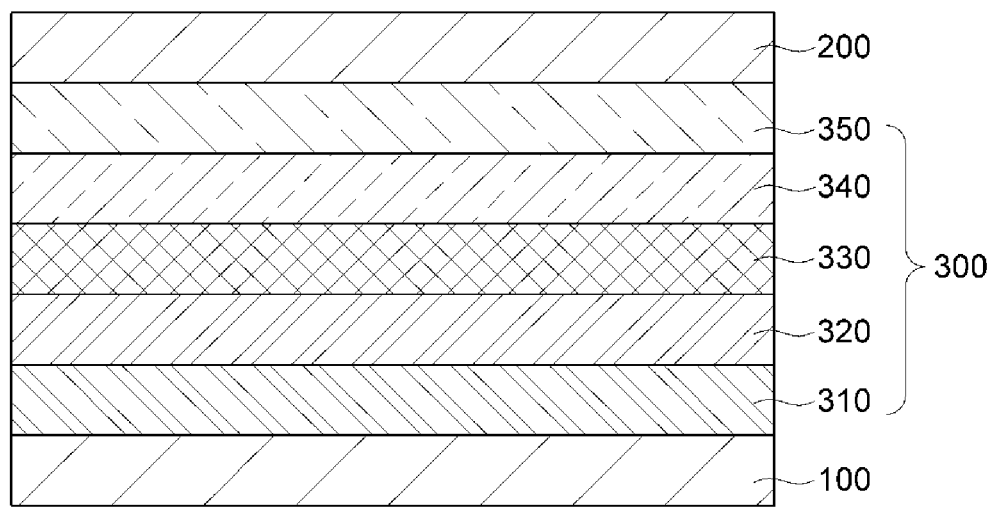

ORGANIC COMPOUND AND ORGANIC ELECTROLUMINESCENCE DEVICE USING THE SAME

CROSS-REFERENCE TO RELATED APPLICATIONS

This application is a National Stage of International Application No. PCT/KR2019/009219 filed Jul. 25, 2019, claiming priority based on Korean Patent Application No. 10-2019-0011770 filed Jan. 30, 2019.

TECHNICAL FIELD

The present invention relates to a novel organic light emitting compound and an organic electroluminescence device using the same, and more particularly, to a compound having excellent thermal stability, electrochemical stability, and hole transporting ability, and an organic electroluminescence device which includes the compound in at least one organic layer and thus has improved characteristics such as luminous efficiency, driving voltage, and lifespan.

DISCUSSION OF RELATED ART

In organic electroluminescence devices (hereinafter, "EL devices"), upon application of voltage between two electrodes, holes are injected from an anode to an organic layer and electrons are injected from a cathode into the organic layer. Injected holes and electrons meet each other to form excitons, and light emission occurs when the excitons fall to a ground state. In such a case, materials used for the organic layer may be classified into, for example, light emitting materials, hole injection materials, hole transporting materials, electron transporting materials and electron injection materials depending on their function.

Light emitting materials of an organic EL device may be classified into blue-, green- and red-light emitting materials depending on their emission colors. Besides, yellow and orange light emitting materials may also be used as such a light emitting material for realizing better natural colors. In addition, a host/dopant system may be employed in the light emitting material to increase color purity and luminous efficiency through energy transferring. Dopant materials may be classified into fluorescent dopants using organic materials and phosphorescent dopants using metal complex compounds which include heavy atoms such as Ir and Pt. The developed phosphorescent materials may improve the luminous efficiency theoretically up to four times as compared to fluorescent materials, so attention is given to phosphorescent dopants as well as phosphorescent host materials.

To date, NPB, BCP and Alq$_3$, represented by the following Chemical Formulas, for example, are widely known as materials used in the hole injection layer, the hole transporting layer, the hole blocking layer and the electron transporting layer, and anthracene derivatives have been reported as fluorescent dopant/host materials for light emitting materials. Particularly, metal complex compounds including Ir, such as FIrpic, Ir(ppy)$_3$, and Ir(btp)$_2$(acac), are known as phosphorescent dopant materials for efficiency improvement among light emitting materials, and they are used as blue, green and red dopant materials. Up to this day, CBP has shown excellent properties as a phosphorescent host material.

However, conventional materials, despite their good luminescence properties, have low glass transition temperatures and poor thermal stability and thus are not satisfactory in terms of life characteristics of organic EL devices. Accordingly, there is a demand for the development of an organic layer material having excellent performance.

DETAILED DESCRIPTION OF THE INVENTION

Technical Objectives

The present invention is directed to a novel organic compound applicable to an electroluminescence device and used as a material for a hole transporting layer by having excellent properties such as thermal stability, electrochemical stability, and hole transporting ability.

The present invention is also directed to an organic electroluminescence device including the novel organic compound, thereby exhibiting a low driving voltage and high luminous efficiency and having an improved lifespan.

Technical Solution to the Problem

The present invention provides an organic compound represented by the following Chemical Formula 1:

[Chemical Formula 1]

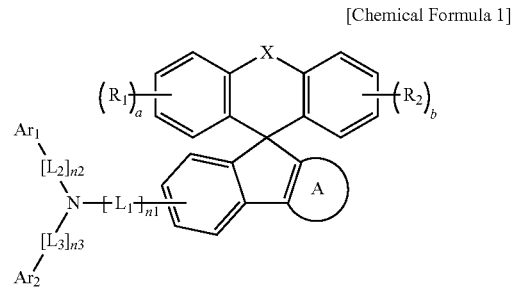

(where in Chemical Formula 1, X is O or S,
each of a and b is an integer ranging from 0 to 4,
R$_1$ and R$_2$ are the same as or different from each other, each independently being selected from the group consisting of hydrogen, deuterium, a halogen group, a cyano group, a nitro group, an amino group, a C$_1$ to C$_{40}$ alkyl group, a C$_2$ to C$_{40}$ alkenyl group, a C$_2$ to C$_{40}$ alkynyl group, a C$_3$ to C$_{40}$ cycloalkyl group, a heterocycloalkyl group having 3 to 40 nuclear atoms, a C$_6$ to C$_{60}$ aryl group, a heteroaryl group having 5 to 60 nuclear atoms, a C$_1$ to C$_{40}$ alkyloxy group, a C$_6$ to C$_{60}$ aryloxy group, a C$_1$ to C$_{40}$ alkylsilyl group, a C$_6$ to C$_{60}$ arylsilyl group, a C$_1$ to C$_{40}$ alkylboron group, a C$_6$ to C$_{60}$ arylboron group, a C$_6$ to C$_{60}$ arylphosphine group, a C$_6$ to C$_{60}$ arylphosphine oxide group, and a C$_6$ to C$_{60}$ arylamine group,
ring A is a C$_6$ to C$_{40}$ polycyclic aromatic ring,
each of n1 to n3 is an integer ranging from 0 to 3,
L$_1$ to L$_3$ are the same as or different from each other, each independently selected from the group consisting of a single bond, a C$_6$ to C$_{18}$ arylene group and a heteroarylene group having 5 to 18 nuclear atoms,
Ar$_1$ and Ar$_2$ are the same as or different from each other, each independently being selected from the group consisting of a C$_6$ to C$_{60}$ aryl group and a heteroaryl group having 5 to 60 nuclear atoms, and
the polycyclic aromatic ring of the ring A, the arylene group and the heteroarylene group of L$_1$ to L$_3$, the aryl group and the heteroaryl group of $Ar_1$ and $Ar_2$, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ and $R_2$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other).

In addition, the present invention is also directed to an organic electroluminescence device including (i) an anode, (ii) a cathode, and (iii) one or more organic layers interposed between the anode and the cathode, wherein at least one of the one or more organic layers includes a compound represented by the Chemical Formula 1.

Effects of the Invention

According to one or more embodiments of the present invention, a compound has excellent properties such as thermal stability, electrochemical stability, and hole transporting ability, thus applicable to a material for an organic layer of an electroluminescence device.

In addition, according to one or more embodiments of the present invention, an organic electroluminescence device including the compound of the present invention in the organic layer is improved in terms of luminous efficiency, driving voltage, and lifespan, thus applicable to a full-color display panel and the like.

BRIEF DESCRIPTION OF DRAWINGS

FIG. 1 is a cross-sectional view illustrating an organic electroluminescence device according to an embodiment of the present invention.

FIG. 2 is a schematic cross-sectional view illustrating an organic electroluminescence device according to another embodiment of the present invention.

| Reference signs | |
|---|---|
| 100: Anode | 200: Cathode |
| 300: Organic layer | 310: Hole injection layer |
| 320: Hole transporting layer | 330: Light emitting layer |
| 340: Electron transporting layer | 350: Electron injection layer |

MODES FOR CARRYING OUT THE INVENTION

Hereinafter, the present invention will be described in detail.
<Novel Compound>
The present invention provides a novel organic compound that is excellent in electrochemical stability, thermal stability, and carrier transporting ability (especially, hole transporting ability) and thus applicable to a material for a high-efficiency hole transporting layer.

Specifically, the compound represented by Chemical Formula 1 according to the present invention includes a core structure in which a monocyclic or polycyclic aromatic ring such as a benzene ring or a naphthalene ring is fused at a benzene part on one side of fluorene and an amine group substituted with aryl and/or heteroaryl is introduced to a benzene part on another side of fluorene directly or by a linker, in a spiro[fused aromatic ring fused with fluorene-xanthene] moiety or a spiro[fused aromatic ring fused with fluorene-thioxathene] moiety.

Since the compound represented by Chemical Formula 1 has a monocyclic or polycyclic aromatic ring such as a benzene ring and a naphthalene ring fused at the benzene part on one side of fluorene in the spiro[fused aromatic ring fused with fluorene-xanthene] moiety or the spiro[fused aromatic ring fused with fluorene-thioxathene] moiety, leading to a high hole mobility, the compound represented by Chemical Formula 1 has excellent hole transporting ability. In addition, the compound represented by Chemical Formula 1 has a HOMO energy level ranging from about 5.0 to 5.6 eV and a LUMO energy level ranging from about 1.7 to 2.5 eV. This is between HOMO and LUMO energy levels of the hole injection layer and the light emitting layer, injection and transferring of holes may become smooth. Accordingly, when an organic electroluminescence device (hereinafter, "EL device") includes the compound of the present invention as a hole transporting material, the luminous efficiency of the organic EL device may be improved, and the driving voltage may be lowered, thereby increasing the lifespan.

In addition, since the compound of Chemical Formula 1 has an amine group substituted with aryl and/or heteroaryl introduced to the benzene part on another side of fluorene, in the spiro[fused aromatic ring fused with fluorene-xanthene] moiety or the spiro[fused aromatic ring fused with fluorene-thioxathene] moiety, luminous efficiency may be further improved due to physicochemical properties such as amorphous properties and high refractive index properties. In addition, since the compound of Chemical Formula 1 has a high glass transition temperature (Tg), it is not only excellent in stability, but also excellent in electrochemical stability.

As described above, the compound represented by Chemical Formula 1 according to the present invention is excellent in terms of thermal stability, electrochemical stability, and hole transporting ability. Accordingly, the compound represented by Chemical Formula 1 of the present invention may be used as an organic layer material of an organic EL device, preferably a material for a hole transporting layer material or a hole transporting auxiliary layer, and more preferably a material for a hole transporting layer. The performance and lifespan characteristics of the organic EL device including the compound of the present invention may be greatly improved, and the performance of a full-color organic light emitting panel to which the organic EL device is applied may also be maximized.

In the compound represented by Chemical Formula 1, X is O or S. Compared to the case where X is N or C, the compound of Chemical Formula 1 has excellent amphoteric properties of electrons and holes, and thus has excellent carrier transporting ability. Accordingly, when the compound of Chemical Formula 1 according to the present invention is used as a material for a hole transporting layer, an effect of improving efficiency and driving voltage may be increased by improving hole transporting ability.

In addition, in the compound represented by Chemical Formula 1, each of a and b is an integer ranging from 0 to 4.

In such an embodiment, when each of a and b is 0, it means that hydrogens each are not substituted with the substituents $R_1$ and $R_2$, and when each of a and b is an integer ranging from 1 to 4, the plurality of $R_1$ and the plurality of $R_2$ are the same as or different from each other and each independently are selected from the group consisting of deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group. In such an embodiment, each of the heterocycloalkyl group and the heteroaryl group includes at least one heteroatom selected from the group consisting of N, S, O and Se. In an example, each of a and b is 0, and $R_1$ and $R_2$ are hydrogen.

In the compound represented by Chemical Formula 1, the ring A may be a $C_6$ to $C_{60}$ polycyclic aromatic ring, preferably a $C_6$ to $C_{40}$ polycyclic aromatic ring, and more preferably a $C_6$ to $C_{40}$ bicyclic to octacyclic polycyclic aromatic ring. In such an embodiment, each ring in the polycyclic aromatic ring may be the same as or different from each other. Specifically, examples of the ring A may be, but not limited to, a naphthalene ring, an anthracene ring, a tetracene ring, a pyrene ring, a phenanthrene ring, a phenalene ring, a benzoanthracene ring, a benzopyrene ring, a triphenylene ring, a chrysene ring, a pentaphene ring, a pentacene ring, and a fused ring of two thereof.

In an embodiment, the compound represented by Chemical Formula 1 may be, but not limited to, embodied as a compound represented by Chemical Formula 2 below:

[Chemical Formula 2]

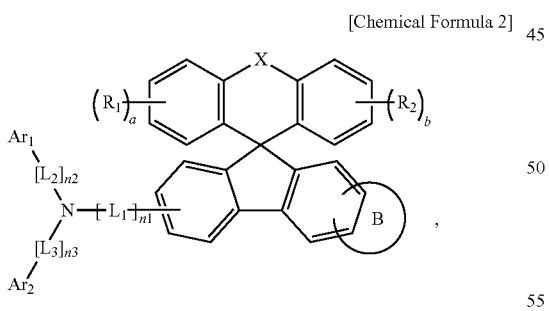

where in Chemical Formula 2,
X, $R_1$, $R_2$, a, b, $L_1$ to $L_3$, n1 to n3, $Ar_1$ and $Ar_2$ are as defined in Chemical Formula 1, respectively,
the ring B is a $C_6$ to $C_{40}$ monocyclic aromatic ring or a $C_6$ to $C_{40}$ polycyclic aromatic ring, and may preferably be, but not limited to, a benzene ring, a naphthalene ring, an anthracene ring, a tetracene ring, a pyrene ring, a phenanthrene ring, a phenalene ring, a benzoanthracene ring, a benzopyrene ring, a triphenylene ring, a chrysene ring, a pentaphene ring, a pentacene ring, and a fused ring of two thereof. In such an embodiment,
each ring in the polycyclic aromatic ring may be the same as or different from each other.

More specifically, the compound represented by Chemical Formula 1 according to the present invention may be, but not limited to, embodied as a compound represented by any one of the following Chemical Formulas 3 to 5:

[Chemical Formula 3]

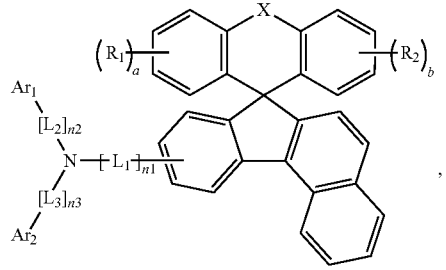

[Chemical Formula 4]

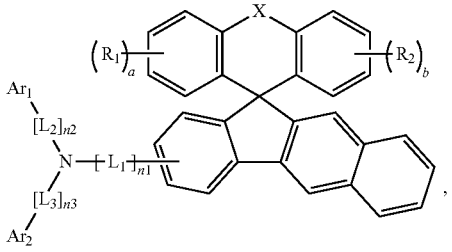

[Chemical Formula 5]

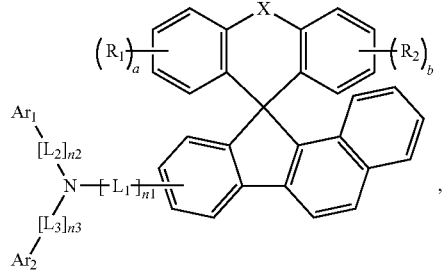

wherein in Chemical Formulas 3 to 5,
X, $R_1$, $R_2$, a, b, $L_1$ to $L_3$, n1 to n3, $Ar_1$ and $Ar_2$ are as defined in Chemical Formula 1, respectively.

Further, in the compound represented by Chemical Formula 1, each of n1 to n3 is an integer ranging from 0 to 3, preferably 0 or 1.

In such an embodiment, when each of n1 to n3 is 0, it means that each of $L_1$ to $L_3$ is a single bond, and when each of n1 to n3 is an integer ranging from 1 to 3, $L_1$ to $L_3$ are divalent linkers, the same as or different from each other, and each independently selected from the group consisting of a $C_6$ to $C_{18}$ arylene group and a heteroarylene group having 5 to 18 nuclear atoms. For example, in Chemical Formula 1, $L_1$ to $L_3$ may be the same as or different from each other, and may each independently be a single bond or a phenylene group.

In particular, when $L_1$ is a phenylene group, a

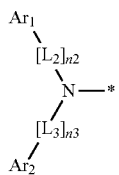

moiety and a

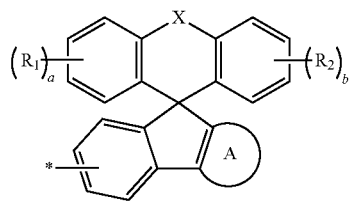

moiety may be introduced at a para position with respect to $L_1$. In such a case, the compound of Chemical Formula 1 maximizes hole transporting ability and facilitates hole transferring between molecules, and thus a driving voltage of the organic EL device may be lowered.

In addition, in the compound represented by Chemical Formula 1, $Ar_1$ and $Ar_2$ are the same as or different from each other and are each independently selected from the group consisting of a $C_6$ to $C_{60}$ aryl group and a heteroaryl group having 5 to 60 nuclear atoms. For example, $Ar_1$ and $Ar_2$ may be the same as or different from each other, and may each independently be selected from, but not limited to, the group consisting of the following substituents A-1 to A-3:

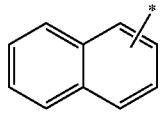 A-1

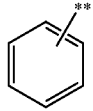 A-2

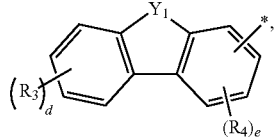 A-3 wherein in Chemical Formula A-3,
$Y_1$ is selected from the group consisting of O, S, C($Ar_3$)($Ar_4$), and N($Ar_5$),
d is an integer ranging from 0 to 4,
e is an integer ranging from 0 to 3,
$R_3$ and $R_4$ are the same as or different from each other, each independently being selected from the group consisting of hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_3$ and $R_4$ may each be independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and preferably, substituted or unsubstituted with one or more kinds of substituents selected from the group consisting of deuterium, halogen, a cyano group, a nitro group, a $C_1$ to $C_{20}$ alkyl group, a $C_6$ to $C_{30}$ aryl group, a heteroaryl group having 5 to 30 nuclear atoms, and when the substituents are plural in number, the substituents are the same as or different from each other.

In addition, in the compound represented by Chemical Formula 1, the polycyclic aromatic ring of the ring A, the arylene group and the heteroarylene group of $L_1$, the aryl group and the heteroaryl group of $Ar_1$ and $Ar_2$, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ and $R_2$ may each be independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and preferably, substituted or unsubstituted with one or more kinds of substituents selected from the group consisting of deuterium, halogen, a cyano group, a nitro group, a $C_1$ to $C_{20}$ alkyl group, a $C_6$ to $C_{30}$ aryl group, a heteroaryl group having 5 to 30 nuclear atoms. In such an embodiment, when the substituents are plural in number, the substituents are the same as or different from each other. In such an embodiment, the heterocycloalkyl group and the heteroaryl group each include at least one heteroatom selected from the group consisting of N, S, O and Se.

The compound represented by Chemical Formula 1 may be, but not limited to, embodied as a compound represented by Chemical Formula 6 or 7 below:

[Chemical Formula 6]

[Chemical Formula 7]

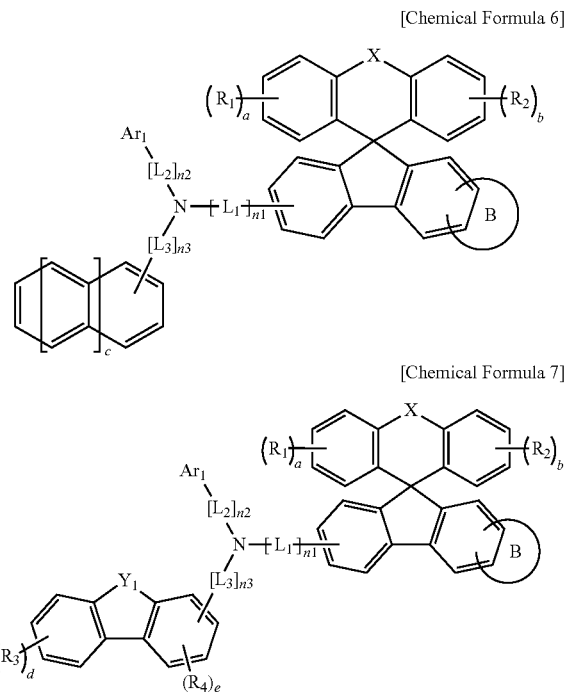

In Chemical Formulas 6 and 7,

X, $R_1$, $R_2$, a, b, $L_1$ to $L_3$, n1 to n3, and $Ar_1$ are as defined in Chemical Formula 1, respectively, the ring B is as defined in Chemical Formula 2, c is 0 or 1, $Y_1$ is selected from the group consisting of O, S, $C(Ar_3)(Ar_4)$, and $N(Ar_5)$, d is an integer ranging from 0 to 4, e is an integer ranging from 0 to 3, $R_3$, $R_4$, $Ar_3$ to $Ar_5$ are the same as or different from each other, each independently being selected from the group consisting of hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and the monocyclic and polycyclic aromatic rings of the ring B, the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_3$, $R_4$, $Ar_3$ to $Ar_5$ may each independently be substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and preferably, substituted or unsubstituted with one or more kinds of substituents selected from the group consisting of deuterium, halogen, a cyano group, a nitro group, a $C_1$ to $C_{20}$ alkyl group, a $C_6$ to $C_{30}$ aryl group, a heteroaryl group having 5 to 30 nuclear atoms, and when the substituents are plural in number, the substituents are the same as or different from each other.

The compound represented by Chemical Formula 1 may be, but not limited to, embodied as a compound represented by any one of the following Chemical Formulas 8 to 13:

[Chemical Formula 8]

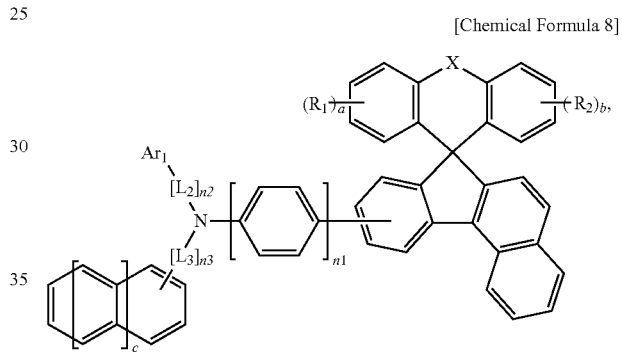

[Chemical Formula 9]

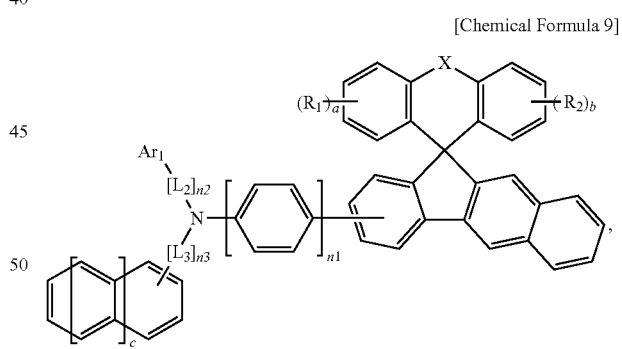

[Chemical Formula 10]

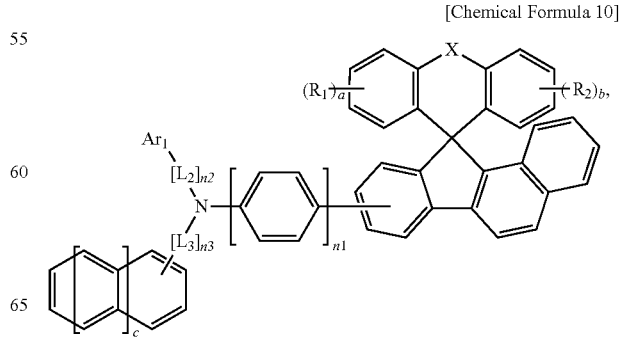

[Chemical Formula 11]

[Chemical Formula 12]

[Chemical Formula 13]

wherein in Chemical Formulas 8 to 13,

X, $R_1$, $R_2$, a, b, $L_2$ to $L_3$, n1 to n3, and $Ar_1$ are as defined in Chemical Formula 1, respectively, and $Y_1$, c, d, e, $R_3$ and $R_4$ are as defined in Chemical Formulas 6 and 7, respectively.

The compound represented by Chemical Formula 1 may be, but not limited to, embodied as a compound represented by any one of the following Chemical Formulas 14 to 22:

[Chemical Formula 14]

[Chemical Formula 15]

[Chemical Formula 16]

[Chemical Formula 17]

[Chemical Formula 18]
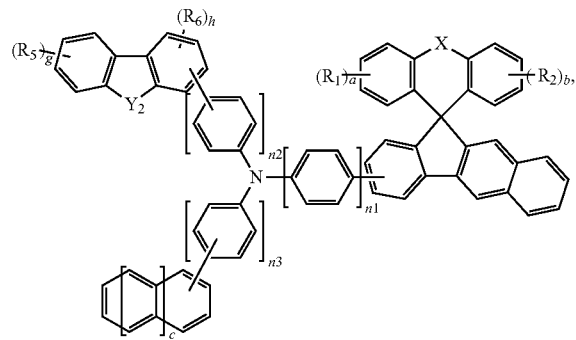
[Chemical Formula 19]
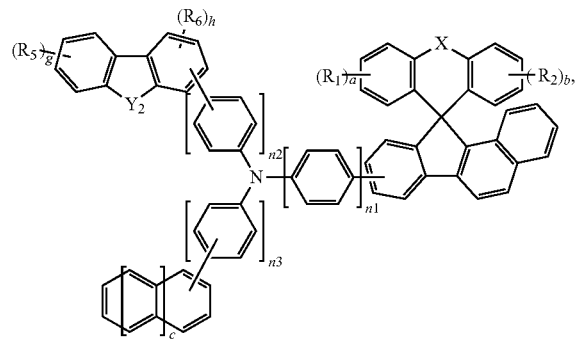
[Chemical Formula 20]
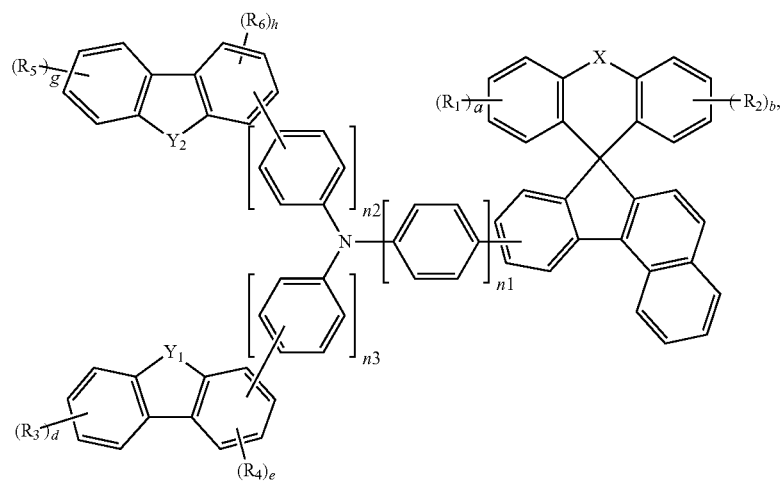
[Chemical Formula 21]
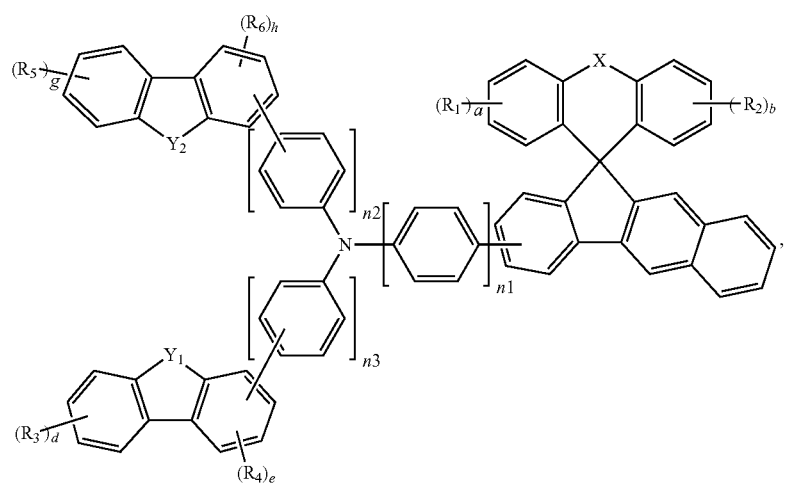

[Chemical Formula 22]

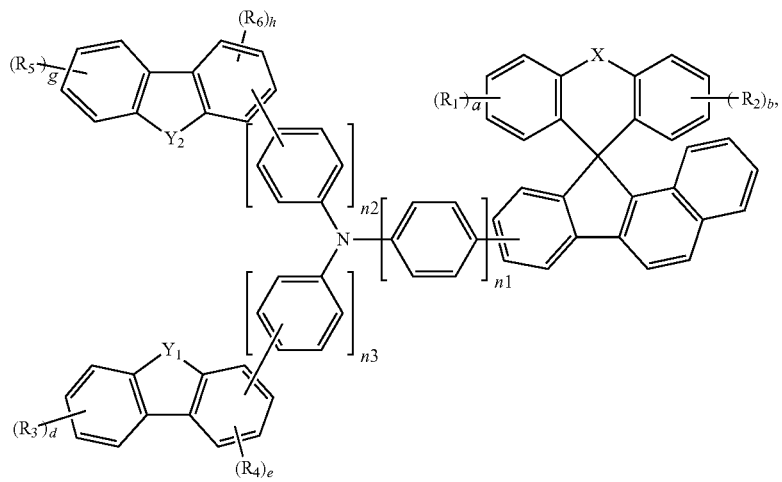

where in Chemical Formulas 14 to 22,

X, $R_1$, $R_2$, a, b, and n1 to n3 are as defined in Chemical Formula 1, respectively, $Y_1$, c, d, e, $R_3$, and $R_4$ are as defined in Chemical Formulas 6 and 7, respectively, f is 0 or 1, $Y_2$ is selected from the group consisting of O, S, C($Ar_6$)($Ar_7$), and N($Ar_8$), g is an integer ranging from 0 to 4, h is an integer ranging from 0 to 3, $R_5$, $R_6$ and $Ar_6$ to $Ar_8$ are the same as or different from each other, each independently being selected from the group consisting of hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_5$, $R_6$ and $Ar_6$ to $Ar_8$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and preferably, substituted or unsubstituted with one or more kinds of substituents selected from the group consisting of deuterium, halogen, a cyano group, a nitro group, a $C_1$ to $C_{20}$ alkyl group, a $C_6$ to $C_{30}$ aryl group, a heteroaryl group having 5 to 30 nuclear atoms, and when the substituents are plural in number, the substituents are the same as or different from each other The compound represented by Chemical Formula 1 according to the present invention described above may be further embodied as the following compounds, such as compounds 1 to 259, but embodiments are not limited thereto.

(1)

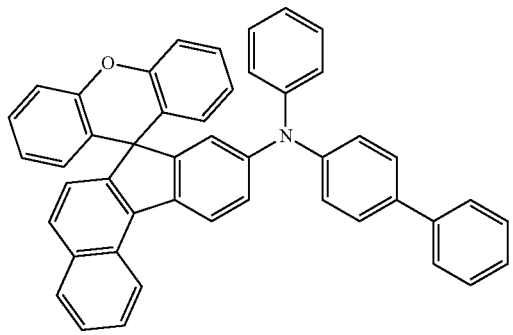

(2)

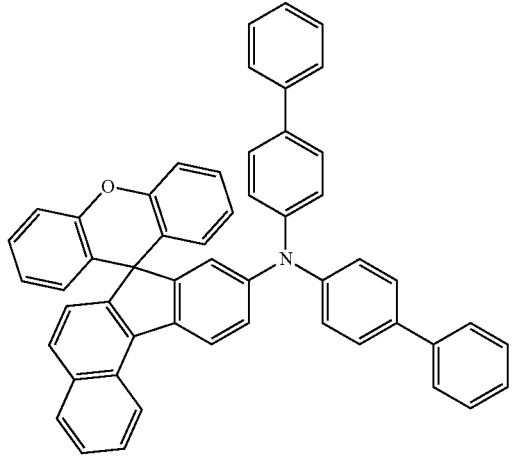

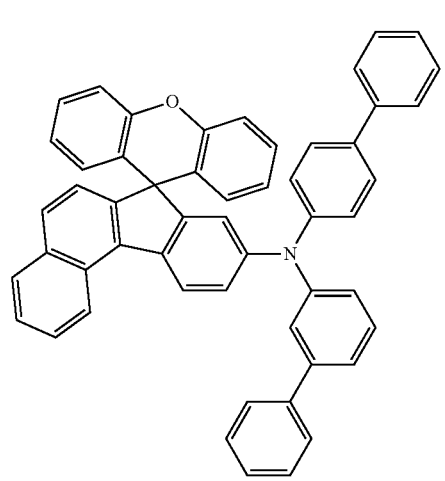
(3)
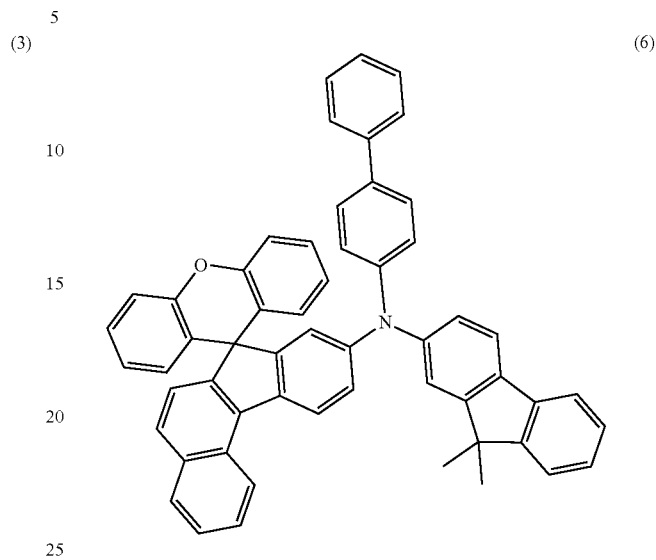
(6)
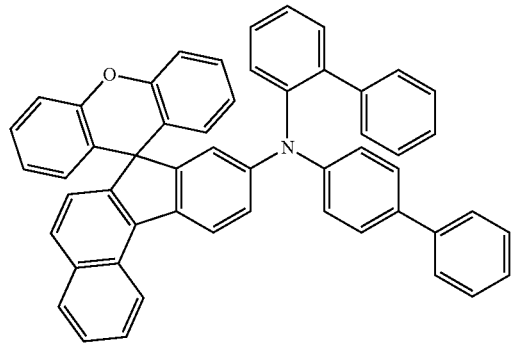
(4)
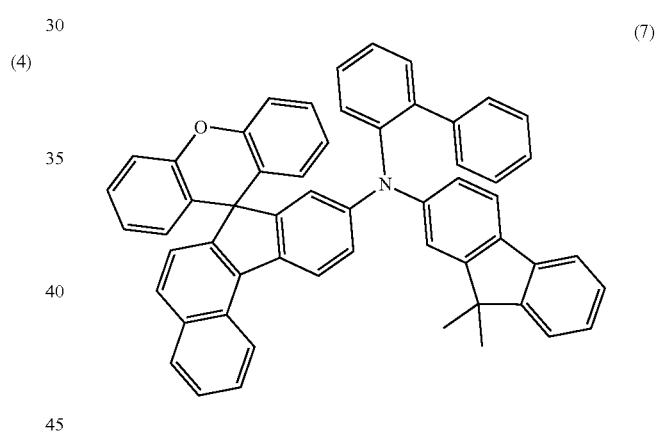
(7)
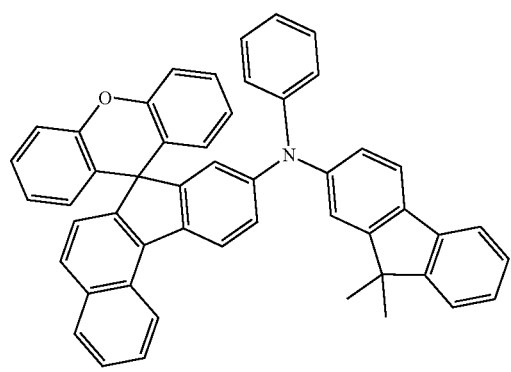
(5)
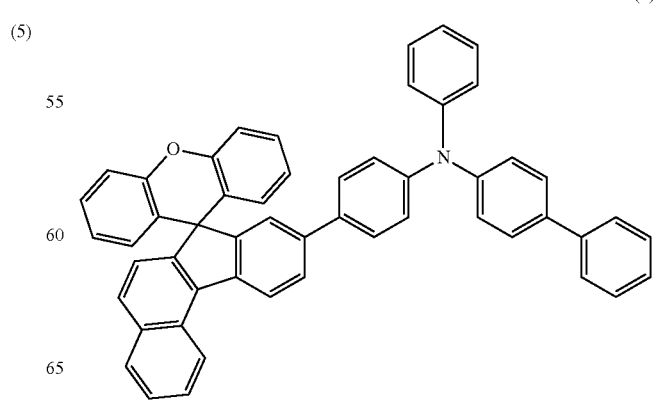
(8)

(9)
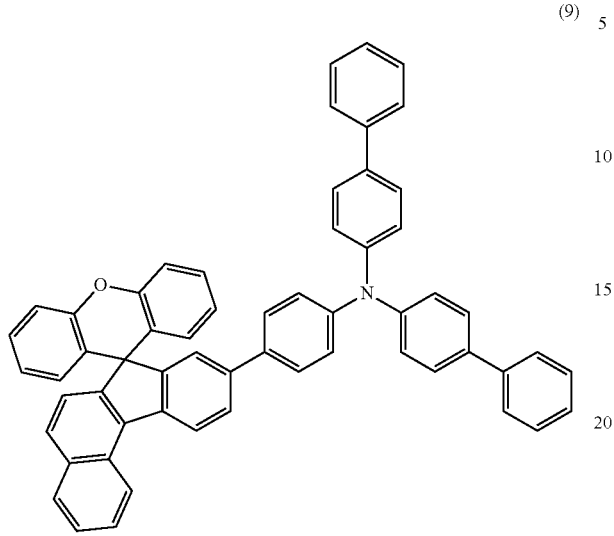
(10)
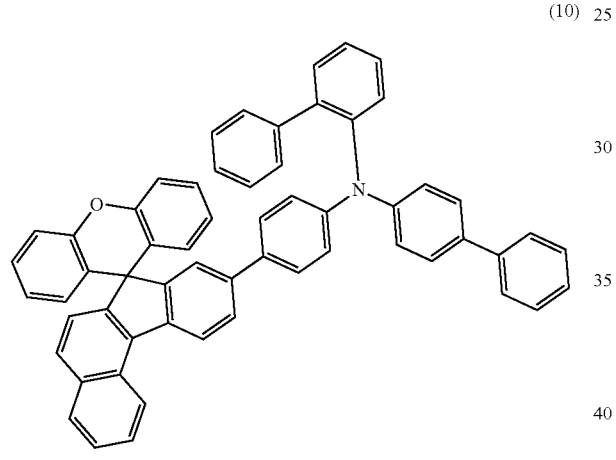
(11)
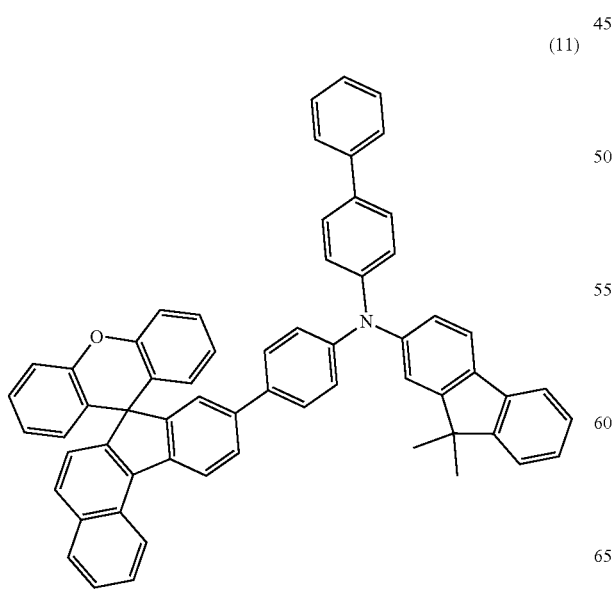
(12)
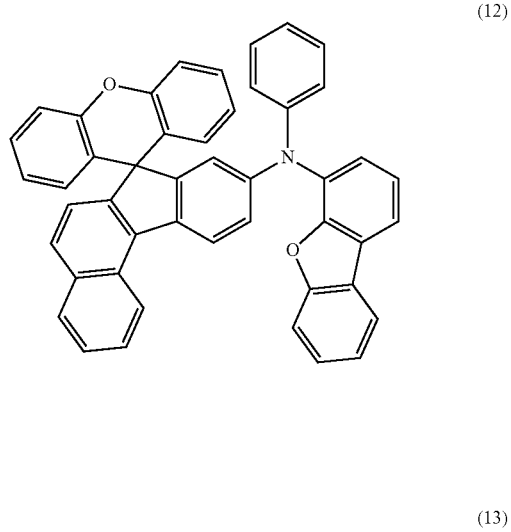
(13)
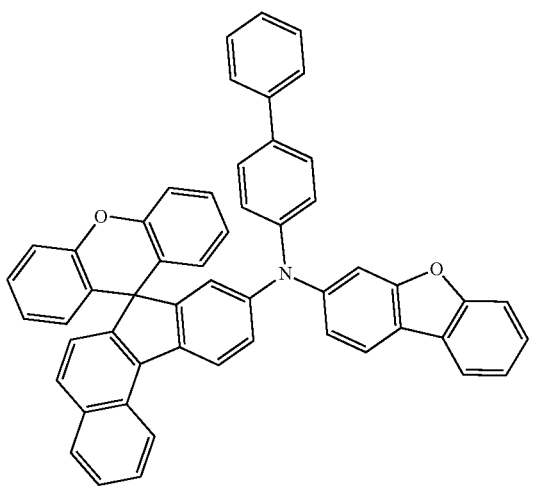
(14)
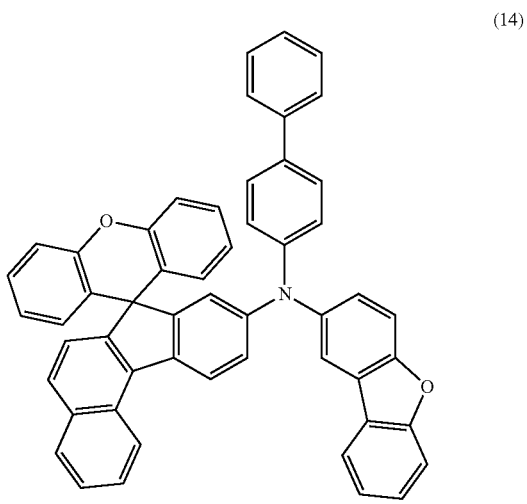

(15)
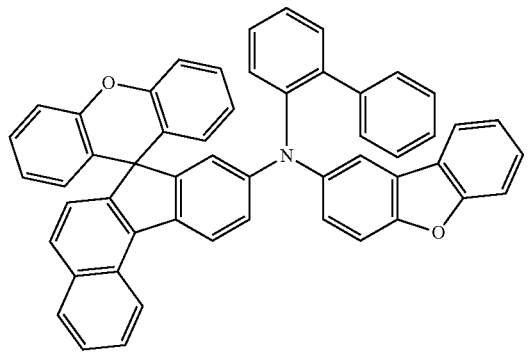
(16)
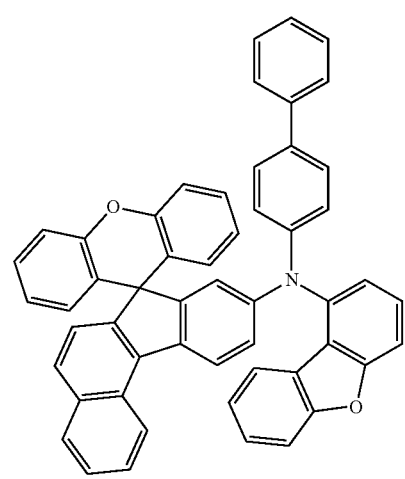
(17)
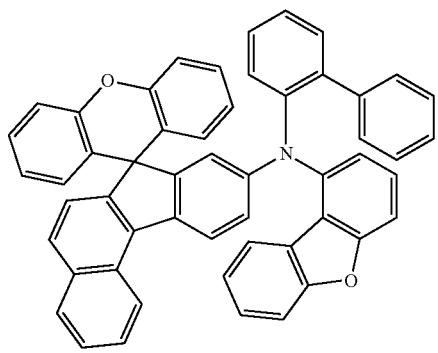
(18)
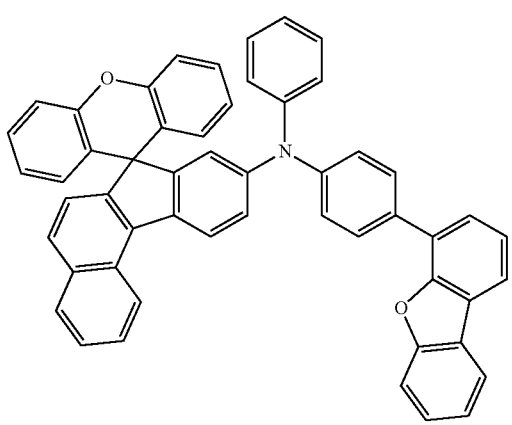
(19)
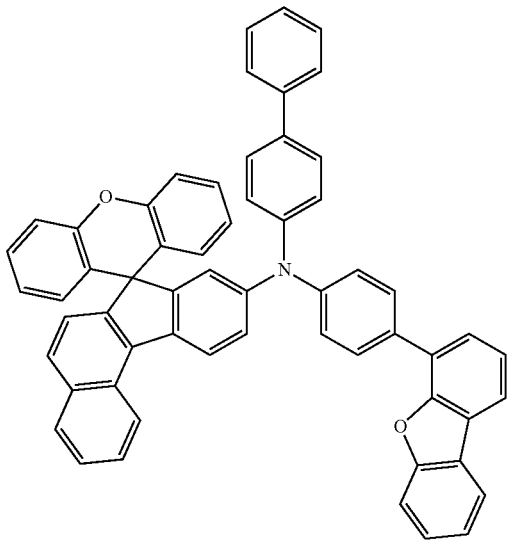
(20)
(21)
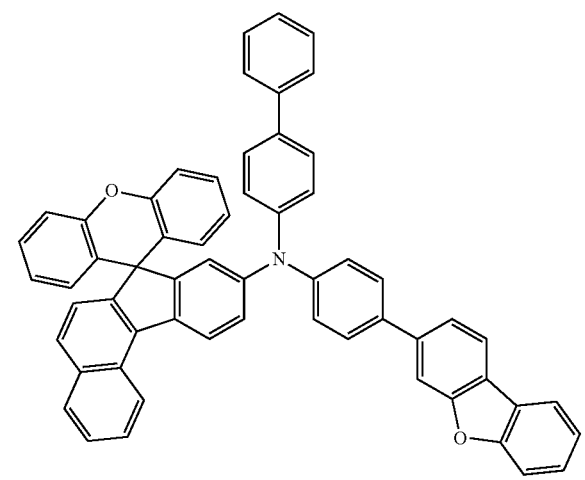

(22)
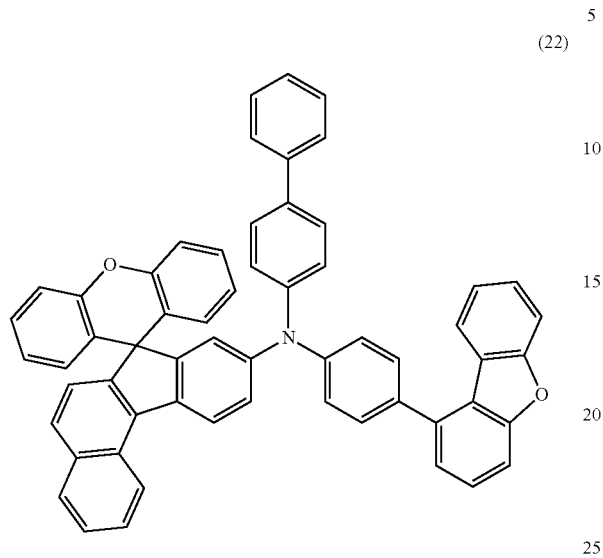
(23)
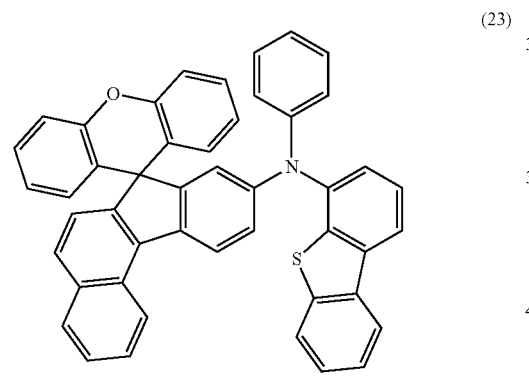
(24)
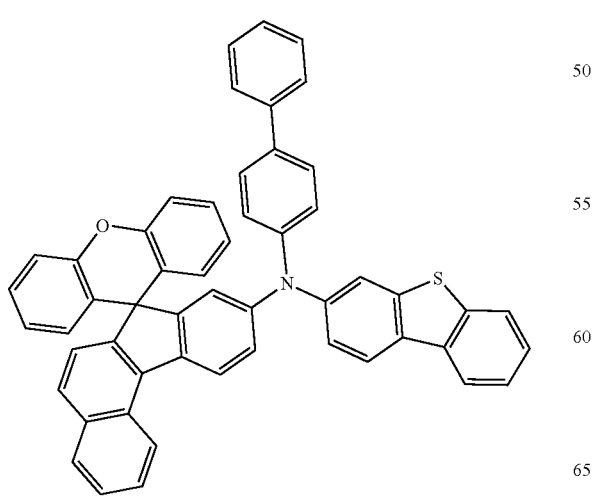
(25)
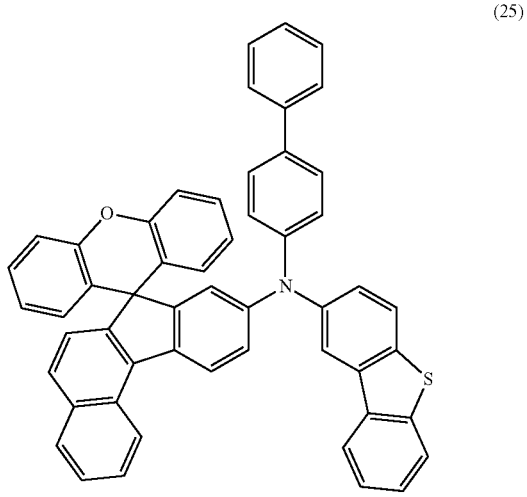
(26)
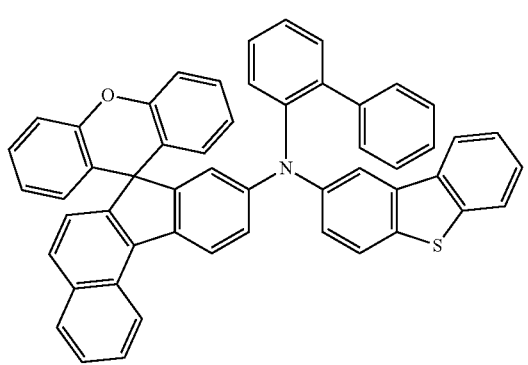
(27)
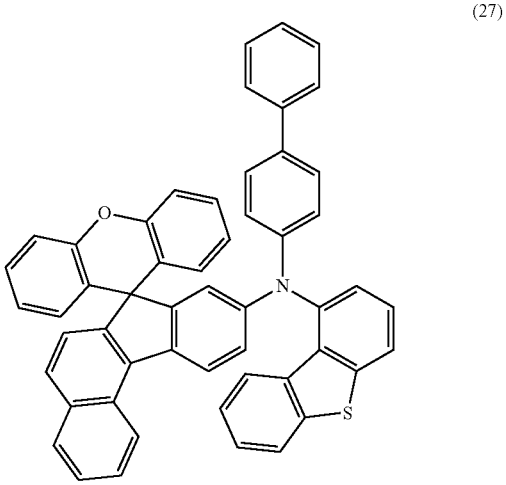

(28) 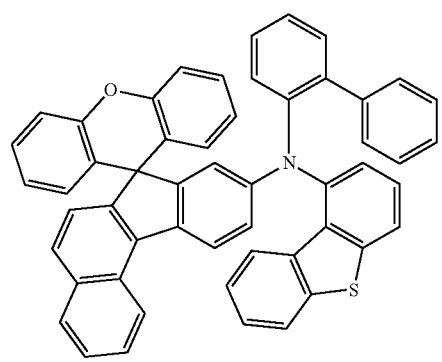
(29) 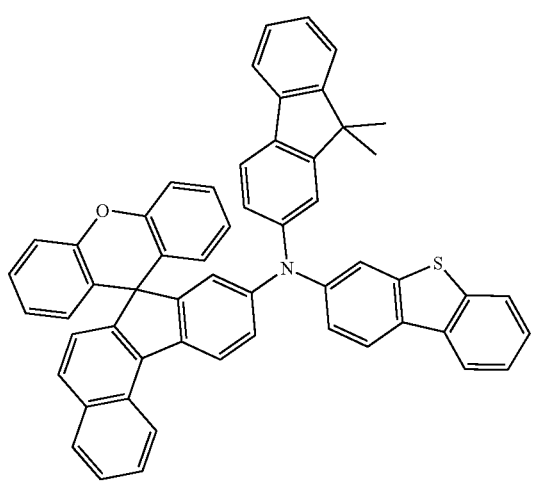
(30) 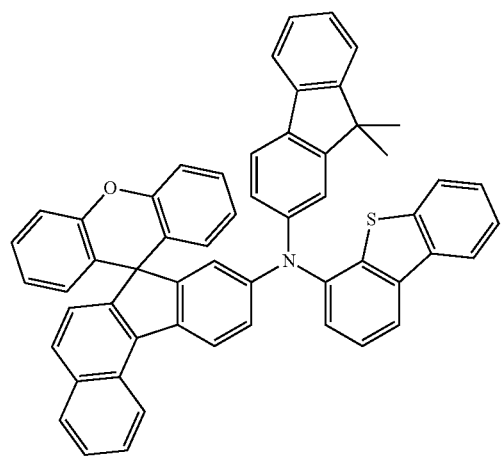
(31) 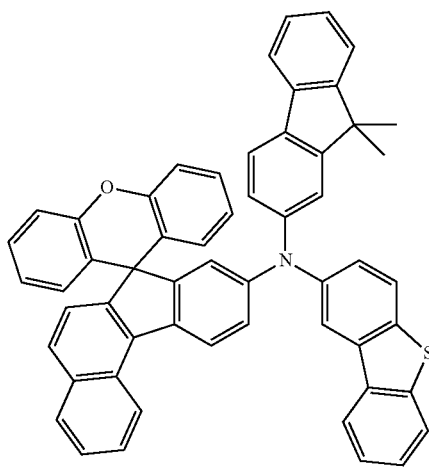
(32) 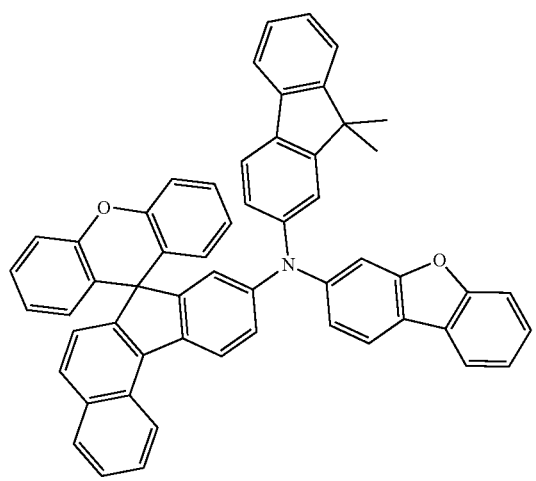
(33) 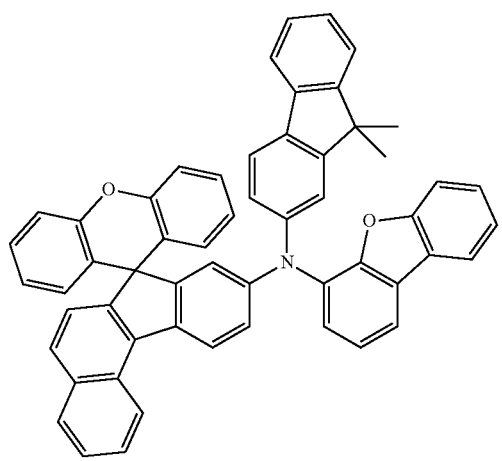

(34)
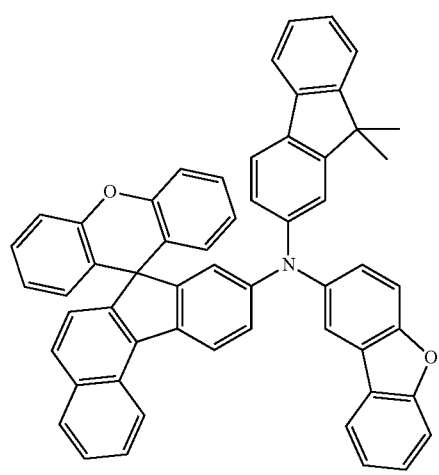
(35)
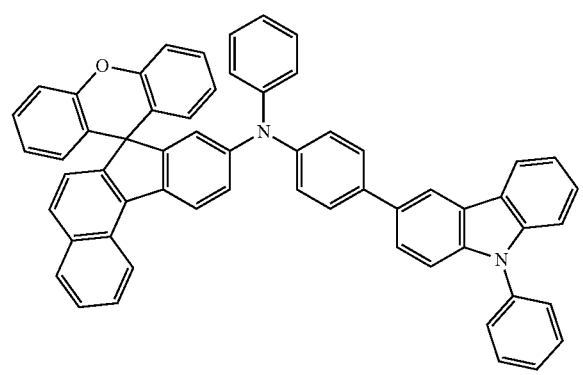
(36)
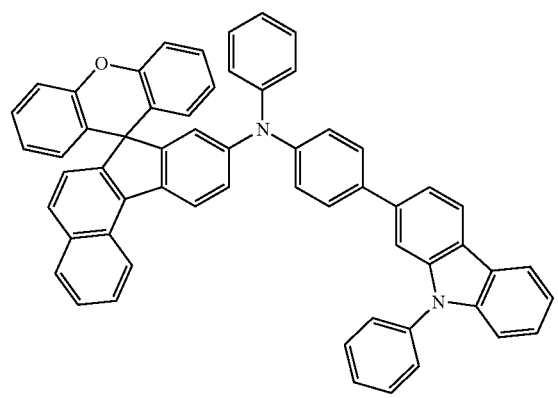
(37)
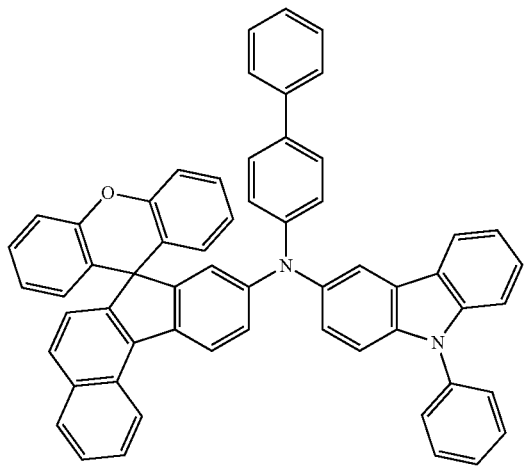
(38)
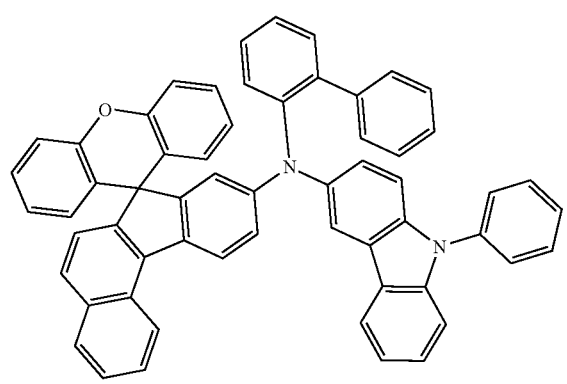
(39)
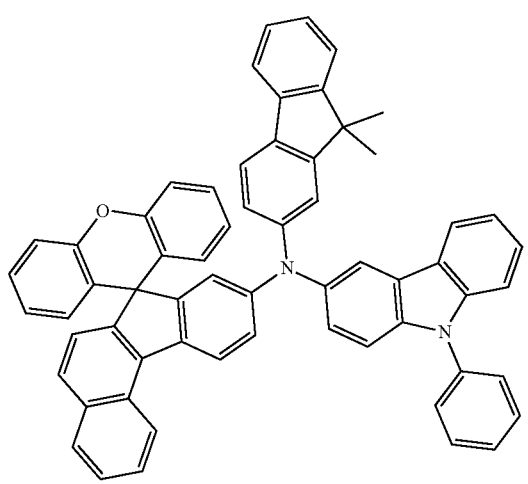

(40)
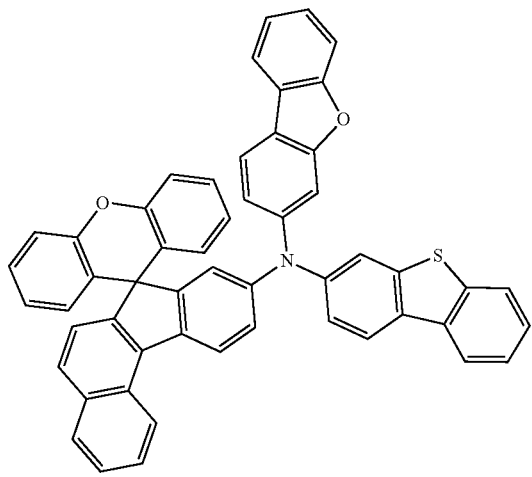
(41)
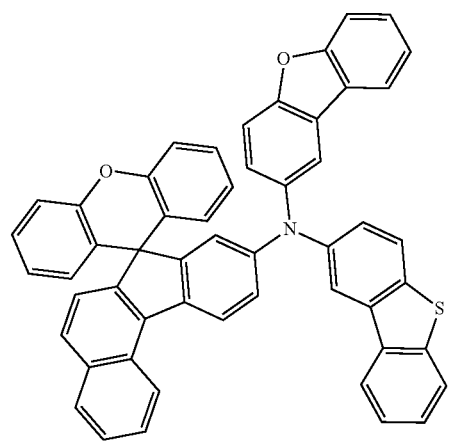
(42)
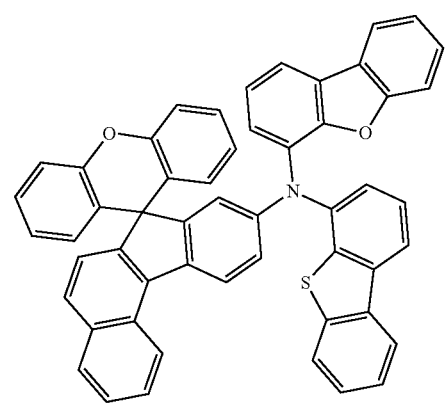
(43)
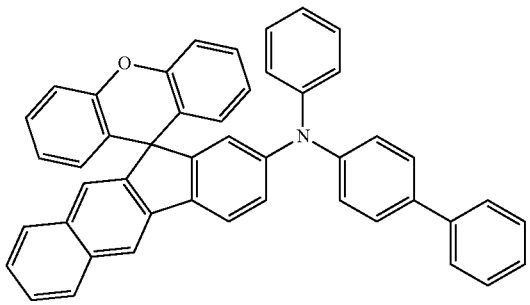
(44)
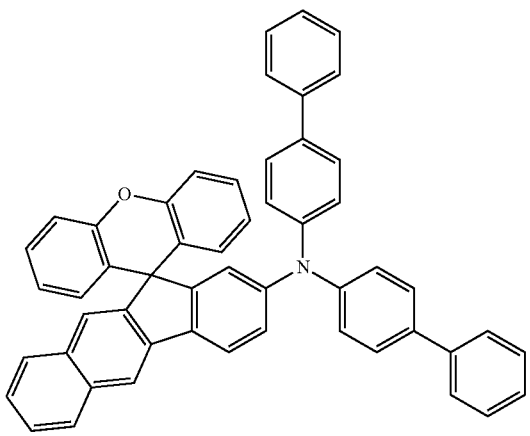
(45)
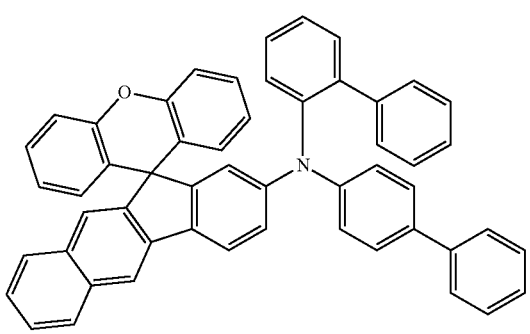
(46)
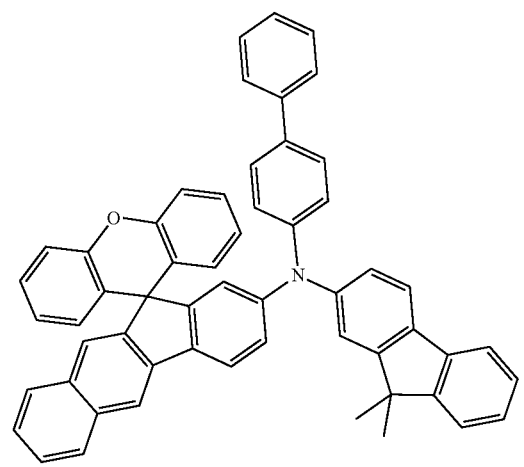

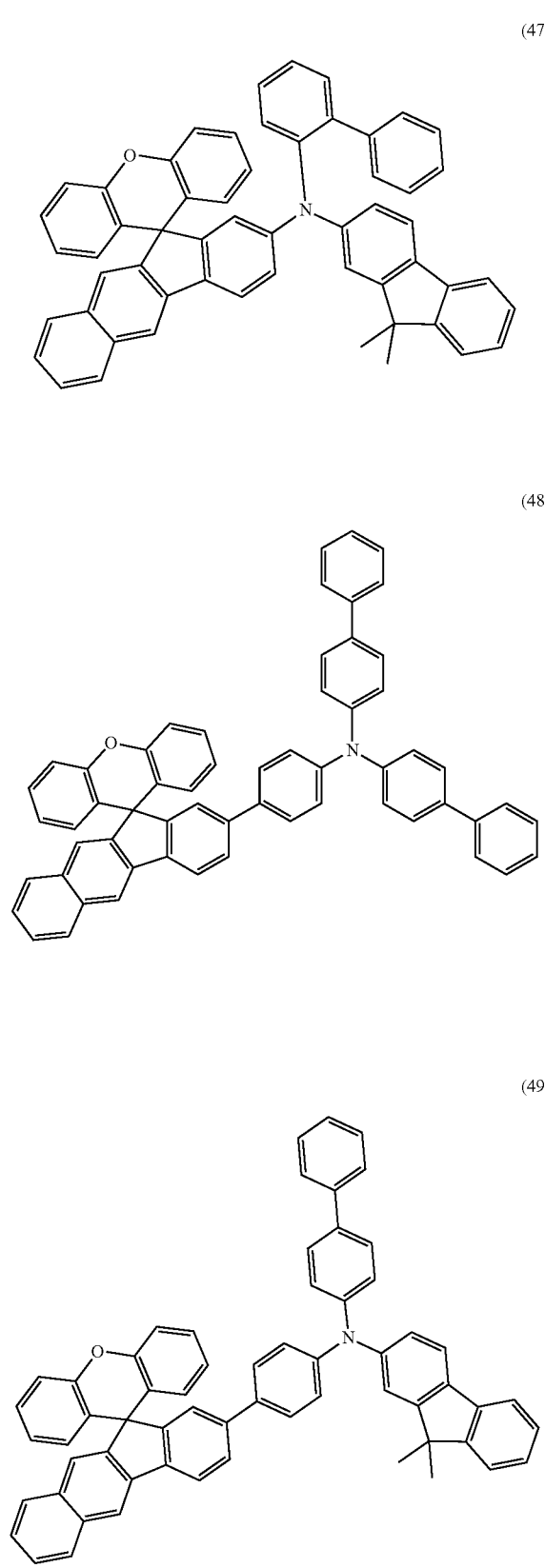
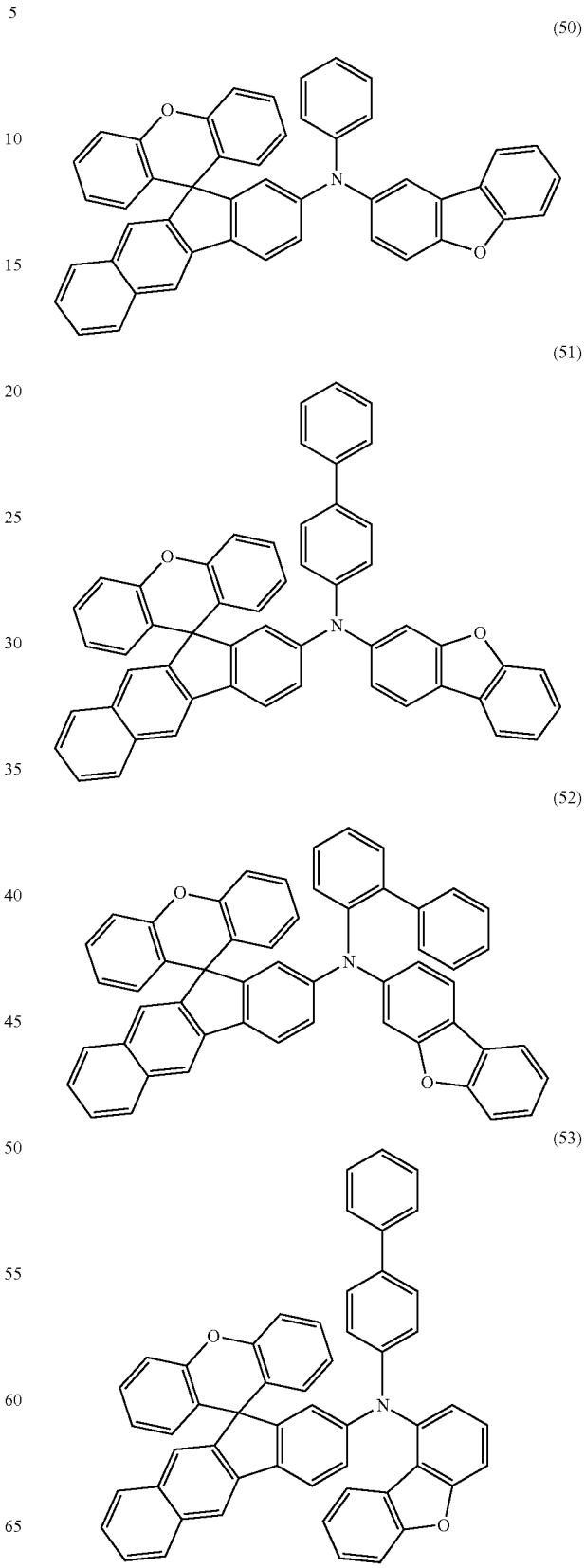

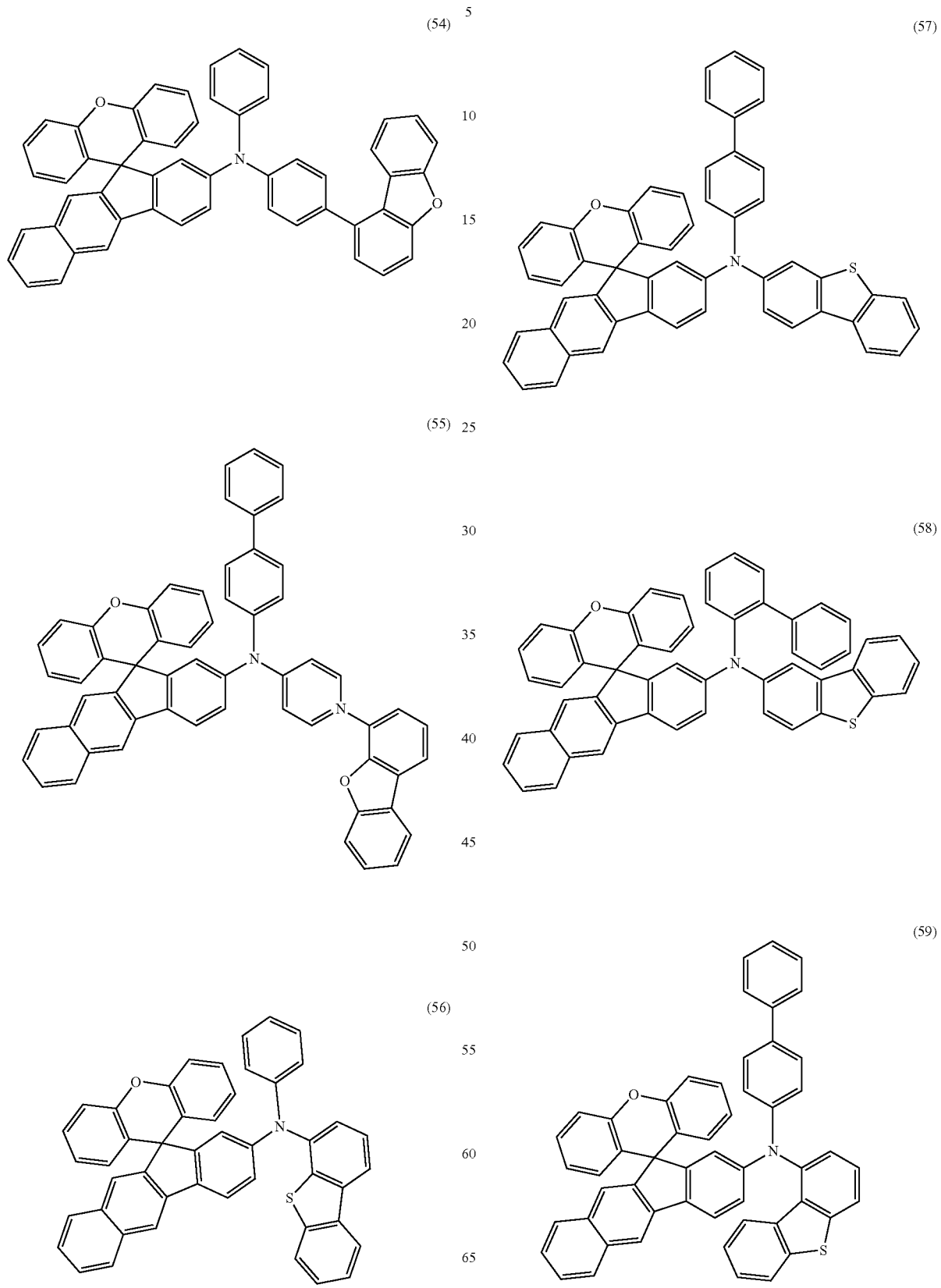

(60)
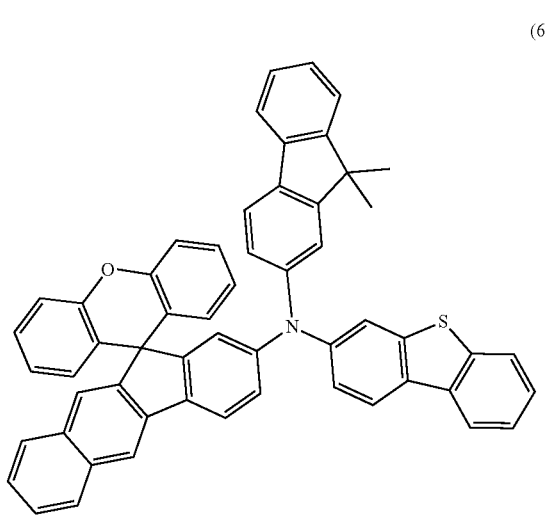
(61)
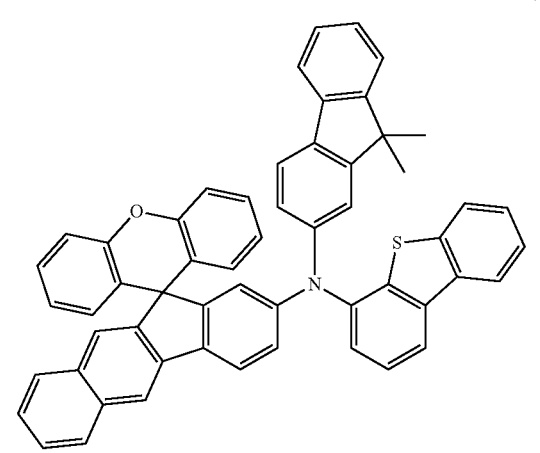
(62)
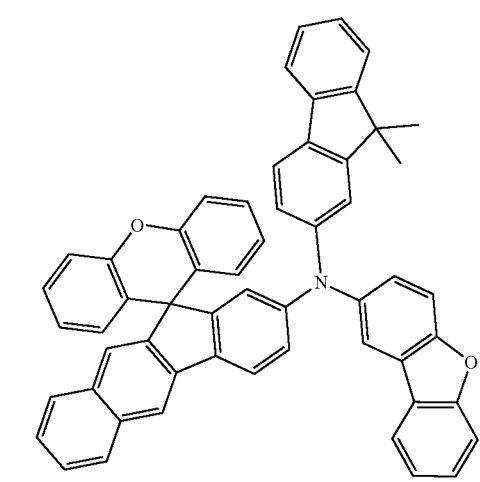
(63)
(64)
(65)
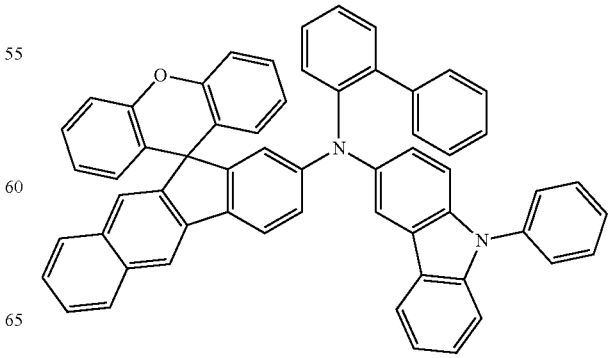

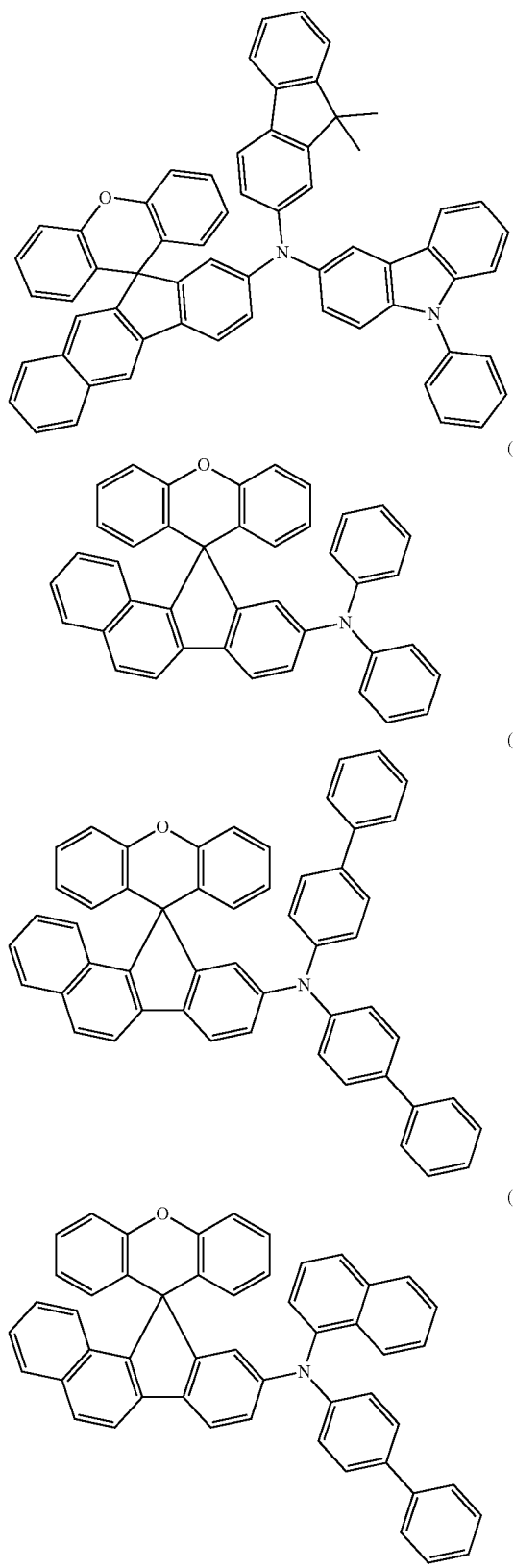
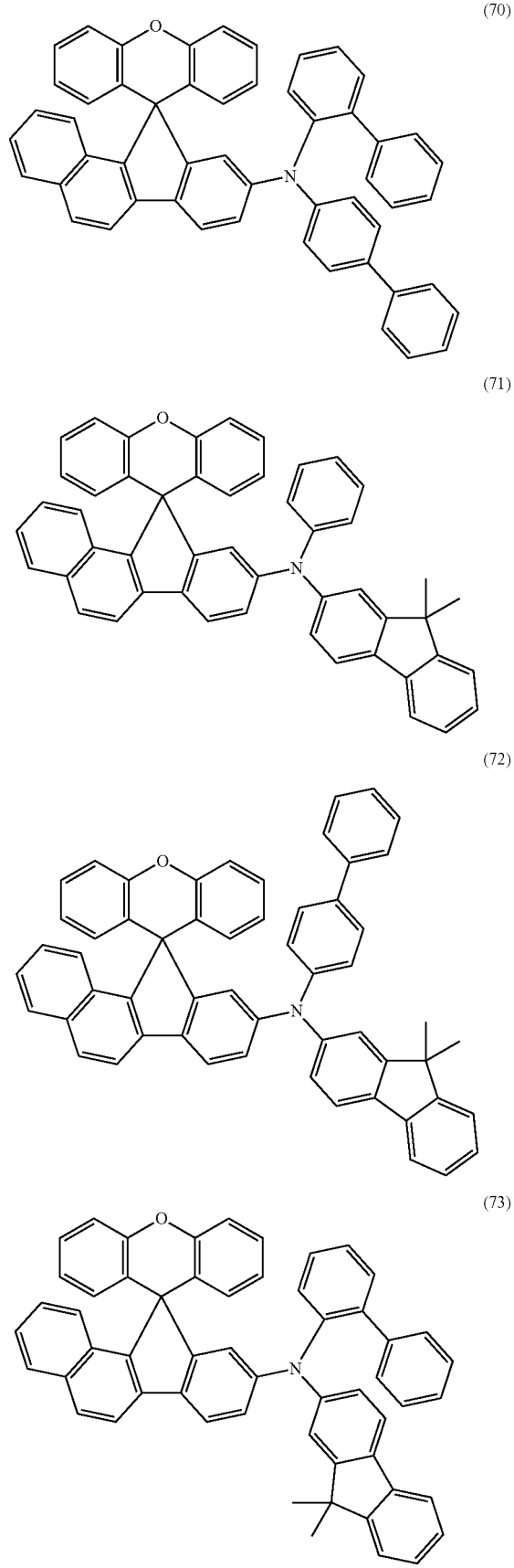

(74) 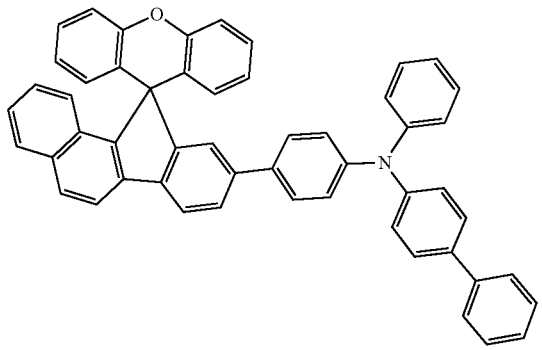
(75) 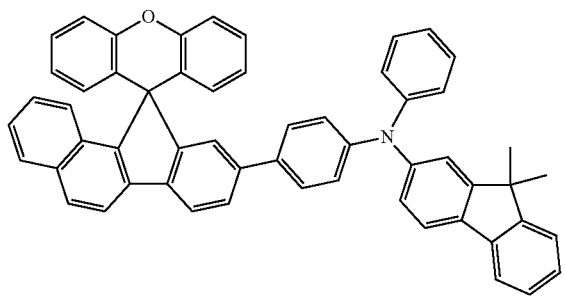
(76) 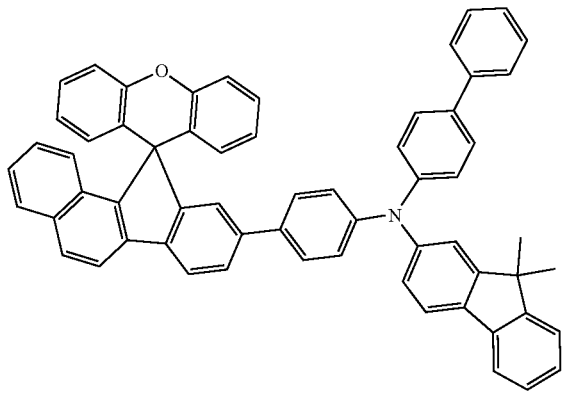
(77) 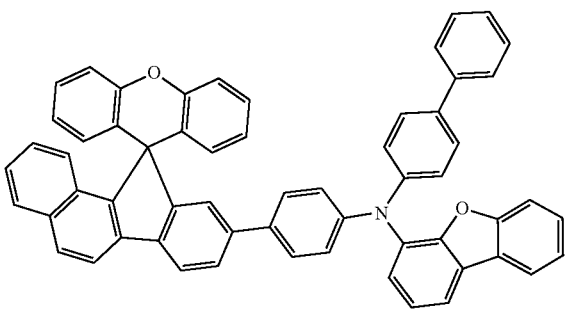
(78) 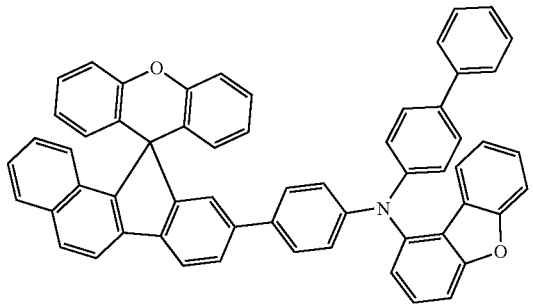
(79) 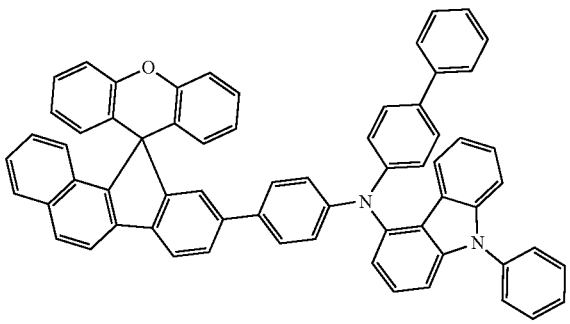
(80) 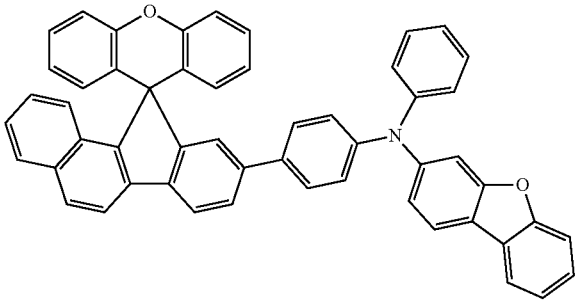
(81) 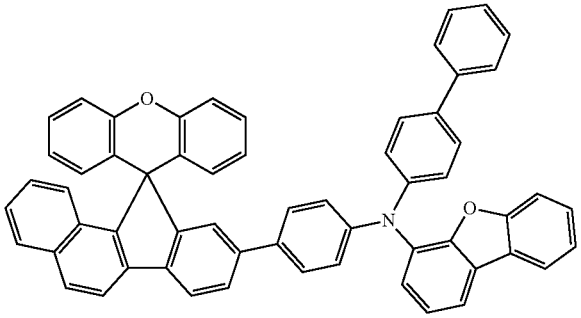

(82)
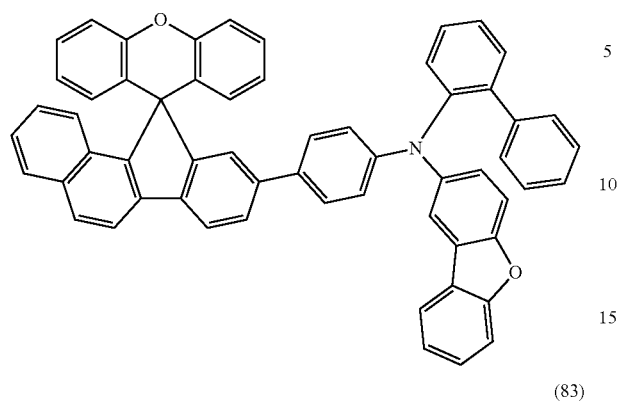
(83)
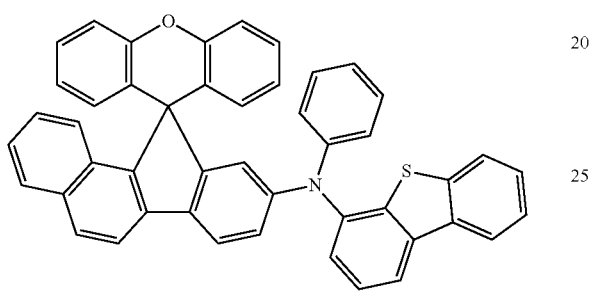
(84)
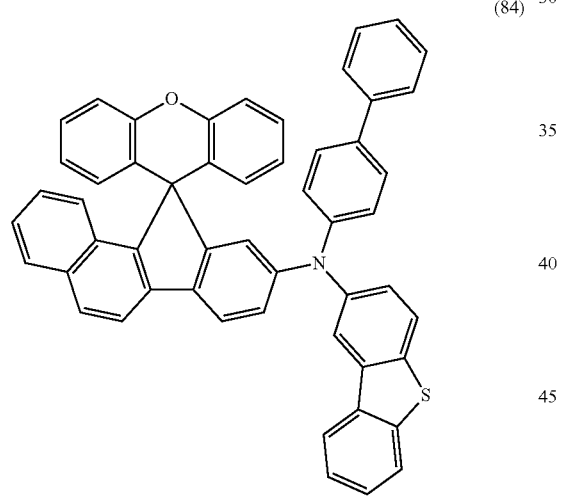
(85)
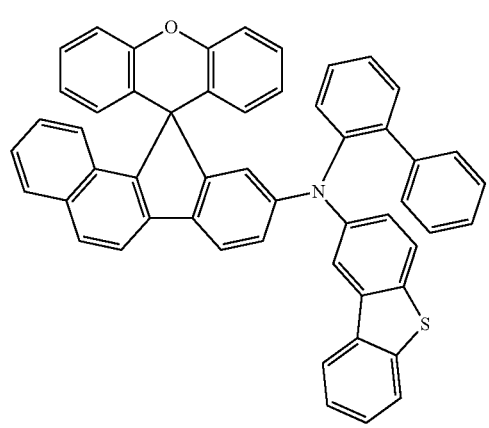
(86)
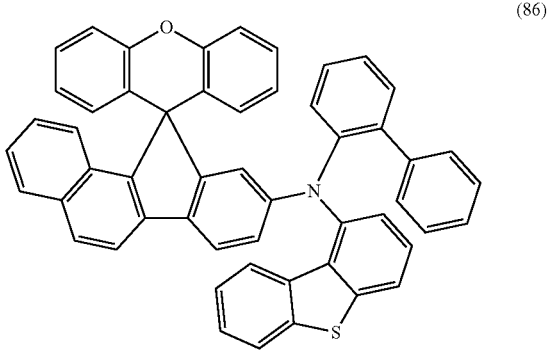
(87)
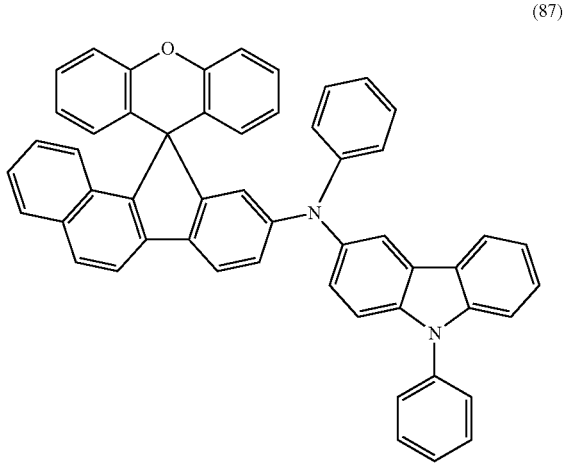
(88)
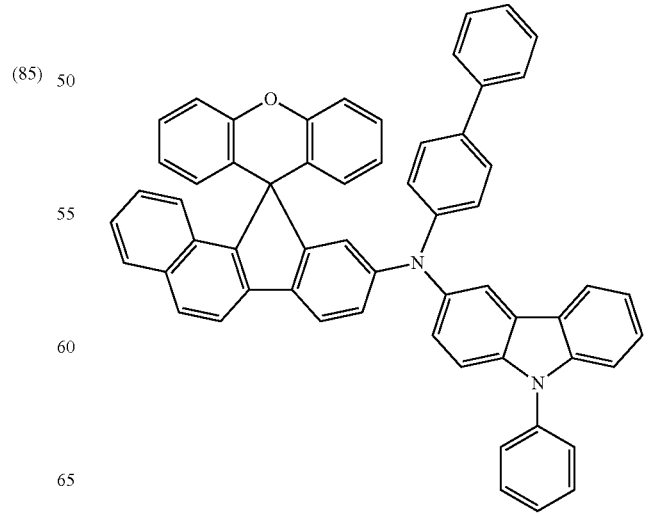

-continued
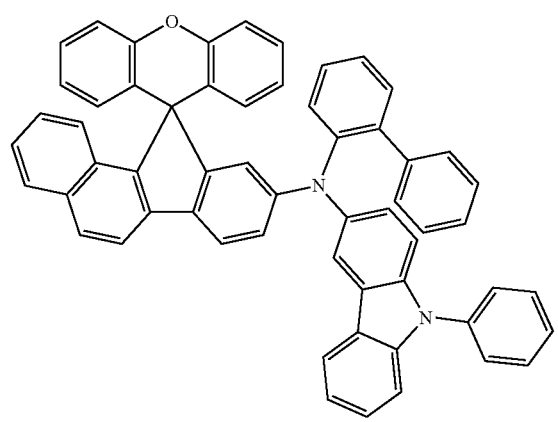
(89)
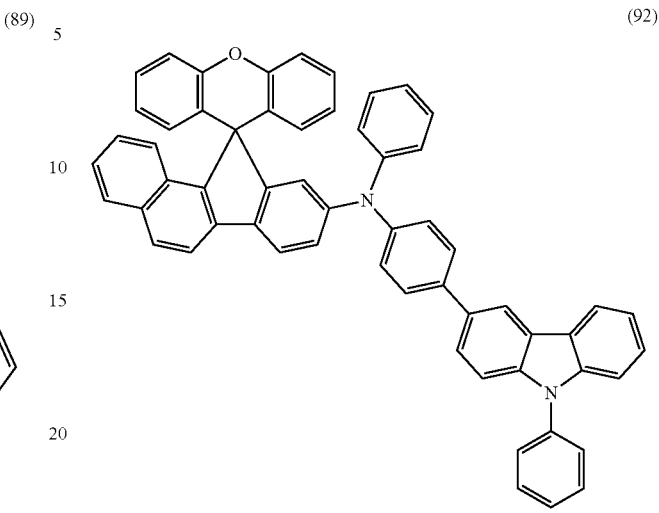
(92)
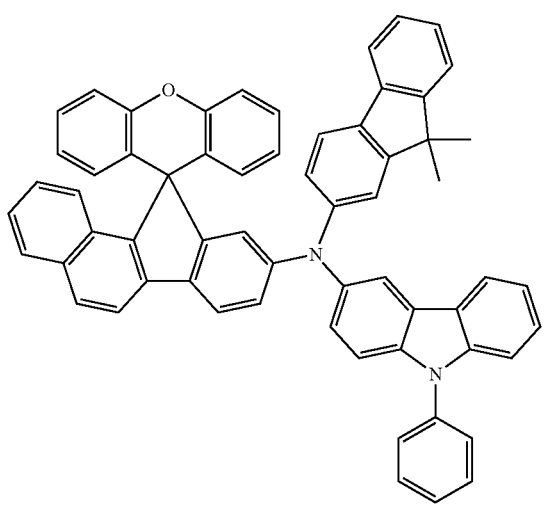
(90)
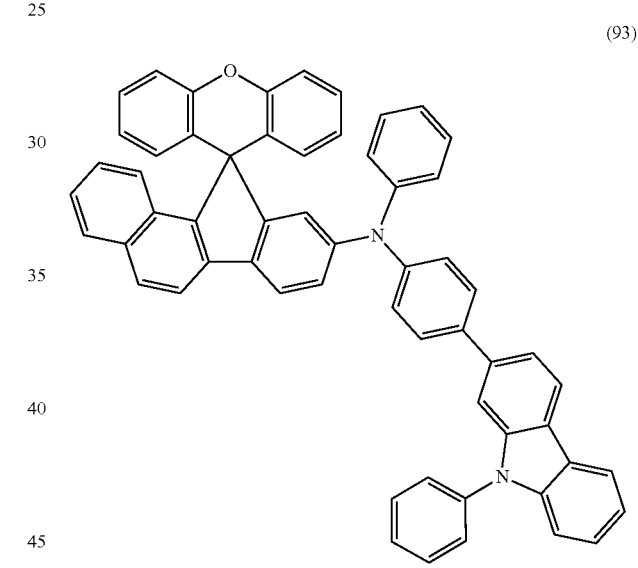
(93)
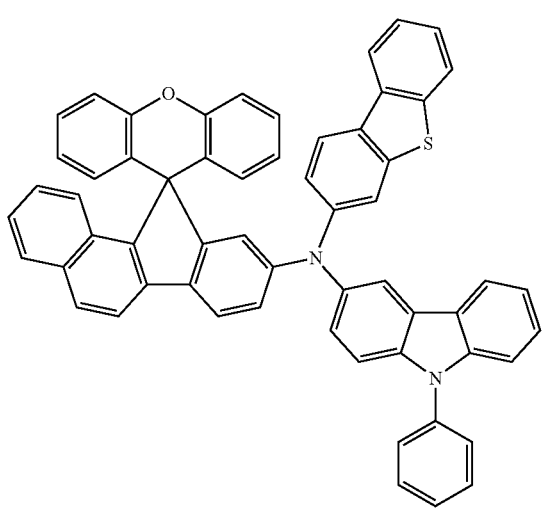
(91)
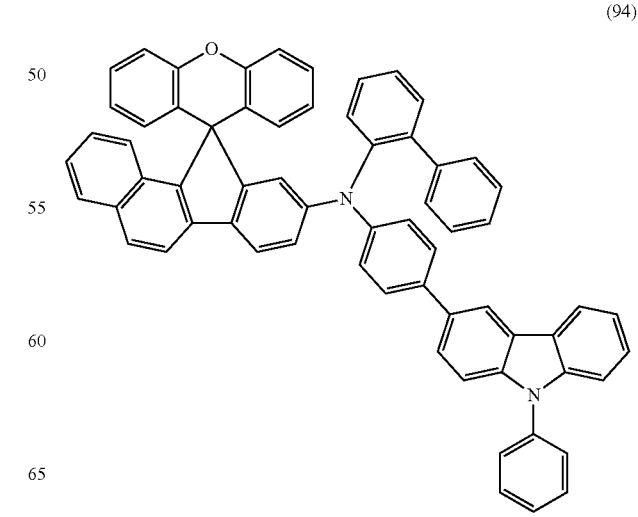
(94)

(95)
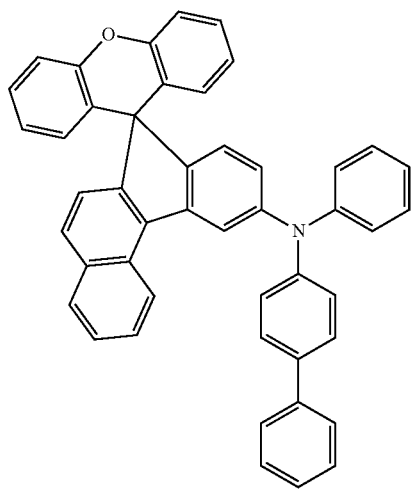
(96)
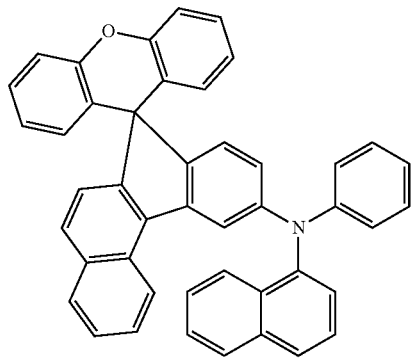
(97)
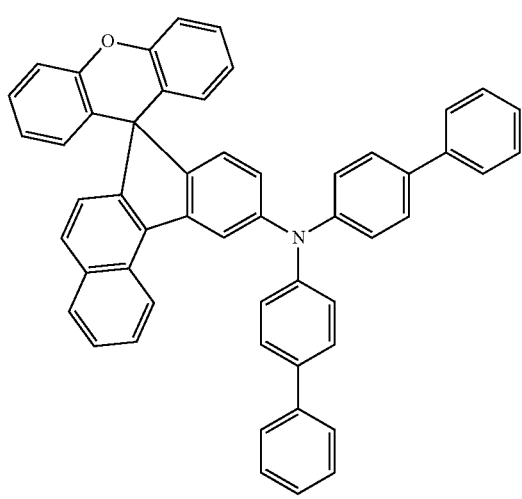
(98)
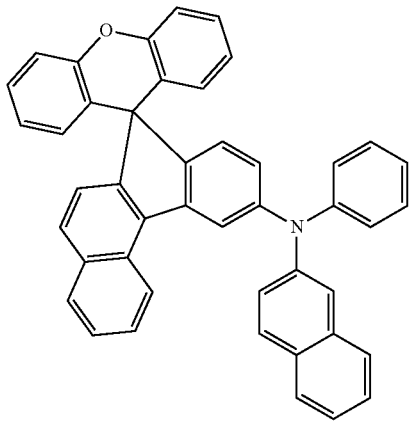
(99)
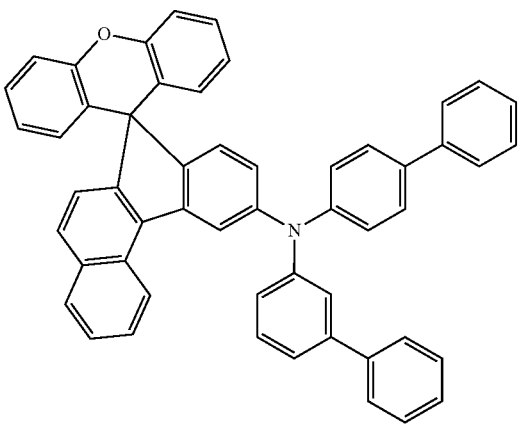
(100)
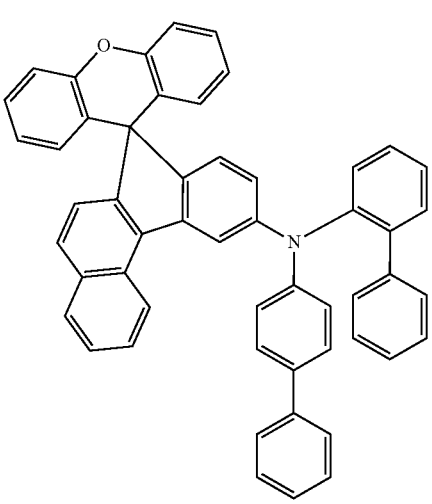

(101)
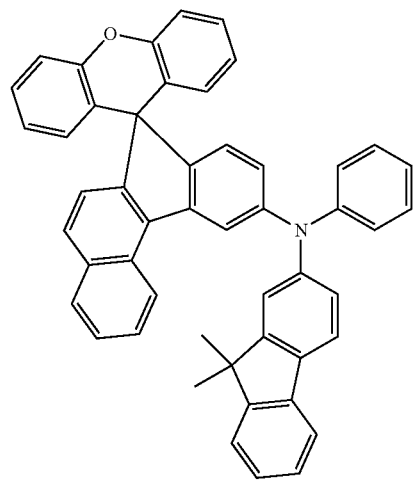
(102)
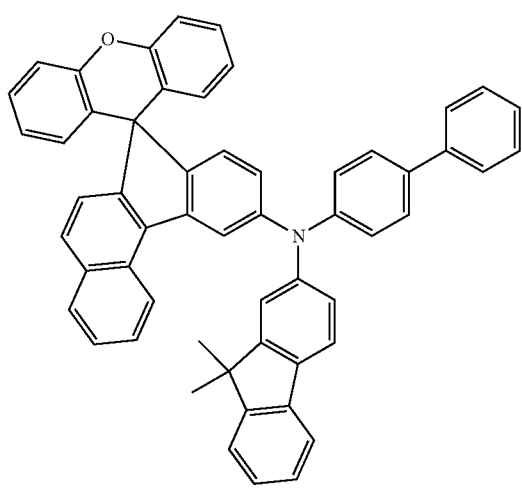
(103)
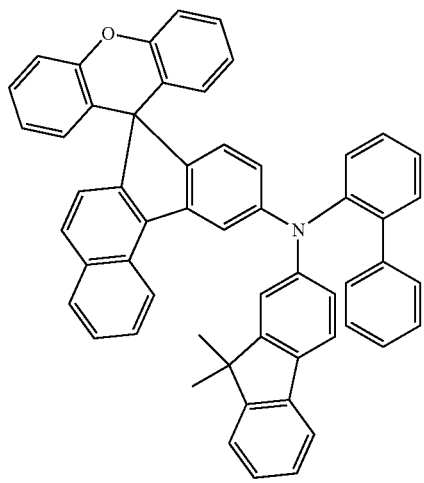
(104)
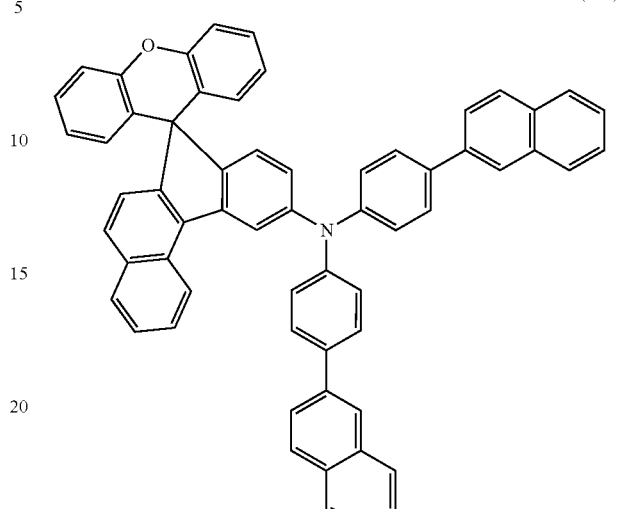
(105)
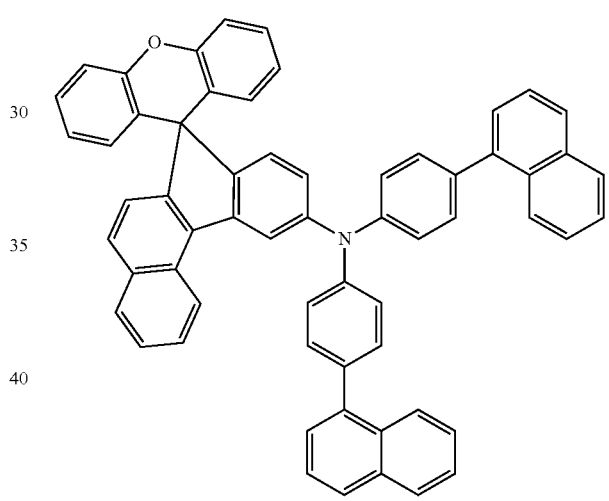
(106)

(107)
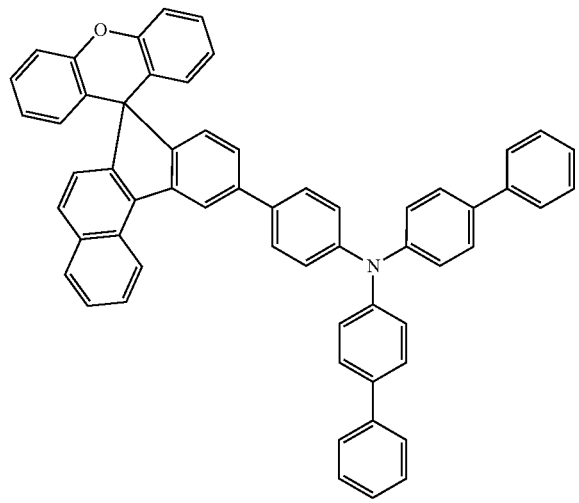
(108)
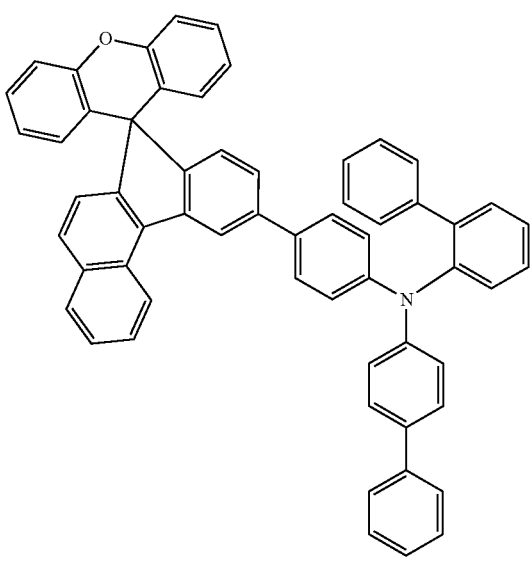
(109)
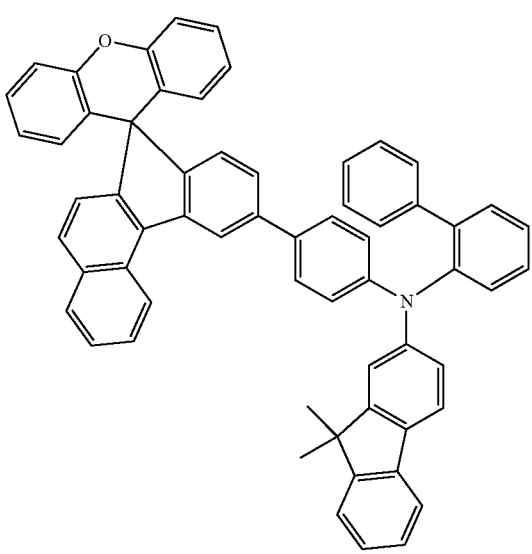
(110)
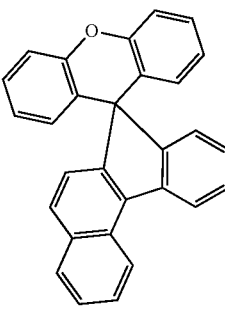
(111)
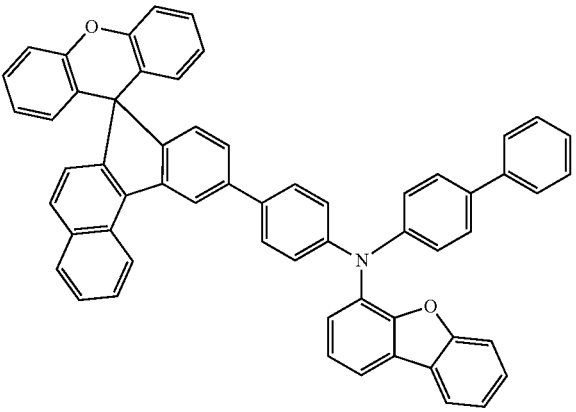
(112)
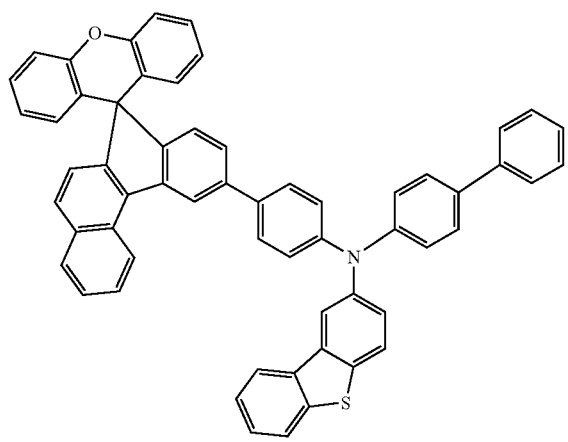

(113)
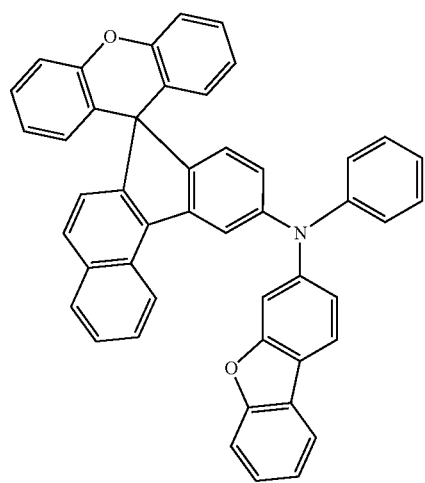
(114)
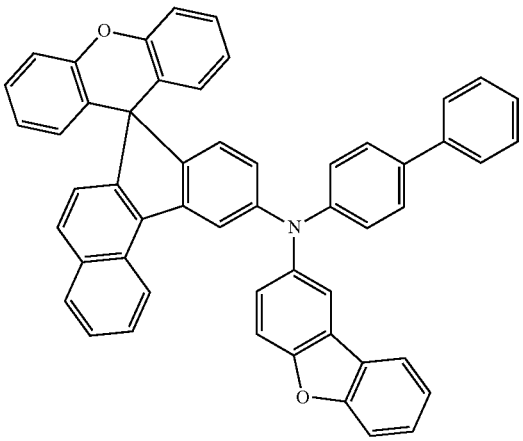
(115)
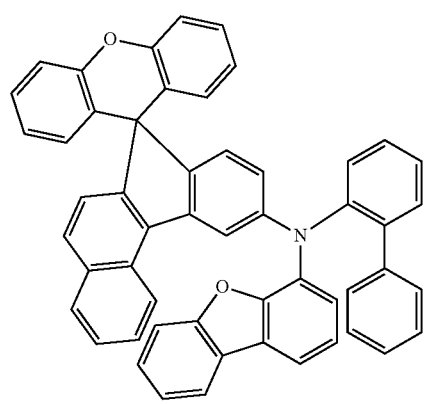
(116)
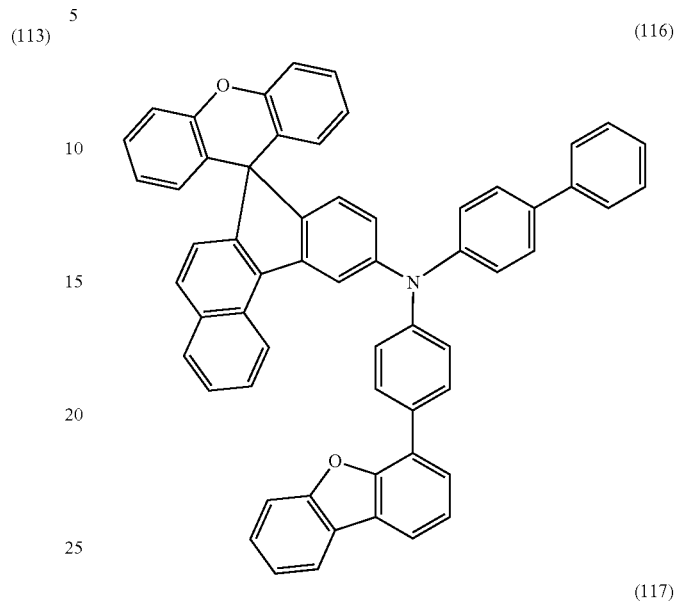
(117)
(118)
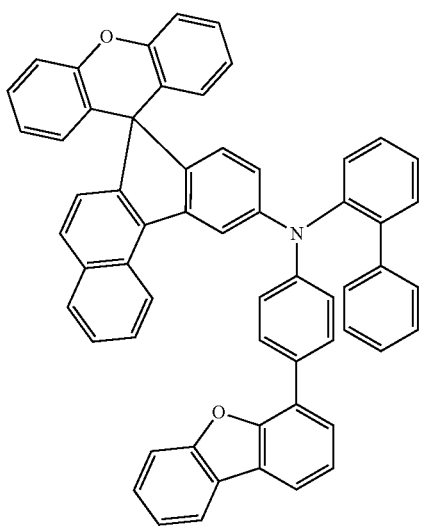

(119) 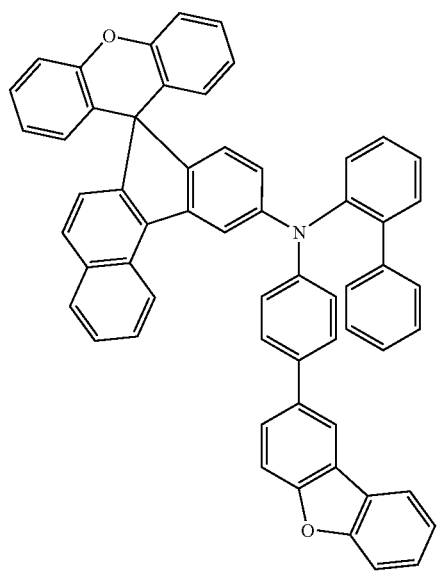
(120) 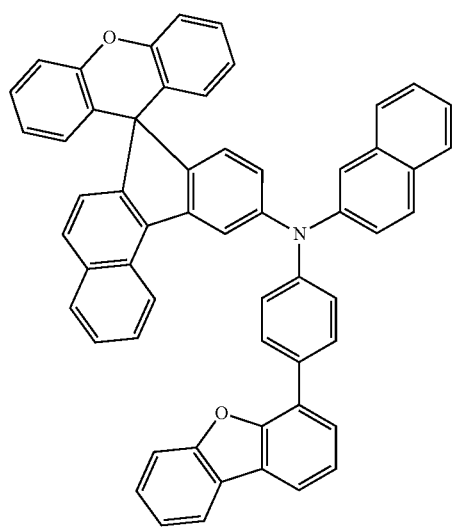
(121) 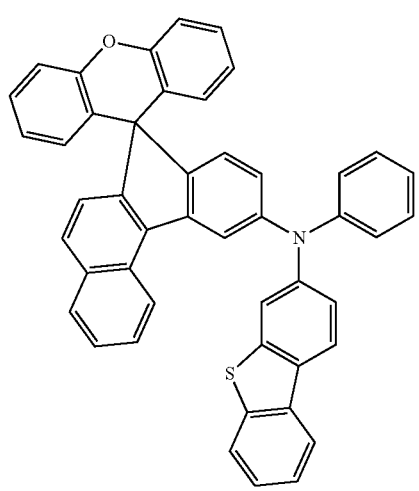
(122) 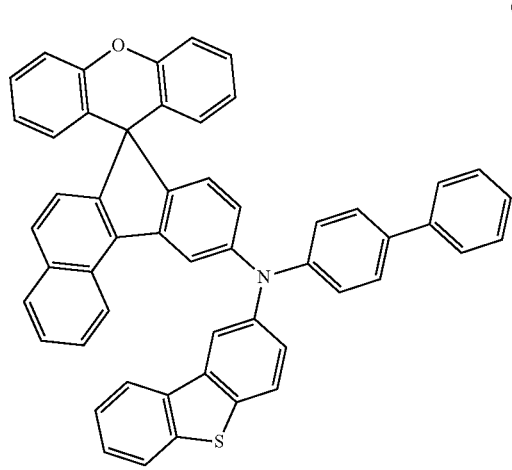
(123) 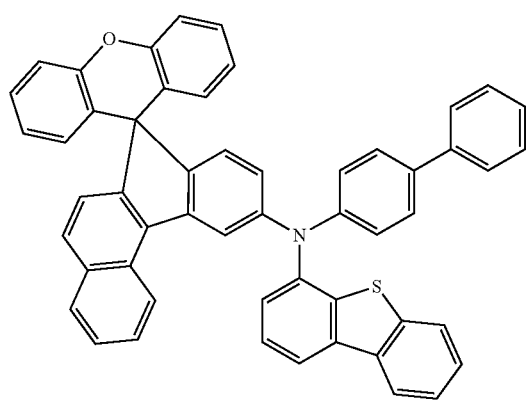
(124) 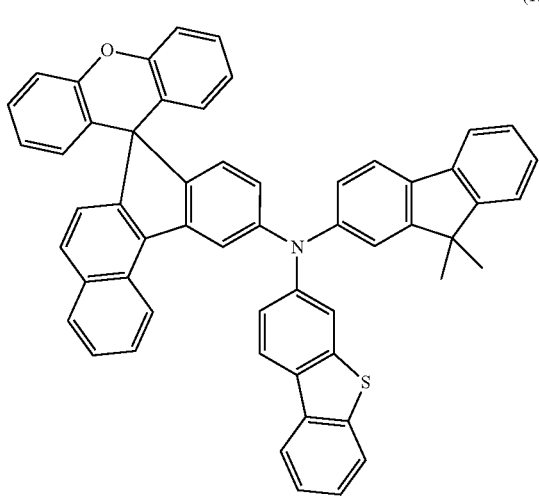

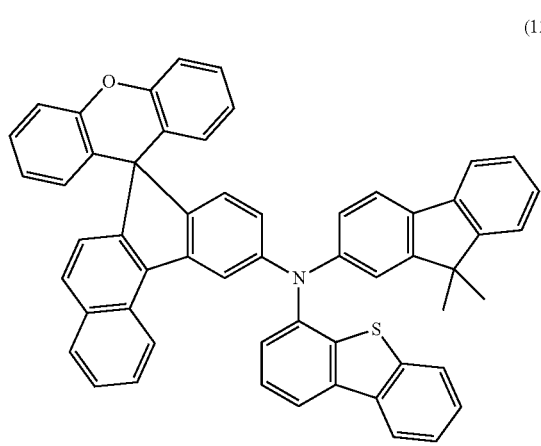
(125)
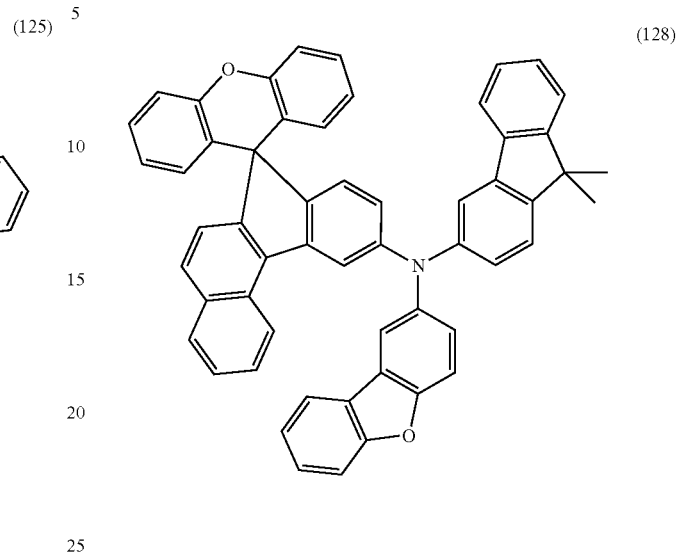
(128)
(126)
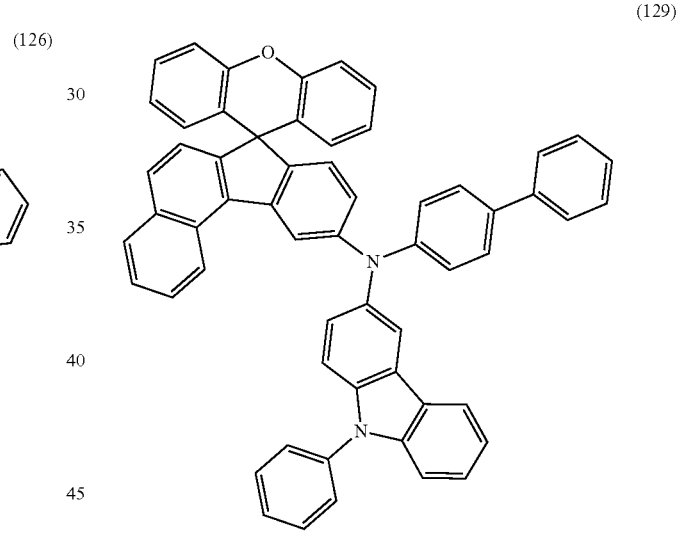
(129)
(127)
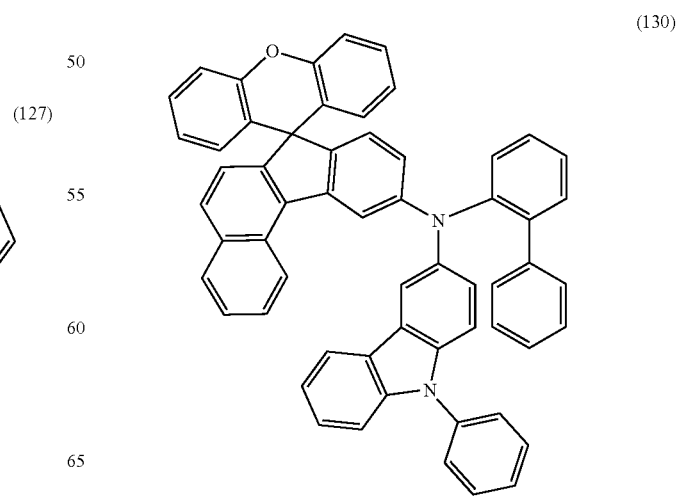
(130)

(131)
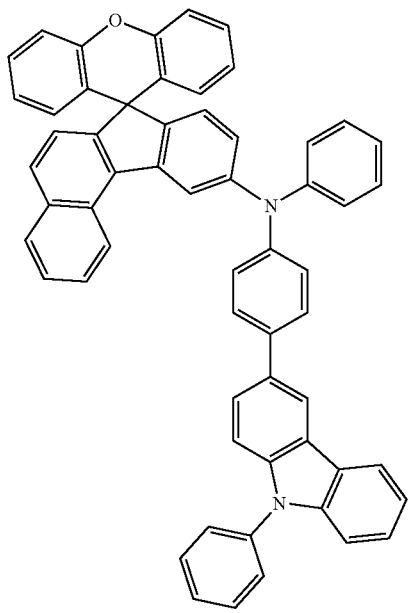
(132)
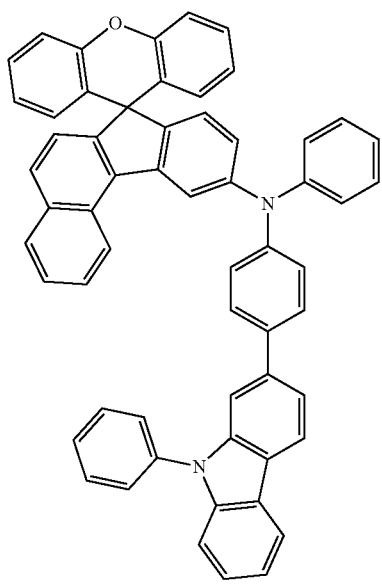
(133)
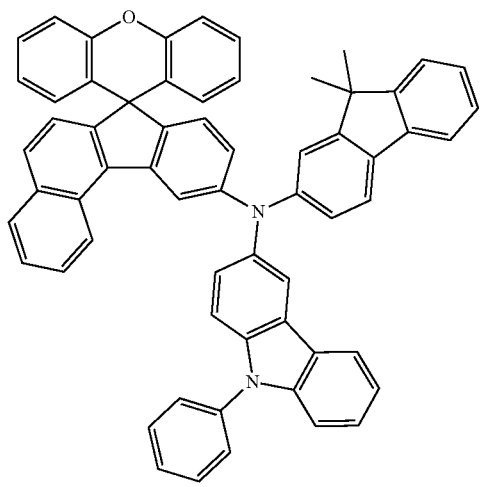
(134)
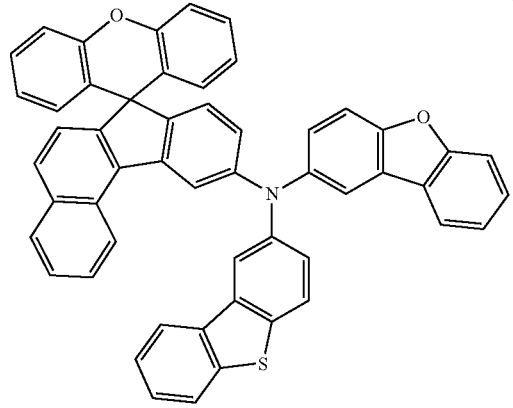
(135)
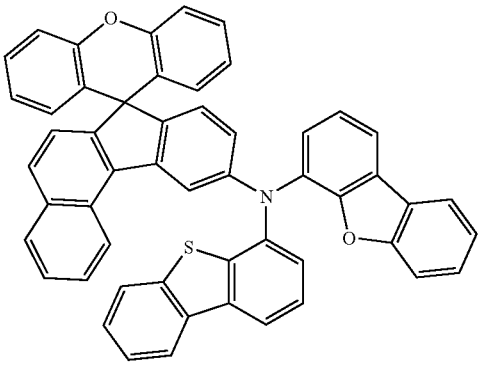
(136)
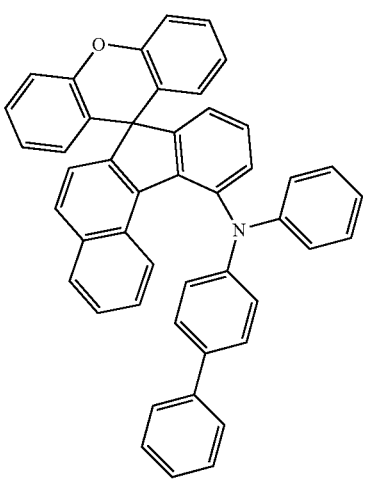

(137)
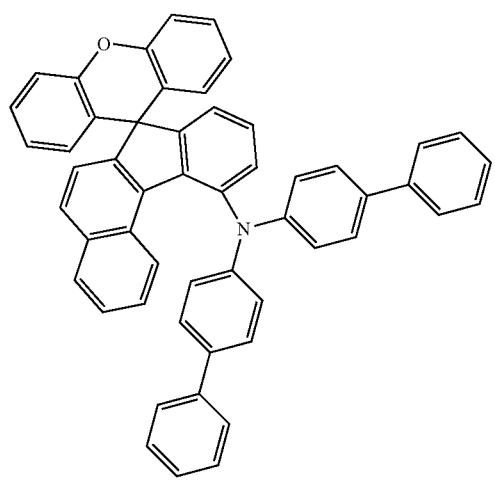
(140)
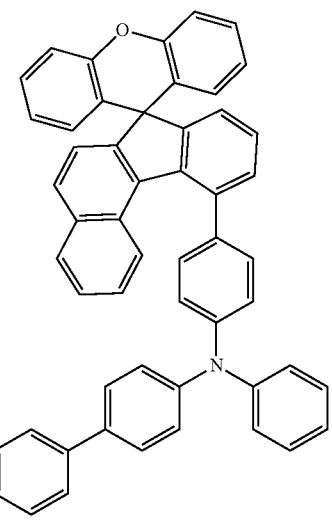
(138)
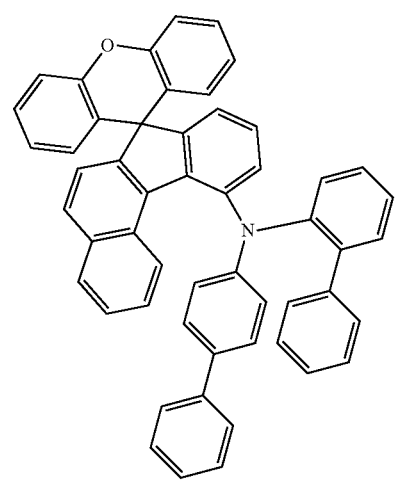
(141)
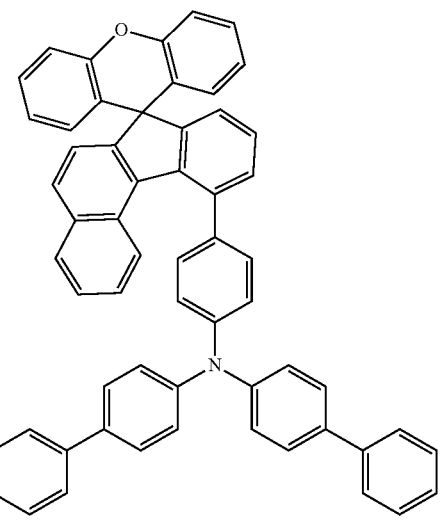
(139)
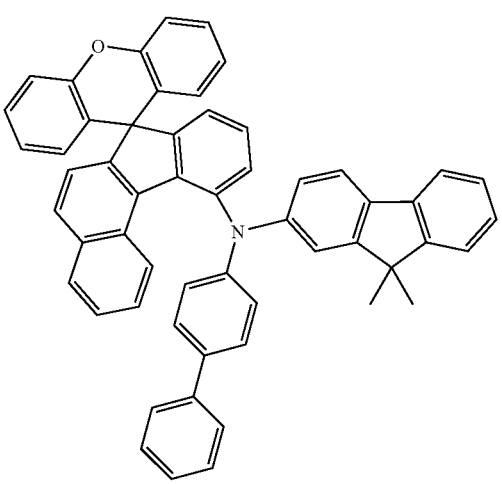
(142)
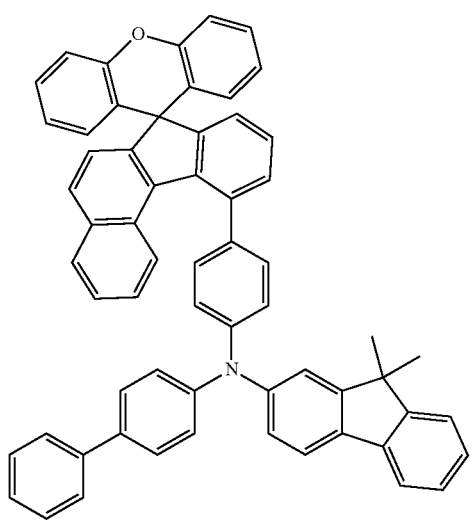

-continued
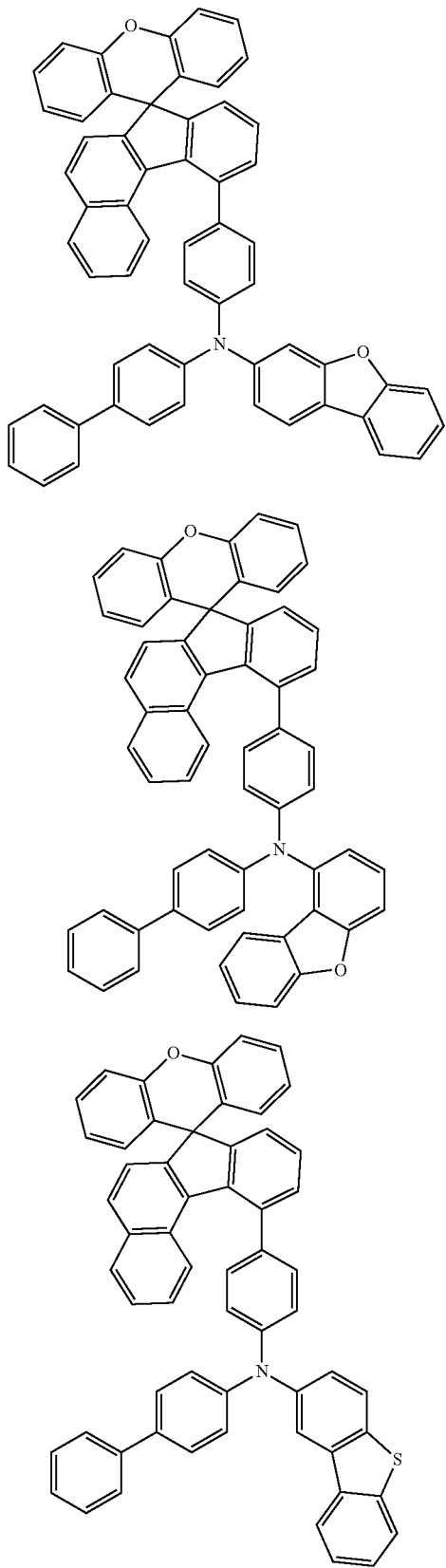
(143)
(144)
(145)
-continued
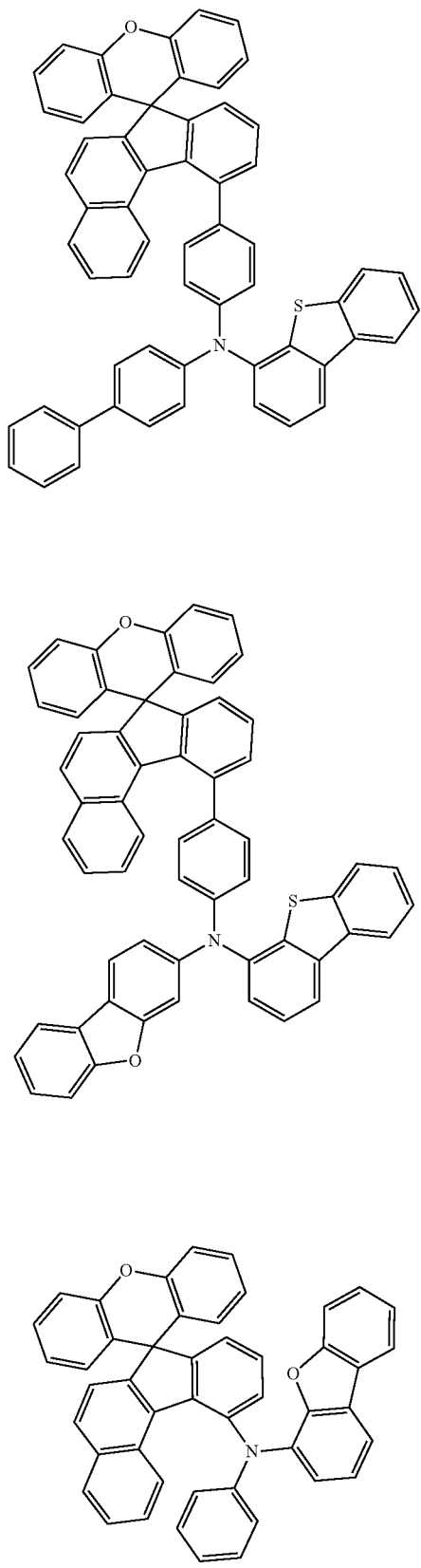
(146)
(147)
(148)

(149)
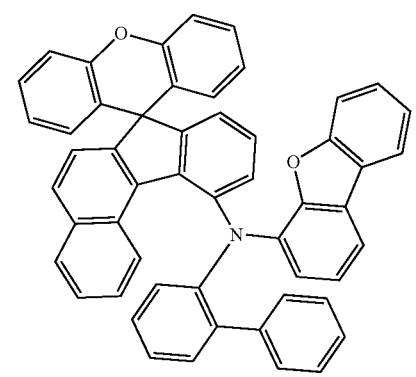
(150)
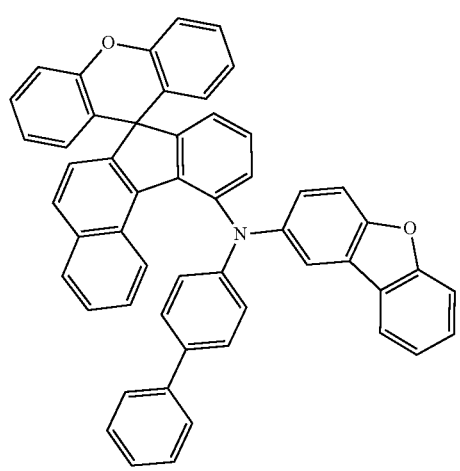
(151)
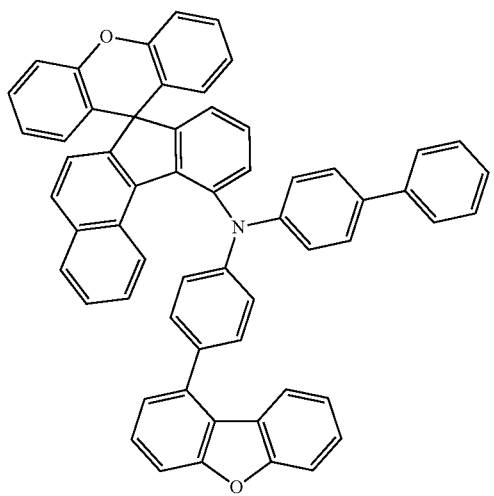
(152)
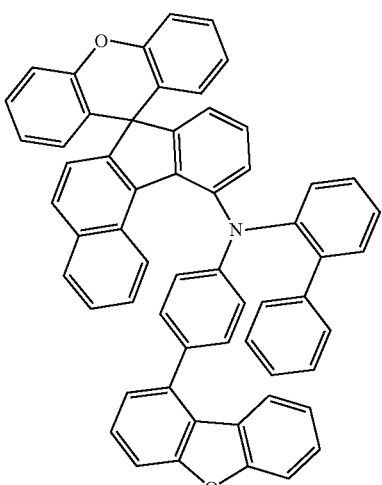
(153)
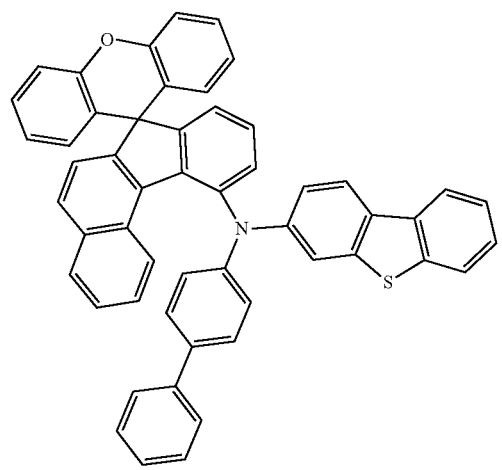
(154)
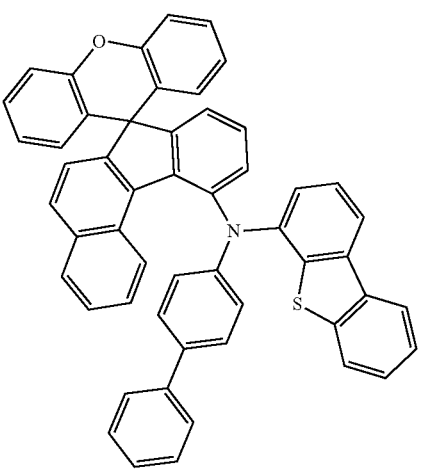

(155)
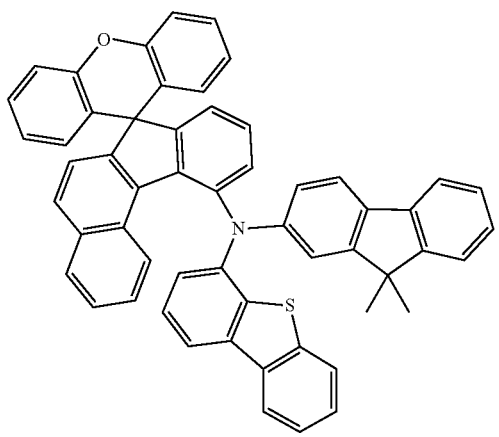
(156)
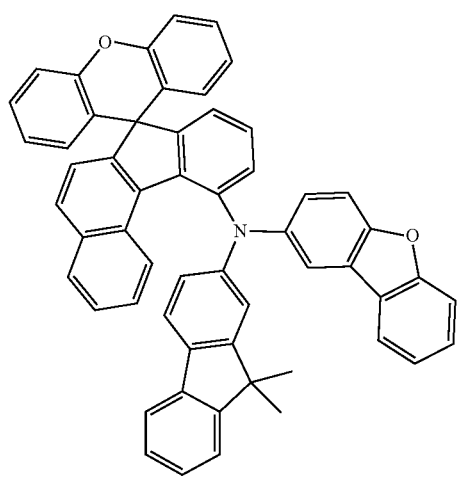
(157)
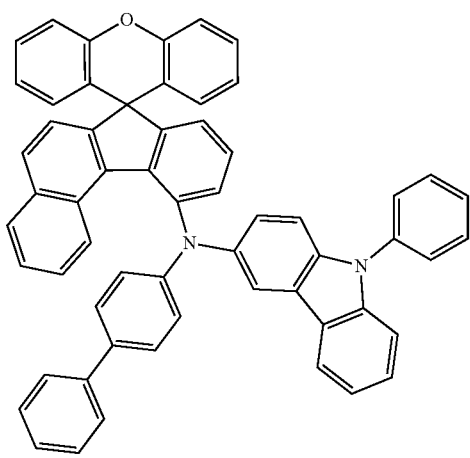
(158)
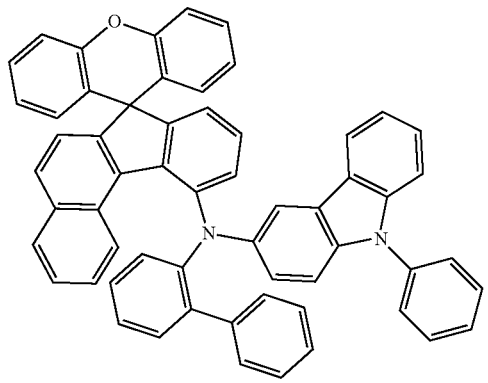
(159)
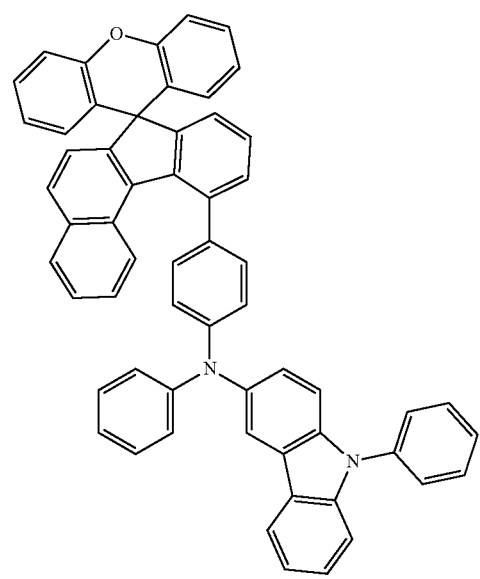
(160)
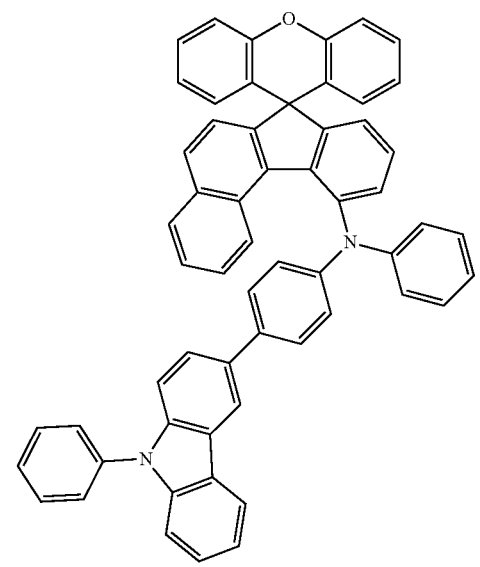

(161)
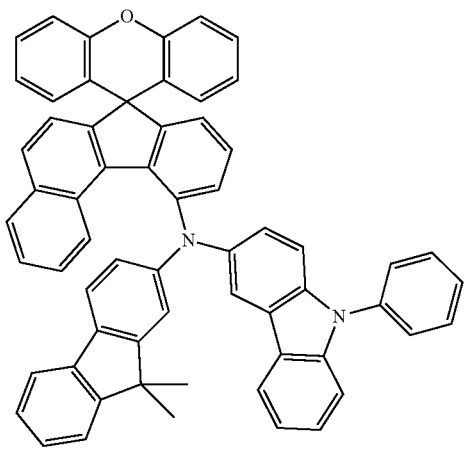
(162)
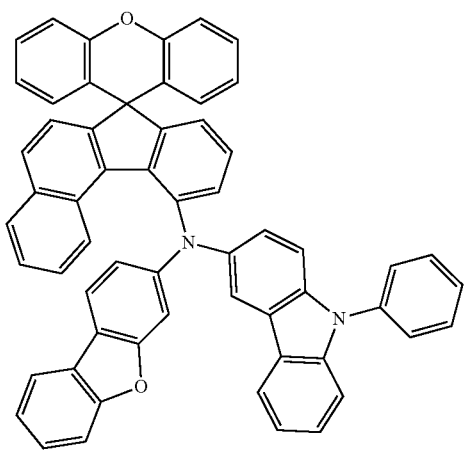
(163)
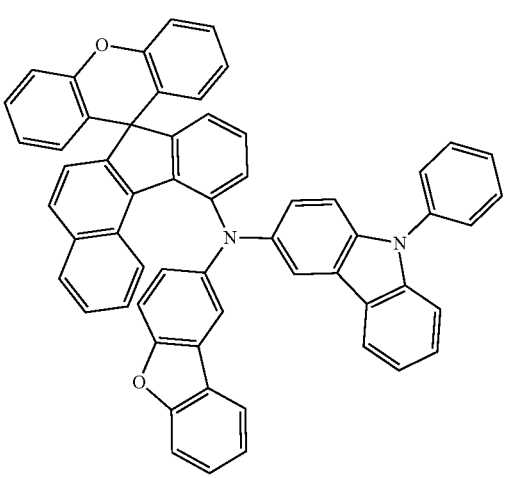
(164)
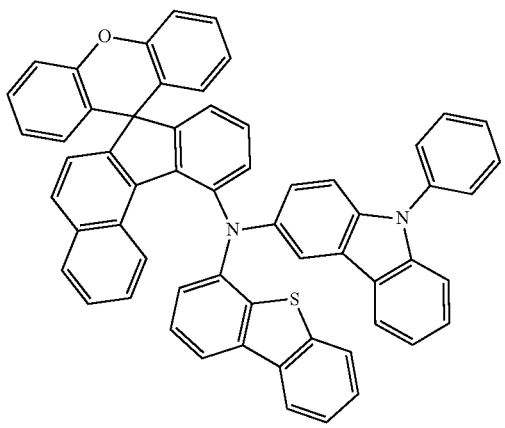
(165)
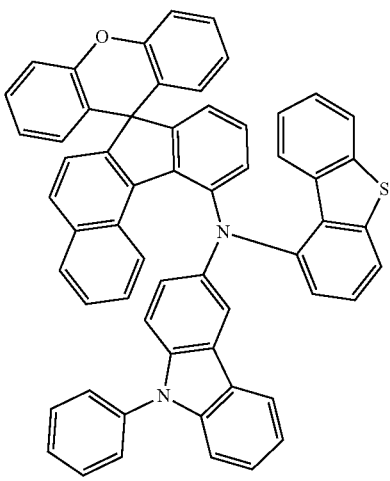
(166)
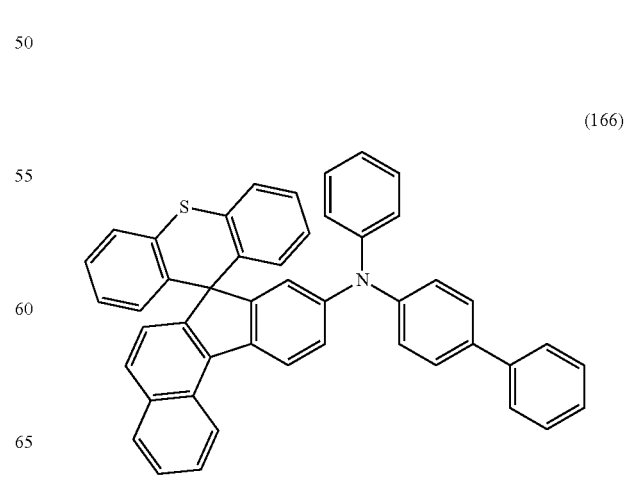

(167)
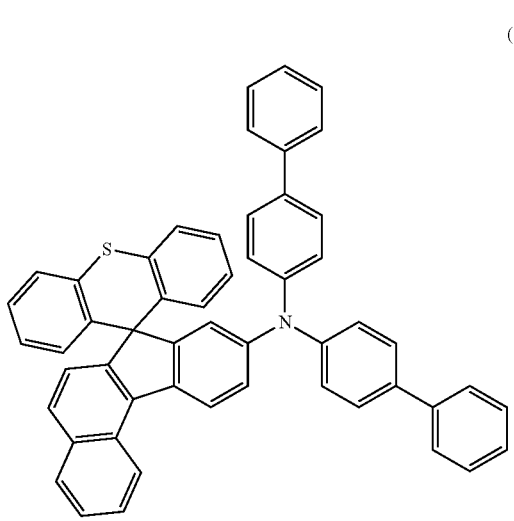
(168)
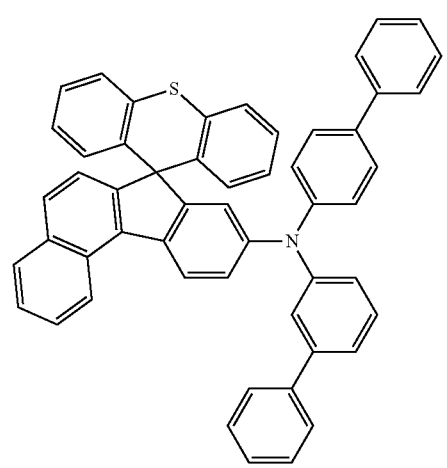
(169)
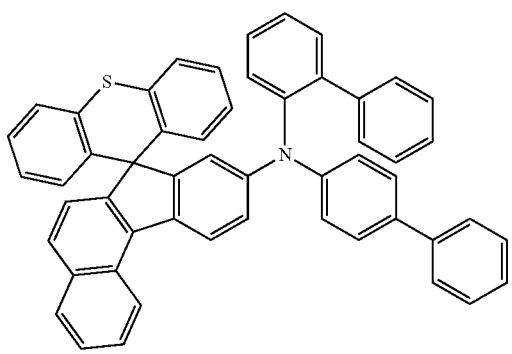
(170)
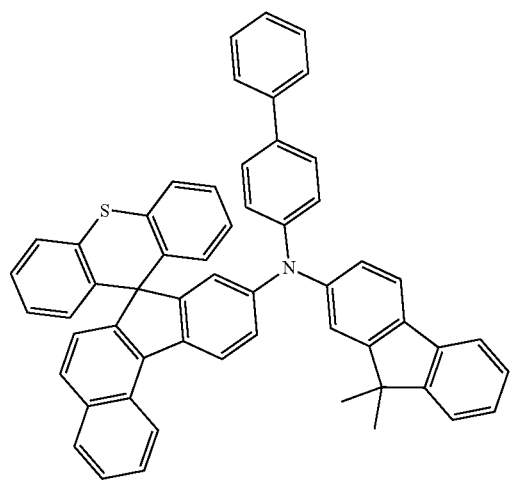
(171)
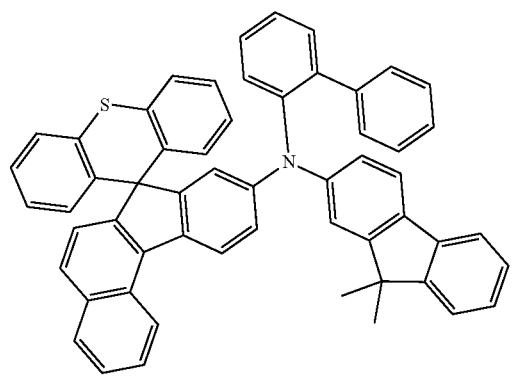
(172)
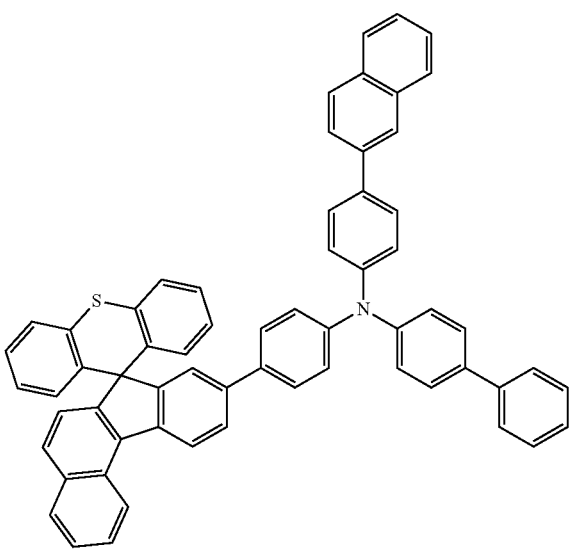

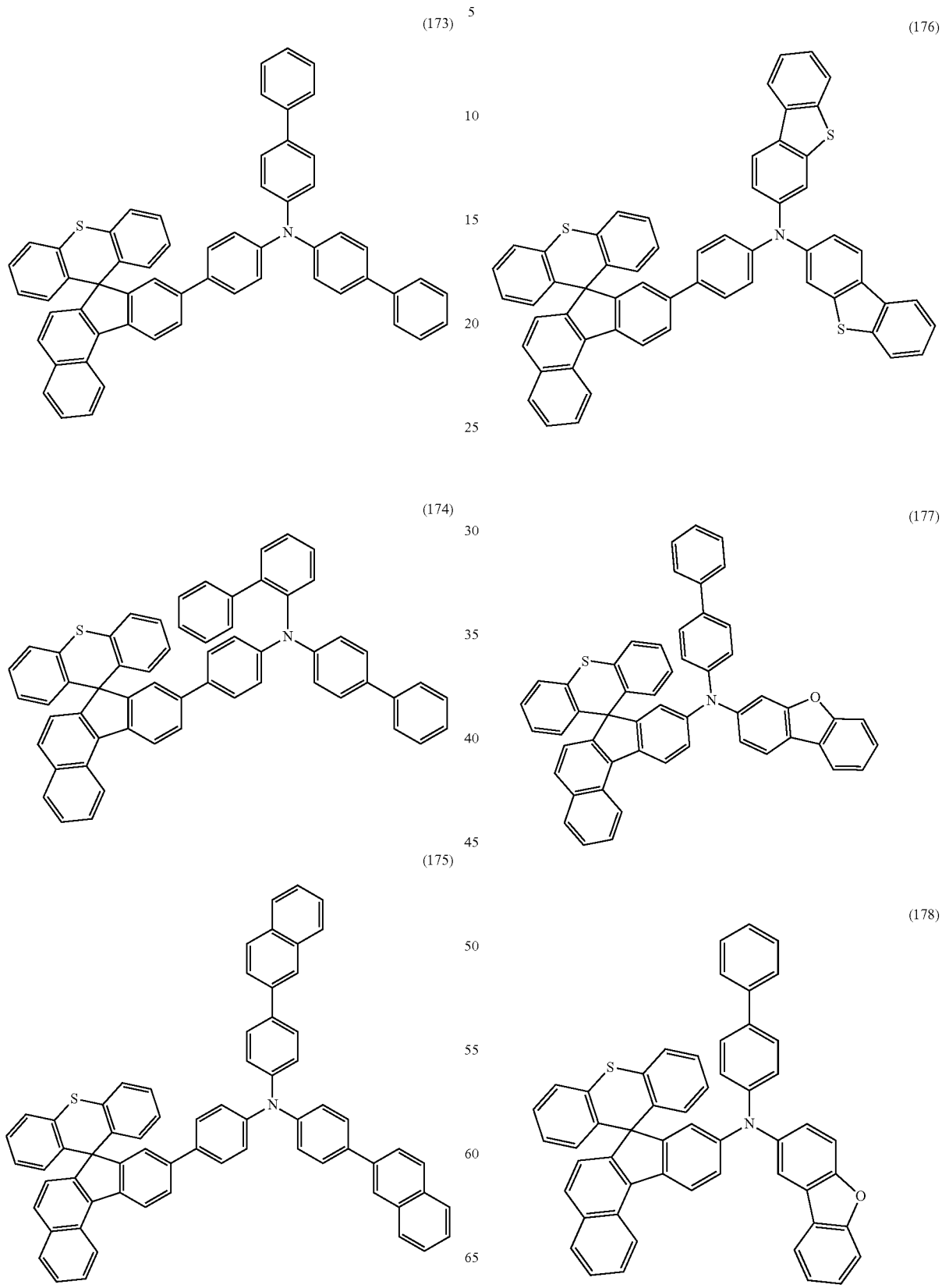

(179)
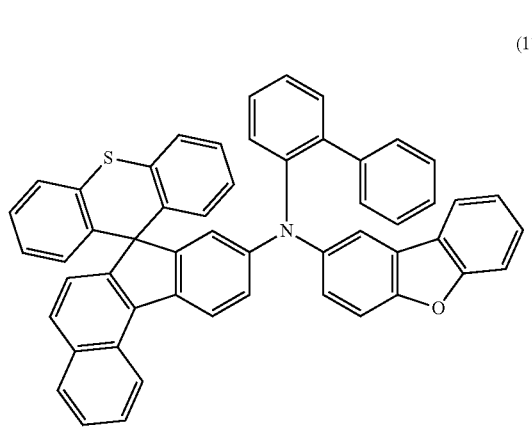
(180)
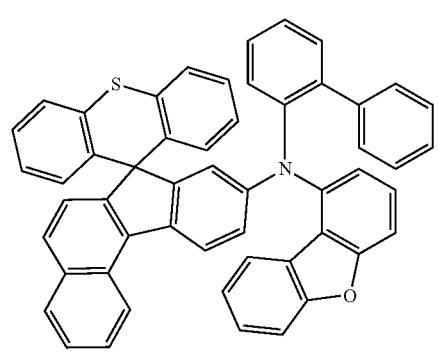
(181)
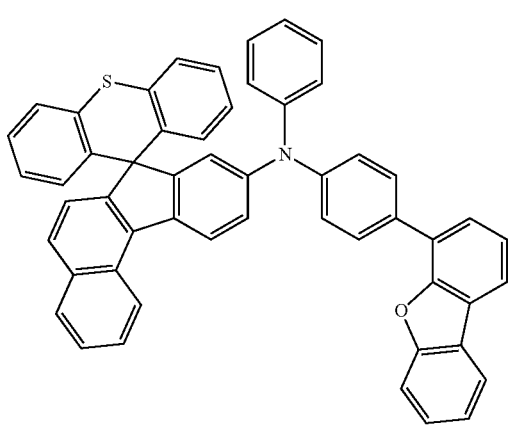
(182)
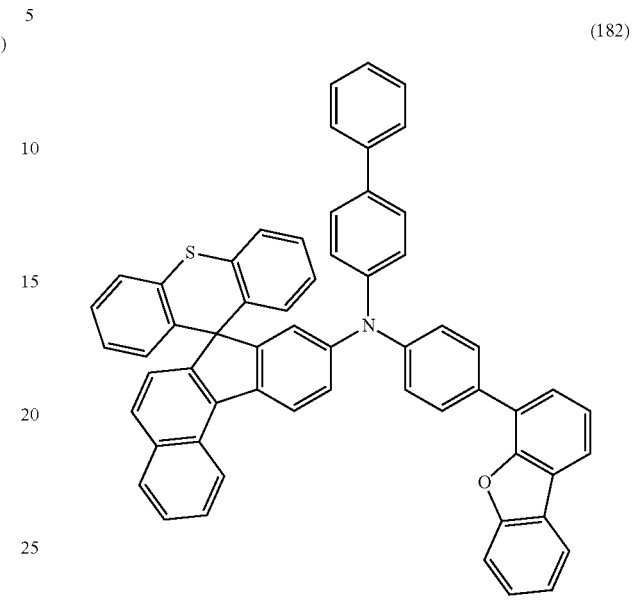
(183)
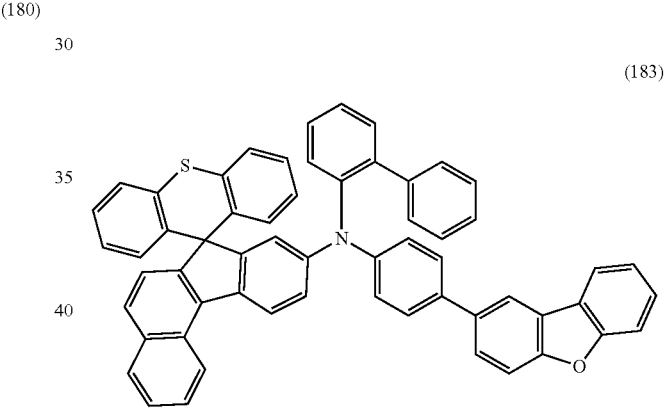
(184)
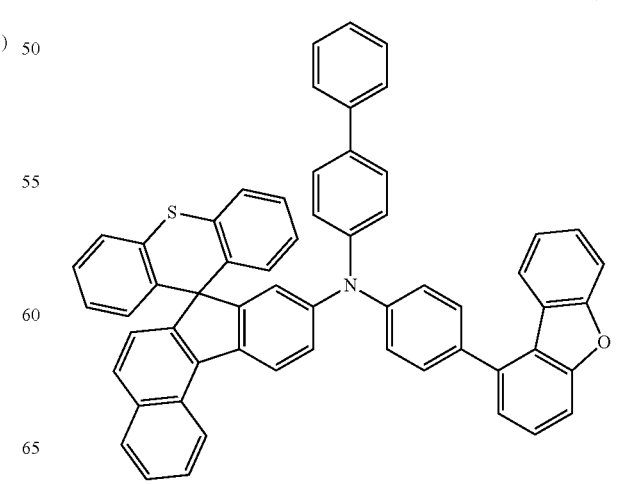

-continued
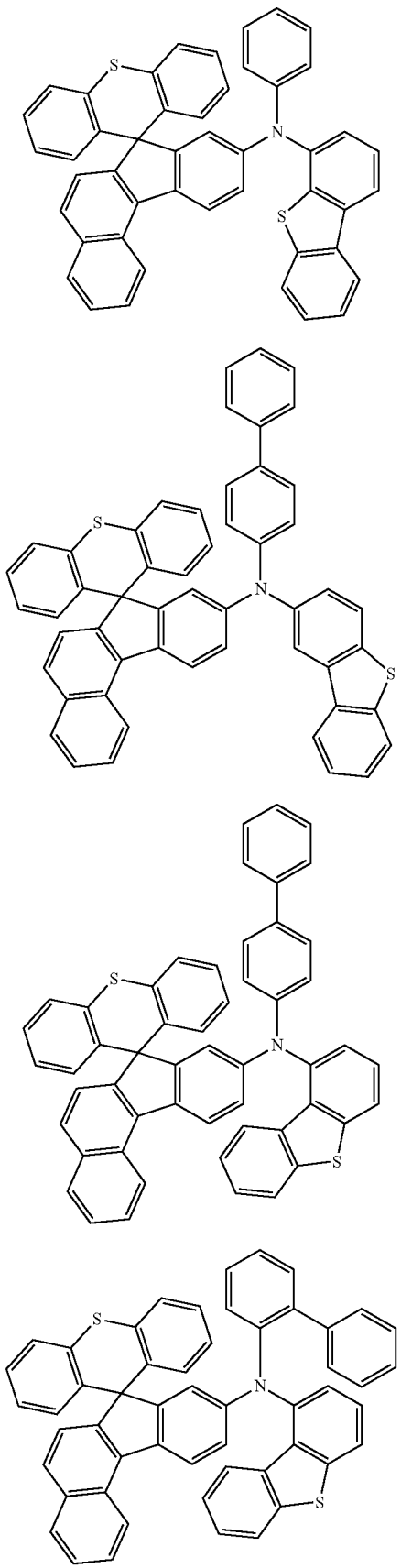
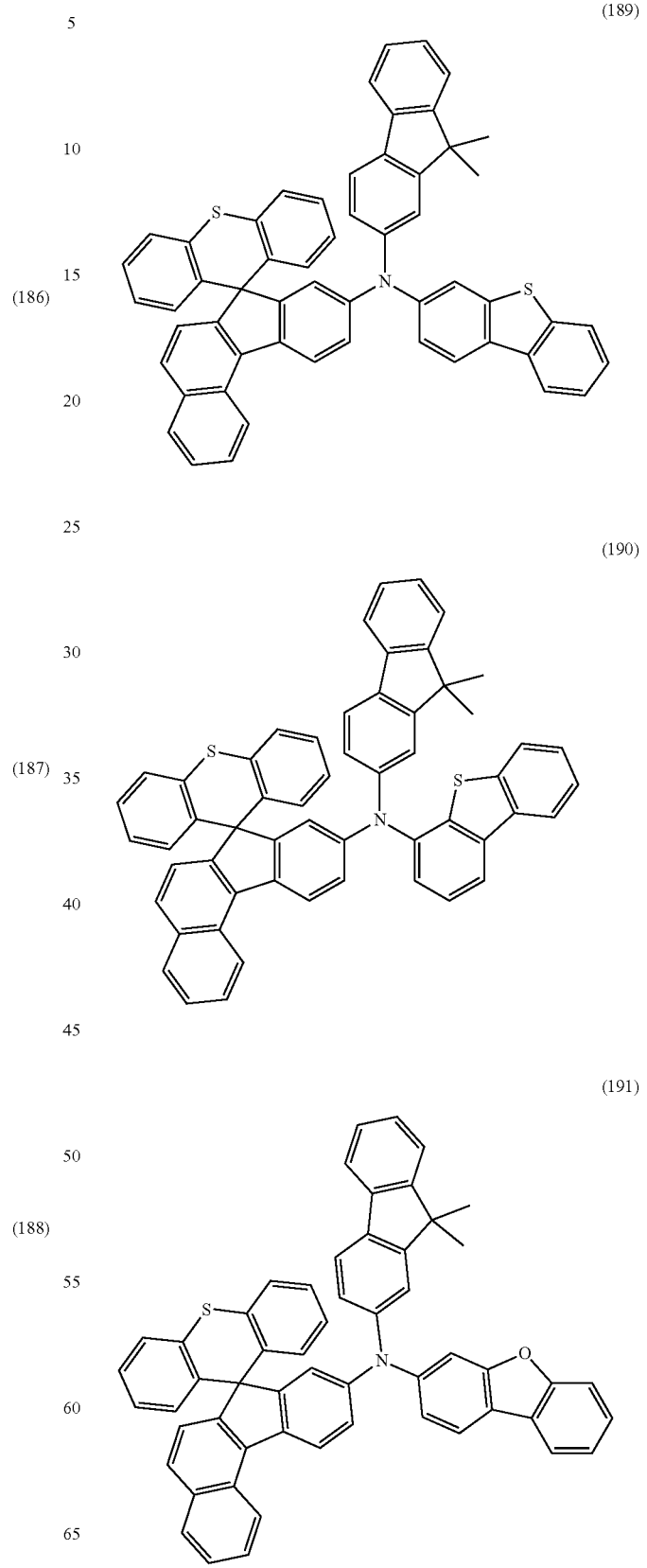

(192)
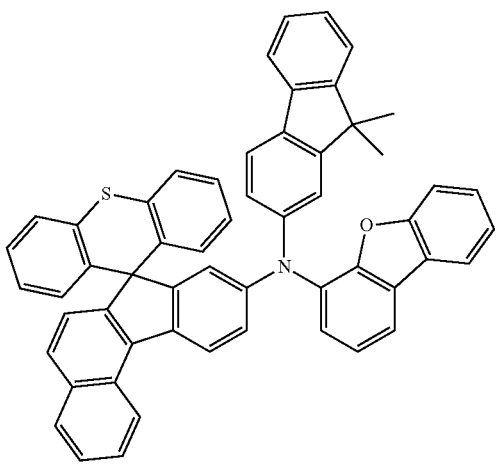
(193)
(194)
(195)
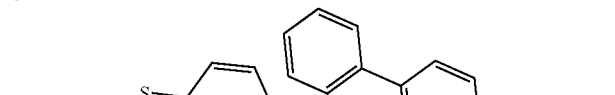
(196)
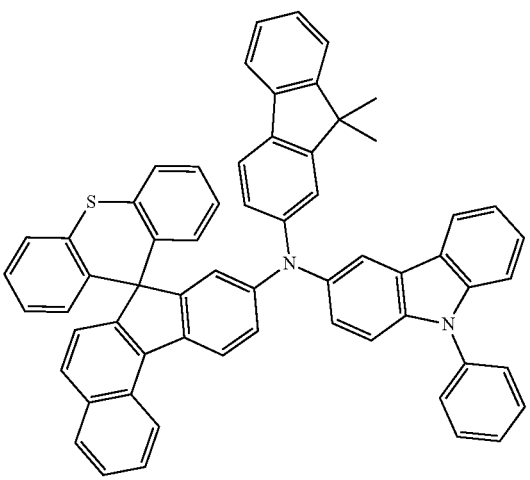
(197)
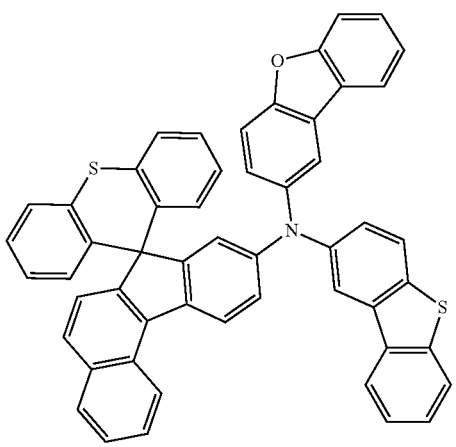
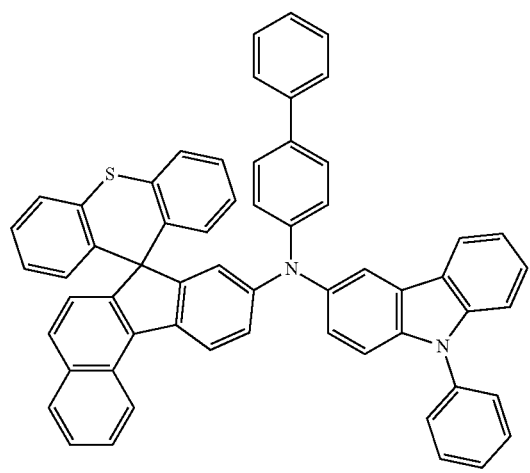

(198)
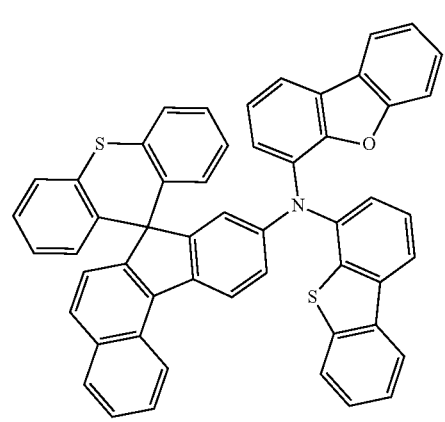
(199)
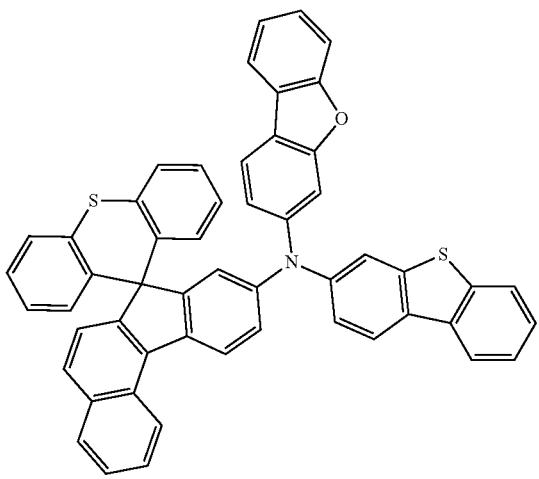
(200)
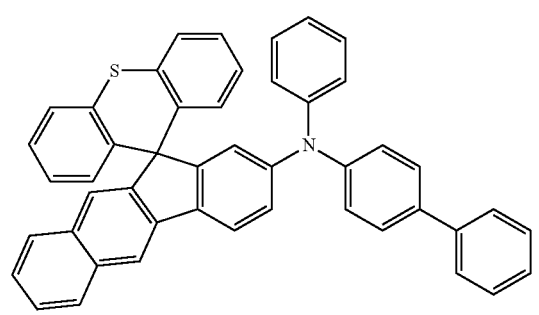
(201)
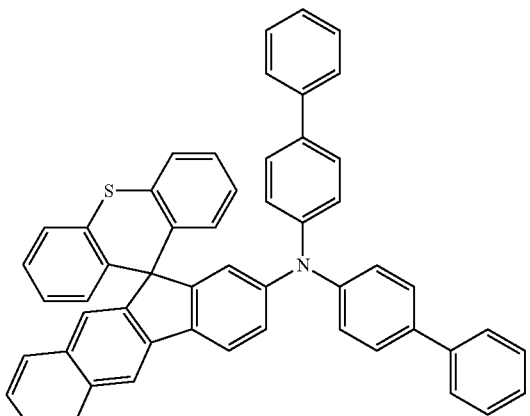
(202)
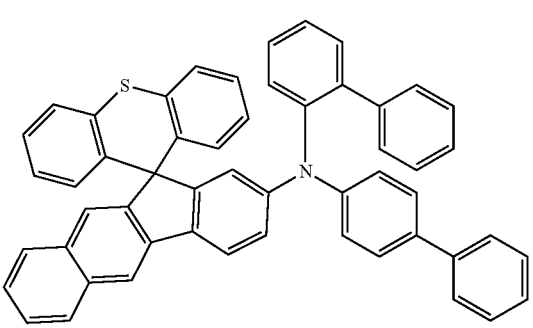
(203)
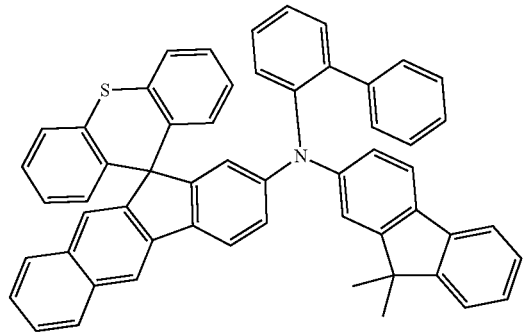
(204)
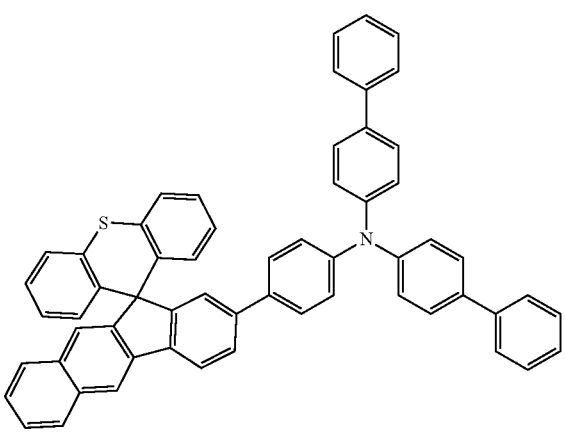

(205)
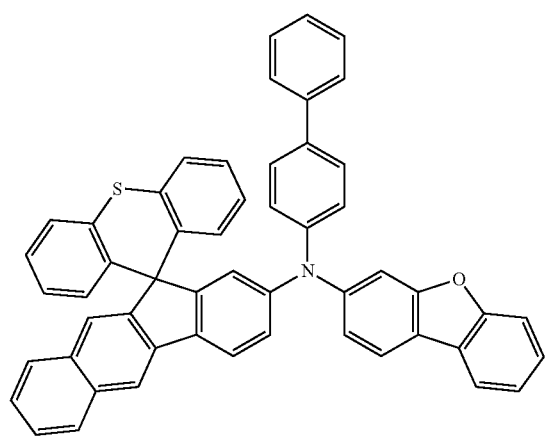
(208)
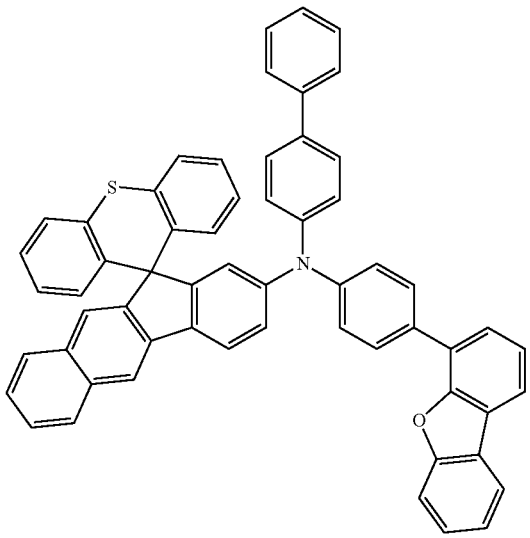
(206)
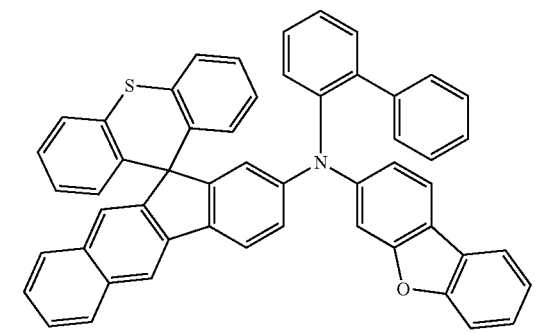
(209)
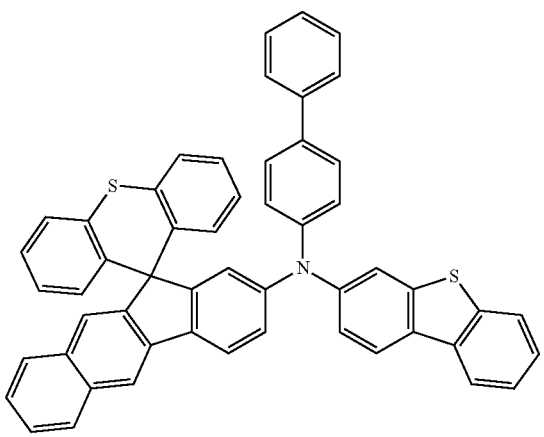
(207)
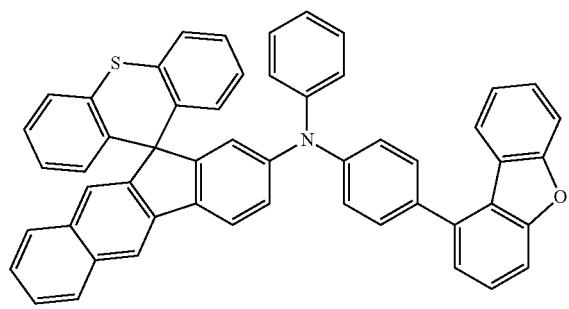
(210)
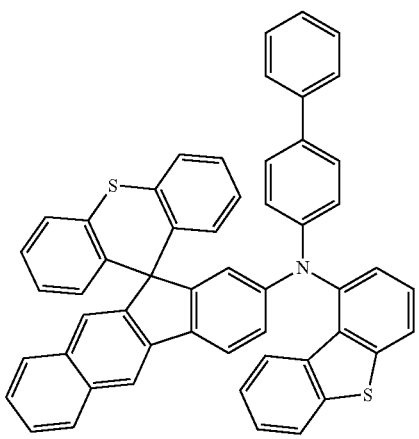

(211)
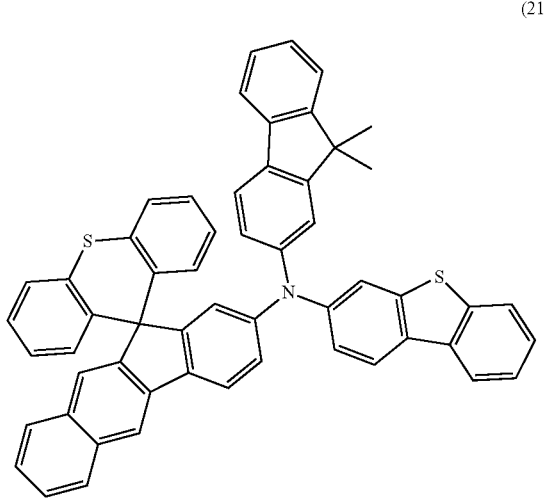
(212)
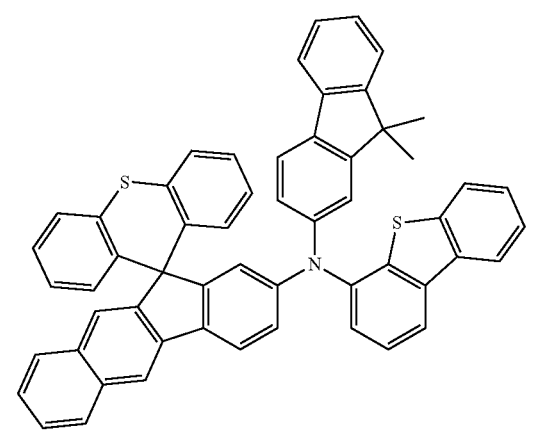
(213)
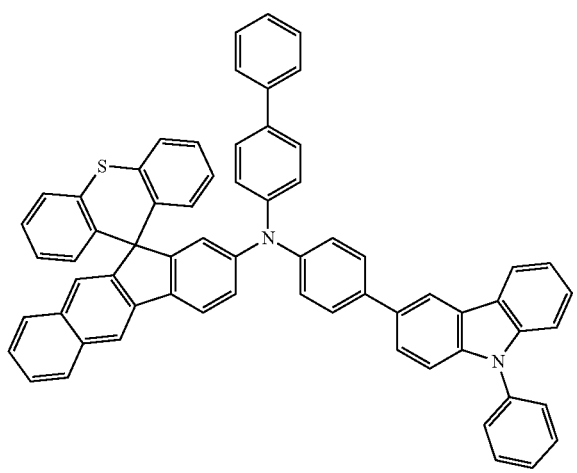
(214)
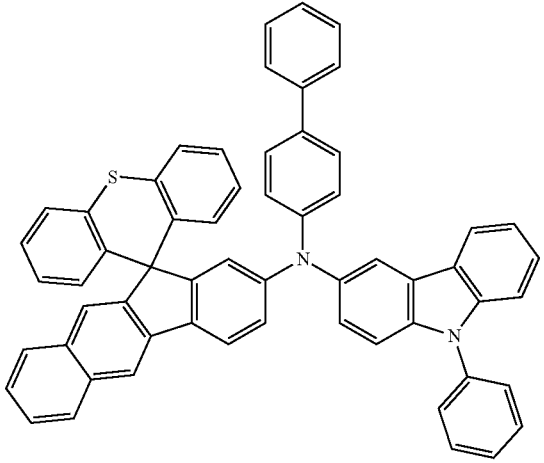
(215)
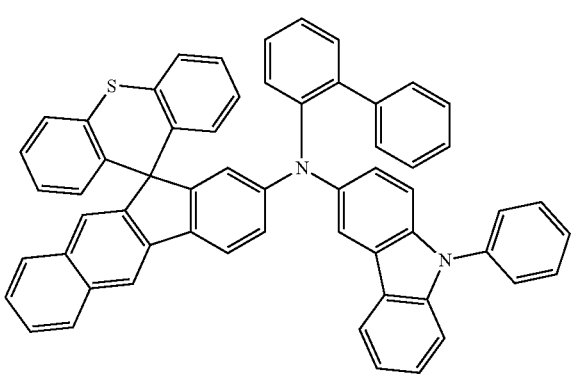
(216)
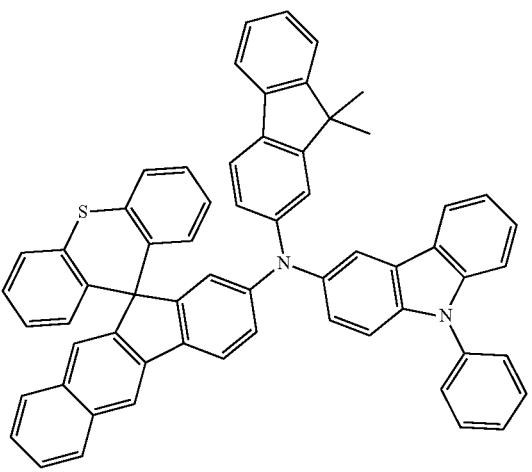

(217)
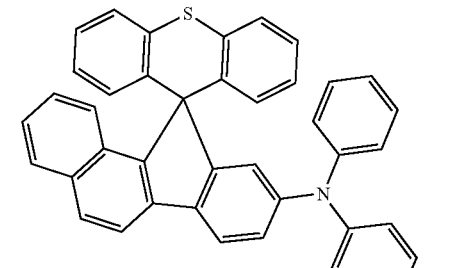
(218)
(219)
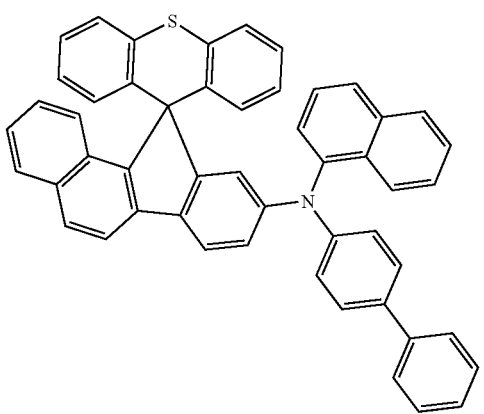
(220)
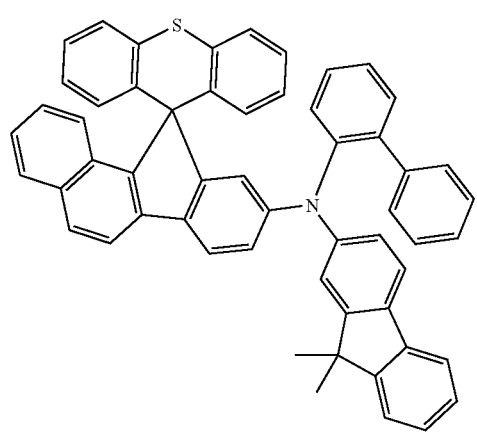
(221)
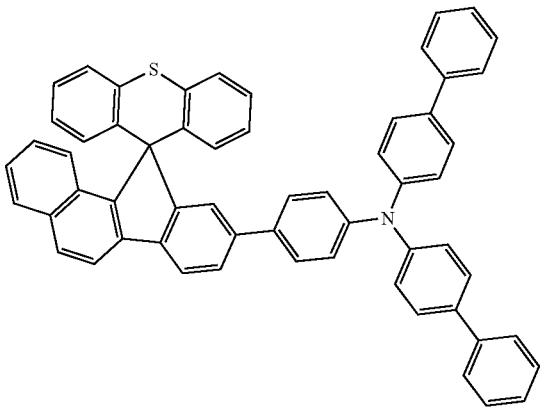
(222)
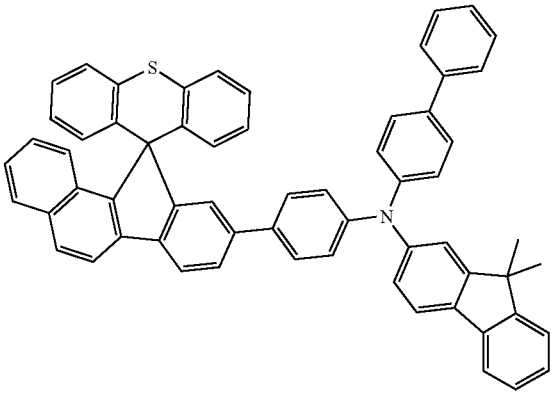
(223)
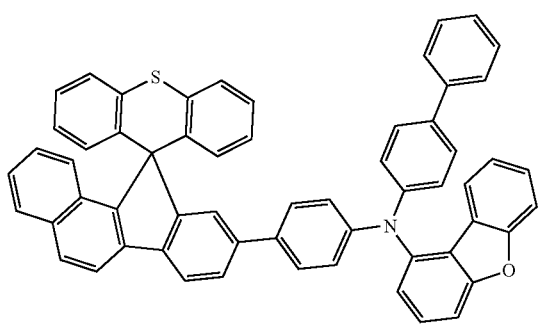
(224)
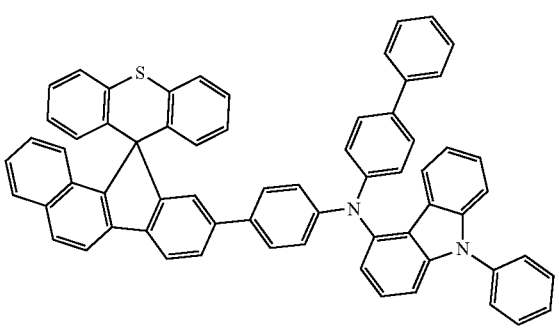

(225)
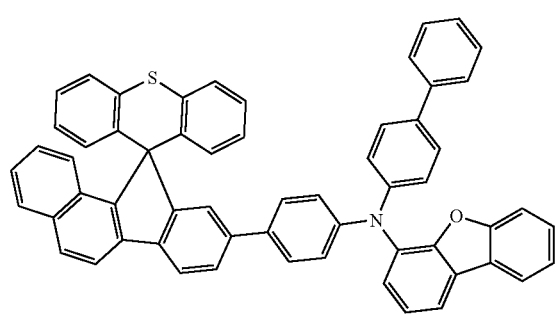
(226)
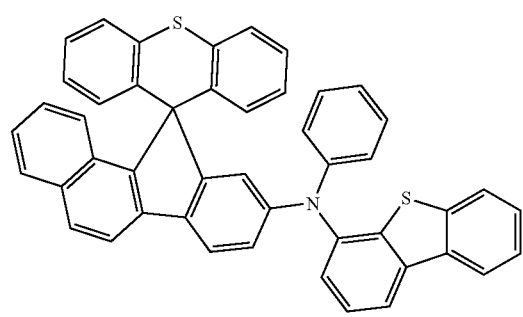
(227)
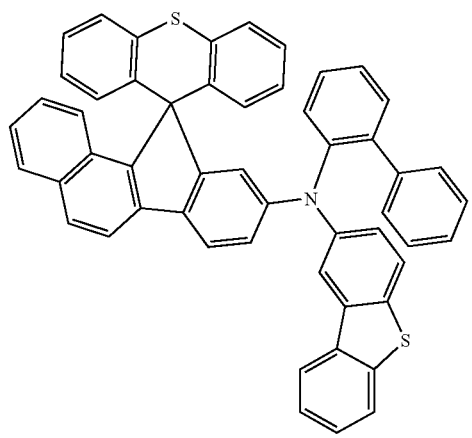
(228)
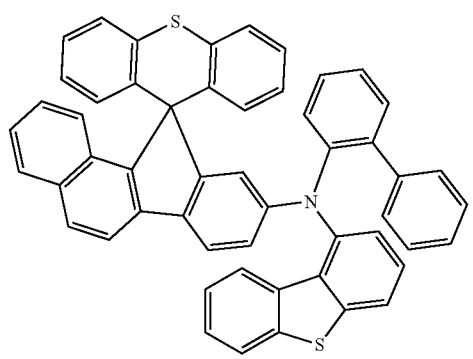
(229)
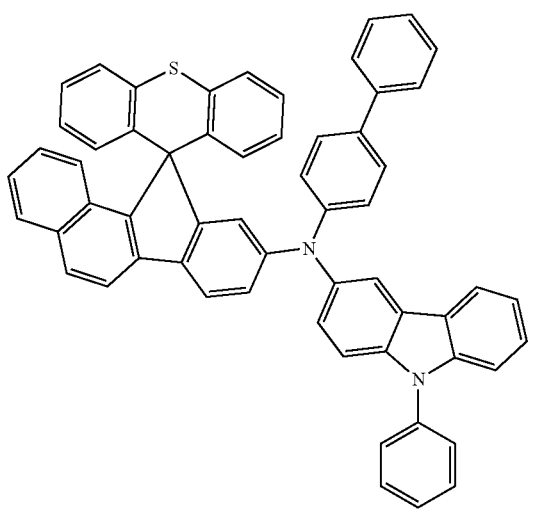
(230)
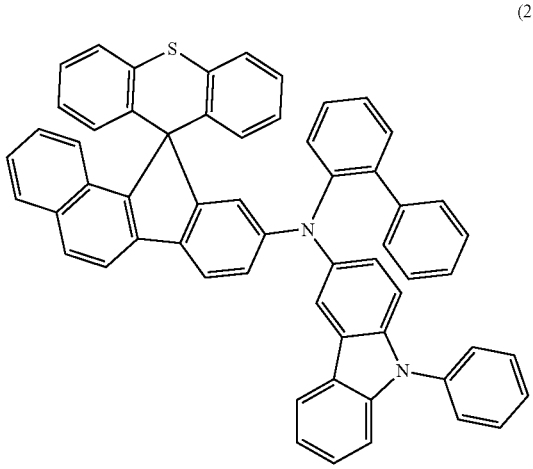
(231)
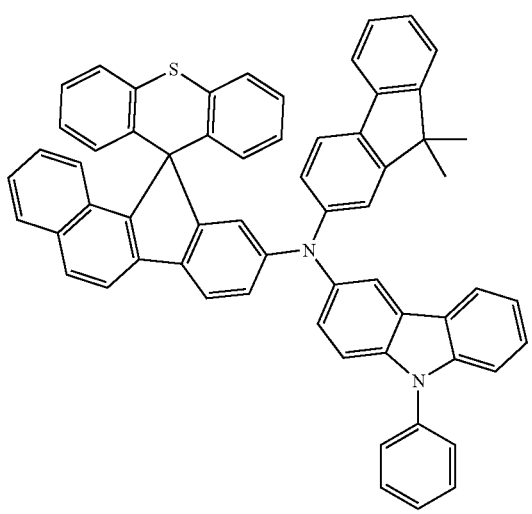

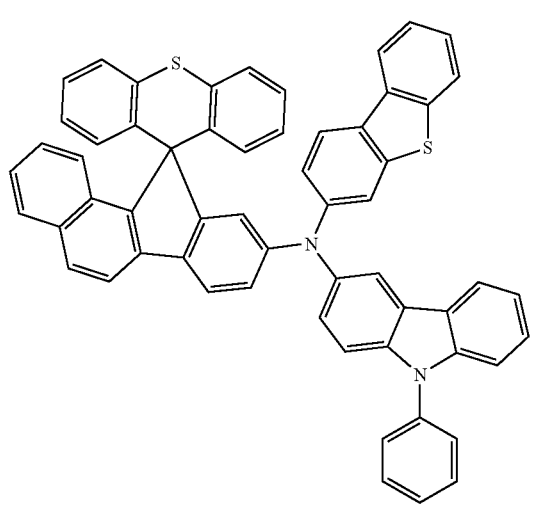
(232)
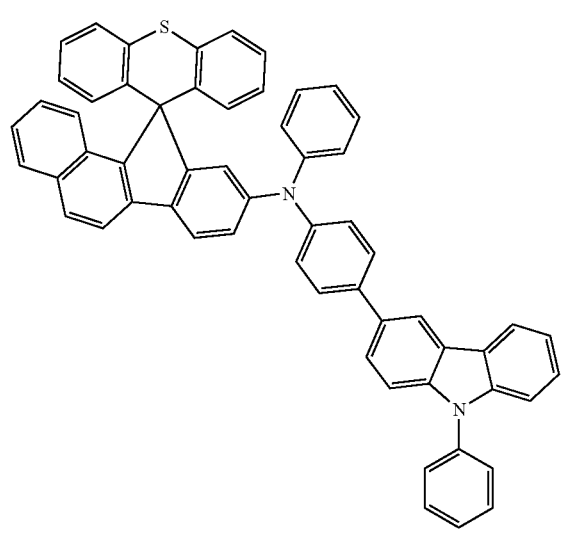
(233)
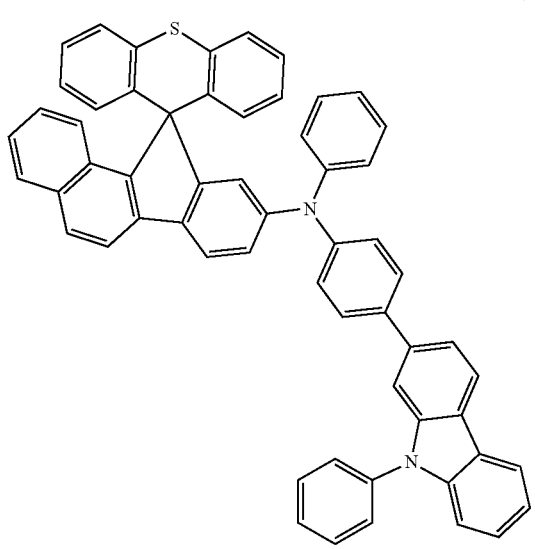
(234)
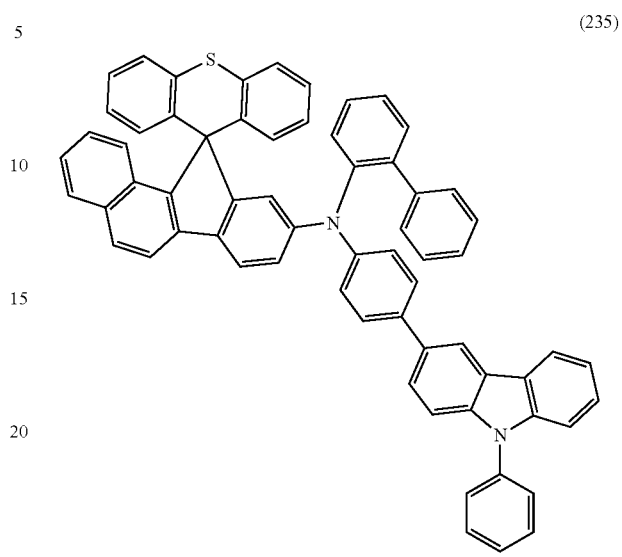
(235)
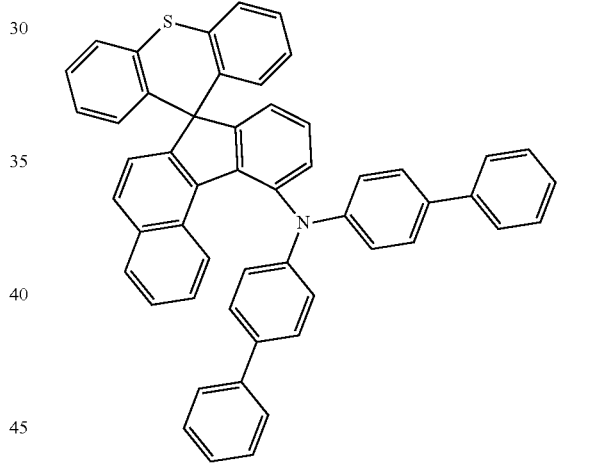
(236)
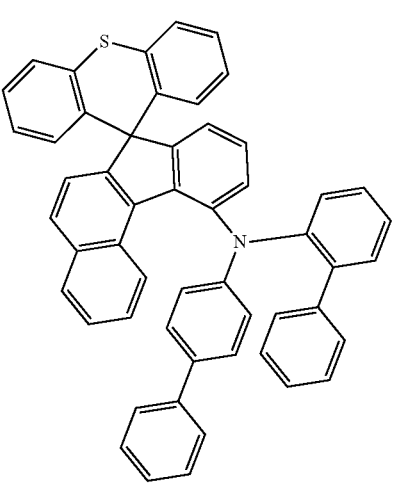
(237)

(238) 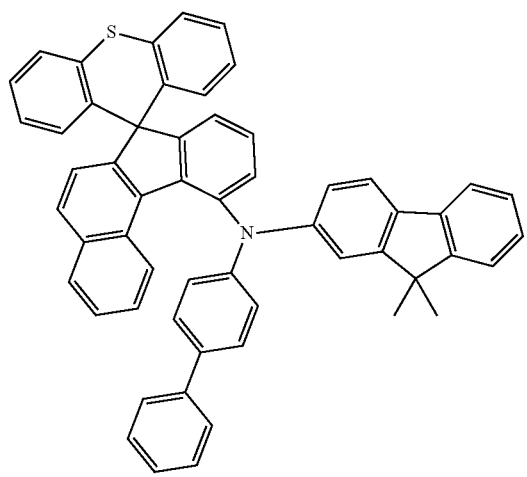
(239) 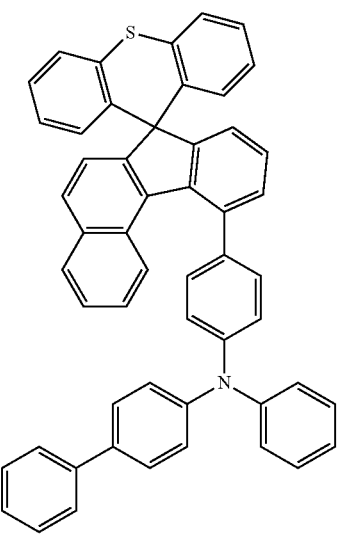
(240) 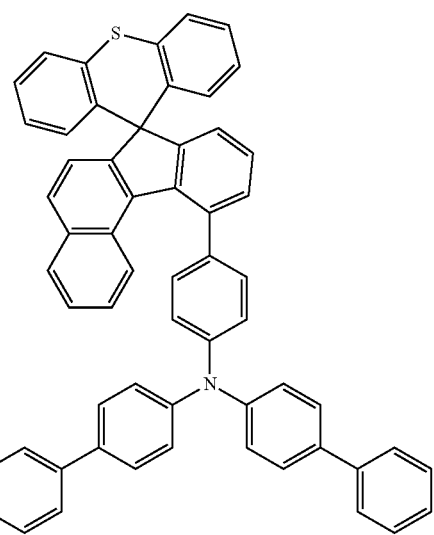
(241) 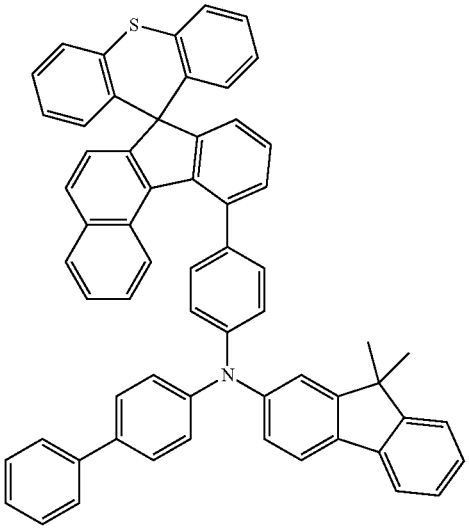
(242) 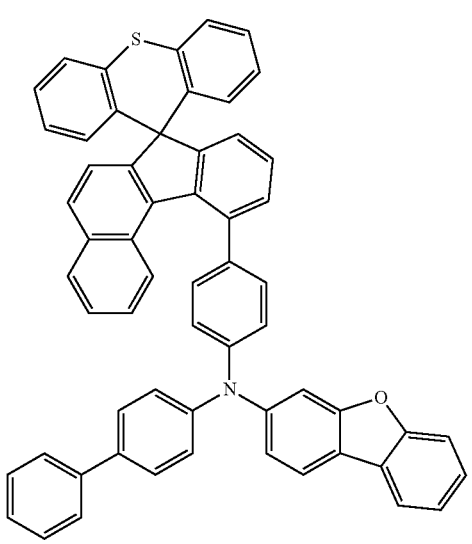
(243) 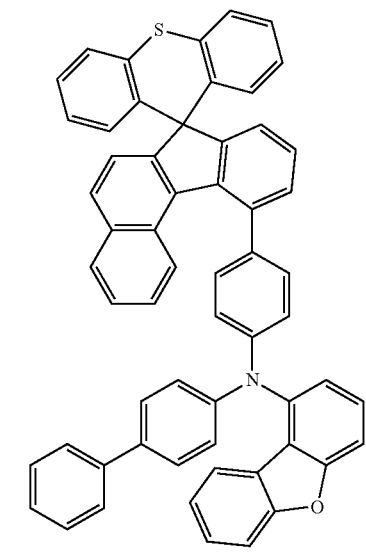

(244) 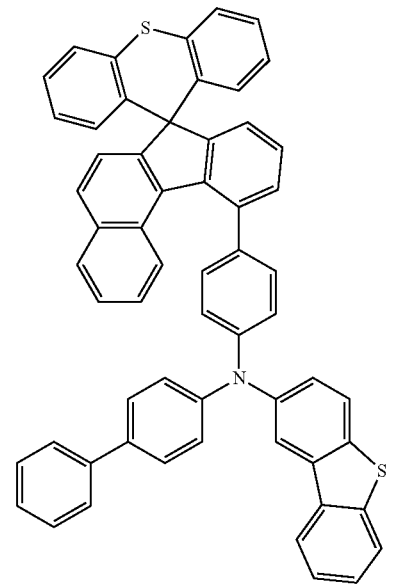
(245) 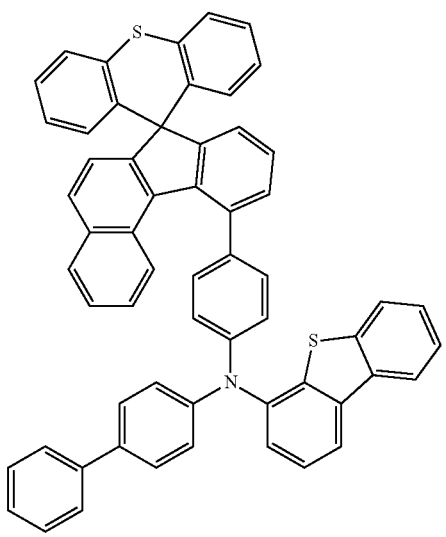
(246) 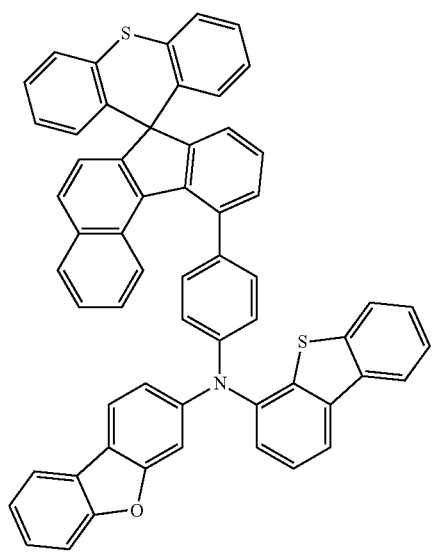
(247) 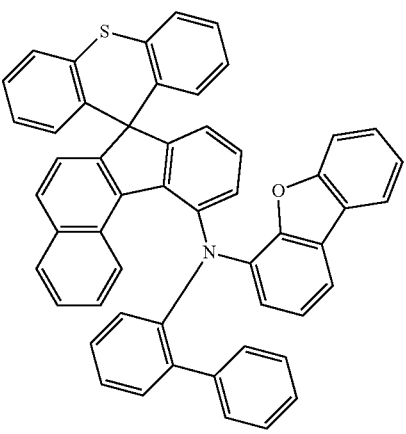
(248) 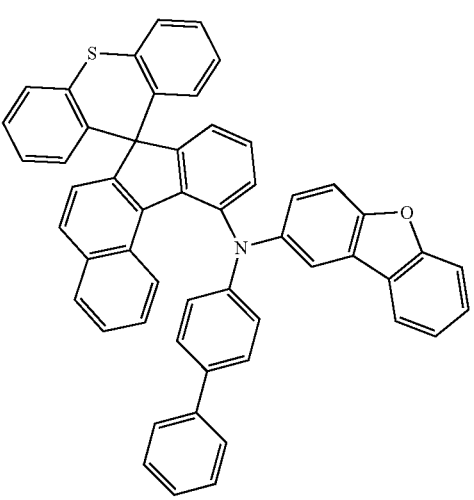
(249) 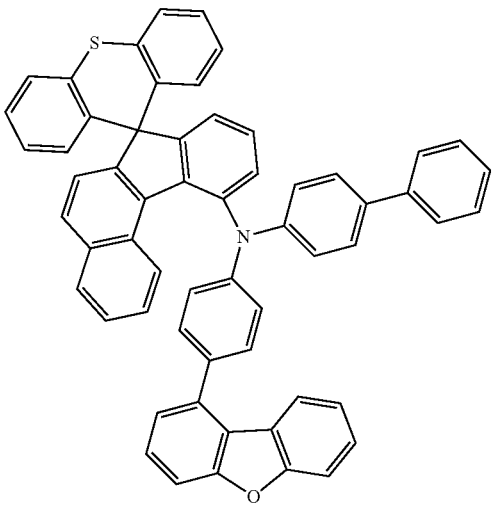

(250)
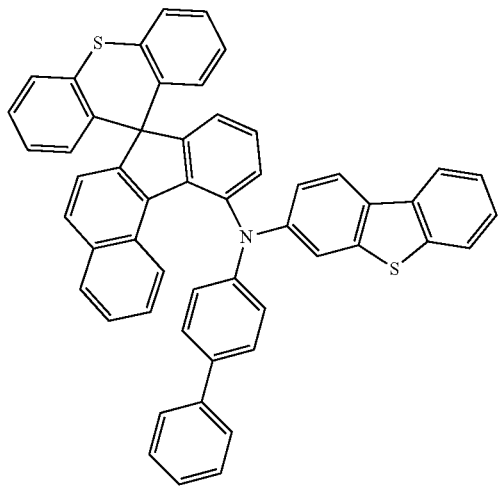
(251)
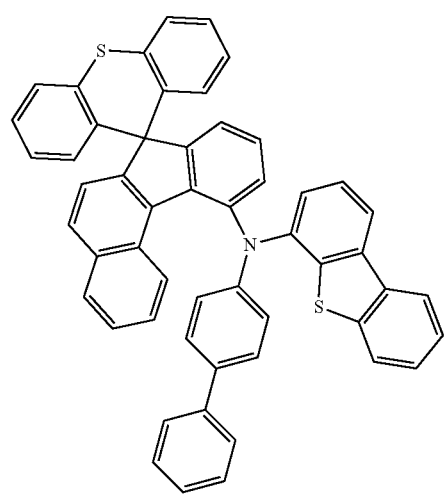
(252)
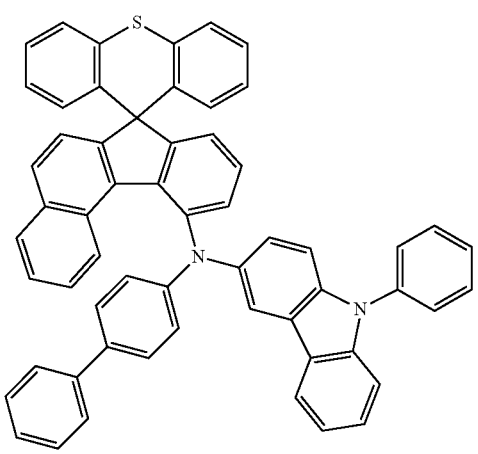
(253)
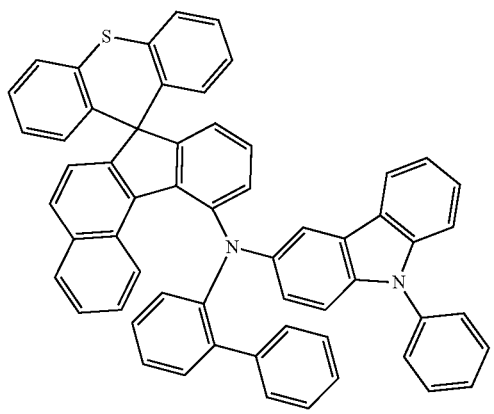
(254)
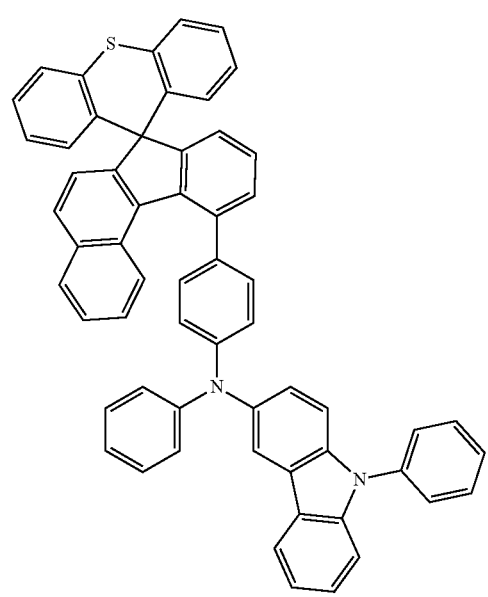
(255)
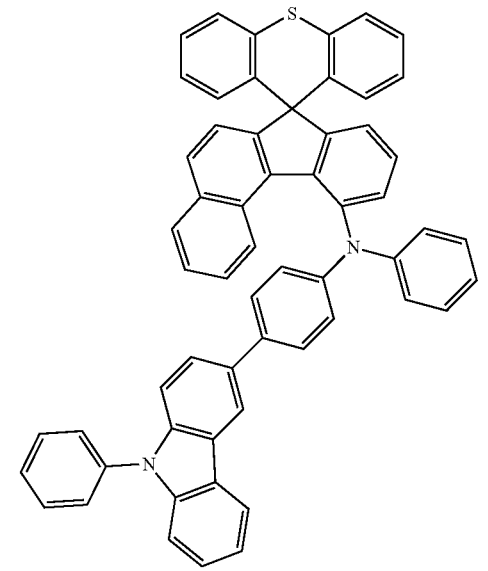

-continued (256) 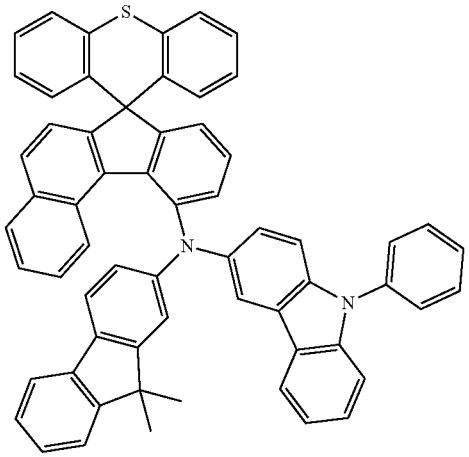

(257) 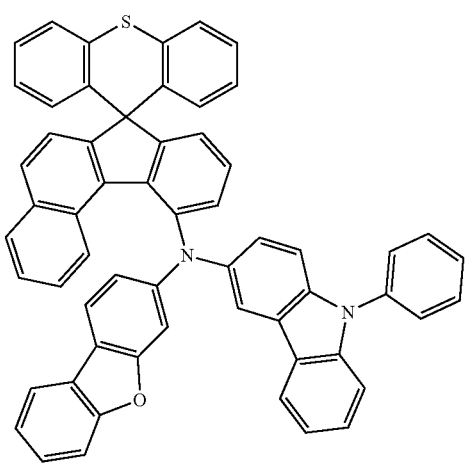

(258) 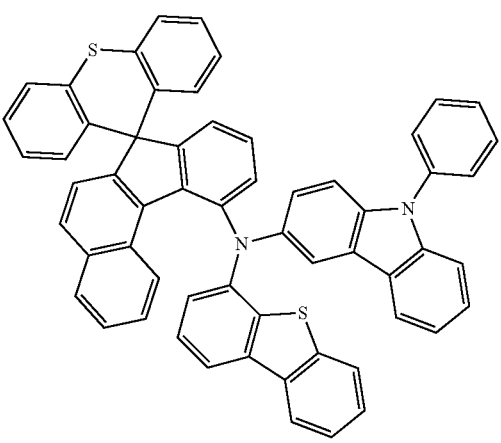

-continued (259) 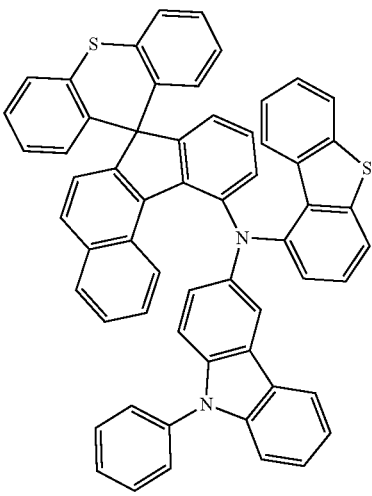

As used herein, "alkyl" refers to a monovalent substituent derived from a saturated, linear or branched hydrocarbon having 1 to 40 carbon atoms. Examples of such alkyl may include, but are not limited to, methyl, ethyl, propyl, isobutyl, sec-butyl, pentyl, iso-amyl, hexyl or the like.

As used herein, "alkenyl" refers to a monovalent substituent derived from an unsaturated, linear or branched hydrocarbon having 2 to 40 carbon atoms, having at least one carbon-carbon double bond. Examples of such alkenyl may include, but are not limited to, vinyl, allyl, isopropenyl, 2-butenyl or the like.

As used herein, "alkynyl" refers to a monovalent substituent derived from an unsaturated, linear or branched hydrocarbon having 2 to 40 carbon atoms, having at least one carbon-carbon triple bond. Examples of such alkynyl may include, but are not limited to, ethynyl, 2-propynyl or the like.

As used herein, "cycloalkyl" refers to a monovalent substituent derived from a monocyclic or polycyclic non-aromatic hydrocarbon having 3 to 40 carbon atoms. Examples of such cycloalkyl may include, but are not limited to, cyclopropyl, cyclopentyl, cyclohexyl, norbornyl, adamantine or the like.

As used herein, "heterocycloalkyl" refers to a monovalent substituent derived from a non-aromatic hydrocarbon having 3 to 40 nuclear atoms, where one or more carbons in the ring, preferably one to three carbons, are substituted with a heteroatom such as N, O, S or Se. Examples of such heterocycloalkyl may include, but are not limited to, morpholine, piperazine or the like.

As used herein, "aryl" refers to a monovalent substituent derived from a $C_6$ to $C_{60}$ aromatic hydrocarbon which is in a structure with a single ring or two or more rings combined with each other. In addition, a form in which two or more rings are pendant (e.g., simply attached) to or fused with each other may also be included. Examples of such aryl may include, but are not limited to, phenyl, naphthyl, phenanthryl, anthryl or the like.

As used herein, "heteroaryl" refers to a monovalent substituent derived from a monoheterocyclic or polyheterocyclic aromatic hydrocarbon having 5 to 60 nuclear atoms. In such a case, one or more carbons in the ring, preferably one to three carbons, are substituted with a heteroatom such as N, O, S or Se. In addition, a form in which two or more rings are pendant to or fused with each other may be included, and a form fused with an aryl group may be included. Examples of such heteroaryl may include, but are not limited to, a 6-membered monocyclic ring such as pyridyl, pyrazinyl, pyrimidinyl, pyridazinyl and triazinyl; a polycyclic ring such as phenoxathienyl, indolizinyl, indolyl, purinyl, quinolyl, benzothiazole and carbazolyl; 2-furanyl; N-imidazolyl; 2-isoxazolyl; 2-pyridinyl; 2-pyrimidinyl or the like.

As used herein, "alkyloxy" refers to a monovalent substituent represented by R'O—, where R' is alkyl having 1 to 40 carbon atoms. Such alkyloxy may include a linear, branched or cyclic structure. Examples of such alkyloxy may include, but are not limited to, methoxy, ethoxy, n-propoxy, 1-propoxy, t-butoxy, n-butoxy, pentoxy or the like.

As used herein, "aryloxy" refers to a monovalent substituent represented by RO—, where R is aryl having 6 to 60 carbon atoms. Examples of such aryloxy may include, but are not limited to, phenyloxy, naphthyloxy, diphenyloxy or the like.

As used herein, "alkylsilyl" refers to silyl substituted with alkyl having 1 to 40 carbon atoms and includes di- and tri-alkylsilyl as well as mono-alkylsilyl. In addition, "arylsilyl" refers to silyl substituted with aryl having 5 to 60 carbon atoms and includes poly-arylsilyl such as di- and tri-arylsilyl as well as mono-arylsilyl.

As used herein, "alkylboron group" refers to a boron group substituted with alkyl having 1 to 40 carbon atoms, and "arylboron group" refers to a boron group substituted with aryl having 6 to 60 carbon atoms.

As used herein, "alkylphosphinyl group" refers to a phosphine group substituted with alkyl having 1 to 40 carbon atoms and includes a di-alkylphosphinyl group as well as a mono-alkylphosphinyl group. As used herein, "arylphosphinyl group" refers to a phosphine group substituted with monoaryl or diaryl having 6 to 60 carbon atoms, and includes a di-arylphosphinyl group as well as a mono-arylphosphinyl group.

As used herein, "arylamine" refers to amine substituted with aryl having 6 to 60 carbon atoms and includes di-arylamine as well as mono-arylamine.

<Organic Electroluminescence Device>

Another aspect of embodiments of the present invention is related to an organic EL device including the compound represented by Chemical Formula 1.

More specifically, the organic EL device according to the present invention includes an anode, a cathode, and one or more organic layers interposed between the anode and the cathode. At least one of the one or more organic layers include the compound represented by Chemical Formula 1. In such a case, the compound may be used solely or as a combination of two or more kinds thereof.

For example, the one or more organic layers may be one or more of a hole injection layer, a hole transporting layer, a light emitting layer, a hole blocking layer, an electron transporting layer and an electron injection layer, and at least one of the one or more organic layers includes the compound represented by Chemical Formula 1. Preferably, the organic layer including the compound of Chemical Formula 1 may be a hole transporting layer.

In an embodiment, the one or more organic layers may include a hole injection layer, a hole transporting layer, a light emitting layer, an electron transporting layer, and an electron injection layer, and the hole transporting layer may be a compound represented by Chemical Formula 1.

The compound represented by Chemical Formula 1 may be included in an organic EL device as a material for the hole transporting layer. In such an embodiment, the compound of Chemical Formula 1 has a high glass transition temperature, high hole transporting ability due to high hole mobility, smooth hole injection and transferring properties from the hole injection layer to the light emitting layer due to an appropriate HOMO and LUMO energy level between the hole injection layer and the light emitting layer, and amorphous crystallinity and high refractive index characteristics. Accordingly, the organic EL device including the compound of Chemical Formula 1 may be improved in terms of efficiency (luminous efficiency and power efficiency), lifespan, luminance, driving voltage, and thermal stability.

The structure of the organic EL device of the present invention is not particularly limited, and for example, an anode 100, one or more organic layers 300, and a cathode 200 may be sequentially stacked on a substrate (see FIGS. 1 and 2). In addition, it may have a structure in which an insulating layer or an adhesive layer is inserted at the interface between the electrode and the organic layer.

In an embodiment, as illustrated in FIG. 1, the organic EL device may have a structure in which the anode 100, the hole injection layer 310, the hole transporting layer 320, the light emitting layer 330, the electron transporting layer 340, and the cathode 200 are sequentially stacked. Optionally, as illustrated in FIG. 2, an electron injection layer 350 may be positioned between the electron transporting layer 340 and the cathode 200. In addition, a hole blocking layer (not illustrated) may be positioned between the light emitting layer 330 and the electron transporting layer 340. The organic EL device of the present invention may be prepared by forming organic layers and electrodes using materials and methods known in the art, except that at least one of the organic layers 300 (e.g., the hole transporting layer 320) includes the compound represented by Chemical Formula 1.

The organic layer may be formed by a vacuum deposition method or a solution coating method. Examples of the solution coating method may include, but are not limited to, spin coating, dip coating, doctor blading, inkjet printing, thermal transfer or the like.

The substrate used for preparing the organic electroluminescence device of the present invention is not particularly limited, but silicon wafers, quartz, glass plates, metal plates, plastic films, sheets or the like may be used.

In addition, a material of the anode may include, but not limited to, a metal such as vanadium, chromium, copper, zinc and gold or an alloy thereof; a metal oxide such as zinc oxide, indium oxide, indium tin oxide (ITO) and indium zinc oxide (IZO); a combination of oxide with metal such as ZnO:Al or $SnO_2$:Sb; a conductive polymer such as polythiophene, poly(3-methylthiophene), poly [3,4-(ethylene-1, 2-dioxy) thiophene] (PEDT), polypyrrole and polyaniline; carbon black or the like.

In addition, a material of the cathode may include, but not limited to, a metal such as magnesium, calcium, sodium, potassium, titanium, indium, yttrium, lithium, gadolinium, aluminum, silver, tin and lead or an alloy thereof; a multilayered material such as LiF/Al and $LiO_2$/Al or the like.

In addition, materials of the hole injection layer, the light emitting layer, the electron injection layer, and the electron transporting layer are not particularly limited and conventional materials known in the art may be used.

Hereinafter, the present invention will be described in detail with reference to the following embodiments. However, the following embodiments are merely to illustrate the invention, and the present invention is not limited by the following embodiments.

[Preparation Example 1] Synthesis of 9-bromospiro[benzo[c]fluorene-7,9'-xanthene]

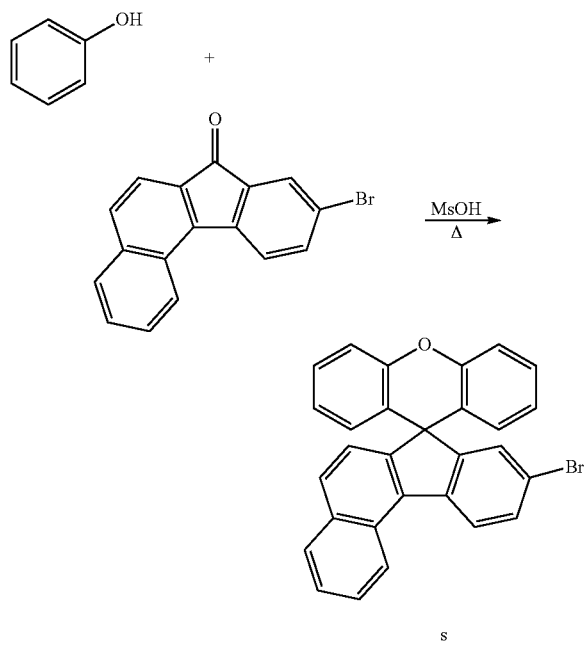

After adding 42 mL (0.65 mol) of methanesulfonic acid (MsOH) to 50 g (0.16 mol) of 9-bromo-7H-benzo[c]fluoren-7-one and 152.2 g (1.62 mol) of phenol, the mixture was heated to reflux at 120° C. for 12 hours. The temperature of the reaction solution obtained by heating to reflux was then cooled to room temperature, and 300 mL of purified water was added to the reaction solution to terminate the reaction of the reaction solution. After completion of the reaction, the mixture was extracted with 1.0 L of $CH_2CL_2$ to separate an organic layer, and the separated organic layer was neutralized with 500 mL of saturated calcium carbonate and washed with distilled water. Thereafter, the washed organic layer was dried over anhydrous $MgSO_4$, distilled under reduced pressure, and purified by silica gel column chromatography, and thus 40.3 g (yield 54%) of a target compound was obtained.

$^1$H-NMR (in $CDCl_3$): δ 7.78 (d, 1H), 7.65 (d, 1H), 7.50 (d, 1H), 7.38 (t, 1H), 7.27 (d, 1H), 7.25 (m, 5H), 7.15 (d, 1H), 6.79 (t, 2H), 6.41 (d, 2H)

[LCMS]: 461

[Preparation Example 2] Synthesis of 2-bromospiro[benzo[b]fluorene-11,9'-xanthene]

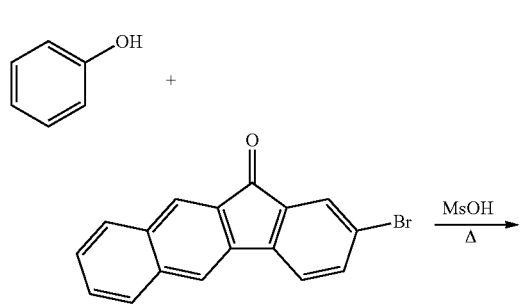

-continued

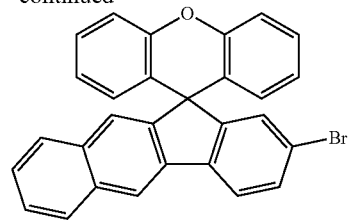

A procedure as in Preparation Example 1 was performed, except that 2-bromo-11H-Benzo[b]fluoren-11-one was used instead of 9-bromo-7H-benzo[c]fluoren-7-one used in Preparation Example 1, and thus 31.3 g (42%) of a target compound was obtained.

[LCMS]: 461

[Preparation Example 2] Synthesis of 9-bromospiro[benzo[a]fluorene-11,9'-xanthene]

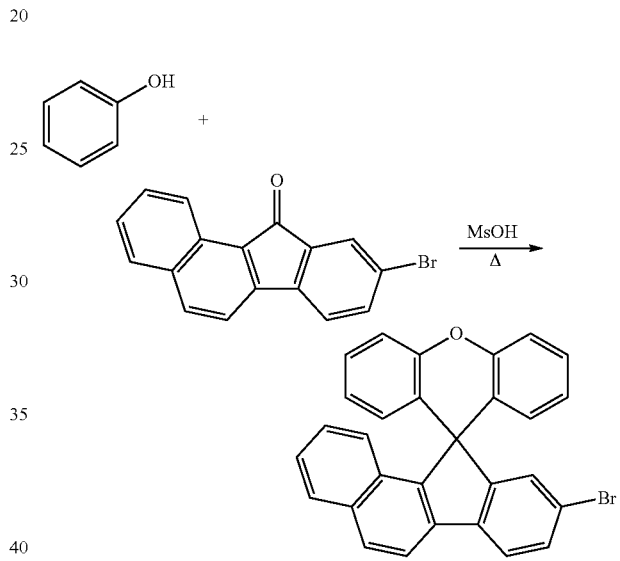

A procedure as in Preparation Example 1 was performed, except that 9-bromo-11H-Benzo[a]fluoren-11-one was used instead of 9-bromo-7H-benzo[c]fluoren-7-one used in Preparation Example 1, and thus 29.1 g (39%) of a target compound corresponding to a structural isomer of Core 1 was obtained.

[LCMS]: 461

[Preparation Example 4] Synthesis of 10-chlorospiro[benzo[c]fluorene-7,9'-xanthene]

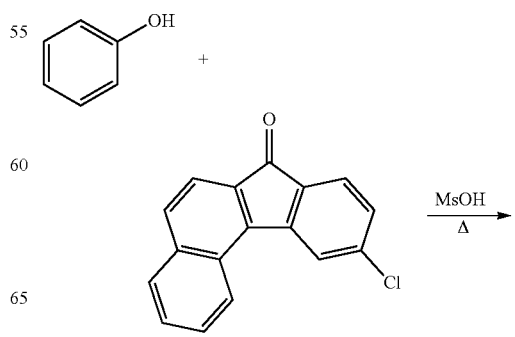

103

-continued

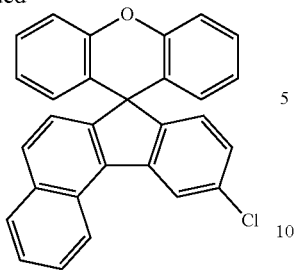

A procedure as in Preparation Example 1 was performed, except that 10-chloro-7H-benzo[c]fluoren-7-one was used instead of 9-bromo-7H-benzo[c]fluoren-7-one used in Preparation Example 1, and thus 35.4 g (45%) of a target compound corresponding to a structural isomer of Core 1 was obtained.

[LCMS]: 416

[Preparation Example 5] Synthesis of 11-chlorospiro[benzo[c]fluorene-7,9'-xanthene]

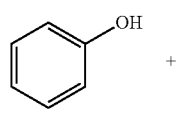
+
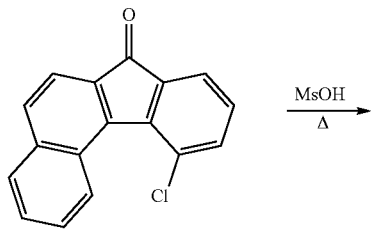

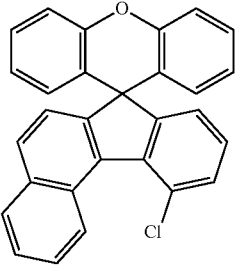

A procedure as in Preparation Example 1 was performed, except that 11-chloro-7H-Benzo[c]fluoren-7-one was used instead of 9-bromo-7H-benzo[c]fluoren-7-one used in Preparation Example 1, and thus 37.0 g (47%) of a target compound corresponding to a structural isomer of Core 1 was obtained.

[LCMS]: 416

[Preparation Example 6] Synthesis of 9-bromospiro[benzo[c]fluorene-7,9'-thioxanthene]

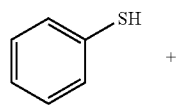
+

104

-continued

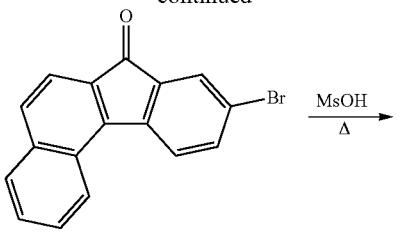

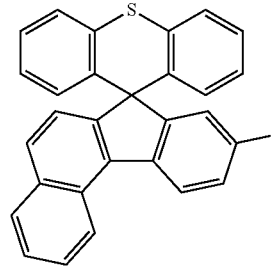

A procedure as in Preparation Example 1 was performed, except that thiophenol was used instead of phenol used in Preparation Example 1, and thus 45.6 g (59%) of a target compound of Core 6 was obtained.

[LCMS]: 477

[Preparation Example 7] Synthesis of 2-bromospiro[benzo[b]fluorene-11,9'-thioxanthene]

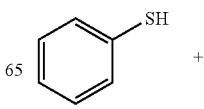
+

A procedure as in Preparation Example 1 was performed, except that thiophenol was used instead of phenol used in Preparation Example 1 and 2-bromo-11H-Benzo[b]fluoren-11-one was used instead of 9-bromo-7H-benzo[c]fluoren-7-one, and thus 42.5 g (55%) of a target compound corresponding to a structural isomer of Core 6 was obtained.

[Preparation Example 8] Synthesis of 9-bromospiro[benzo[a]fluorene-11,9'-thioxanthene]

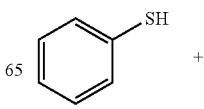
+

105
-continued

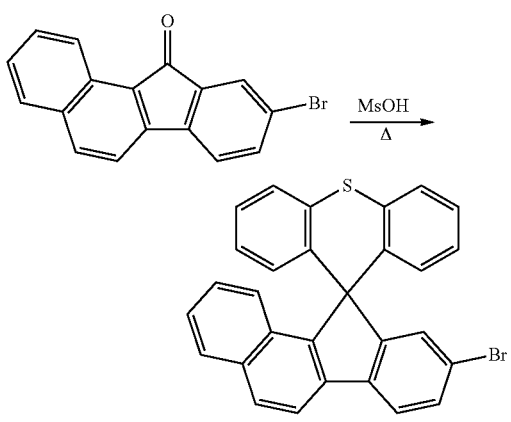

A procedure as in Preparation Example 1 was performed, except that thiophenol was used instead of phenol used in Preparation Example 1 and 9-bromo-11H-Benzo[a]fluoren-11-one was used instead of 9-bromo-7H-benzo[c]fluoren-7-one, and thus 31.7 g (41%) of a target compound corresponding to a structural isomer of Core 6 was obtained.

[LCMS]: 477

[Preparation Example 9] Synthesis of 11-chlorospiro[benzo[c]fluorene-7,9'-thioxanthene]

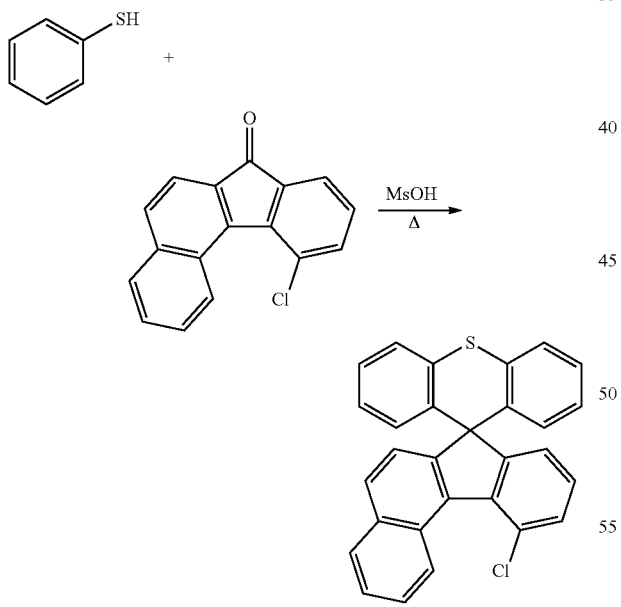

A procedure as in Preparation Example 1 was performed, except that thiophenol was used instead of phenol used in Preparation Example 1 and 11-chloro-7H-benzo[c]fluoren-7-one was used instead of 9-bromo-7H-benzo[c]fluoren-7-one, and thus 40.9 g (50%) of a target compound corresponding to a structural isomer of Core 6 was obtained.

[LCMS]: 432

106

[Preparation Example 10] Synthesis of 4,4,5,5-tetramethyl-2-(spiro[benzo[c]fluorene-7,9'-xanthen]-9-yl)-1,3,2-dioxaborolane

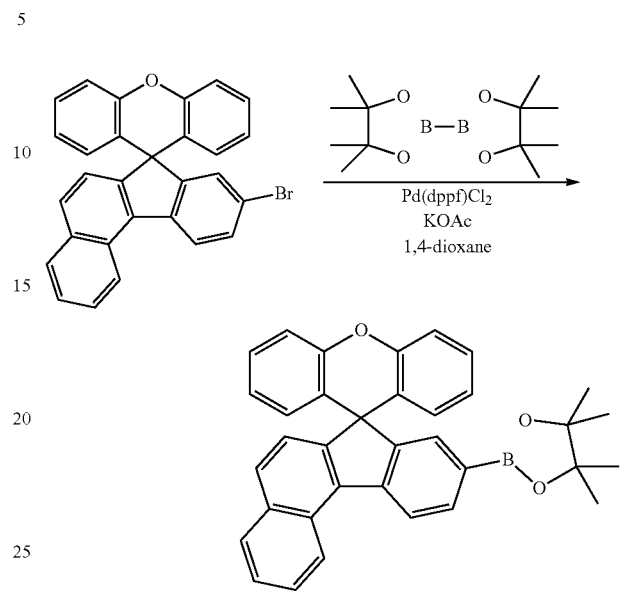

500 mL of 1,4-dioxane was added to 25.0 g (54.2 mmol) of 9-bromospiro[benzo[c]fluorene-7,9'-xanthene] obtained in [Preparation Example 1] and 16.5 g (65.1 mmol) of 4,4,4',4',5,5,5',5'-octamethyl-2,2'-bi(1,3,2-dioxaborolane).

Thereafter, 2.3 g (2.8 mmol) of [1,1'-Bis(diphenylphosphino)ferrocene]dichloropalladium(II) (Pd(dppf)Cl$_2$) and 16.0 g (163 mmol) of potassium acetate (KOAc) were added to the mixture, and the mixture was heated to reflux at 130° C. for 4 hours. Then, the temperature of the reaction solution obtained by heating to reflux was cooled to room temperature, 500 mL of an aqueous ammonium chloride solution was added to the reaction solution to terminate the reaction, followed by extraction with 1.0 L of ethyl acetate (EA), and the extracted material was then washed with distilled water to obtain an organic layer. Thereafter, the obtained organic layer was dried over anhydrous MgSO$_4$, distilled under reduced pressure, and purified by silica gel column chromatography, and thus 18.2 g (yield 66%) of a target compound was obtained.

[LCMS]: 508

[Preparation Example 11] Synthesis of 4,4,5,5-tetramethyl-2-(spiro[benzo[a]fluorene-11,9'-xanthen]-9-yl)-1,3,2-dioxaborolane

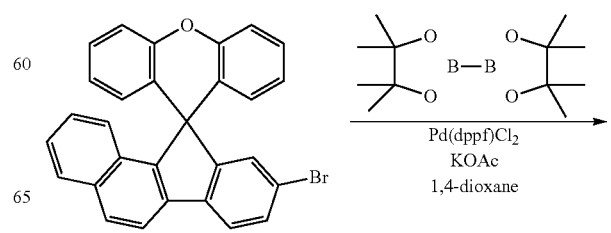

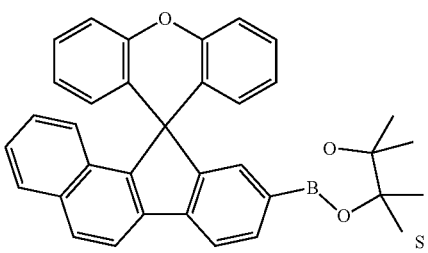

A procedure as in Preparation Example 10 was performed, except that 9-bromospiro[benzo[a]fluorene-11,9'-xanthene]obtained in Preparation Example 3 was used instead of 9-bromospiro[benzo[c]fluorene-7,9'-xanthene] used in Preparation Example 10, and thus 32.8 g (58%) of a target compound corresponding to a structural isomer of Core 10 was obtained.

[LCMS]: 508

[Preparation Example 12] Synthesis of 4,4,5,5-tetramethyl-2-(spiro[benzo[c]fluorene-7,9'-xanthen]-10-yl)-1,3,2-dioxaborolane

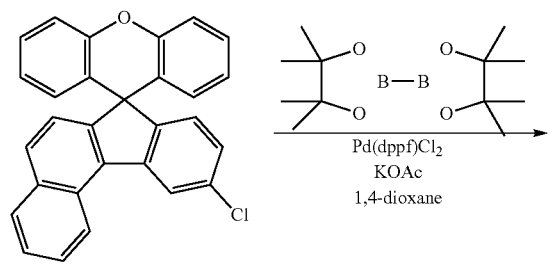

A procedure as in Preparation Example 10 was performed, except that 10-chlorospiro[benzo[c]fluorene-7,9'-xanthene]obtained in Preparation Example 4 was used instead of 9-bromospiro[benzo[c]fluorene-7,9'-xanthene] used in Preparation Example 10, and thus 26.9 g (63%) of a target compound corresponding to a structural isomer of Core 10 was obtained.

[LCMS]: 508

[Preparation Example 13] Synthesis of 4,4,5,5-tetramethyl-2-(spiro[benzo[c]fluorene-7,9'-thioxanthen]-11-yl)-1,3,2-dioxaborolane

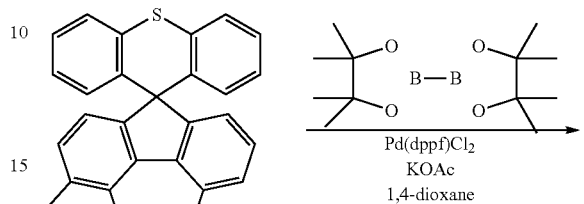

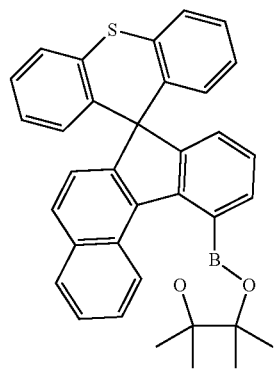

A procedure as in Preparation Example 10 was performed, except that 11-chlorospiro[benzo[c]fluorene-7,9'-thioxanthene]obtained in Preparation Example 9 was used instead of 9-bromospiro[benzo[c]fluorene-7,9'-xanthene] used in Preparation Example 10, and thus 29.5 g (70%) of a target compound corresponding to Core 11 was obtained.

[LCMS]: 524

[Synthesis Example 1] Synthesis of Compound 2

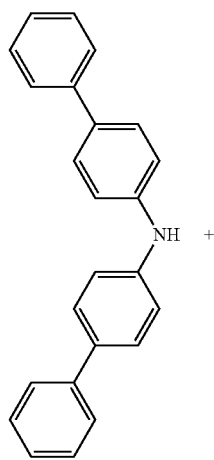

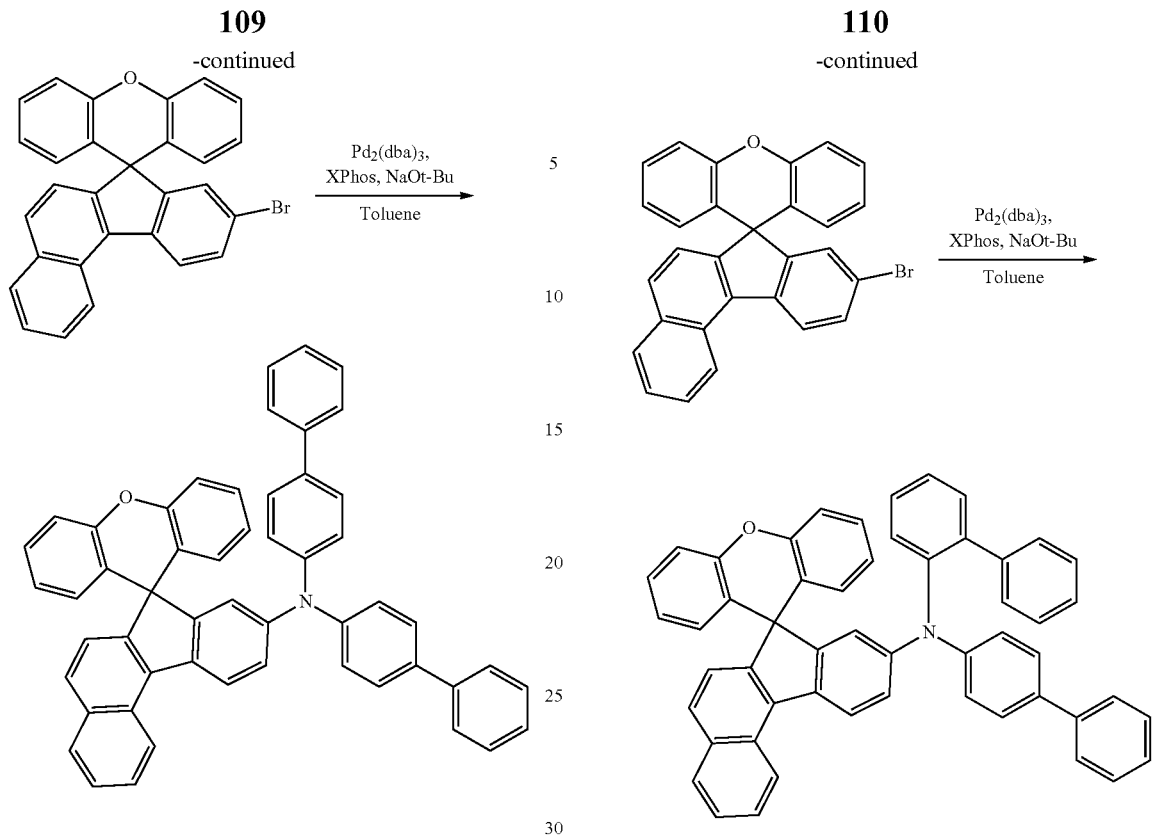

After adding 100 mL of toluene to 10.0 g (21.7 mmol) of 9-bromospiro[benzo[c]fluorene-7,9'-xanthene] obtained in Preparation Example 1 and 7.0 g (21.7 mmol) of di([1,1'-biphenyl]-4-yl)amine, 1.0 g (1.1 mmol) of $Pd_2(dba)_3$, 1.04 g (2.2 mmol) of XPhos, and 4.2 g (43.4 mmol) of NaOt-Bu were added to the mixture, and then the mixture was heated to reflux at 120° C. for 3 hours. Then, the temperature of the reaction solution heated to reflux was cooled to room temperature, and then 300 mL of purified water was added to the reaction solution to terminate the reaction. After completion of the reaction, the obtained mixture was extracted with 500 mL of E.A., and washed with distilled water to obtain an organic layer. The obtained organic layer was dried over anhydrous $MgSO_4$, distilled under reduced pressure, and purified by silica gel column chromatography to obtain 11.1 g (yield 73%) of a target compound.

[LCMS]: 701

[Synthesis Example 2] Synthesis of Compound 4

A procedure as in Synthesis Example 1 was performed, except that N-([1,1'-biphenyl]-4-yl)-[1,1'-biphenyl]-2-amine was used instead of di([1,1'-biphenyl]-4-yl)amine used in Synthesis Example 1, and thus 9.9 g (yield 65%) of a target compound was obtained.

[LCMS]: 701

[Synthesis Example 3] Synthesis of Compound 7

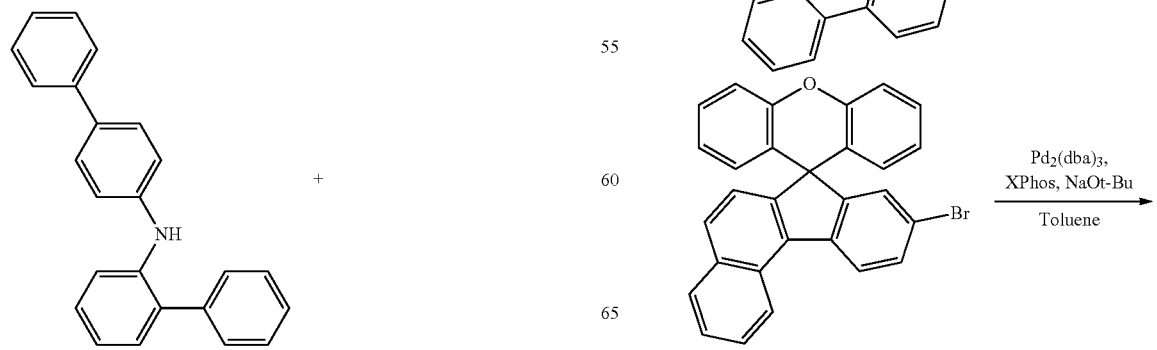

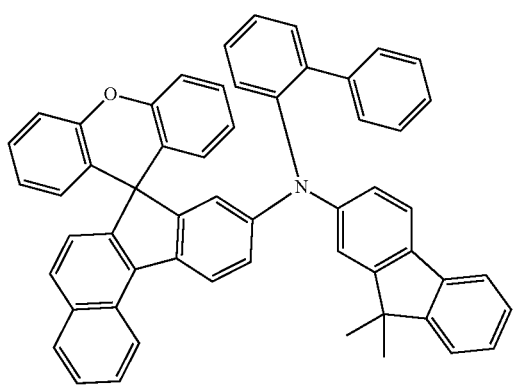

A procedure as in Synthesis Example 1 was performed, except that N-([1,1'-biphenyl]-2-yl)-9,9-dimethyl-9H-fluoren-2-amine was used instead of di([1,1'-biphenyl]-4-yl)amine used in Synthesis Example 1, and thus 8.5 g (yield 70%) of a target compound was obtained.

[LCMS]: 741

[Synthesis Example 4] Synthesis of Compound 11

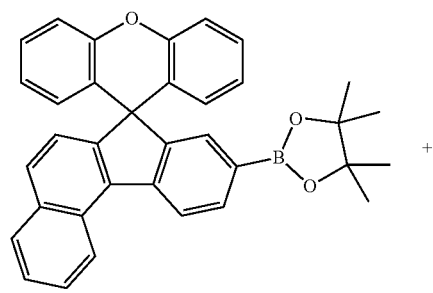

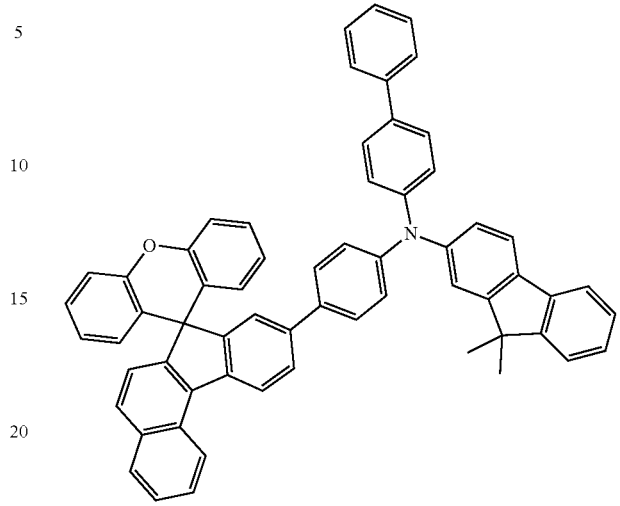

After adding 600 mL of dioxane and 150 mL of H₂O to 15 g (29.5 mmol) of 4,4,5,5-tetramethyl-2-(spiro[benzo[c]fluorene-7,9'-xanthen]-9-yl)-1,3,2-dioxaborolane of Preparation Example 10 and 15.3 g (32.5 mmol) of N-([1,1'-biphenyl]-4-yl)-N-(4-chlorophenyl)-9,9-dimethyl-9H-fluoren-2-amine, 1.7 g (1.5 mmol) of Pd(PPh₃)₄ and 12.2 g (88.5 mmol) of K₂CO₃ were added thereto, followed by heating to reflux at 120° C. for 3 hours. Then, the temperature of the reaction solution heated to reflux was cooled to room temperature, and 500 mL of purified water was added to the cooled reaction solution to terminate the reaction. After completion of the reaction, the mixture was extracted with 1.0 L of E.A., and washed with distilled water to obtain an organic layer. The obtained organic layer was dried over anhydrous MgSO₄, distilled under reduced pressure, and purified by silica gel column chromatography to obtain 14.2 g (yield 59%) of a target compound.

[LCMS]: 818

[Synthesis Example 5] Synthesis of Compound 14

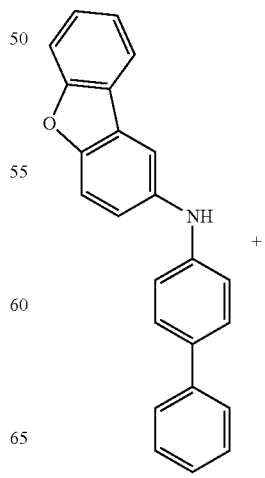

113
-continued

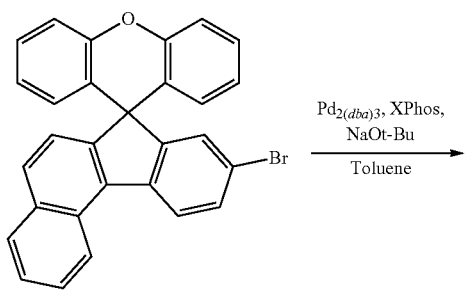

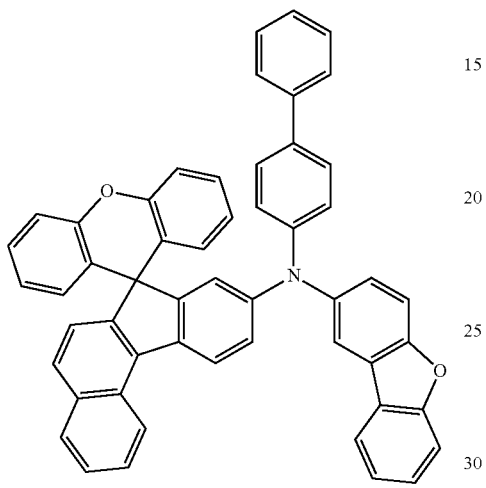

A procedure as in Synthesis Example 1 was performed, except that N-([1,1'-biphenyl]-4-yl)dibenzo[b,d]furan-2-amine was used instead of di([1,1'-biphenyl]-4-yl)amine used in Synthesis Example 1, and thus 7.7 g (yield 62%) of a target compound was obtained.

[LCMS]: 715

[Synthesis Example 6] Synthesis of Compound 19

114
-continued

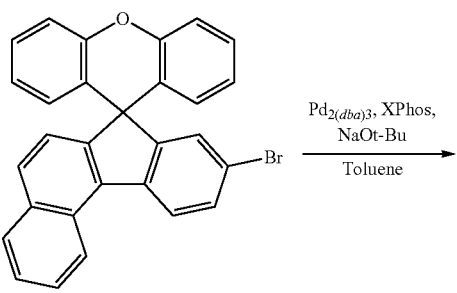

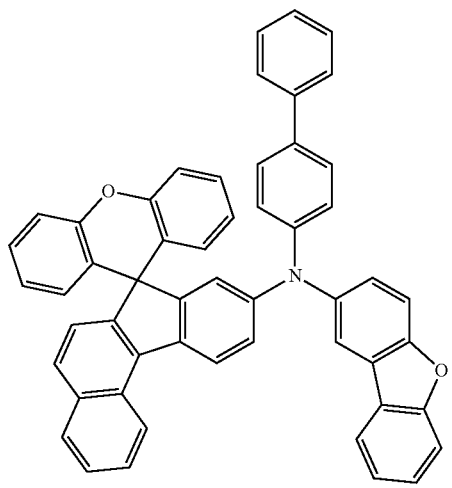

A procedure as in Synthesis Example 1 was performed, except that N-(4-(dibenzo[b,d]furan-4-yl)phenyl)-[1,1'-biphenyl]-4-amine was used instead of di([1,1'-biphenyl]-4-yl)amine used in Synthesis Example 1, and thus 10.2 g (yield 55%) of a target compound was obtained.

[LCMS]: 791

[Synthesis Example 7] Synthesis of Compound 25

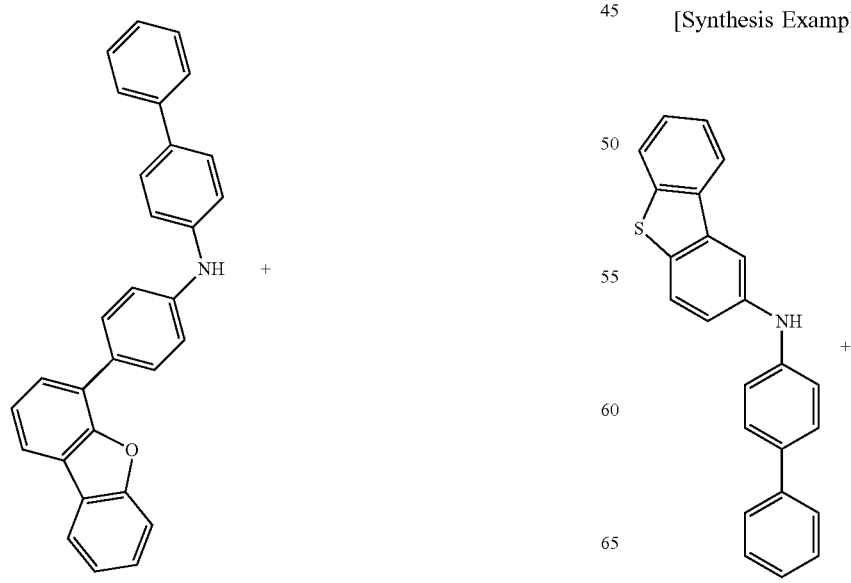

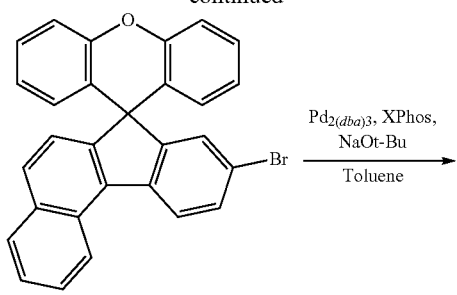

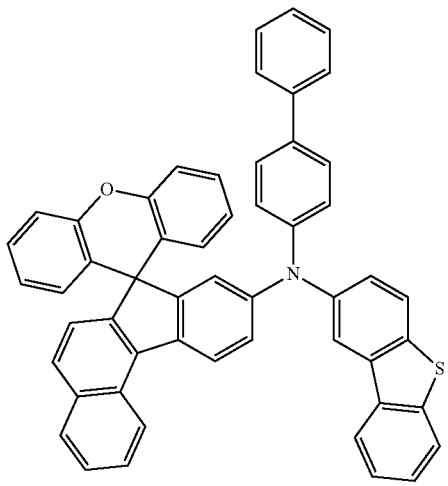

A procedure as in Synthesis Example 1 was performed, except that N-([1,1'-biphenyl]-4-yl)dibenzo[b,d]thiophen-2-amine was used instead of di([1,1'-biphenyl]-4-yl)amine used in Synthesis Example 1, and thus 5.2 g (yield 72%) of a target compound was obtained.

[LCMS]: 731

[Synthesis Example 8] Synthesis of Compound 29

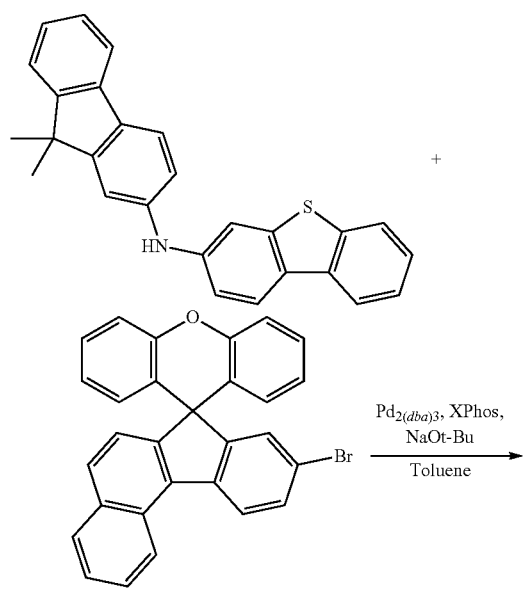

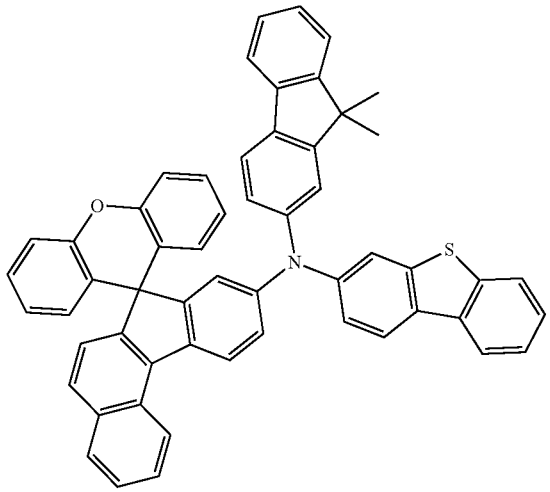

A procedure as in Synthesis Example 1 was performed, except that N-(9,9-dimethyl-9H-fluoren-2-yl)dibenzo[b,d]thiophen-3-amine was used instead of di([1,1'-biphenyl]-4-yl)amine used in Synthesis Example 1, and thus 6.6 g (yield 75%) of a target compound was obtained.

[LCMS]: 771

[Synthesis Example 9] Synthesis of Compound 34

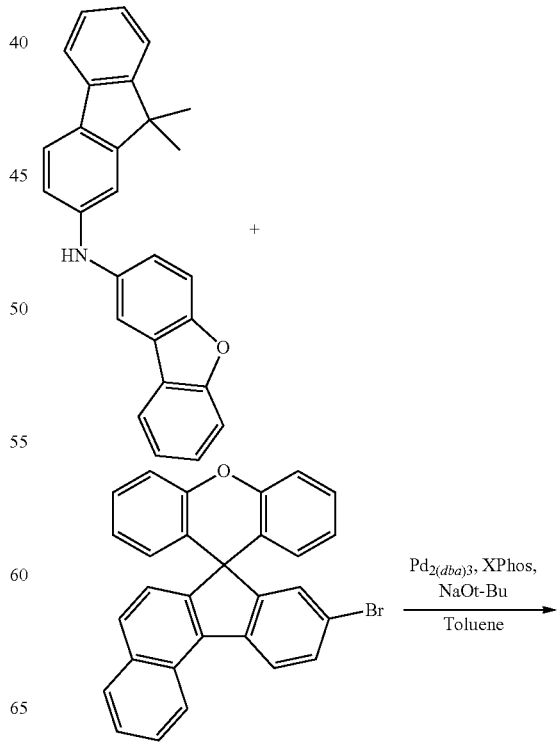

117

-continued

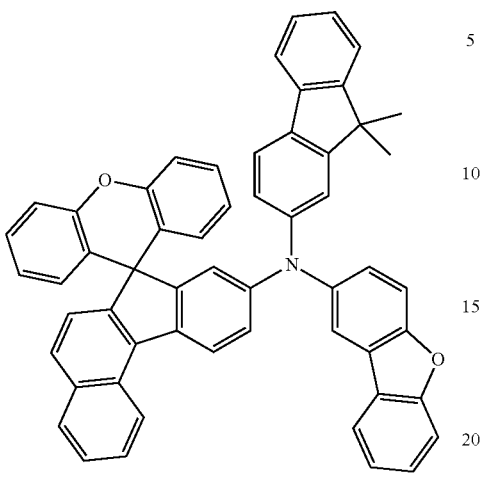

A procedure as in Synthesis Example 1 was performed, except that N-(9,9-dimethyl-9H-fluoren-2-yl)dibenzo[b,d]furan-2-amine was used instead of di([1,1'-biphenyl]-4-yl)amine used in Synthesis Example 1, and thus 9.1 g (yield 64%) of a target compound was obtained.

[LCMS]: 755

[Synthesis Example 10] Synthesis of Compound 37

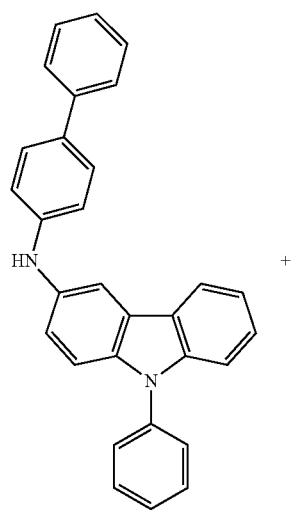

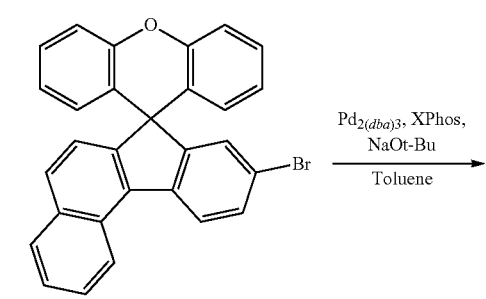

118

-continued

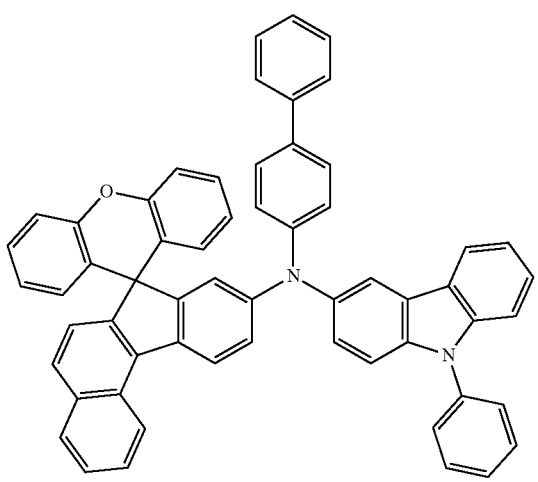

A procedure as in Synthesis Example 1 was performed, except that N-([1,1'-biphenyl]-4-yl)-9-phenyl-9H-carbazol-3-amine was used instead of di([1,1'-biphenyl]-4-yl)amine used in Synthesis Example 1, and thus 8.6 g (yield 69%) of a target compound was obtained.

LCMS]: 790

[Synthesis Example 11] Synthesis of Compound 42

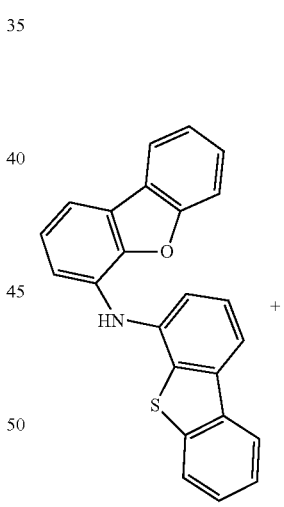

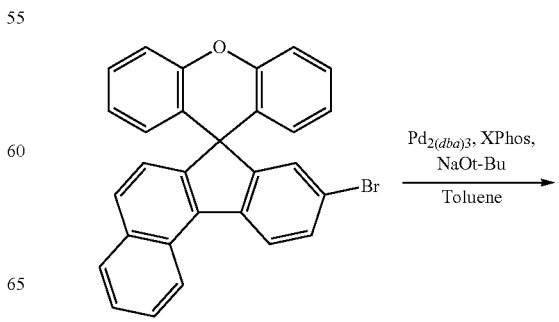

-continued

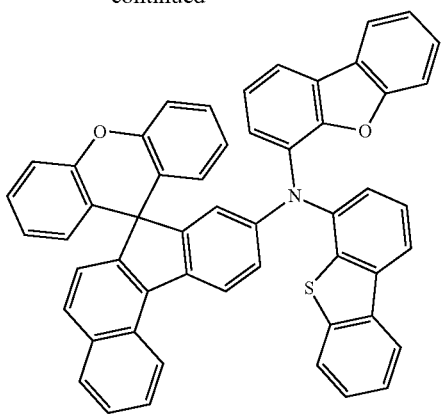

A procedure as in Synthesis Example 1 was performed, except that N-(dibenzo[b,d]thiophen-4-yl)dibenzo[b,d]furan-4-amine was used instead of di([1,1'-biphenyl]-4-yl)amine used in Synthesis Example 1, and thus 10.4 g (yield 61%) of a target compound was obtained.

[LCMS]: 745

[Synthesis Example 12] Synthesis of Compound 45

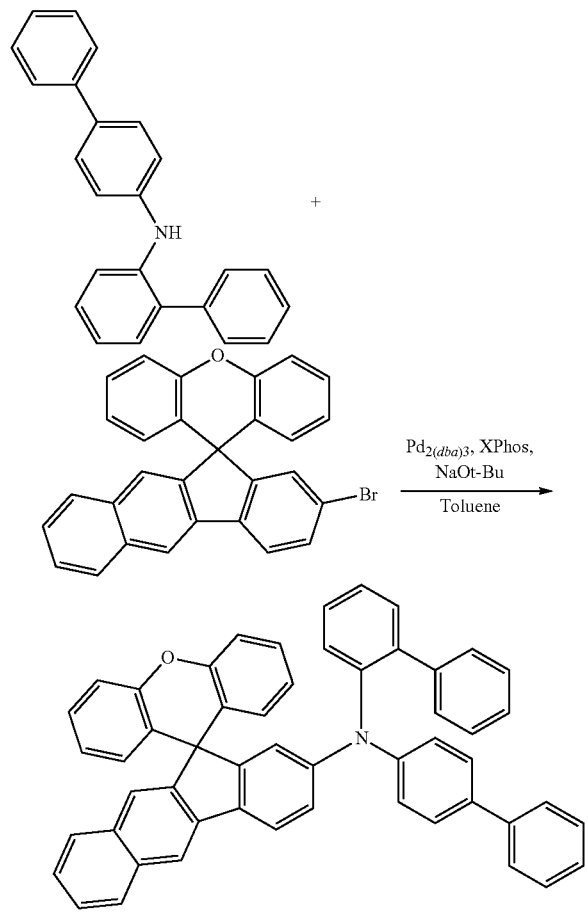

A procedure as in Synthesis Example 1 was performed, except that 2-bromospiro[benzo[b]fluorene-11,9'-xanthene] of Preparation Example 2 was used instead of 9-bromospiro[benzo[c]fluorene-7,9'-xanthene] used in Synthesis Example 1 and N-([1,1'-biphenyl]-4-yl)-[1,1'-biphenyl]-2-amine was used instead of di([1,1'-biphenyl]-4-yl)amine, and thus 4.9 g (yield 75%) of a target compound was obtained.

[LCMS]: 701

[Synthesis Example 13] Synthesis of Compound 52

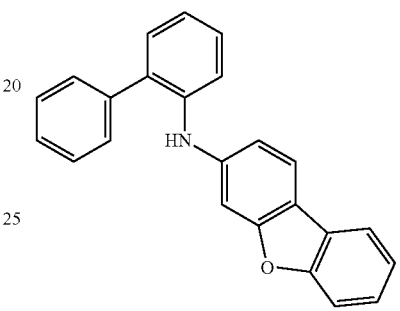

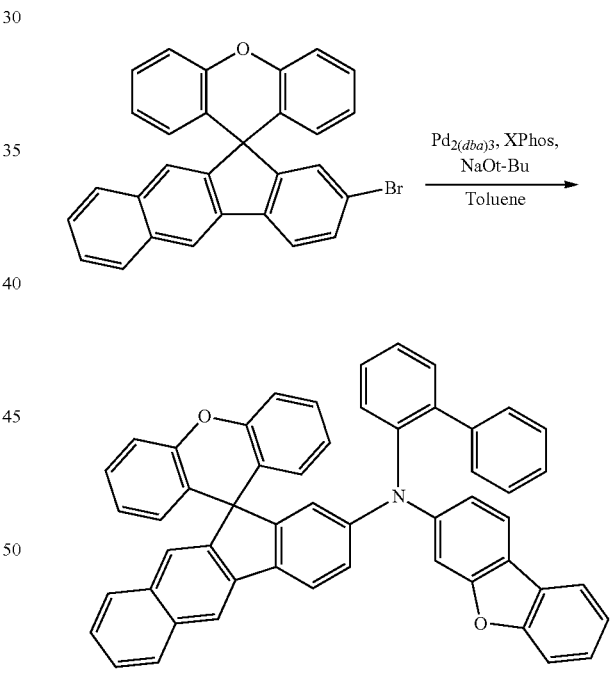

A procedure as in Synthesis Example 1 was performed, except that 2-bromospiro[benzo[b]fluorene-11,9'-xanthene] of Preparation Example 2 was used instead of 9-bromospiro[benzo[c]fluorene-7,9'-xanthene] used in Synthesis Example 1 and N-([1,1'-biphenyl]-2-yl)dibenzo[b,d]furan-3-amine was used instead of di([1,1'-biphenyl]-4-yl)amine, and thus 7.5 g (yield 52%) of a target compound was obtained.

[LCMS]: 715

[Synthesis Example 14] Synthesis of Compound 54

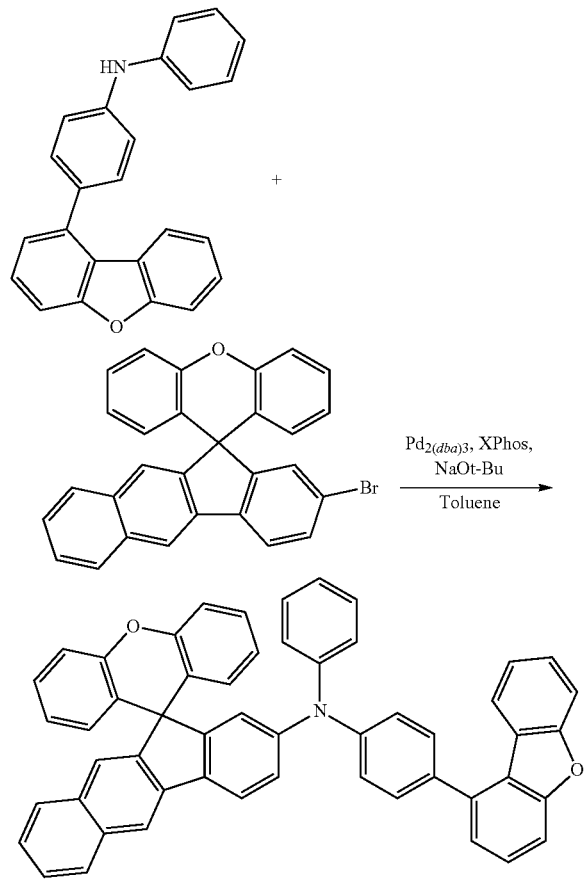

A procedure as in Synthesis Example 1 was performed, except that 2-bromospiro[benzo[b]fluorene-11,9'-xanthene] of Preparation Example 2 was used instead of 9-bromospiro[benzo[c]fluorene-7,9'-xanthene] used in Synthesis Example 1 and 4-(dibenzo[b,d]furan-1-yl)-N-phenylaniline was used instead of di([1,1'-biphenyl]-4-yl)amine, and thus 11.4 g (yield 76%) of a target compound was obtained.

[LCMS]: 715

[Synthesis Example 15] Synthesis of Compound 59

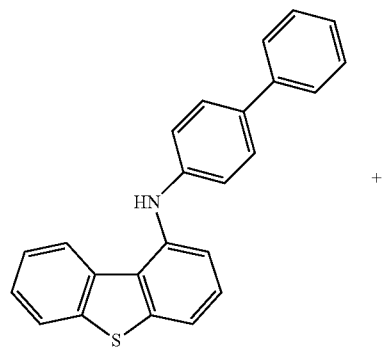

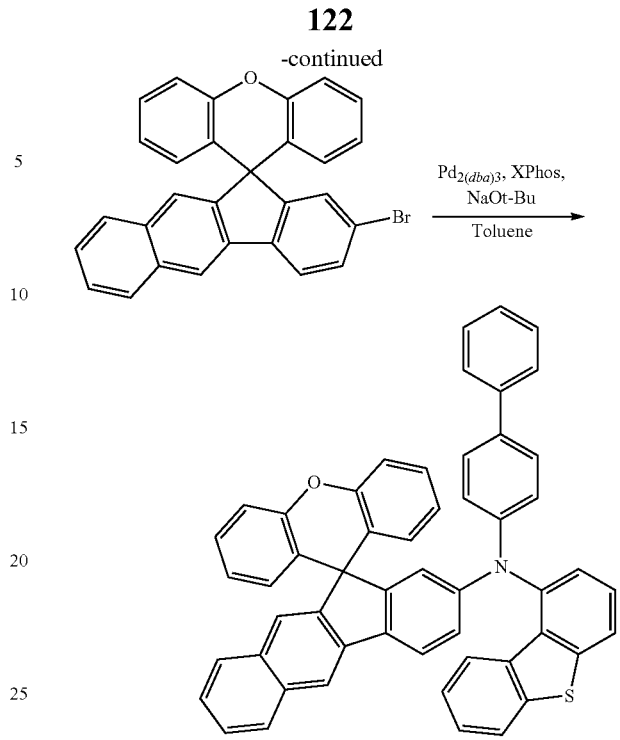

A procedure as in Synthesis Example 1 was performed, except that 2-bromospiro[benzo[b]fluorene-11,9'-xanthene] of Preparation Example 2 was used instead of 9-bromospiro[benzo[c]fluorene-7,9'-xanthene] used in Synthesis Example 1 and N-([1,1'-biphenyl]-4-yl)dibenzo[b,d]thiophen-1-amine was used instead of di([1,1'-biphenyl]-4-yl)amine, and thus 8.5 g (yield 59%) of a target compound was obtained.

[LCMS]: 731

[Synthesis Example 16] Synthesis of Compound 65

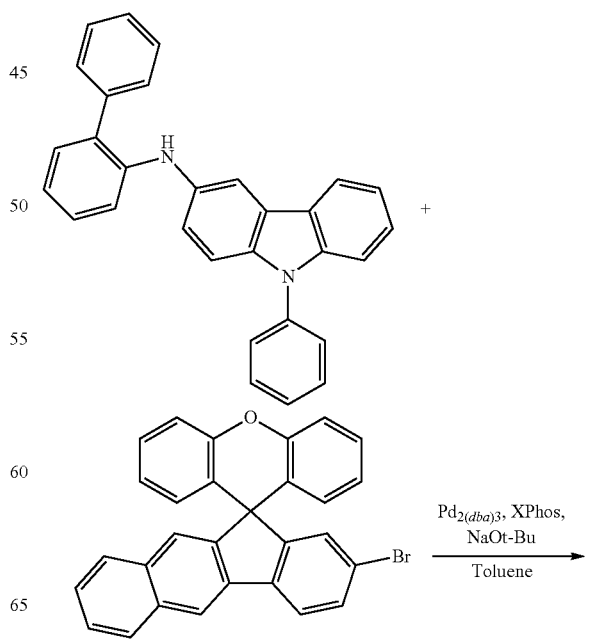

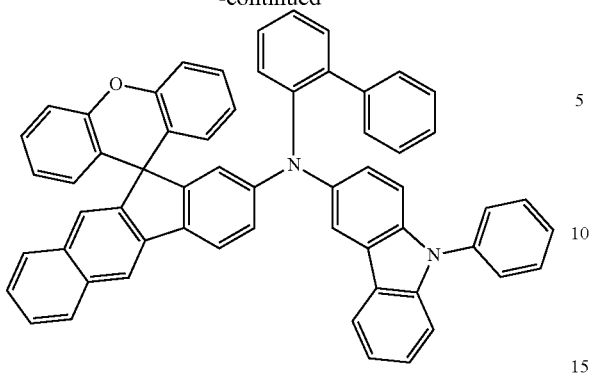

A procedure as in Synthesis Example 1 was performed, except that 2-bromospiro[benzo[b]fluorene-11,9'-xanthene] of Preparation Example 2 was used instead of 9-bromospiro[benzo[c]fluorene-7,9'-xanthene] used in Synthesis Example 1 and N-([1,1'-biphenyl]-2-yl)-9-phenyl-9H-carbazol-3-amine was used instead of di([1,1'-biphenyl]-4-yl)amine, and thus 3.9 g (yield 71%) of a target compound was obtained.

[LCMS]: 790

[Synthesis Example 17] Synthesis of Compound 69

A procedure as in Synthesis Example 1 was performed, except that 9-bromospiro[benzo[a]fluorene-11,9'-xanthene] of Preparation Example 3 was used instead of 9-bromospiro[benzo[c]fluorene-7,9'-xanthene] used in Synthesis Example 1 and N-([1,1'-biphenyl]-4-yl)naphthalen-1-amine was used instead of di([1,1'-biphenyl]-4-yl)amine, and thus 5.6 g (yield 62%) of a target compound was obtained.

[LCMS]: 675

[Synthesis Example 18] Synthesis of Compound 77

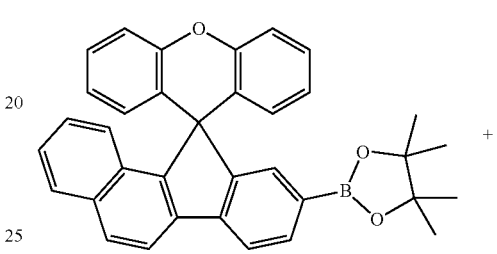

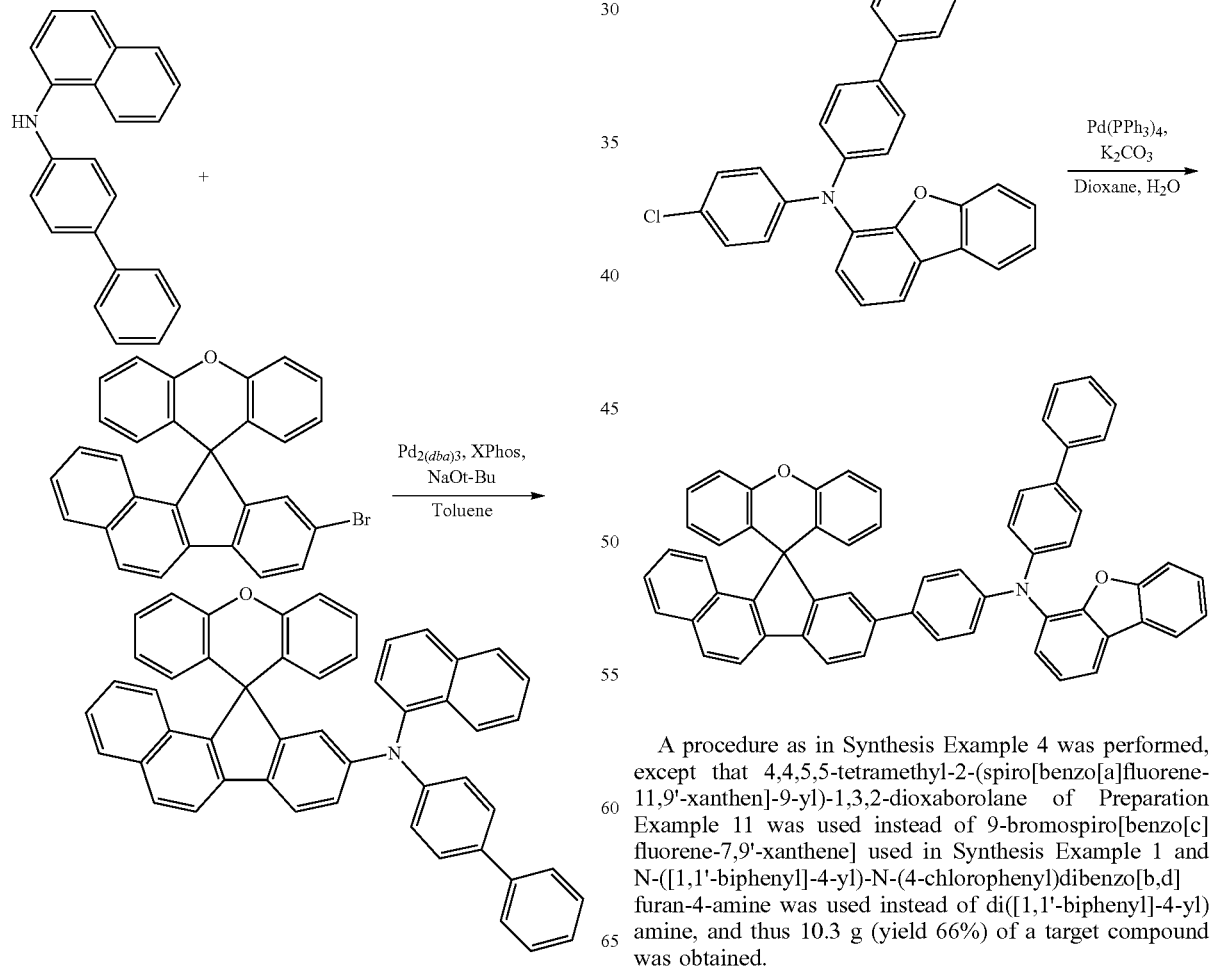

A procedure as in Synthesis Example 4 was performed, except that 4,4,5,5-tetramethyl-2-(spiro[benzo[a]fluorene-11,9'-xanthen]-9-yl)-1,3,2-dioxaborolane of Preparation Example 11 was used instead of 9-bromospiro[benzo[c]fluorene-7,9'-xanthene] used in Synthesis Example 1 and N-([1,1'-biphenyl]-4-yl)-N-(4-chlorophenyl)dibenzo[b,d]furan-4-amine was used instead of di([1,1'-biphenyl]-4-yl)amine, and thus 10.3 g (yield 66%) of a target compound was obtained.

[LCMS]: 791

[Synthesis Example 19] Synthesis of Compound 82

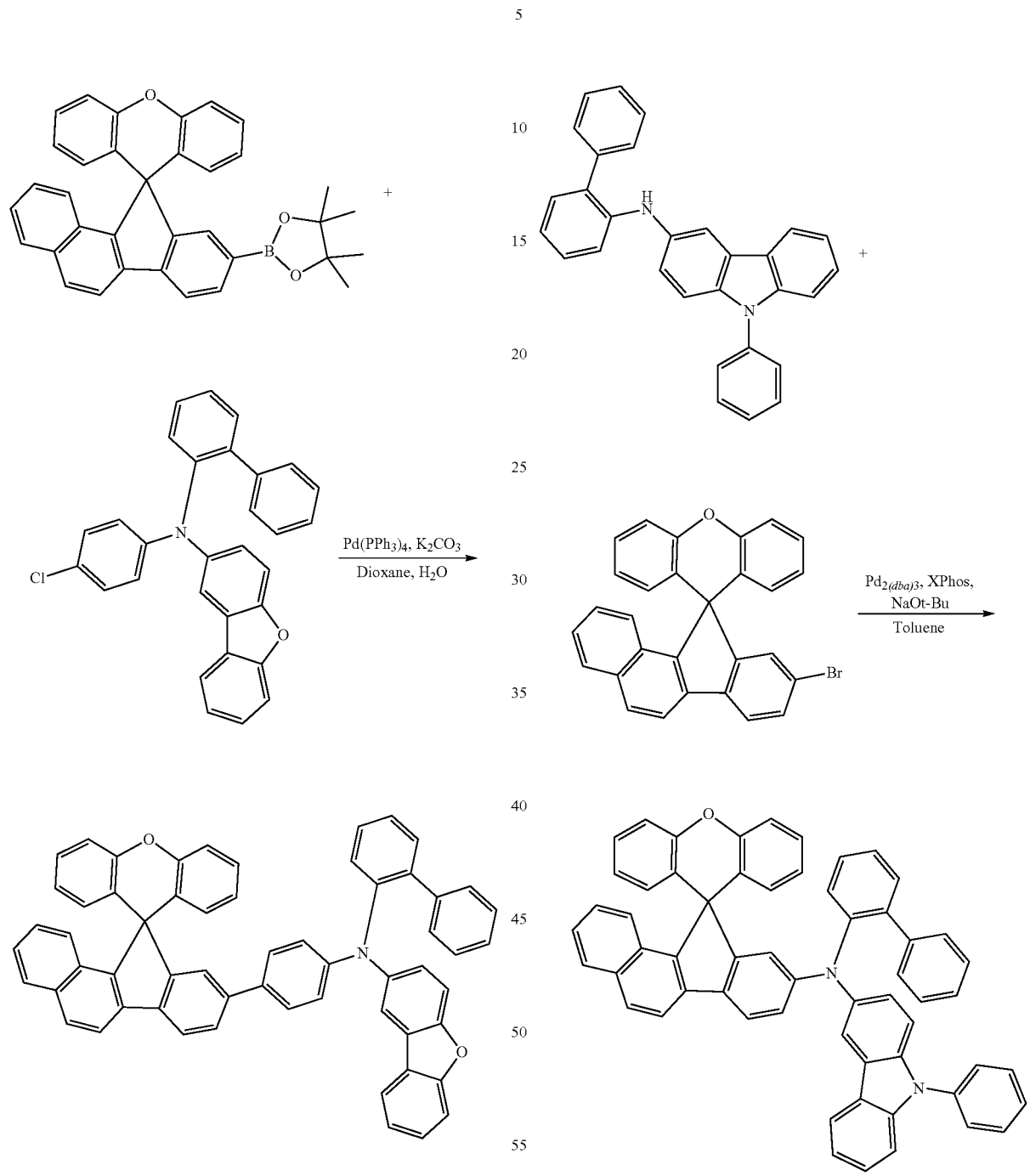

[Synthesis Example 20] Synthesis of Compound 89

A procedure as in Synthesis Example 4 was performed, except that 4,4,5,5-tetramethyl-2-(spiro[benzo[a]fluorene-11,9'-xanthen]-9-yl)-1,3,2-dioxaborolane of Preparation Example 11 was used instead of 9-bromospiro[benzo[c]fluorene-7,9'-xanthene] used in Synthesis Example 1 and N-([1,1'-biphenyl]-2-yl)-N-(4-chlorophenyl)dibenzo[b,d]furan-2-amine was used instead of di([1,1'-biphenyl]-4-yl)amine, and thus 7.0 g (yield 62%) of a target compound was obtained.

[LCMS]: 791

A procedure as in Synthesis Example 1 was performed, except that 9-bromospiro[benzo[a]fluorene-11,9'-xanthene] of Preparation Example 3 was used instead of 9-bromospiro[benzo[c]fluorene-7,9'-xanthene] used in Synthesis Example 1 and N-([1,1'-biphenyl]-2-yl)-9-phenyl-9H-carbazol-3-amine was used instead of di([1,1'-biphenyl]-4-yl)amine, and thus 4.5 g (yield 69%) of a target compound was obtained.

[LCMS]: 790

[Synthesis Example 21] Synthesis of Compound 94

[Synthesis Example 22] Synthesis of Compound 96

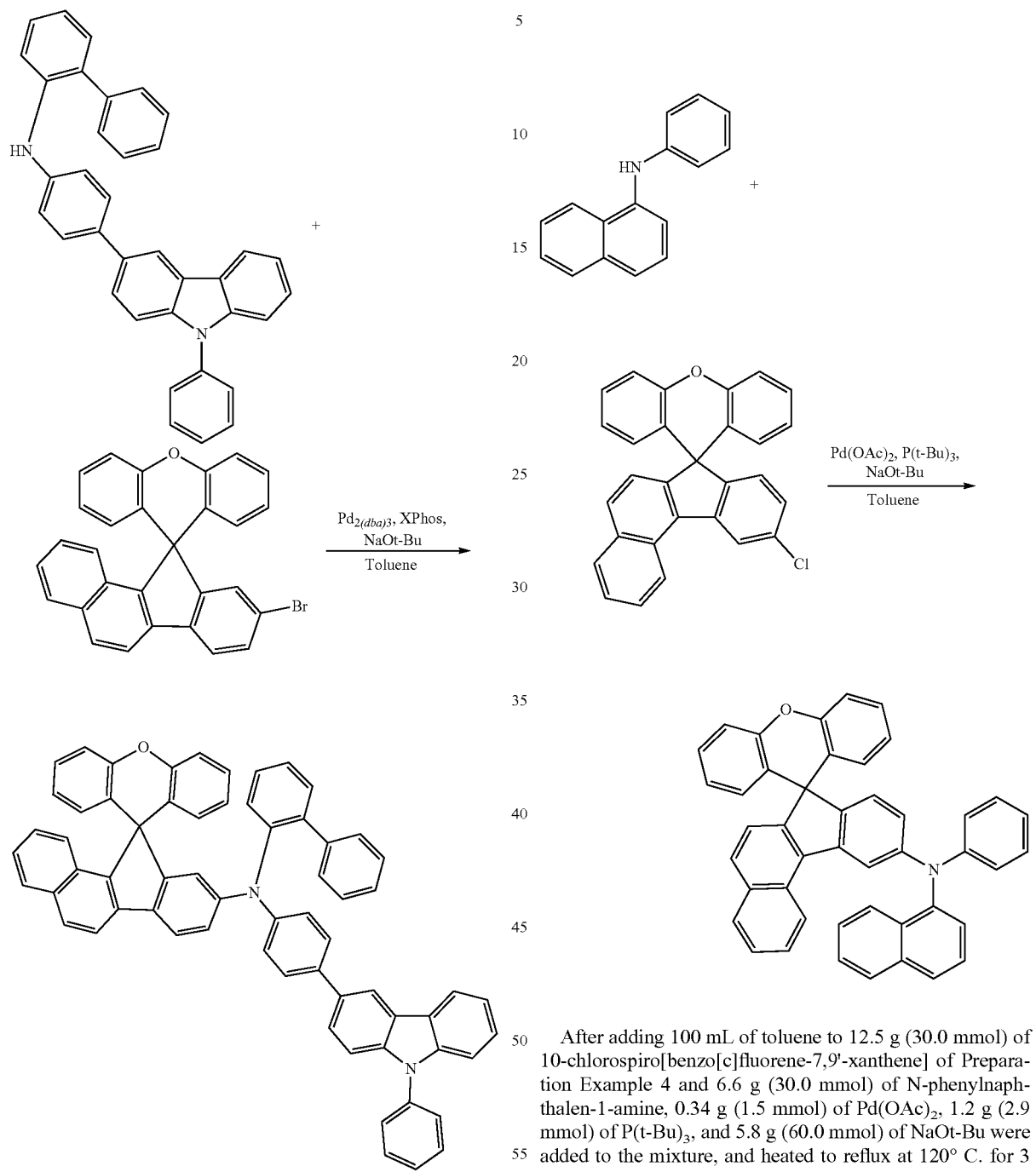

A procedure as in Synthesis Example 1 was performed, except that 9-bromospiro[benzo[a]fluorene-11,9'-xanthene] of Preparation Example 3 was used instead of 9-bromospiro[benzo[c]fluorene-7,9'-xanthene] used in Synthesis Example 1 and N-(4-(9-phenyl-9H-carbazol-3-yl)phenyl)-[1,1'-biphenyl]-2-amine was used instead of di([1,1'-biphenyl]-4-yl)amine, and thus 3.5 g (yield 77%) of a target compound was obtained.

[LCMS]: 867

After adding 100 mL of toluene to 12.5 g (30.0 mmol) of 10-chlorospiro[benzo[c]fluorene-7,9'-xanthene] of Preparation Example 4 and 6.6 g (30.0 mmol) of N-phenylnaphthalen-1-amine, 0.34 g (1.5 mmol) of Pd(OAc)$_2$, 1.2 g (2.9 mmol) of P(t-Bu)$_3$, and 5.8 g (60.0 mmol) of NaOt-Bu were added to the mixture, and heated to reflux at 120° C. for 3 hours. Then, the temperature of the reaction solution heated to reflux was cooled to room temperature, and 300 mL of purified water was added to the cooled reaction solution to terminate the reaction. After completion of the reaction, the mixture was extracted with 500 mL of E.A., and washed with distilled water to obtain an organic layer. The obtained organic layer was dried over anhydrous MgSO$_4$, distilled under reduced pressure, and purified by silica gel column chromatography to obtain 10.4 g (yield 58%) of a target compound.

[LCMS]: 599

[Synthesis Example 23] Synthesis of Compound 100

[Synthesis Example 24] Synthesis of Compound 105

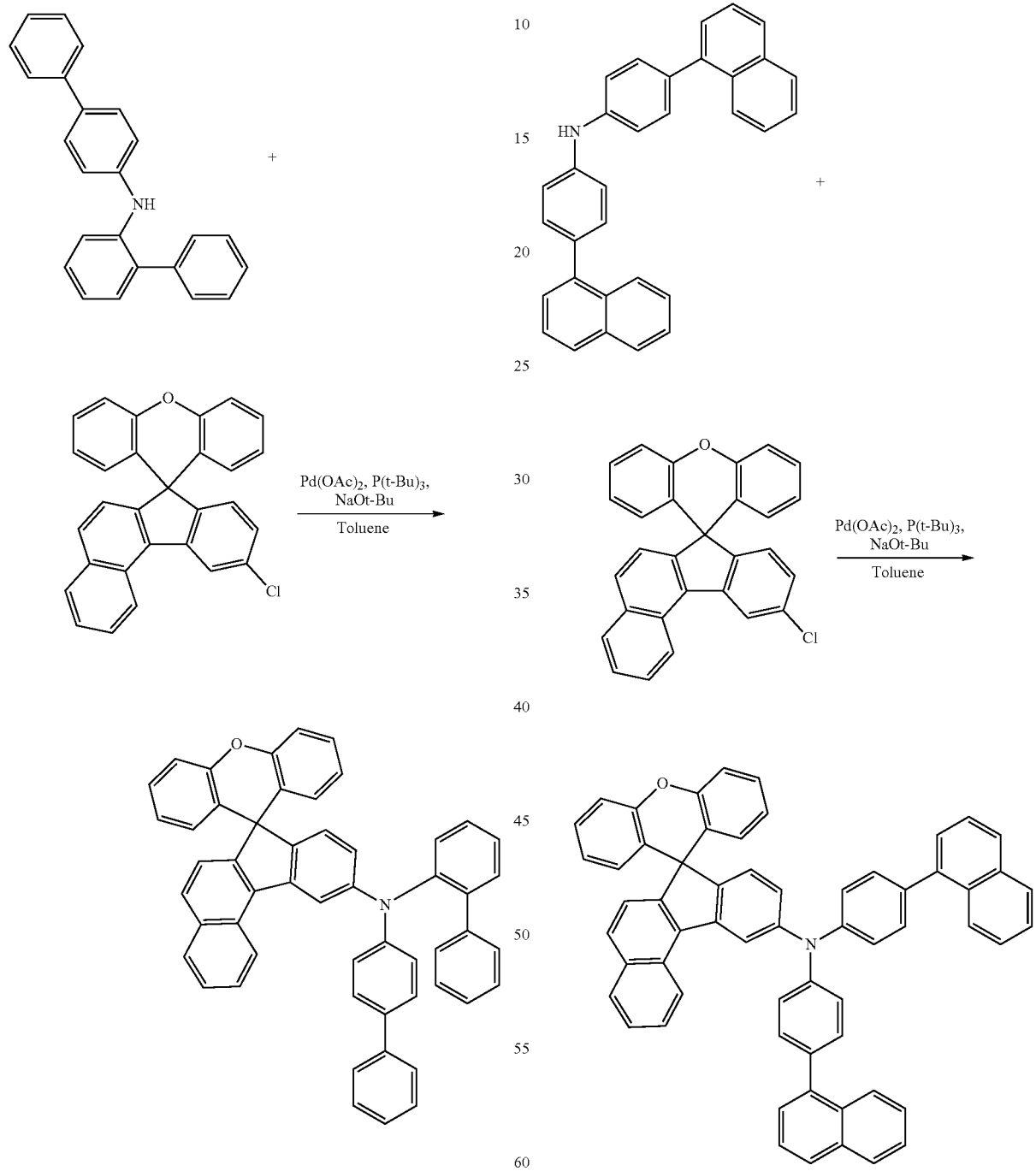

A procedure as in Synthesis Example 22 was performed, except that N-([1,1'-biphenyl]-4-yl)-[1,1'-biphenyl]-2-amine was used instead of N-phenylnaphthalen-1-amine used in Synthesis Example 22, and thus 8.4 g (yield 63%) of a target compound was obtained.

[LCMS]: 701

A procedure as in Synthesis Example 22 was performed, except that bis(4-(naphthalen-1-yl)phenyl)amine was used instead of N-phenylnaphthalen-1-amine used in Synthesis Example 22, and thus 5.0 g (yield 49%) of a target compound was obtained.

[LCMS]: 801

[Synthesis Example 25] Synthesis of Compound 108

[Synthesis Example 26] Synthesis of Compound 117

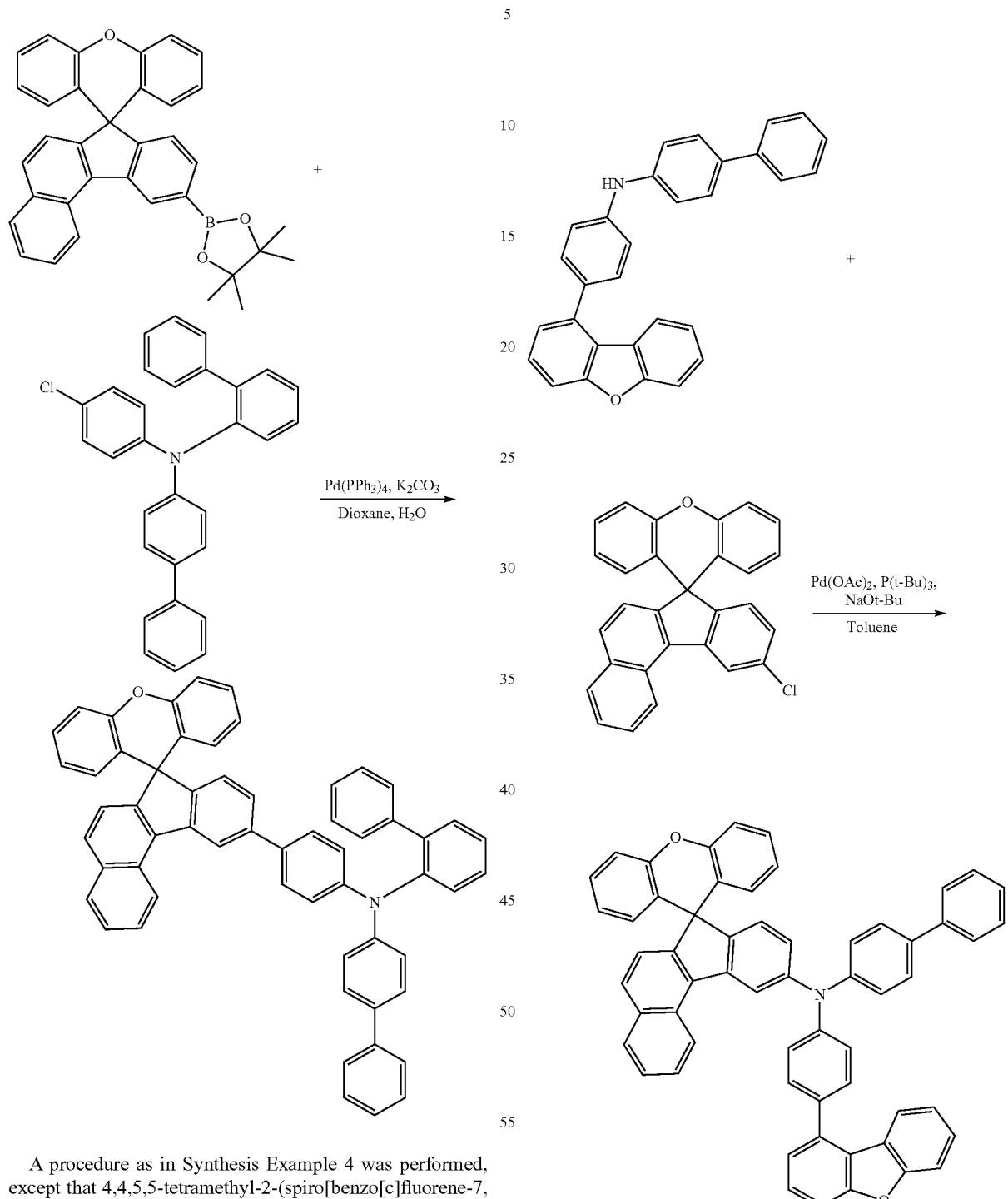

A procedure as in Synthesis Example 4 was performed, except that 4,4,5,5-tetramethyl-2-(spiro[benzo[c]fluorene-7,9'-xanthen]-10-yl)-1,3,2-dioxaborolane of Preparation Example 12 was used instead of 4,4,5,5-tetramethyl-2-(spiro[benzo[c]fluorene-7,9'-xanthen]-9-yl)-1,3,2-dioxaborolane used in Synthesis Example 4 and N-([1,1'-biphenyl]-4-yl)-N-(4-chlorophenyl)-[1,1'-biphenyl]-2-amine was used instead of N-([1,1'-biphenyl]-4-yl)-N-(4-chlorophenyl)-9,9-dimethyl-9H-fluoren-2-amine, and thus 8.2 g (yield 70%) of a target compound was obtained.

[LCMS]: 777

A procedure as in Synthesis Example 22 was performed, except that N-(4-(dibenzo[b,d]furan-1-yl)phenyl)-[1,1'-biphenyl]-4-amine was used instead of N-phenylnaphthalen-1-amine used in Synthesis Example 22, and thus 5.0 g (yield 49%) of a target compound was obtained.

[LCMS]: 791

[Synthesis Example 27] Synthesis of Compound 122

[Synthesis Example 28] Synthesis of Compound 130

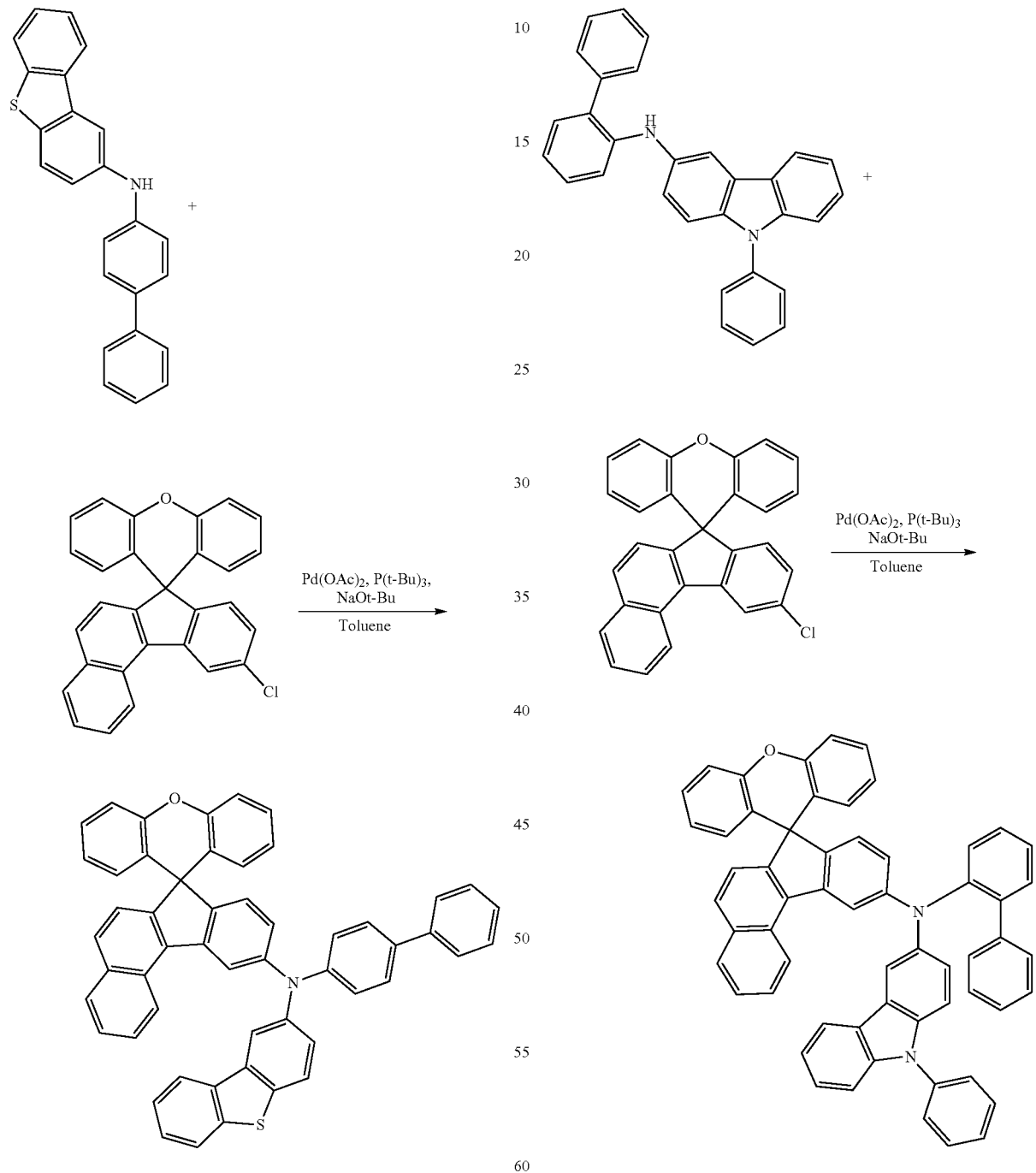

A procedure as in Synthesis Example 22 was performed, except that N-([1,1'-biphenyl]-4-yl)dibenzo[b,d]thiophen-2-amine was used instead of N-phenylnaphthalen-1-amine used in Synthesis Example 22, and thus 10.5 g (yield 55%) of a target compound was obtained.

[LCMS]: 731

A procedure as in Synthesis Example 22 was performed, except that N-([1,1'-biphenyl]-2-yl)-9-phenyl-9H-carbazol-3-amine was used instead of N-phenylnaphthalen-1-amine used in Synthesis Example 22, and thus 9.3 g (yield 59%) of a target compound was obtained.

[LCMS]: 790

[Synthesis Example 29] Synthesis of Compound 139

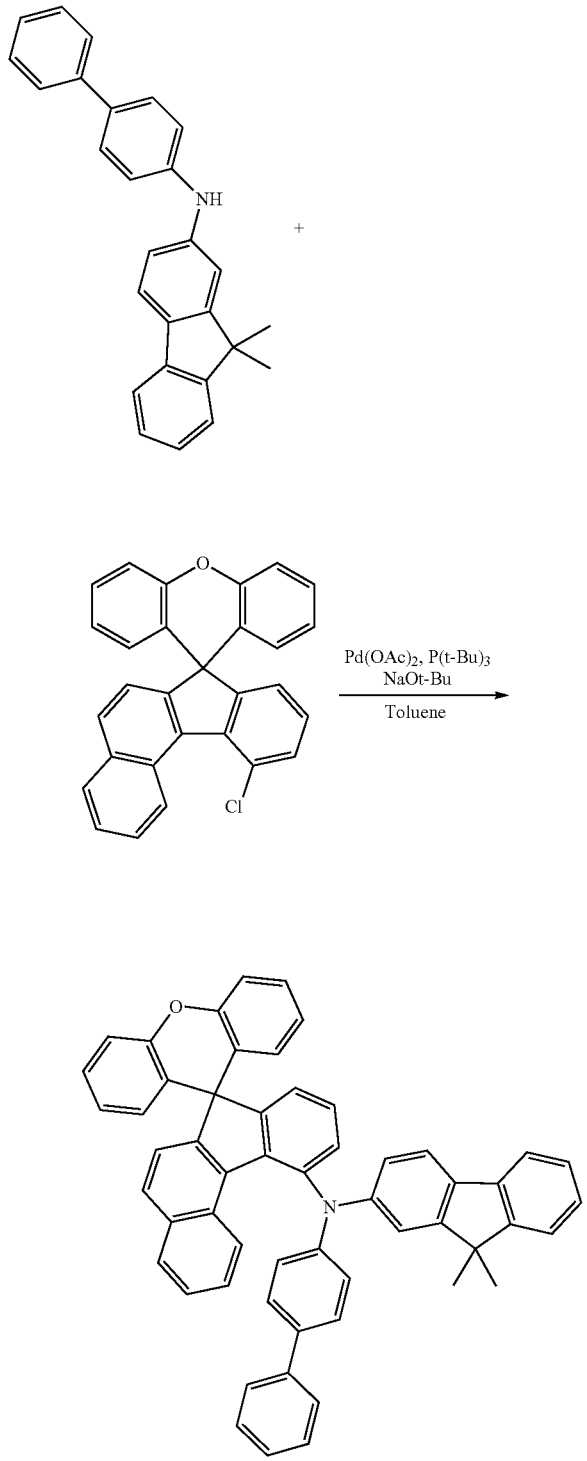 [SMILES: CC1(C)c2ccccc2-c2ccc(Nc3ccc(-c4ccccc4)cc3)cc21 ; "+" ; Clc1cccc2c1-c1c(ccc3ccccc13)C21c2ccccc2Oc2ccccc21 ; CC1(C)c2ccccc2-c2ccc(N(c3ccc(-c4ccccc4)cc3)c3cccc4c3-c3c(ccc5ccccc35)C43c4ccccc4Oc4ccccc43)cc21]

A procedure as in Synthesis Example 22 was performed, except that 11-chlorospiro[benzo[c]fluorene-7,9'-xanthene] of Preparation Example 5 was used instead of 10-chlorospiro[benzo[c]fluorene-7,9'-xanthene] used in Synthesis Example 22 and N-([1,1'-biphenyl]-4-yl)-9,9-dimethyl-9H-fluoren-2-amine was used instead of N-phenylnaphthalen-1-amine, and thus 4.5 g (yield 52%) of a target compound was obtained.

[LCMS]: 741

[Synthesis Example 30] Synthesis of Compound 153

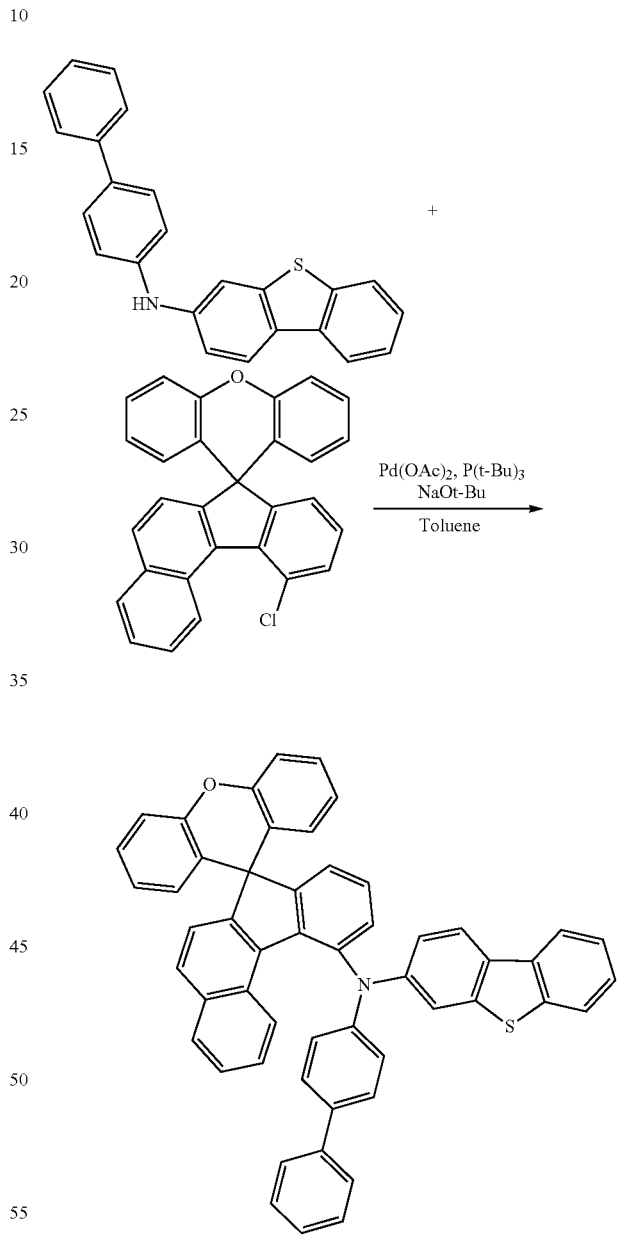

A procedure as in Synthesis Example 22 was performed, except that 11-chlorospiro[benzo[c]fluorene-7,9'-xanthene] of Preparation Example 5 was used instead of 10-chlorospiro[benzo[c]fluorene-7,9'-xanthene] used in Synthesis Example 22 and N-([1,1'-biphenyl]-4-yl)dibenzo[b,d]thiophen-3-amine was used instead of N-phenylnaphthalen-1-amine, and thus 6.6 g (yield 50%) of a target compound was obtained.

[LCMS]: 731

[Synthesis Example 31] Synthesis of Compound 161

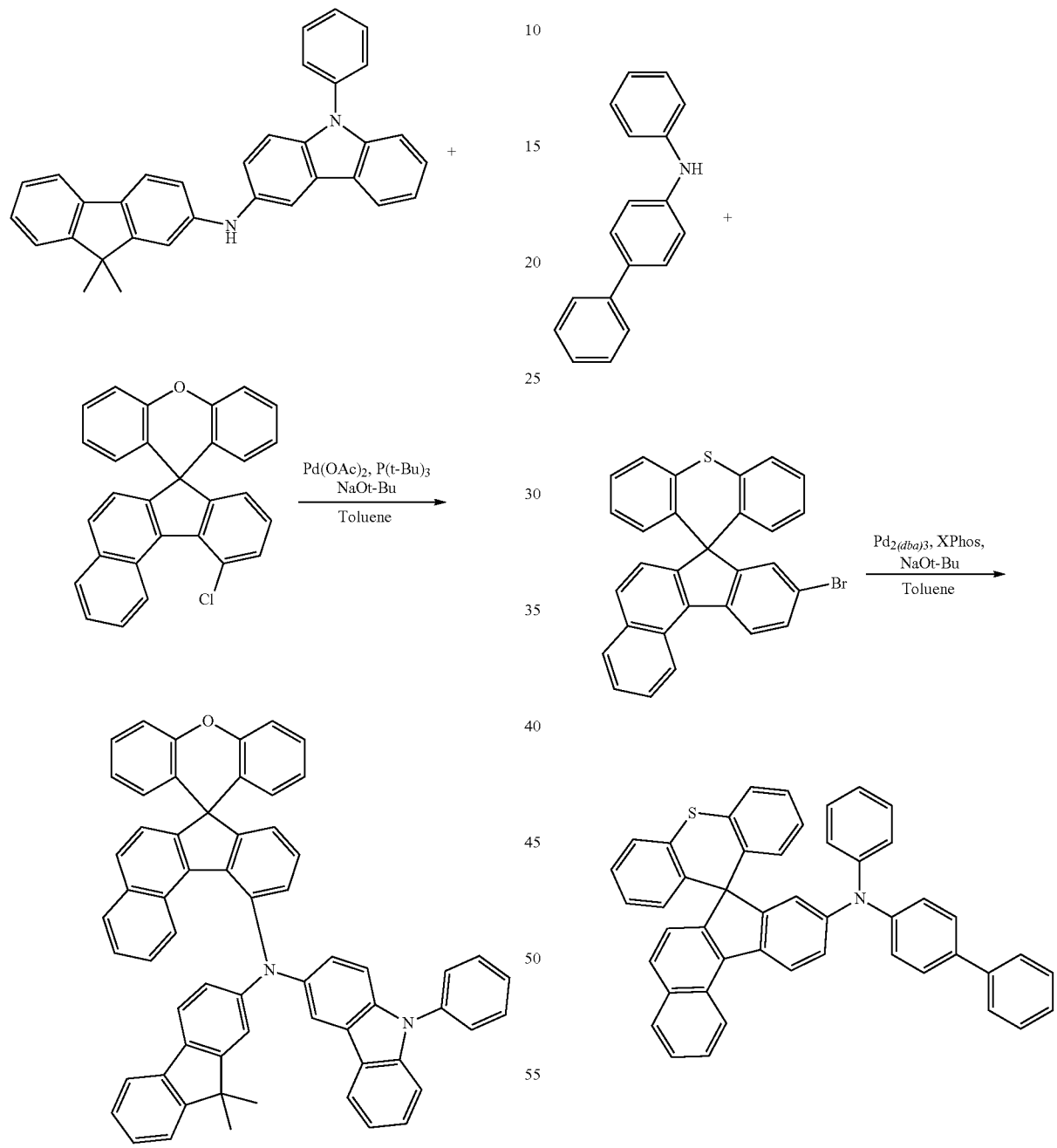

A procedure as in Synthesis Example 22 was performed, except that 11-chlorospiro[benzo[c]fluorene-7,9'-xanthene] of Preparation Example 5 was used instead of 10-chlorospiro[benzo[c]fluorene-7,9'-xanthene] used in Synthesis Example 22 and N-(9,9-dimethyl-9H-fluoren-2-yl)-9-phenyl-9H-carbazol-3-amine was used instead of N-phenylnaphthalen-1-amine, and thus 9.0 g (yield 61%) of a target compound was obtained.

[LCMS]: 831

[Synthesis Example 32] Synthesis of Compound 166

A procedure as in Synthesis Example 1 was performed, except that 9-bromospiro[benzo[c]fluorene-7,9'-thioxanthene] of Preparation Example 6 was used instead of 9-bromospiro[benzo[c]fluorene-7,9'-xanthene] used in Synthesis Example 1 and N-phenyl-[1,1'-biphenyl]-4-amine was used instead of di([1,1'-biphenyl]-4-yl)amine, and thus 8.8 g (yield 58%) of a target compound was obtained.

[LCMS]: 641

[Synthesis Example 33] Synthesis of Compound 171

[Synthesis Example 34] Synthesis of Compound 178

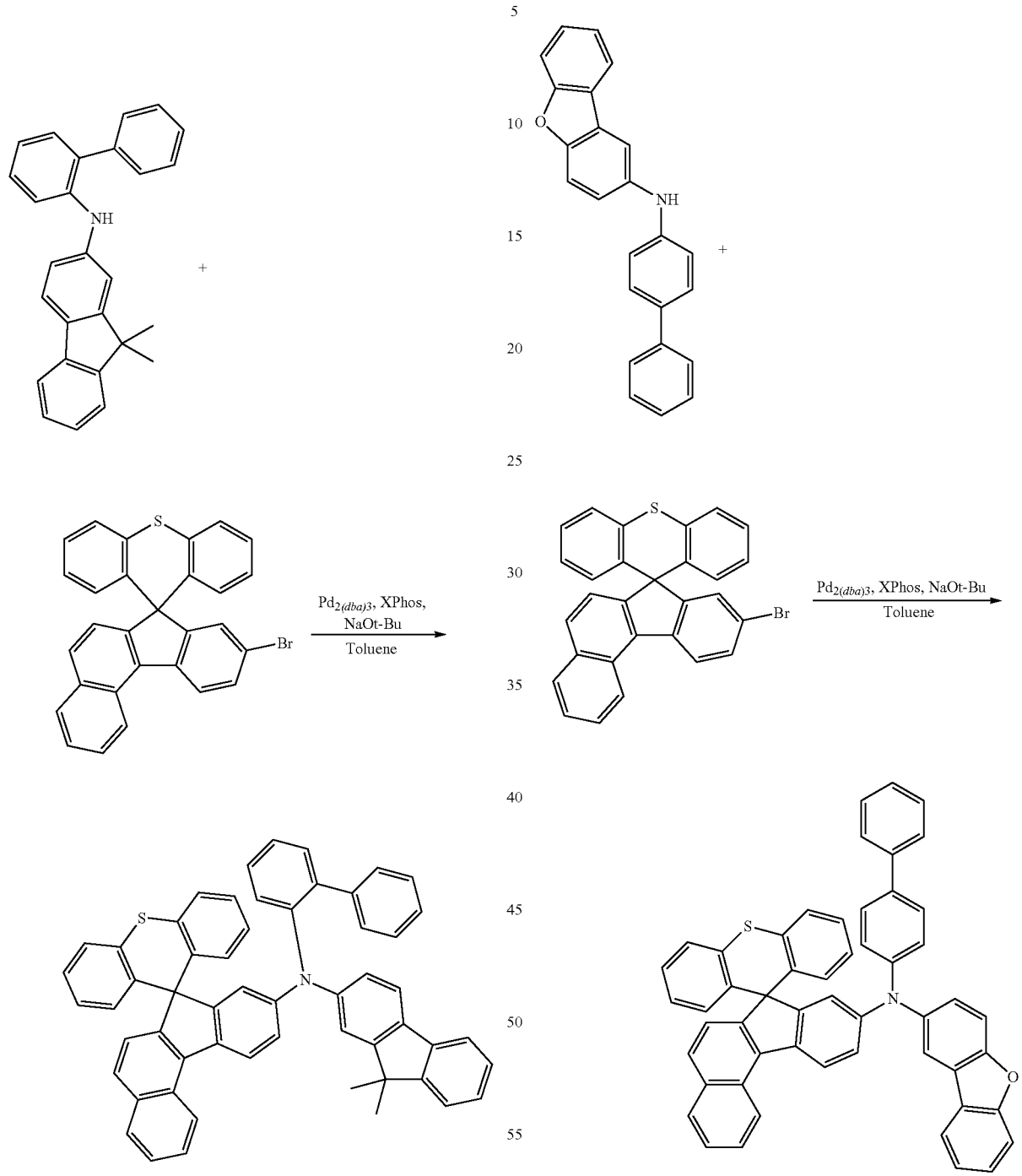

A procedure as in Synthesis Example 1 was performed, except that 9-bromospiro[benzo[c]fluorene-7,9'-thioxanthene] of Preparation Example 6 was used instead of 9-bromospiro[benzo[c]fluorene-7,9'-xanthene] used in Synthesis Example 1 and N-([1,1'-biphenyl]-2-yl)-9,9-dimethyl-9H-fluoren-2-amine was used instead of di([1,1'-biphenyl]-4-yl)amine, and thus 7.2 g (yield 73%) of a target compound was obtained.

[LCMS]: 758

A procedure as in Synthesis Example 1 was performed, except that 9-bromospiro[benzo[c]fluorene-7,9'-thioxanthene] of Preparation Example 6 was used instead of 9-bromospiro[benzo[c]fluorene-7,9'-xanthene] used in Synthesis Example 1 and N-([1,1'-biphenyl]-4-yl)dibenzo[b,d]furan-2-amine was used instead of di([1,1'-biphenyl]-4-yl)amine, and thus 5.5 g (yield 67%) of a target compound was obtained.

[LCMS]: 731

141
[Synthesis Example 35] Synthesis of Compound 187

142
[Synthesis Example 36] Synthesis of Compound 195

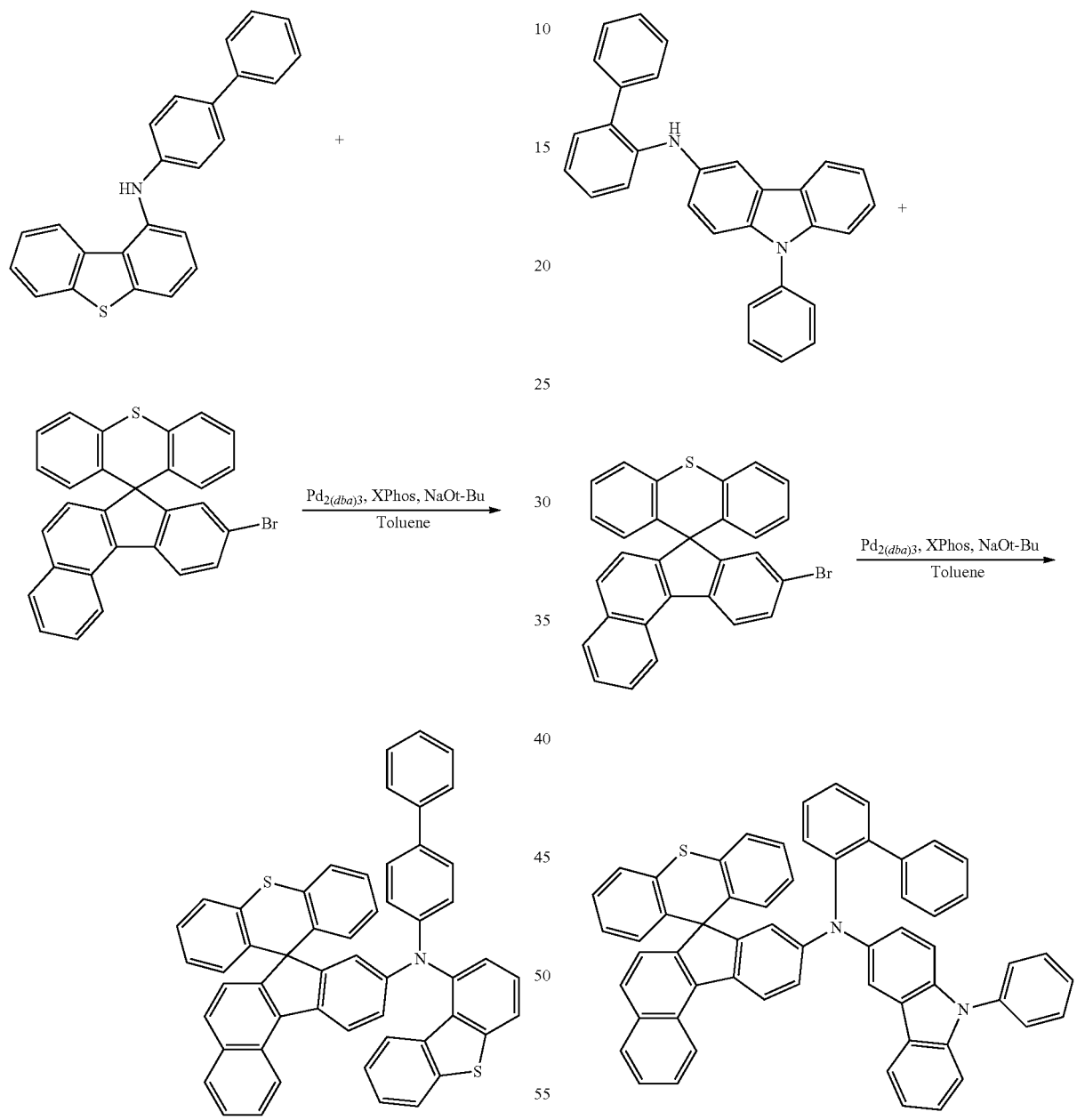

A procedure as in Synthesis Example 1 was performed, except that 9-bromospiro[benzo[c]fluorene-7,9'-thioxanthene] of Preparation Example 6 was used instead of 9-bromospiro[benzo[c]fluorene-7,9'-xanthene] used in Synthesis Example 1 and N-([1,1'-biphenyl]-4-yl)dibenzo[b,d]thiophen-1-amine was used instead of di([1,1'-biphenyl]-4-yl)amine, and thus 3.9 g (yield 60%) of a target compound was obtained.

[LCMS]: 747

A procedure as in Synthesis Example 1 was performed, except that 9-bromospiro[benzo[c]fluorene-7,9'-thioxanthene] of Preparation Example 6 was used instead of 9-bromospiro[benzo[c]fluorene-7,9'-xanthene] used in Synthesis Example 1 and N-([1,1'-biphenyl]-2-yl)-9-phenyl-9H-carbazol-3-amine was used instead of di([1,1'-biphenyl]-4-yl)amine, and thus 5.8 g (yield 49%) of a target compound was obtained.

[LCMS]: 807

[Synthesis Example 37] Synthesis of Compound 199

[Synthesis Example 38] Synthesis of Compound 203

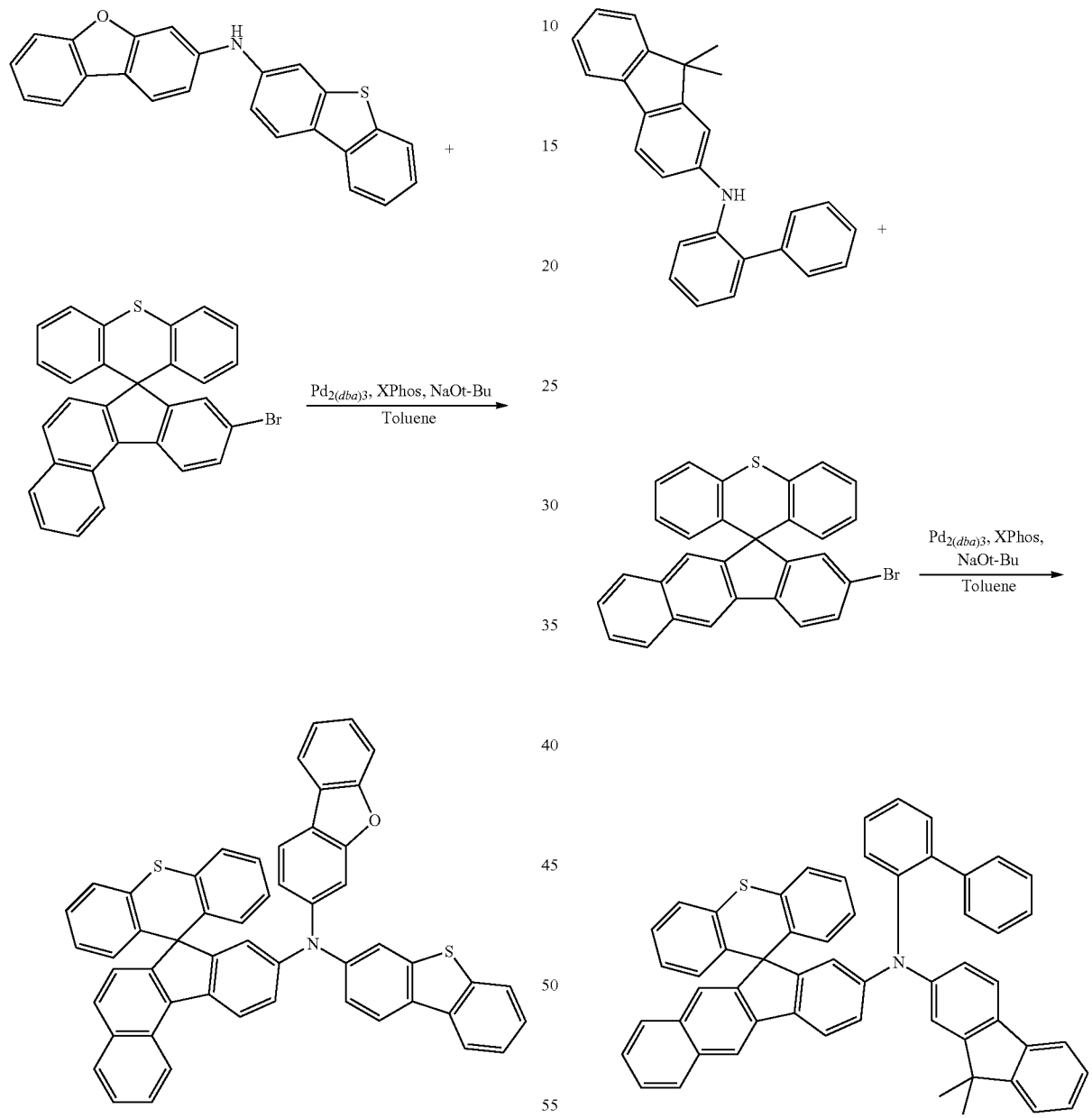

A procedure as in Synthesis Example 1 was performed, except that 9-bromospiro[benzo[c]fluorene-7,9'-thioxanthene] of Preparation Example 6 was used instead of 9-bromospiro[benzo[c]fluorene-7,9'-xanthene] used in Synthesis Example 1 and N-(dibenzo[b,d]thiophen-3-yl)dibenzo[b,d]furan-3-amine was used instead of di([1,1'-biphenyl]-4-yl)amine, and thus 6.1 g (yield 55%) of a target compound was obtained.

[LCMS]: 761

A procedure as in Synthesis Example 1 was performed, except that 2-bromospiro[benzo[b]fluorene-11,9'-thioxanthene] of Preparation Example 7 was used instead of 9-bromospiro[benzo[c]fluorene-7,9'-xanthene] used in Synthesis Example 1 and N-([1,1'-biphenyl]-2-yl)-9,9-dimethyl-9H-fluoren-2-amine was used instead of di([1,1'-biphenyl]-4-yl)amine, and thus 9.3 g (yield 62%) of a target compound was obtained.

[LCMS]: 758

[Synthesis Example 39] Synthesis of Compound 208

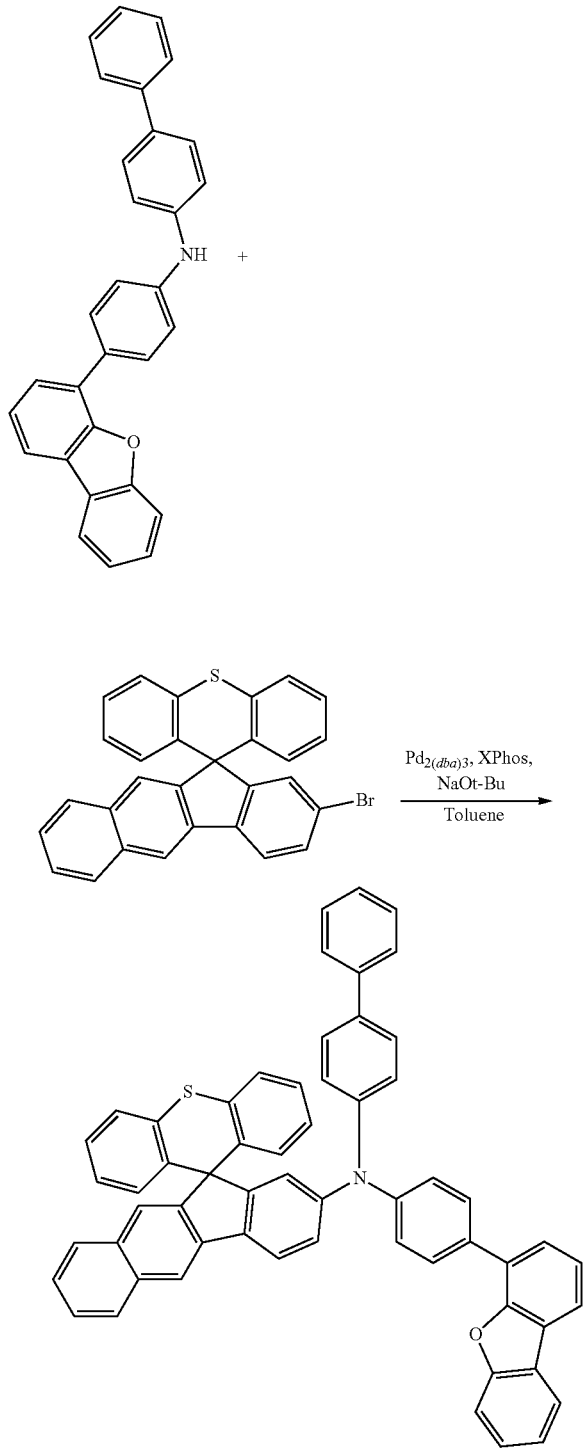

A procedure as in Synthesis Example 1 was performed, except that 2-bromospiro[benzo[b]fluorene-11,9'-thioxanthene] of Preparation Example 7 was used instead of 9-bromospiro[benzo[c]fluorene-7,9'-xanthene] used in Synthesis Example 1 and N-(4-(dibenzo[b,d]furan-4-yl)phenyl)-[1,1'-biphenyl]-4-amine was used instead of di([1,1'-biphenyl]-4-yl)amine, and thus 3.3 g (yield 66%) of a target compound was obtained.

[LCMS]: 808

[Synthesis Example 40] Synthesis of Compound 216

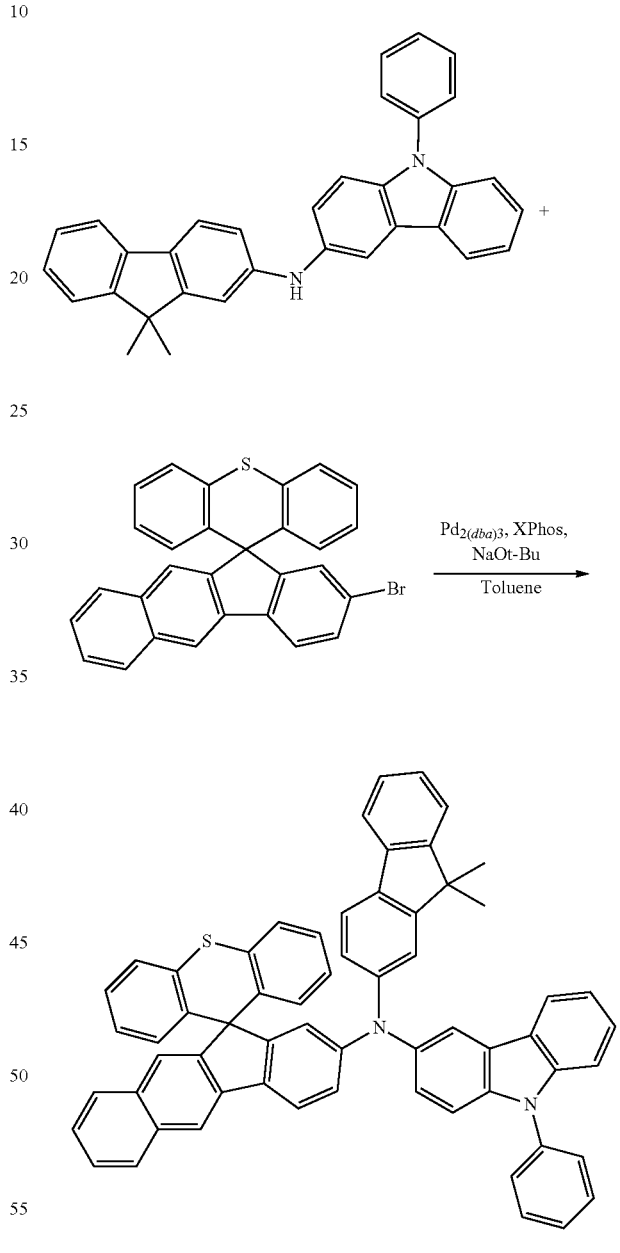

A procedure as in Synthesis Example 1 was performed, except that 2-bromospiro[benzo[b]fluorene-11,9'-thioxanthene] of Preparation Example 7 was used instead of 9-bromospiro[benzo[c]fluorene-7,9'-xanthene] used in Synthesis Example 1 and N-(9,9-dimethyl-9H-fluoren-2-yl)-9-phenyl-9H-carbazol-3-amine was used instead of di([1,1'-biphenyl]-4-yl)amine, and thus 5.5 g (yield 60%) of a target compound was obtained.

[LCMS]: 847

[Synthesis Example 41] Synthesis of Compound 218

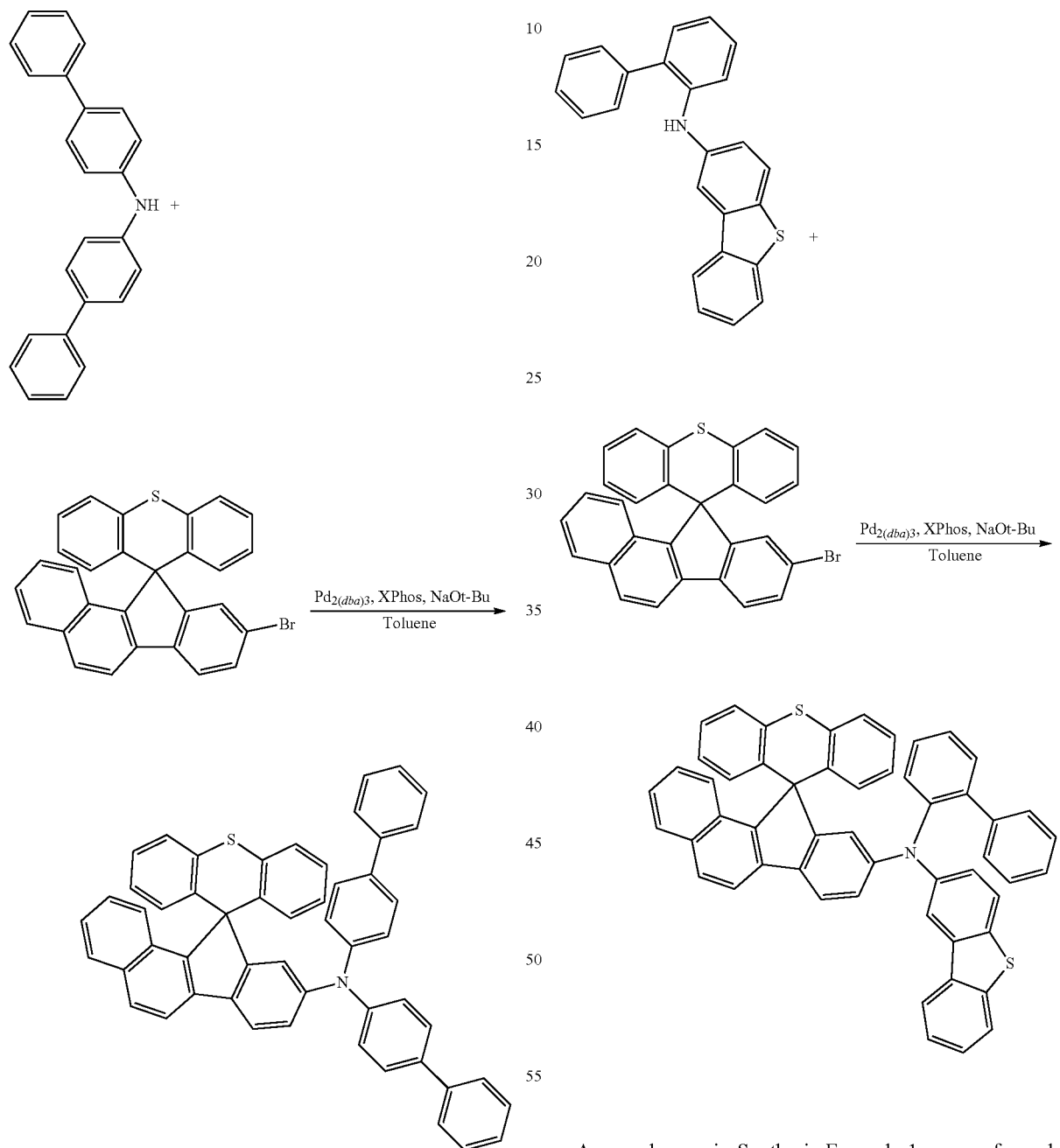

A procedure as in Synthesis Example 1 was performed, except that 9-bromospiro[benzo[a]fluorene-11,9'-thioxanthene] of Preparation Example 8 was used instead of 9-bromospiro[benzo[c]fluorene-7,9'-xanthene] used in Synthesis Example 1, and thus 7.2 g (yield 49%) of a target compound was obtained.

[LCMS]: 717

[Synthesis Example 42] Synthesis of Compound 227

A procedure as in Synthesis Example 1 was performed, except that 9-bromospiro[benzo[a]fluorene-11,9'-thioxanthene] of Preparation Example 8 was used instead of 9-bromospiro[benzo[c]fluorene-7,9'-xanthene] used in Synthesis Example 1 and N-([1,1'-biphenyl]-2-yl)dibenzo[b,d]thiophen-2-amine was used instead of di([1,1'-biphenyl]-4-yl)amine, and thus 6.1 g (yield 65%) of a target compound was obtained.

[LCMS]: 747

[Synthesis Example 43] Synthesis of Compound 229

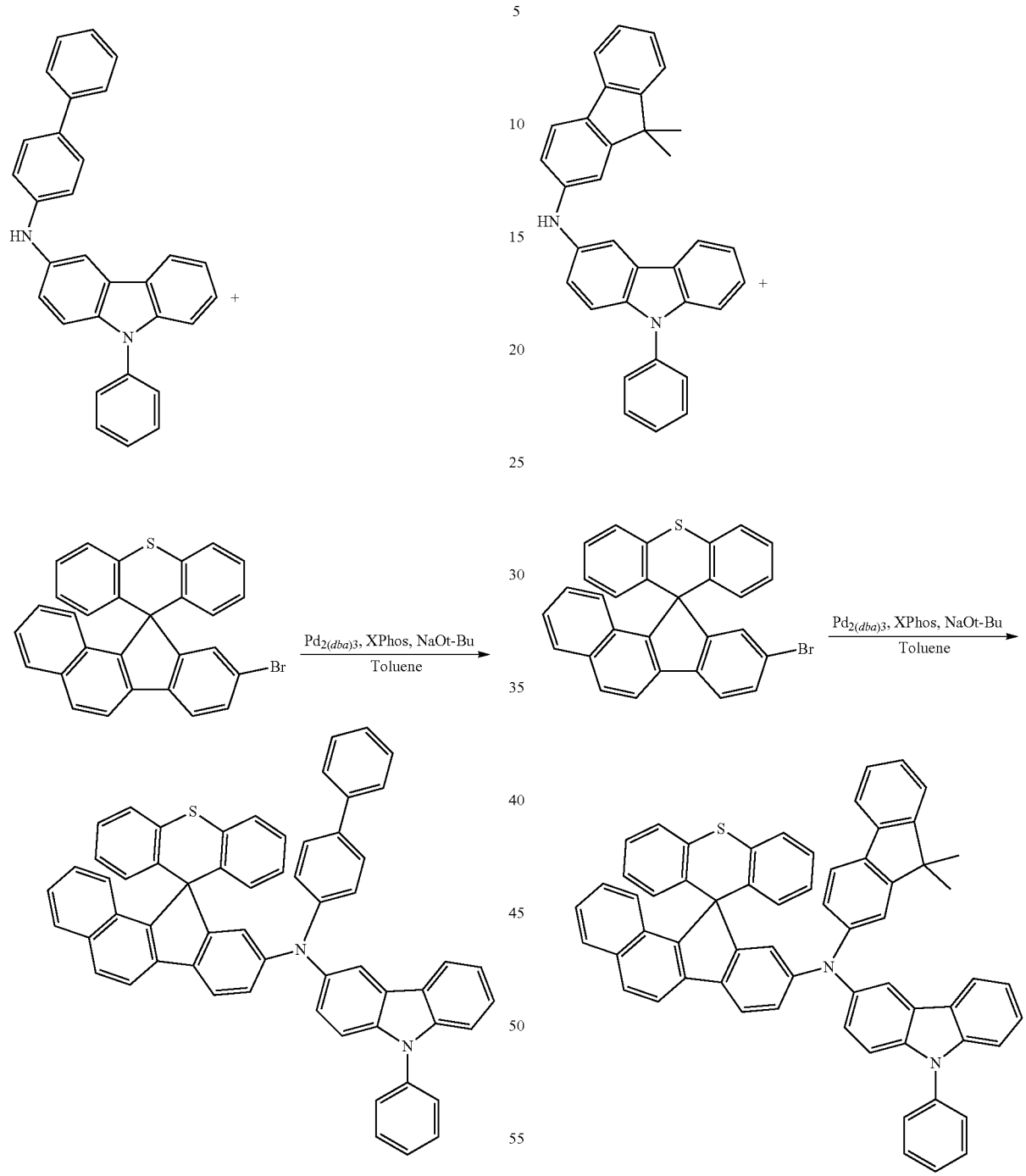

A procedure as in Synthesis Example 1 was performed, except that 9-bromospiro[benzo[a]fluorene-11,9'-thioxanthene] of Preparation Example 8 was used instead of 9-bromospiro[benzo[c]fluorene-7,9'-xanthene] used in Synthesis Example 1 and N-([1,1'-biphenyl]-4-yl)-9-phenyl-9H-carbazol-3-amine was used instead of di([1,1'-biphenyl]-4-yl)amine, and thus 12.1 g (yield 72%) of a target compound was obtained.

[LCMS]: 807

[Synthesis Example 44] Synthesis of Compound 231

A procedure as in Synthesis Example 1 was performed, except that 9-bromospiro[benzo[a]fluorene-11,9'-thioxanthene] of Preparation Example 8 was used instead of 9-bromospiro[benzo[c]fluorene-7,9'-xanthene] used in Synthesis Example 1 and N-(9,9-dimethyl-9H-fluoren-2-yl)-9-phenyl-9H-carbazol-3-amine was used instead of di([1,1'-biphenyl]-4-yl)amine, and thus 9.6 g (yield 66%) of a target compound was obtained.

[LCMS]: 847

[Synthesis Example 45] Synthesis of Compound 237

[Synthesis Example 46] Synthesis of Compound 241

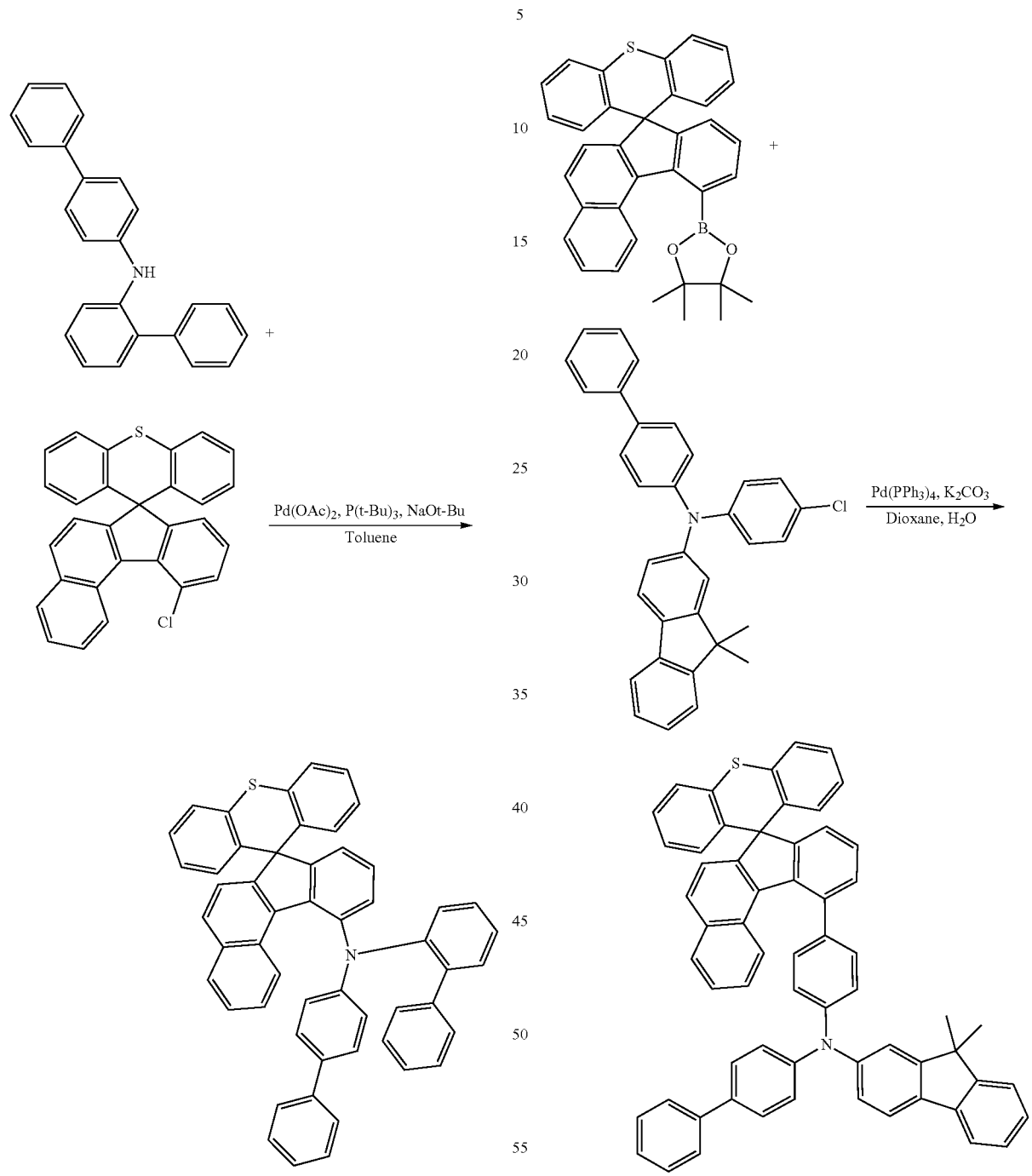

A procedure as in Synthesis Example 1 was performed, except that 11-chlorospiro[benzo[c]fluorene-7,9'-thioxanthene] of Preparation Example 9 was used instead of 9-bromospiro[benzo[c]fluorene-7,9'-xanthene] used in Synthesis Example 1 and N-([1,1'-biphenyl]-4-yl)-[1,1'-biphenyl]-2-amine was used instead of di([1,1'-biphenyl]-4-yl)amine, and thus 6.0 g (yield 55%) of a target compound was obtained.

[LCMS]: 717

A procedure as in Synthesis Example 4 was performed, except that 4,4,5,5-tetramethyl-2-(spiro[benzo[c]fluorene-7,9'-thioxanthen]-11-yl)-1,3,2-dioxaborolane of Preparation Example 13 was used instead of 4,4,5,5-tetramethyl-2-(spiro[benzo[c]fluorene-7,9'-xanthen]-9-yl)-1,3,2-dioxaborolane used in Synthesis Example 4, and thus 8.2 g (yield 49%) of a target compound was obtained.

[LCMS]: 834

[Synthesis Example 47] Synthesis of Compound 244

[Synthesis Example 48] Synthesis of Compound 254

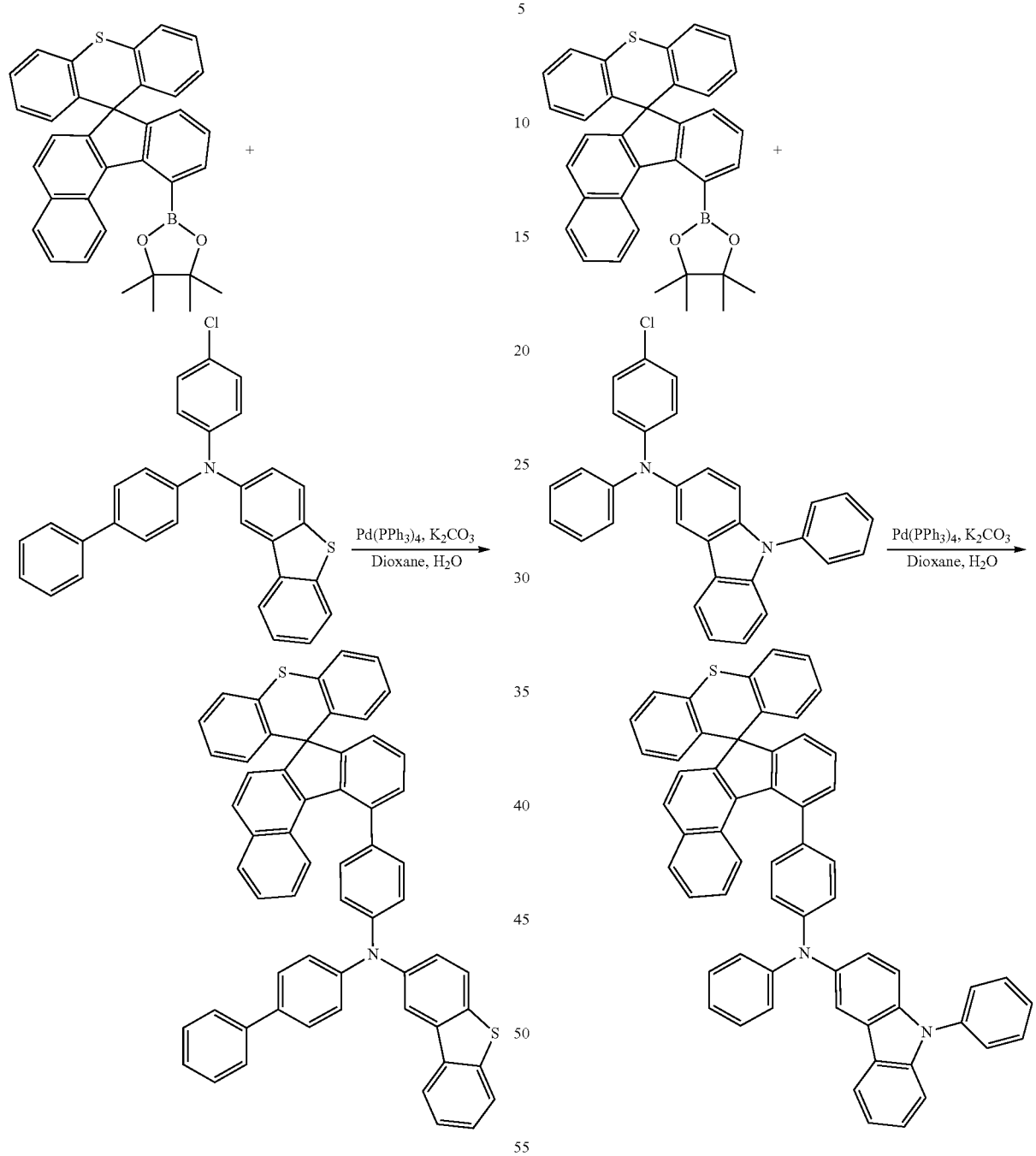

A procedure as in Synthesis Example 4 was performed, except that 4,4,5,5-tetramethyl-2-(spiro[benzo[c]fluorene-7, 9'-thioxanthen]-11-yl)-1,3,2-dioxaborolane of Preparation Example 13 was used instead of 4,4,5,5-tetramethyl-2-(spiro[benzo[c]fluorene-7,9'-xanthen]-9-yl)-1,3,2-dioxaborolane used in Synthesis Example 4 and N-([1,1'-biphenyl]-4-yl)-N-(4-chlorophenyl)dibenzo[b,d]thiophen-2-amine was used instead of N-([1,1'-biphenyl]-4-yl)-N-(4-chlorophenyl)-9,9-dimethyl-9H-fluoren-2-amine, and thus 4.4 g (yield 53%) of a target compound was obtained.

[LCMS]: 824

A procedure as in Synthesis Example 4 was performed, except that 4,4,5,5-tetramethyl-2-(spiro[benzo[c]fluorene-7, 9'-thioxanthen]-11-yl)-1,3,2-dioxaborolane of Preparation Example 13 was used instead of 4,4,5,5-tetramethyl-2-(spiro[benzo[c]fluorene-7,9'-xanthen]-9-yl)-1,3,2-dioxaborolane used in Synthesis Example 4 and N-(4-chlorophenyl)-N,9-diphenyl-9H-carbazol-3-amine was used instead of N-([1, 1'-biphenyl]-4-yl)-N-(4-chlorophenyl)-9,9-dimethyl-9H-fluoren-2-amine, and thus 9.9 g (yield 63%) of a target compound was obtained.

[LCMS]: 807

[Embodiment 1] Preparing of Organic EL Device

The compound 2 synthesized in the above Synthesis Example 1 was subjected to high purity sublimation purification by a commonly known method and then a green organic EL device was prepared as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech), and cleaned for 5 minutes using UV, and then the coated glass substrate was transferred to a vacuum evaporator.

On the ITO transparent glass substrate (electrode) prepared as above, m-MTDATA (60 nm)/Compound 2 (80 nm)/DS-H522+5% DS-501 (300 nm)/BCP (10 nm)/Alq$_3$ (30 nm)/LiF (1 nm)/Al (200 nm) were laminated in the order to manufacture an organic EL device. In such a case, the DS-H522 and DS-501 as used are BG products of Doosan Electronics, and the structures of m-MTDATA, BCP, and Alq$_3$ are as follows.

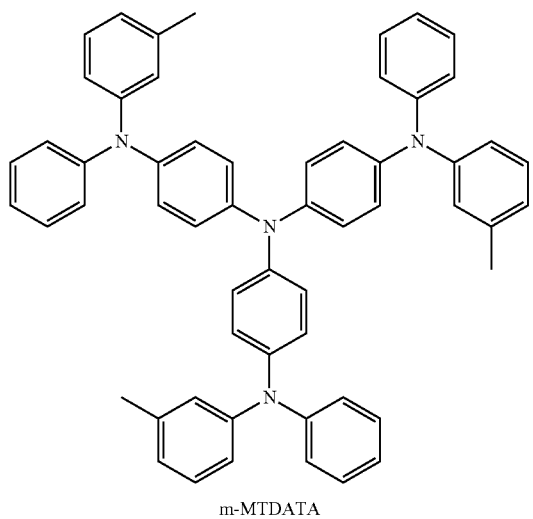

m-MTDATA

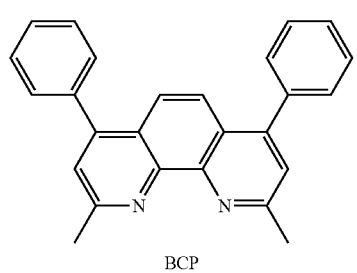

BCP

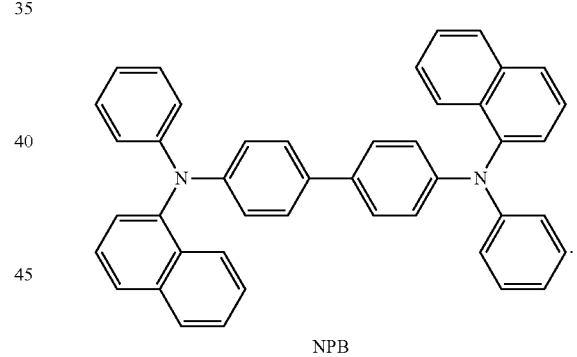

Alq$_3$

[Embodiments 2 to 44] Preparing of an Organic EL Device

Organic EL devices were prepared in the same manner as in Embodiment 1, except that the respective compounds shown in Table 1, instead of Compound 2, were used as a hole transporting material in the forming of a hole transporting layer in Embodiment 1.

[Comparative Example 1] Preparing of Organic EL Device

An organic EL device was prepared in the same manner as in Embodiment 1, except that NPB, instead of Compound 2, was used as a hole transporting material in the forming of the hole transporting layer in Embodiment 1. The structure of the NPB used in such an embodiment is as follows:

NPB

Evaluation Example 1

For each organic EL device prepared in Embodiments 1 to 44 and Comparative Example 1, a driving voltage and current efficiency at a current density of 10 mA/cm$^2$ were measured, and the results are shown in Table 1 below.

TABLE 1

| Sample | Hole transporting layer | Driving voltage (V) | Current efficiency (cd/A) |
|---|---|---|---|
| Embodiment 1 | Compound 2 | 3.6 | 24.8 |
| Embodiment 2 | Compound 4 | 3.8 | 23.5 |
| Embodiment 3 | Compound 7 | 3.8 | 23.9 |
| Embodiment 4 | Compound 11 | 3.7 | 23.8 |
| Embodiment 5 | Compound 14 | 4.0 | 22.9 |

157

TABLE 1-continued

| Sample | Hole transporting layer | Driving voltage (V) | Current efficiency (cd/A) |
|---|---|---|---|
| Embodiment 6 | Compound 19 | 3.9 | 22.4 |
| Embodiment 7 | Compound 25 | 4.0 | 21.9 |
| Embodiment 8 | Compound 34 | 3.5 | 24.0 |
| Embodiment 9 | Compound 37 | 4.2 | 24.8 |
| Embodiment 10 | Compound 42 | 3.9 | 25.1 |
| Embodiment 11 | Compound 45 | 3.8 | 22.3 |
| Embodiment 12 | Compound 52 | 3.7 | 23.1 |
| Embodiment 13 | Compound 54 | 3.9 | 24.5 |
| Embodiment 14 | Compound 59 | 4.1 | 22.5 |
| Embodiment 15 | Compound 65 | 4.3 | 23.6 |
| Embodiment 16 | Compound 69 | 3.5 | 24.7 |
| Embodiment 17 | Compound 82 | 4.2 | 24.4 |
| Embodiment 18 | Compound 89 | 3.9 | 23.3 |
| Embodiment 19 | Compound 96 | 4.5 | 23.4 |
| Embodiment 20 | Compound 100 | 3.7 | 24.1 |
| Embodiment 21 | Compound 105 | 3.8 | 23.3 |
| Embodiment 22 | Compound 108 | 3.8 | 24.5 |
| Embodiment 23 | Compound 117 | 4.0 | 23.3 |
| Embodiment 24 | Compound 122 | 4.1 | 24.0 |
| Embodiment 25 | Compound 130 | 3.7 | 25.0 |
| Embodiment 26 | Compound 139 | 4.1 | 24.8 |
| Embodiment 27 | Compound 153 | 3.9 | 24.1 |
| Embodiment 28 | Compound 161 | 3.8 | 22.8 |
| Embodiment 29 | Compound 166 | 3.7 | 24.5 |
| Embodiment 30 | Compound 171 | 3.7 | 22.8 |
| Embodiment 31 | Compound 178 | 3.9 | 23.5 |
| Embodiment 32 | Compound 187 | 4.4 | 22.1 |
| Embodiment 33 | Compound 195 | 3.9 | 19.8 |
| Embodiment 34 | Compound 203 | 4.1 | 23.5 |
| Embodiment 35 | Compound 208 | 3.9 | 24.4 |
| Embodiment 36 | Compound 216 | 3.8 | 24.7 |
| Embodiment 37 | Compound 218 | 3.6 | 22.9 |
| Embodiment 38 | Compound 227 | 3.9 | 22.4 |
| Embodiment 39 | Compound 229 | 3.8 | 24.0 |
| Embodiment 40 | Compound 231 | 4.1 | 23.8 |
| Embodiment 41 | Compound 237 | 3.9 | 22.3 |
| Embodiment 42 | Compound 241 | 3.5 | 24.7 |
| Embodiment 43 | Compound 244 | 3.7 | 22.1 |
| Embodiment 44 | Compound 254 | 3.9 | 23.9 |
| Comp. example 1 | NPB | 4.8 | 20.5 |

As illustrated in Table 1 above, it was appreciated that the organic EL devices using the compound according to the present invention as a hole transporting layer (organic EL devices prepared in Embodiments 1 to 44, respectively) exhibited excellent performance in terms of the current efficiency and driving voltage, as compared with the organic EL device (organic EL device of Comparative Example 1) that includes the conventional NBP as a material for the hole transporting layer.

The invention claimed is:
1. An organic compound represented by any one of the following Chemical Formulas 3 to 5:

[Chemical Formula 3]

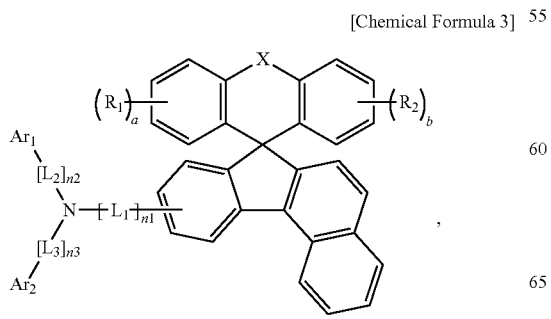

158

[Chemical Formula 4]

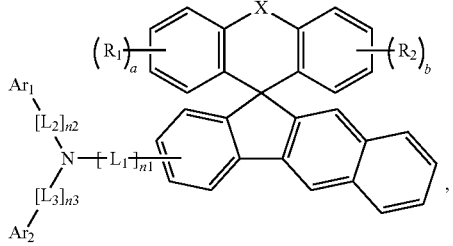

[Chemical Formula 5]

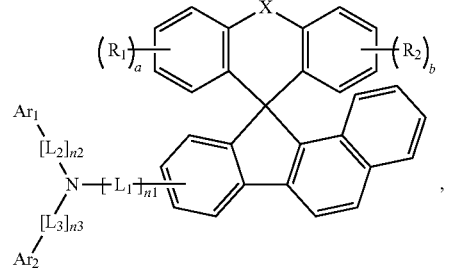

(wherein in Chemical Formulas 3 to 5,
X is O or S,
each of a and b is an integer ranging from 0 to 4,
$R_1$ and $R_2$ are the same as or different from each other, each independently being selected from the group consisting of hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group,
each of n1 to n3 is an integer ranging from 0 to 3,
$L_1$ to $L_3$ are the same as or different from each other, each independently selected from the group consisting of a single bond, a $C_6$ to $C_{18}$ arylene group and a heteroarylene group having 5 to 18 nuclear atoms,
$Ar_1$ and $Ar_2$ are the same as or different from each other, each independently being selected from the group consisting of a $C_6$ to $C_{60}$ aryl group and a heteroaryl group having 5 to 60 nuclear atoms, and
the arylene group and the heteroarylene group of $L_1$ to $L_3$, the aryl group and the heteroaryl group of $Ar_1$ and $Ar_2$, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ and $R_2$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other).

2. The organic compound of claim 1, wherein the compound represented by any one of the Chemical Formulas 3 to 5 is a compound embodied as a compound selected from a group consisting of:

(1)

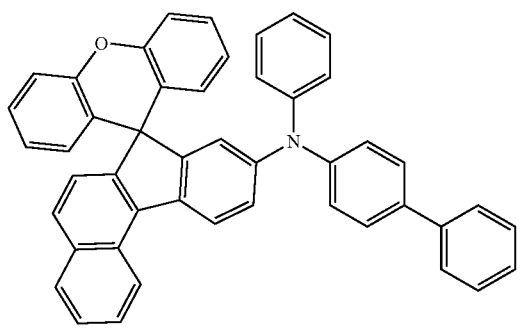

(2)

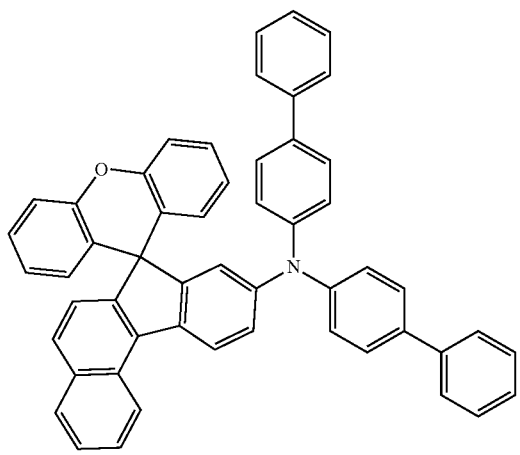

(3)

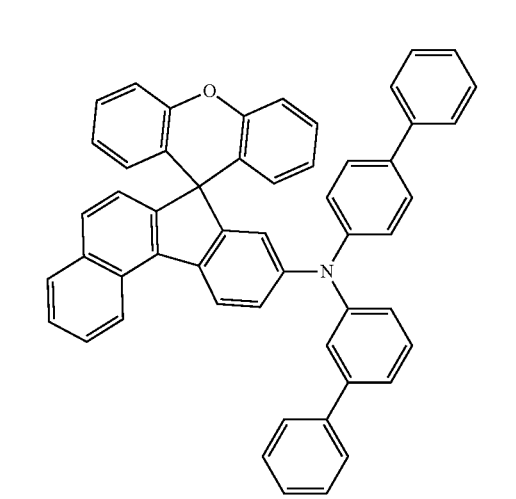

-continued (4)

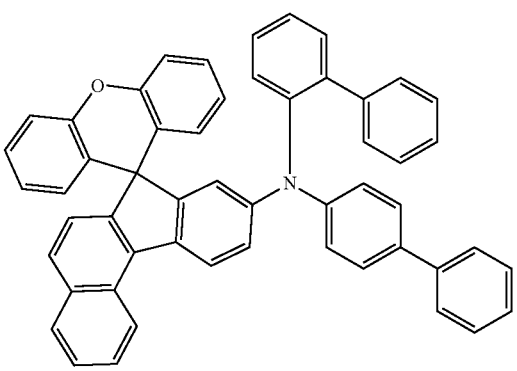

(5)

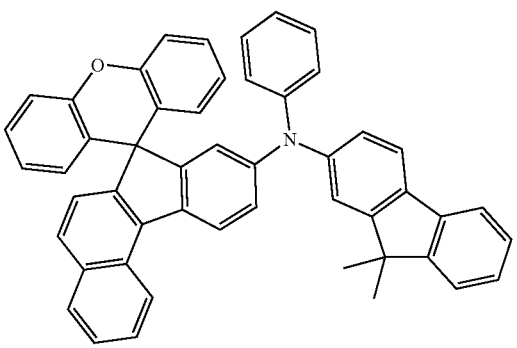

(6)

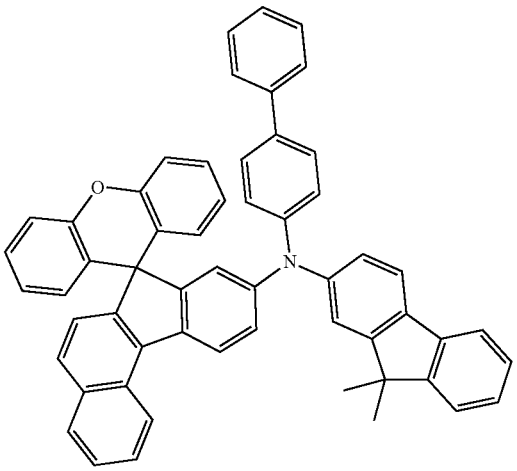

(7)

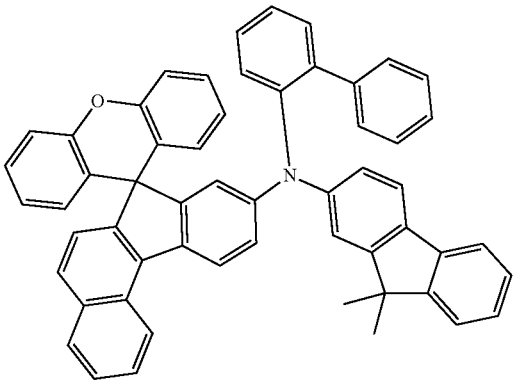

161
-continued
(8)
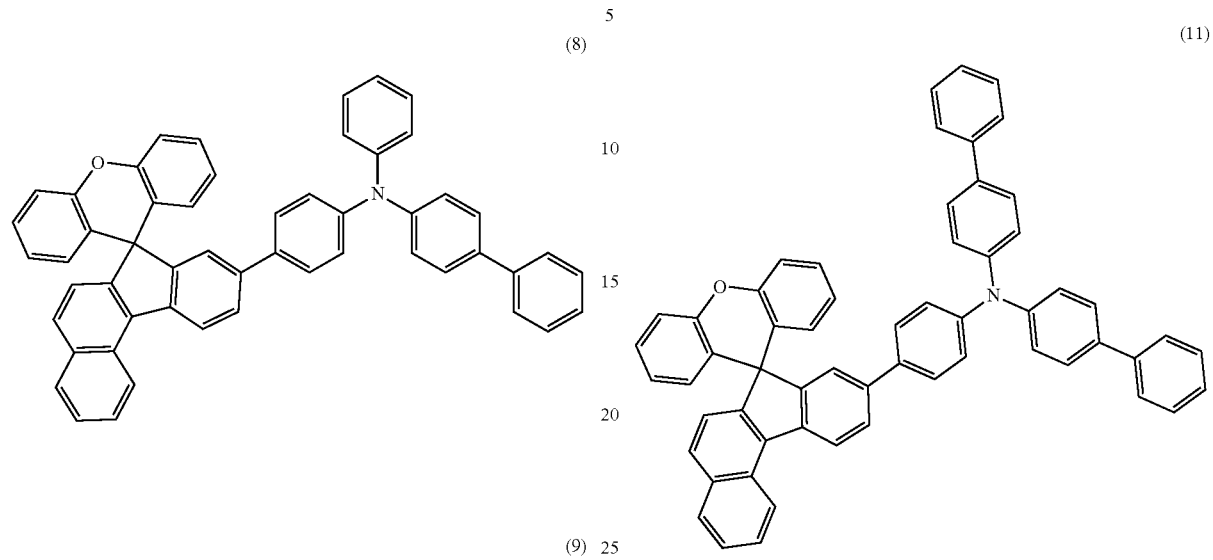
(9)
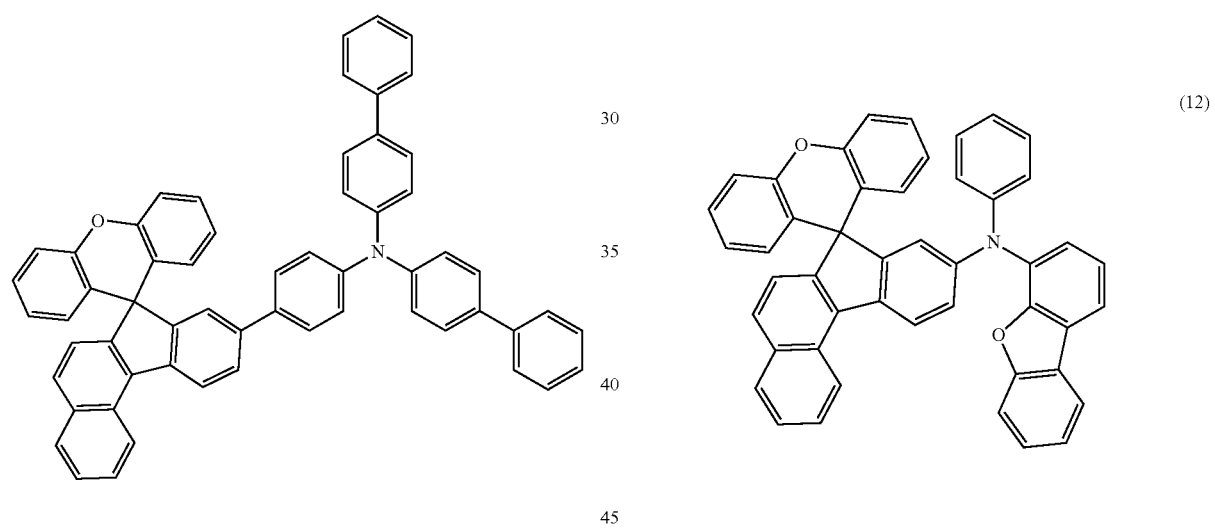
(10)
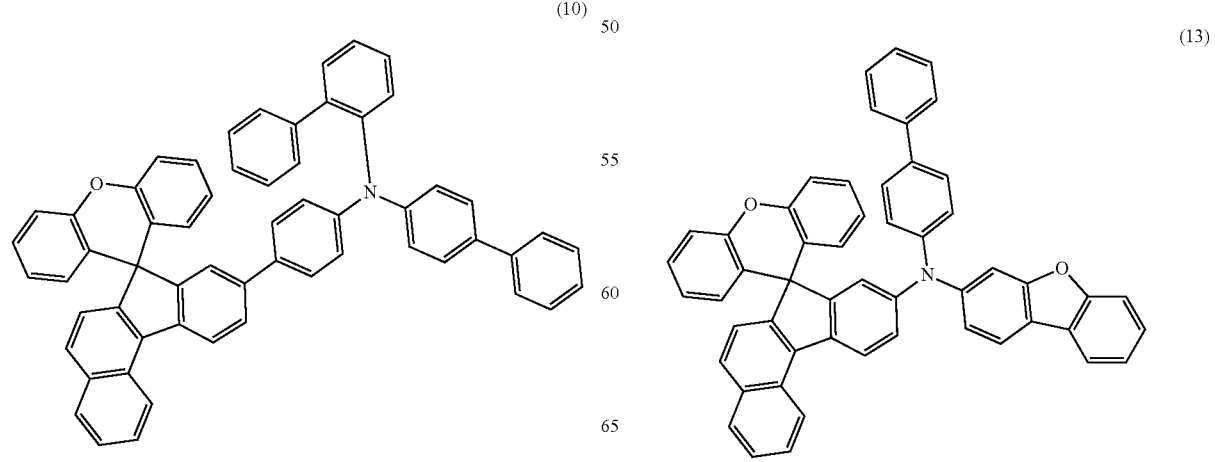
162
-continued
(11)
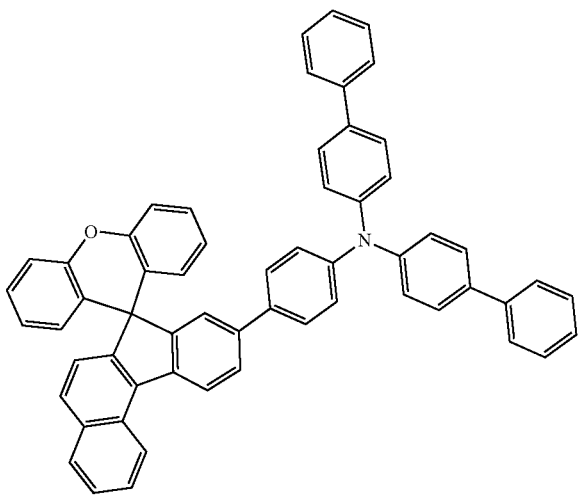
(12)
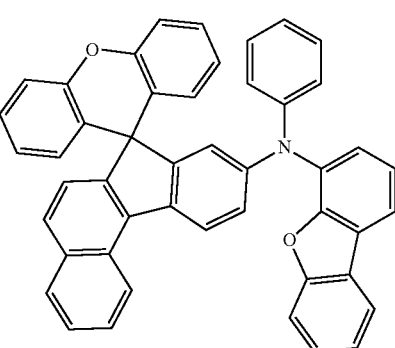
(13)
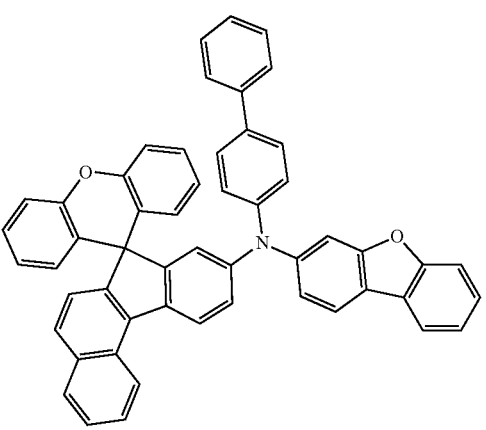

(14)
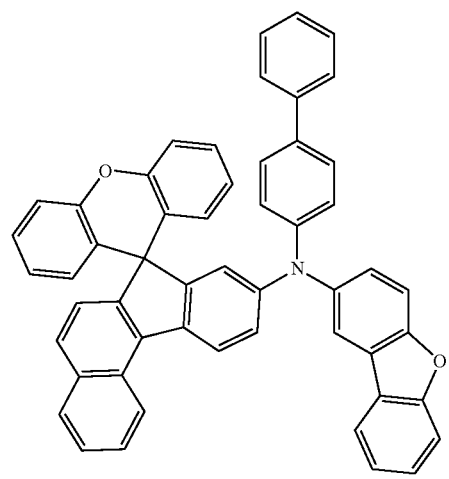
(15)
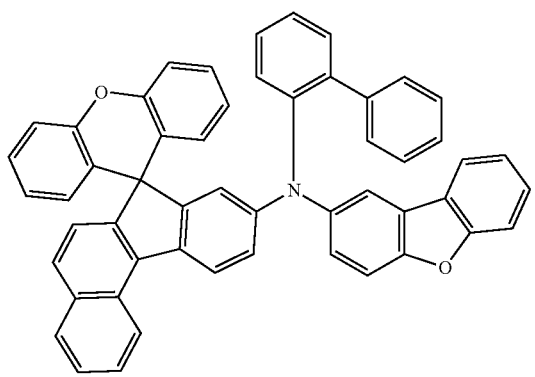
(16)
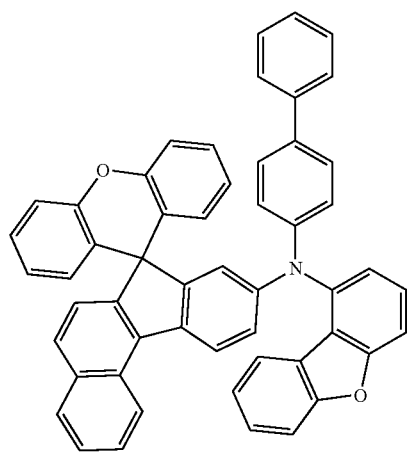
(17)
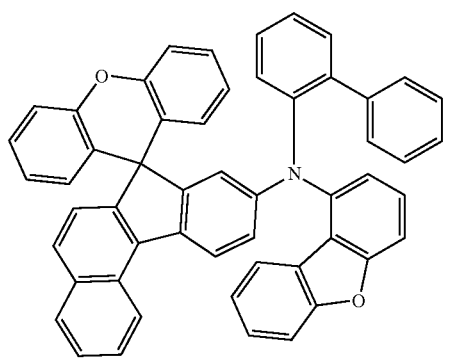
(18)
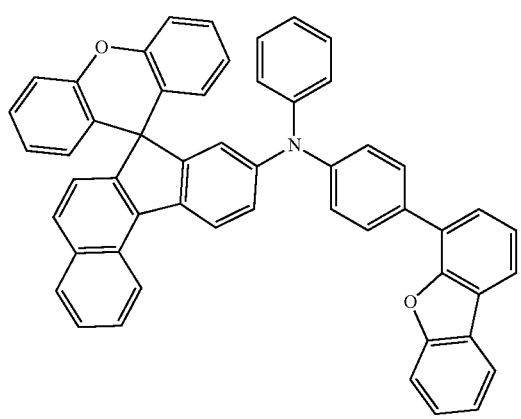
(19)
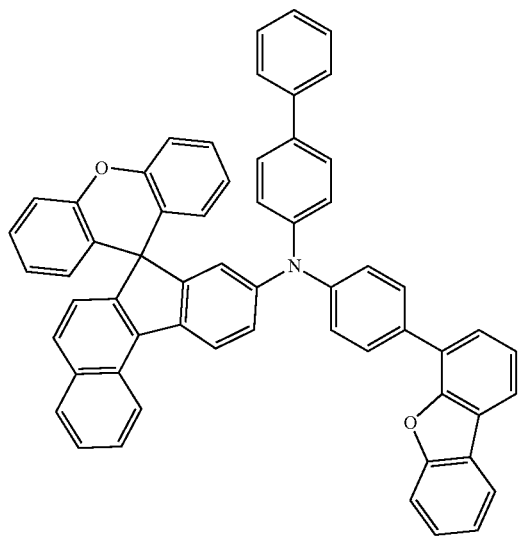

(20)
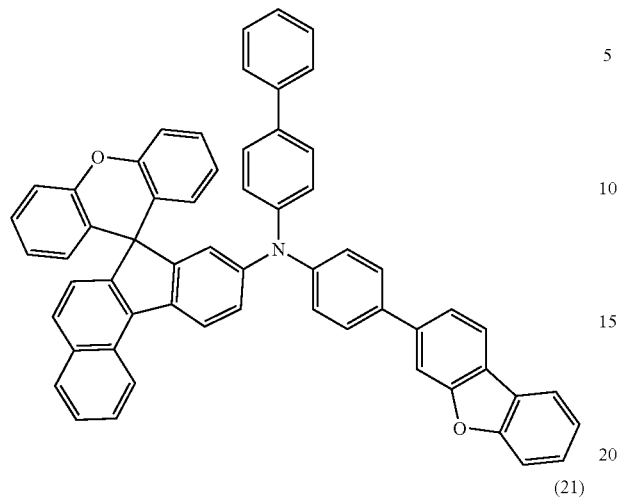
(21)
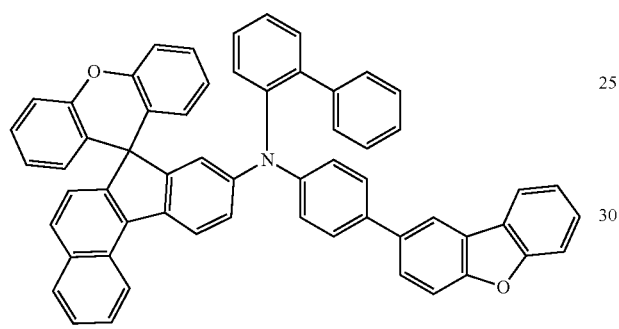
(22)
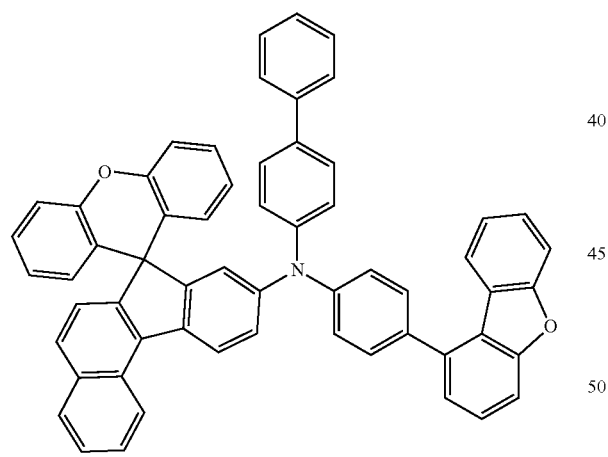
(23)
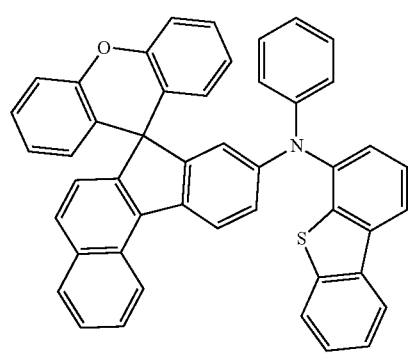
(24)
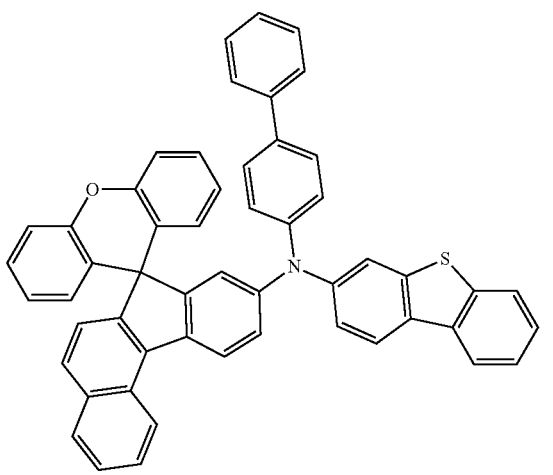
(25)
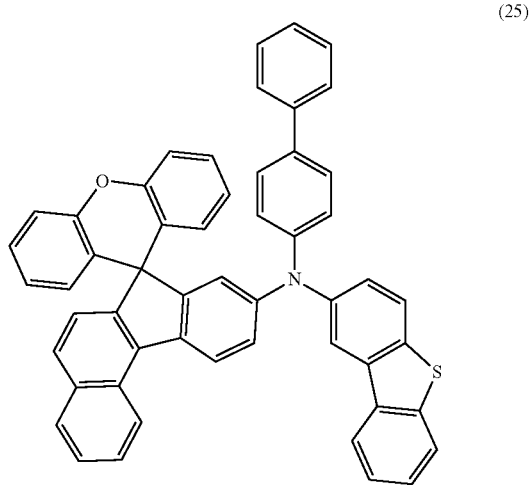
(26)
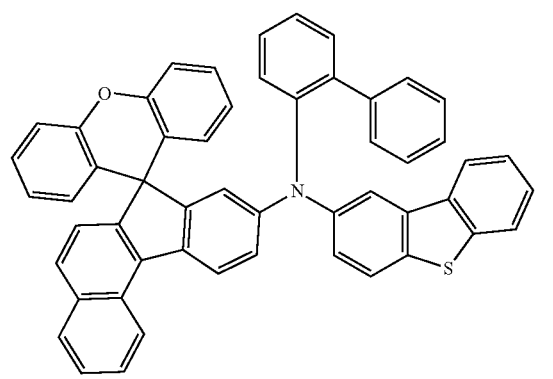

(27)
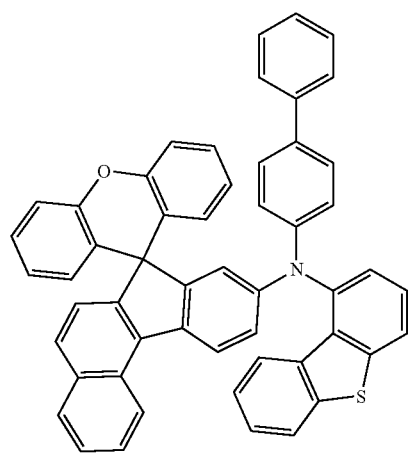
(28)
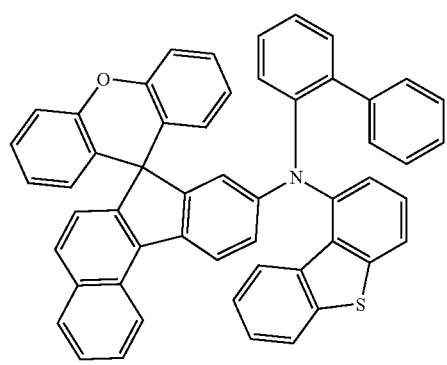
(29)
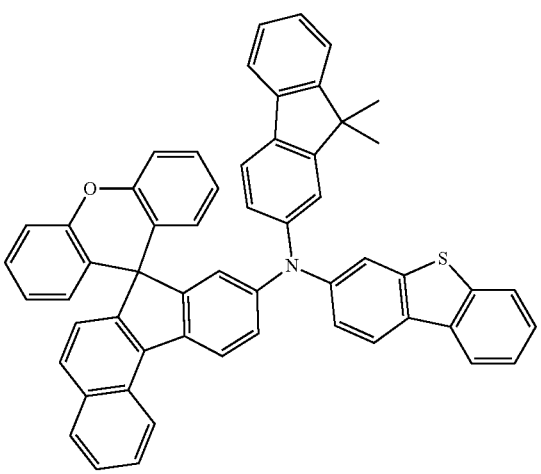
(30)
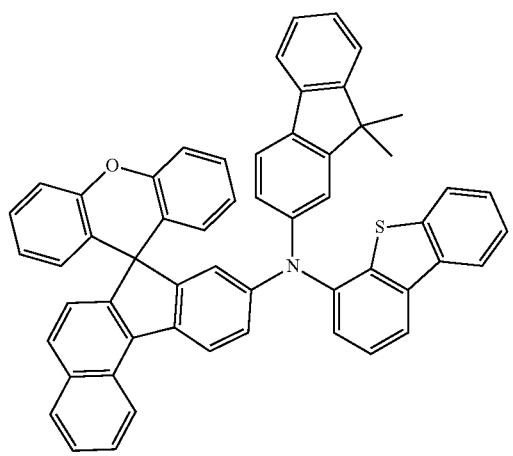
(31)
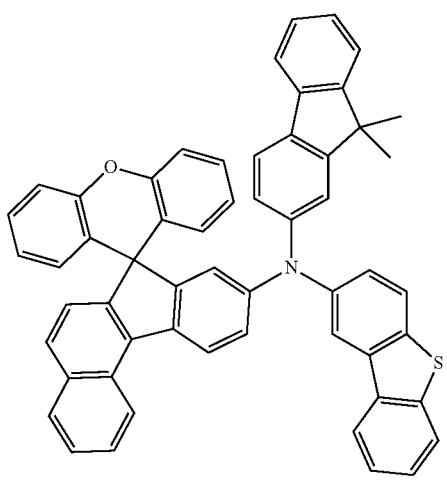
(32)
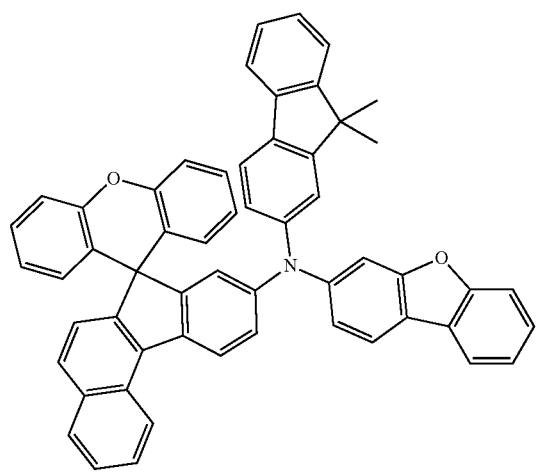

(33)
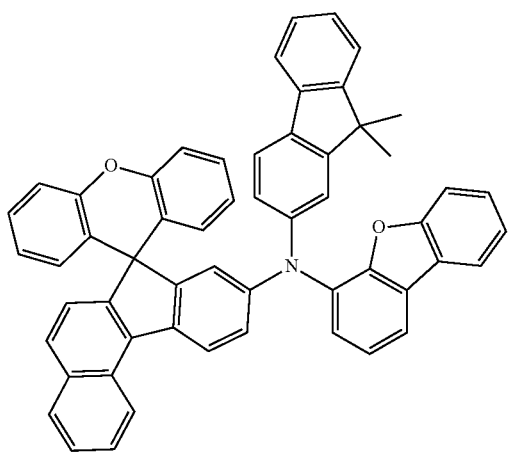
(36)
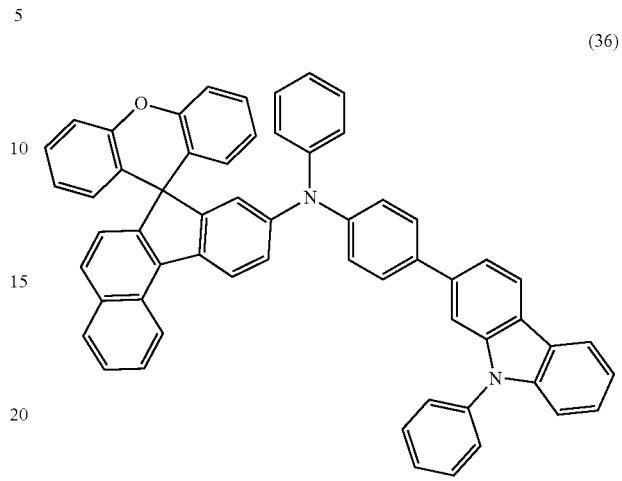
(34)
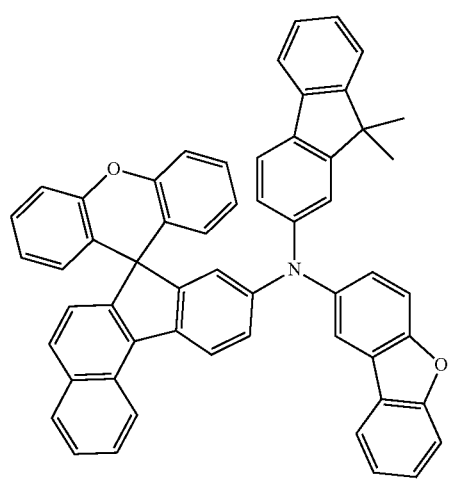
(37)
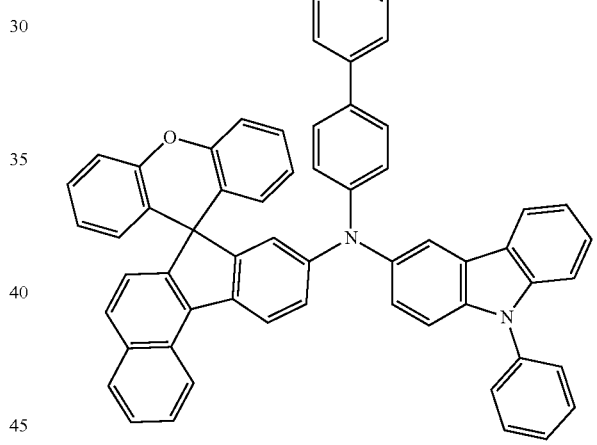
(35)
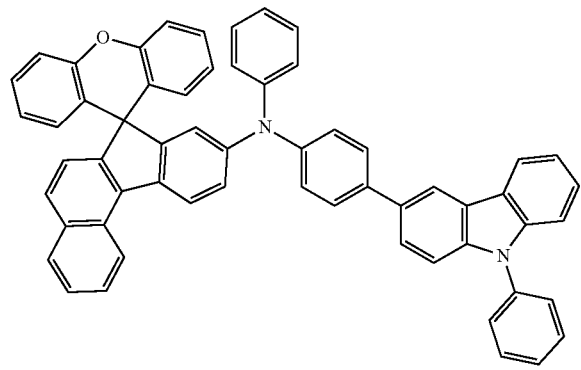
(38)
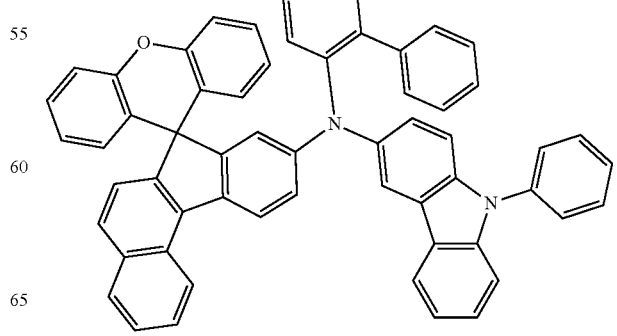

-continued
(39)
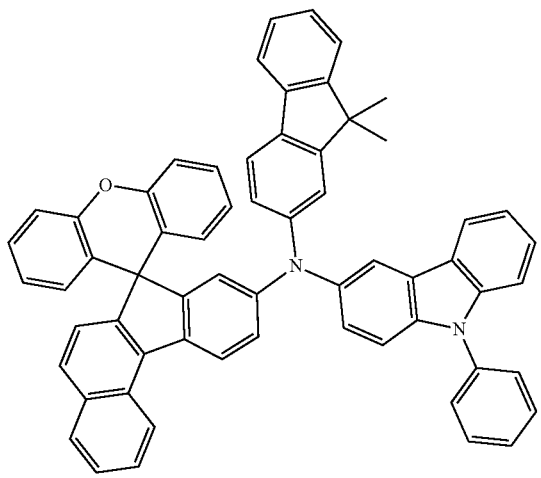
(40)
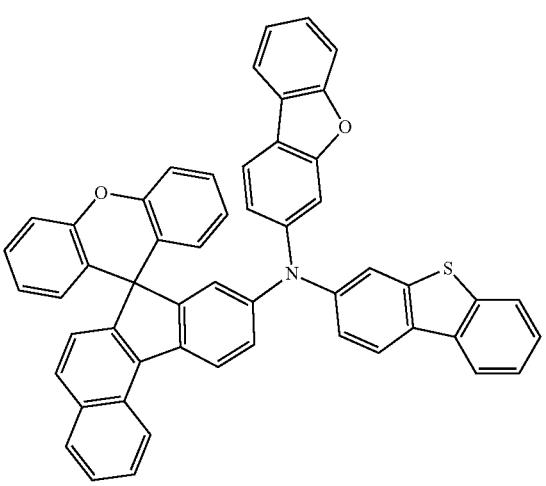
(41)
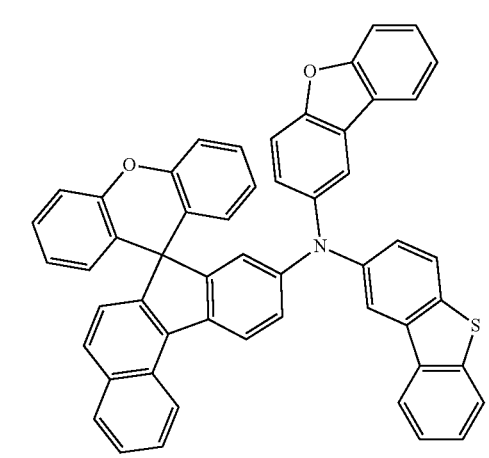
-continued
(42)
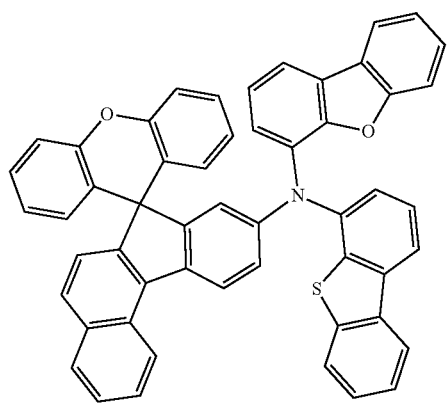
(43)
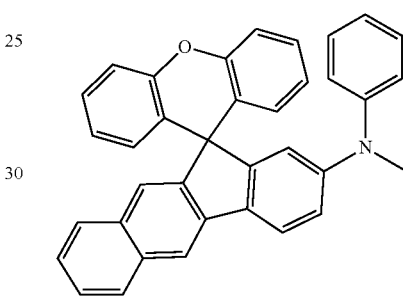
(44)
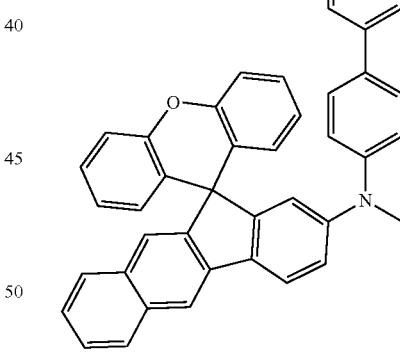
(45)

-continued
(46)
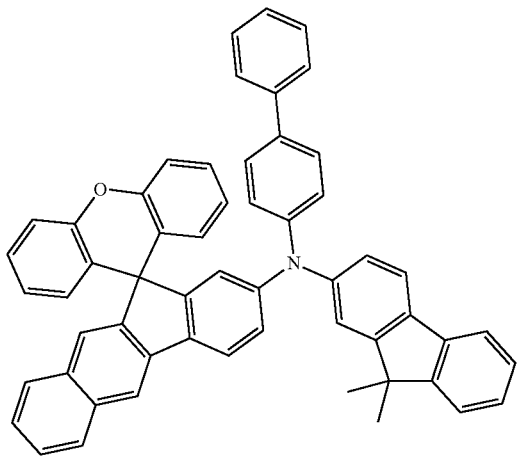
(47)
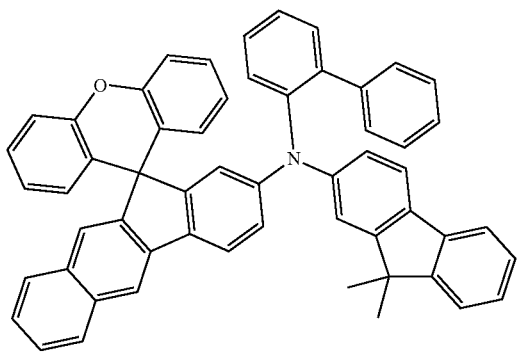
(48)
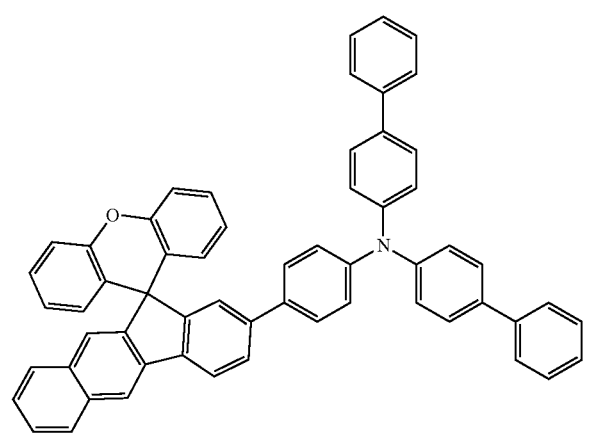
-continued
(49)
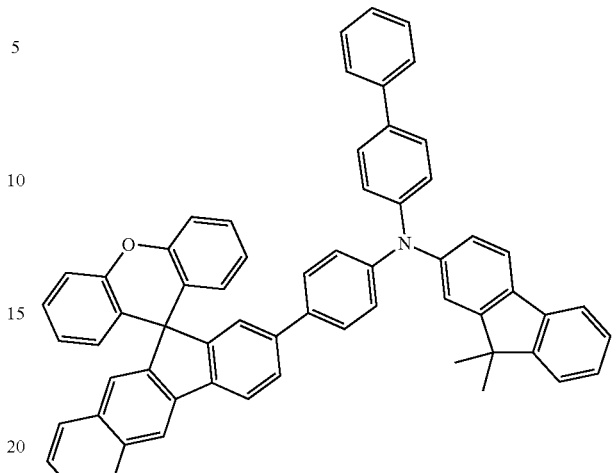
(50)
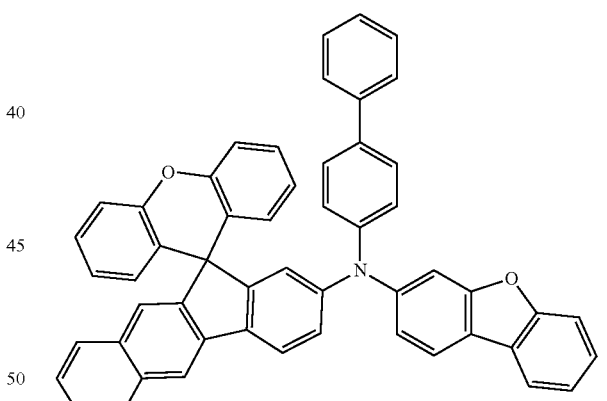
(51)
(52)
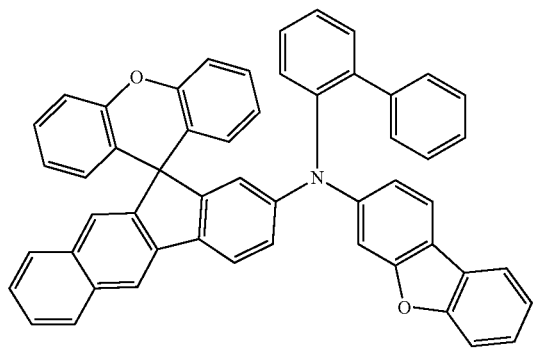

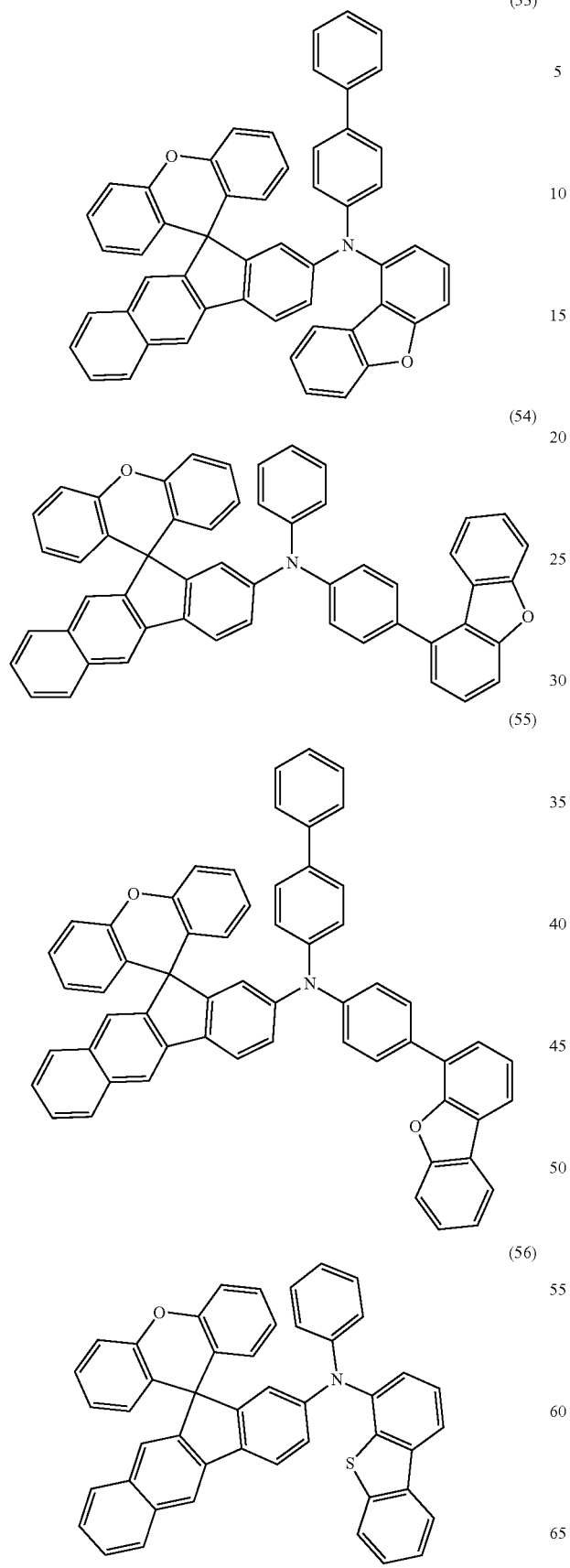
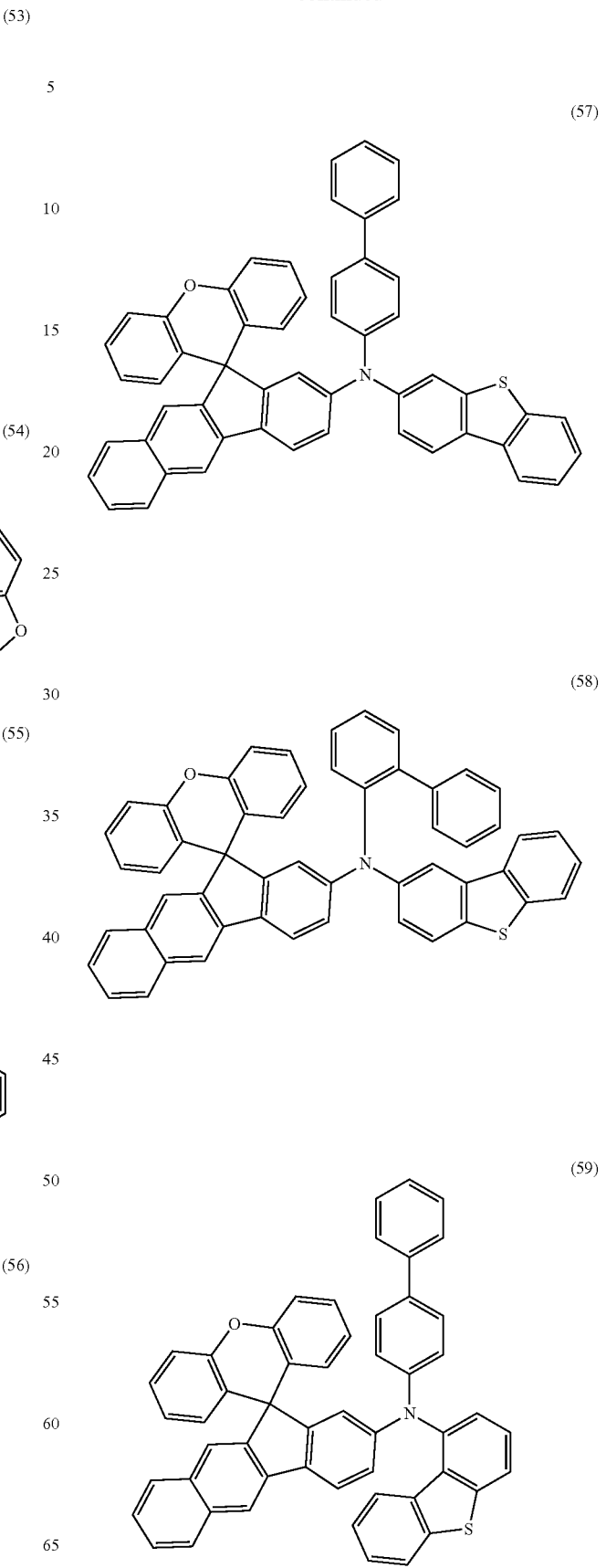

177
-continued
(60)
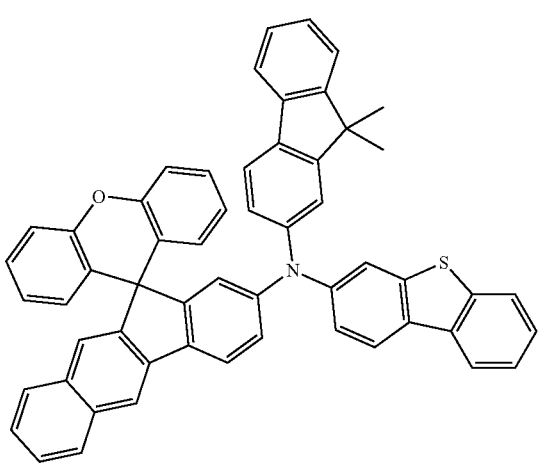
(61)
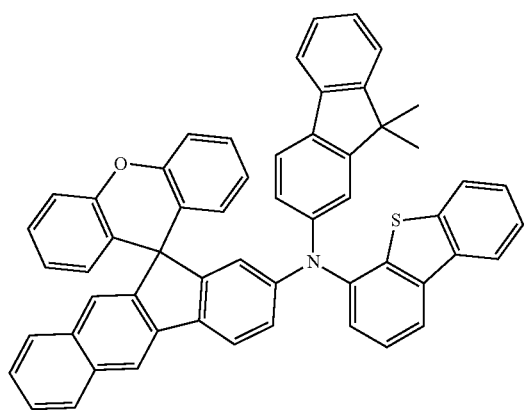
(62)
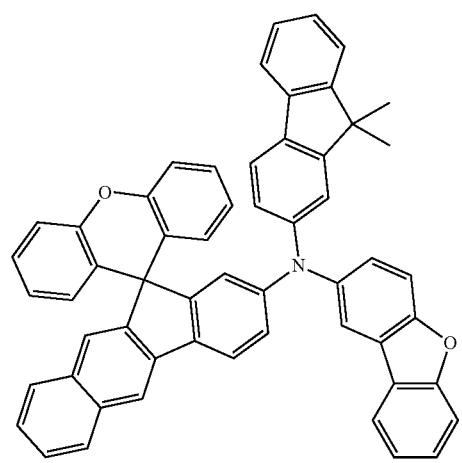
178
-continued
(63)
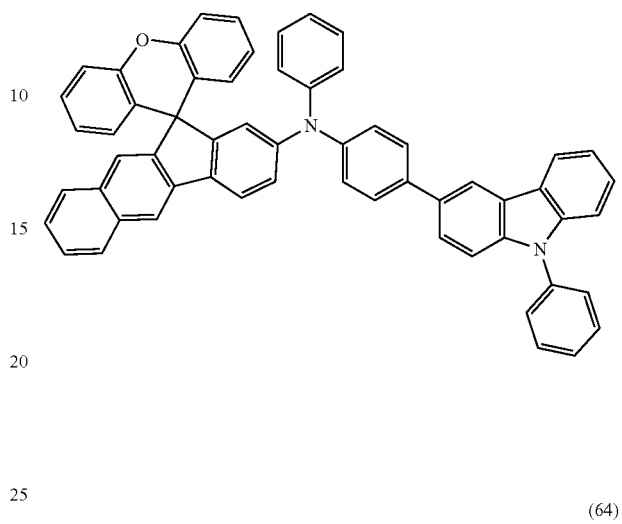
(64)
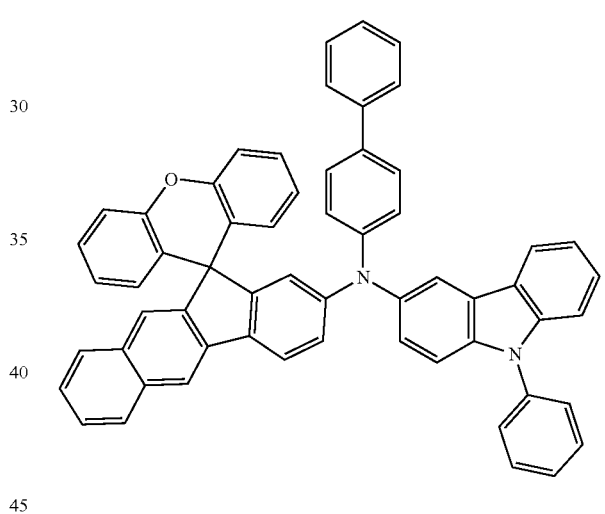
(65)
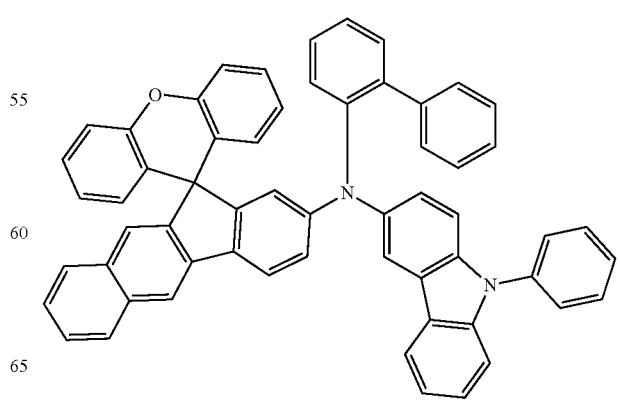

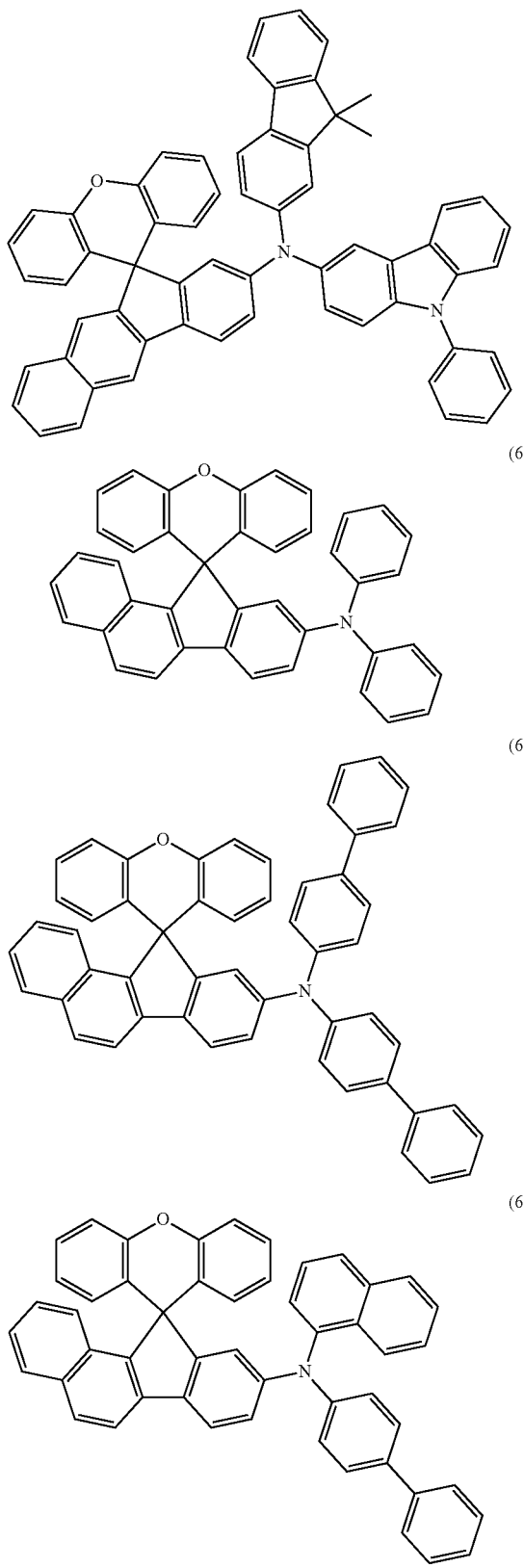
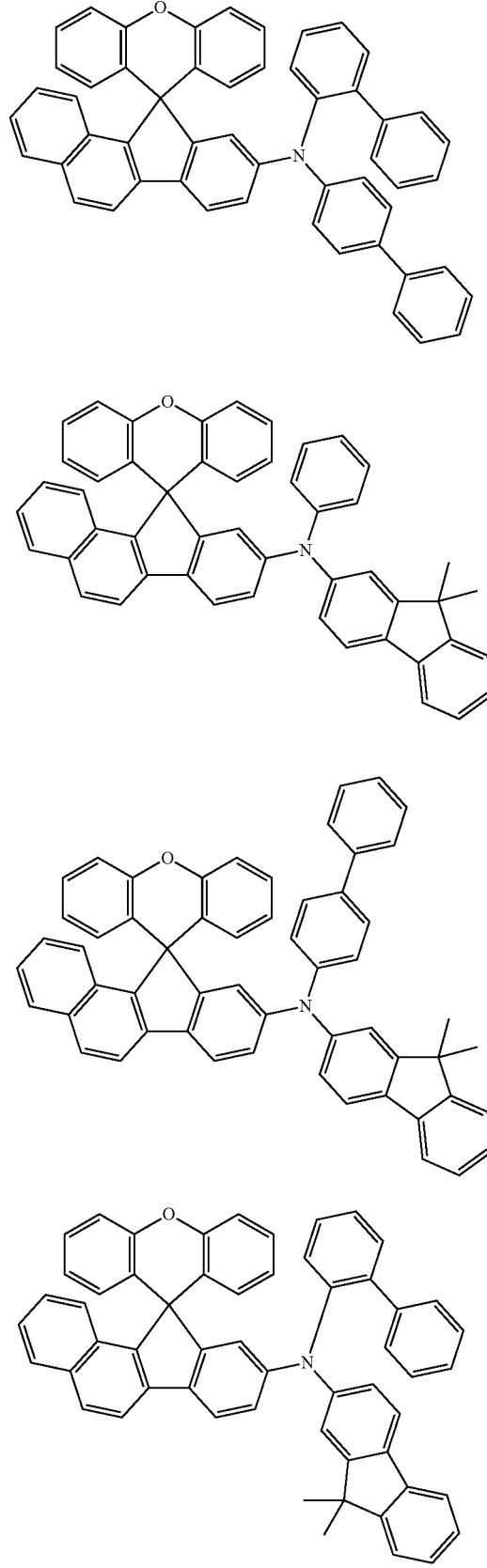

(74)
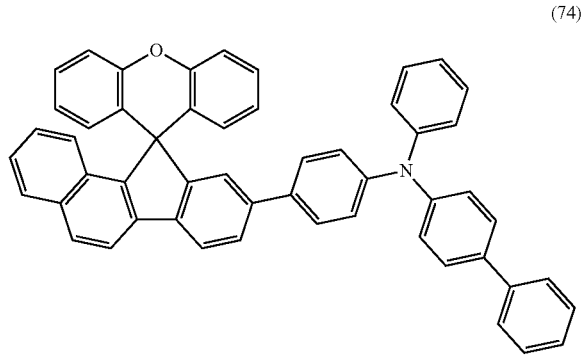
(75)
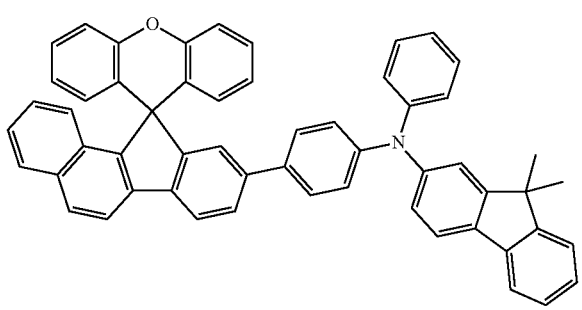
(76)
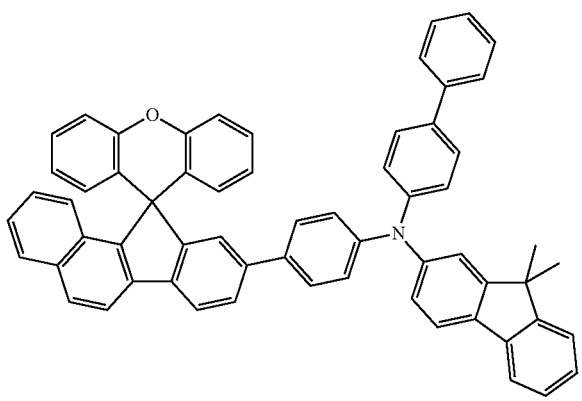
(77)
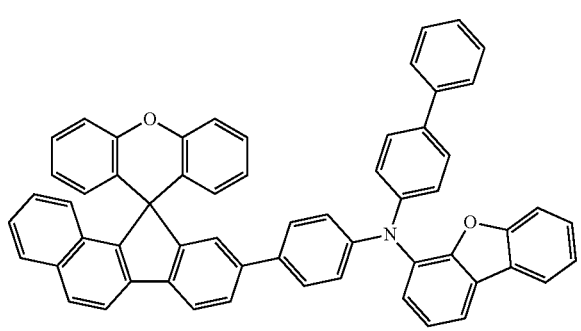
(78)
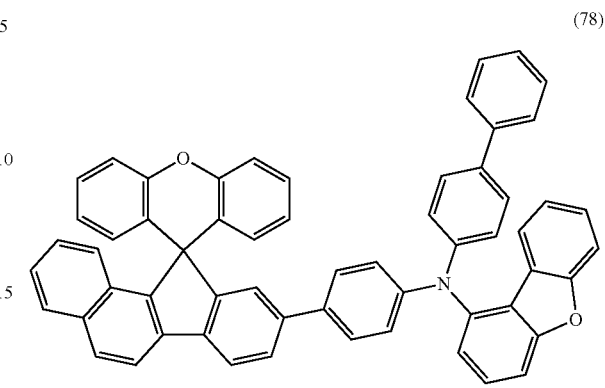
(79)
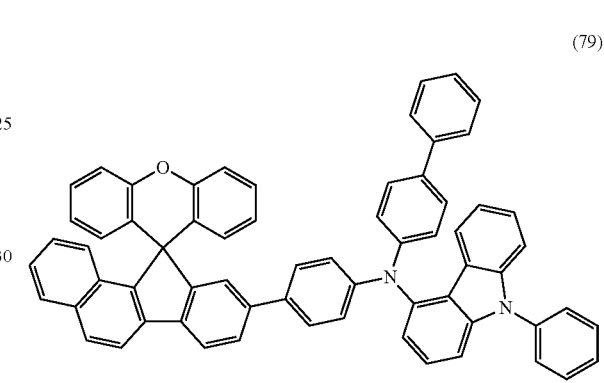
(80)
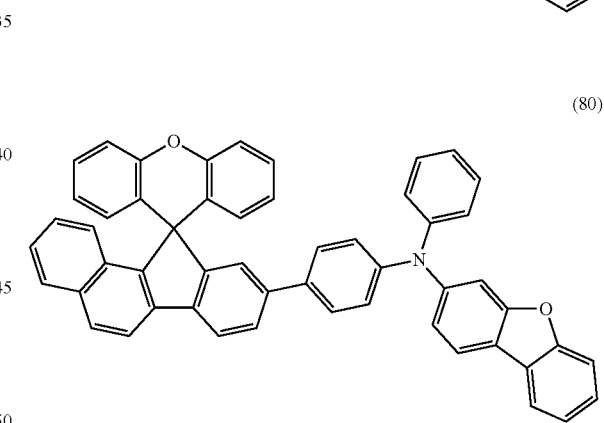
(81)
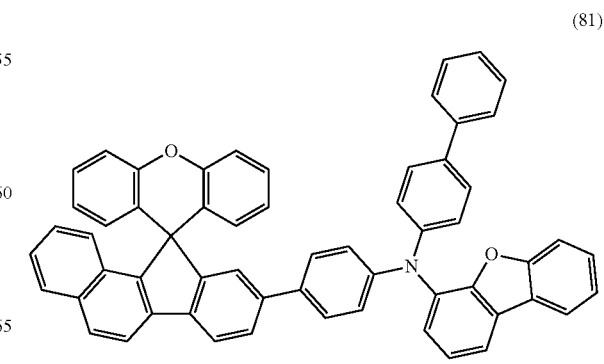

-continued
(82)
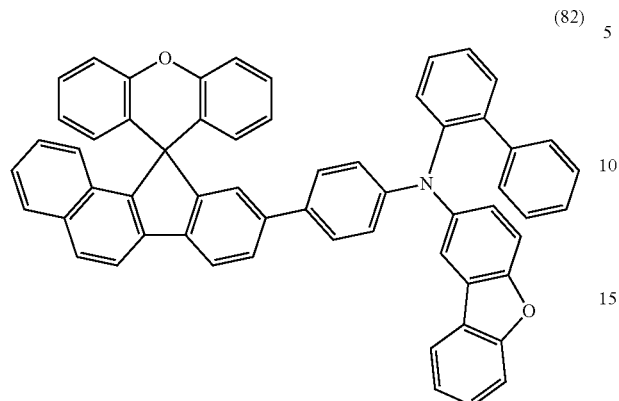
(83)
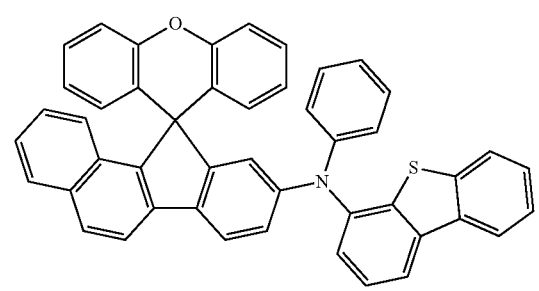
(84)
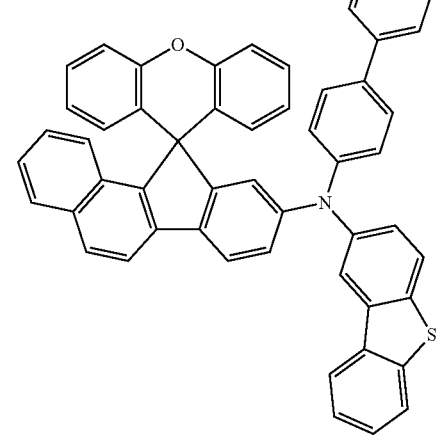
(85)
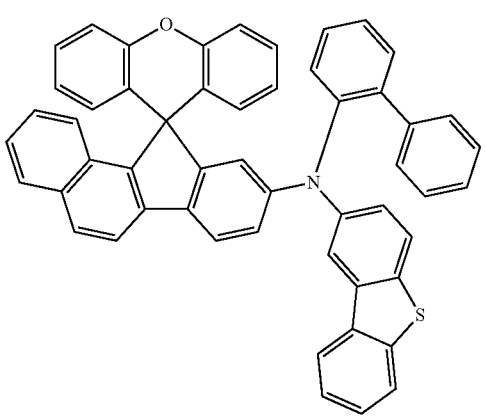
-continued
(86)
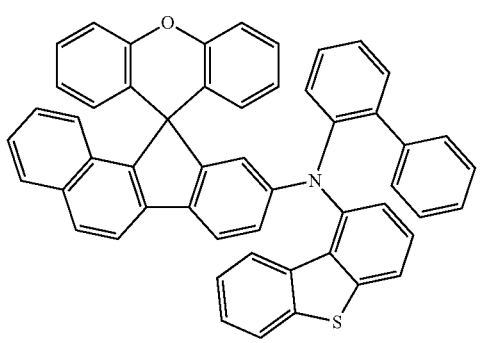
(87)
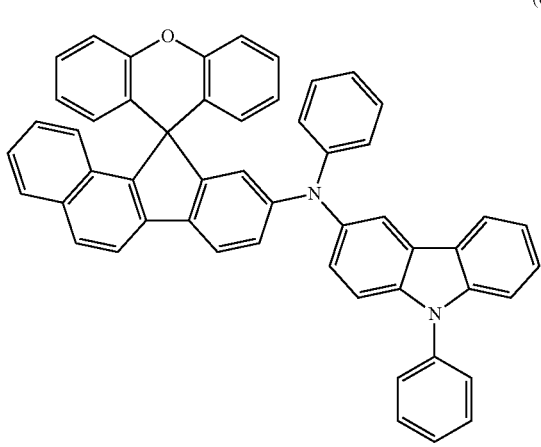
(88)
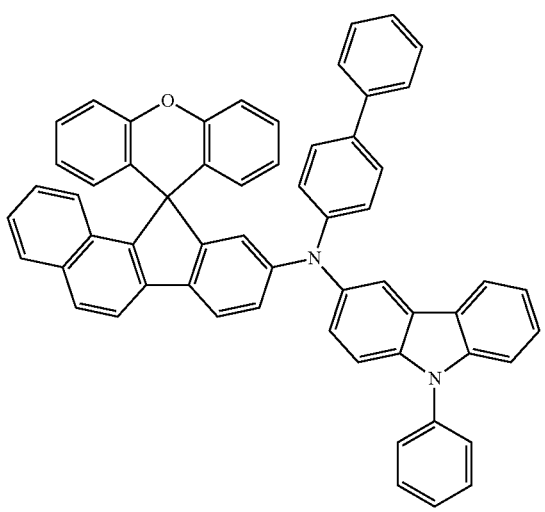

(89)
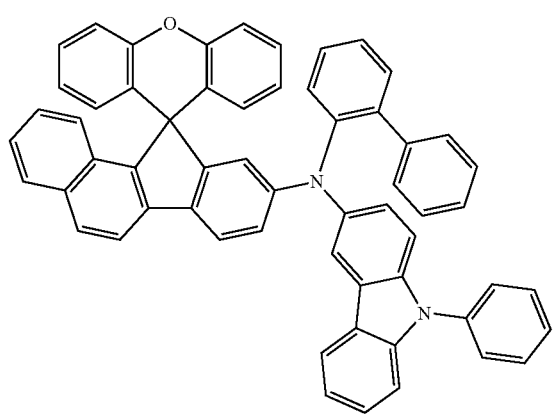
(92)
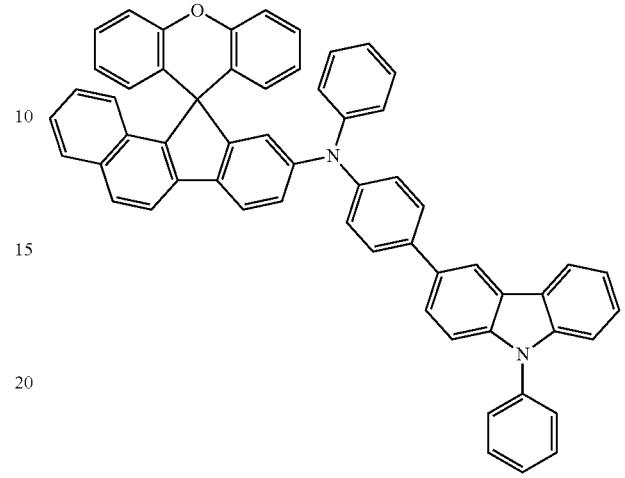
(90)
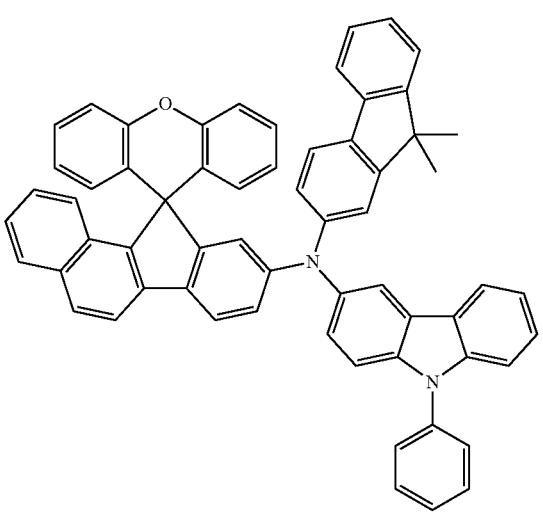
(93)
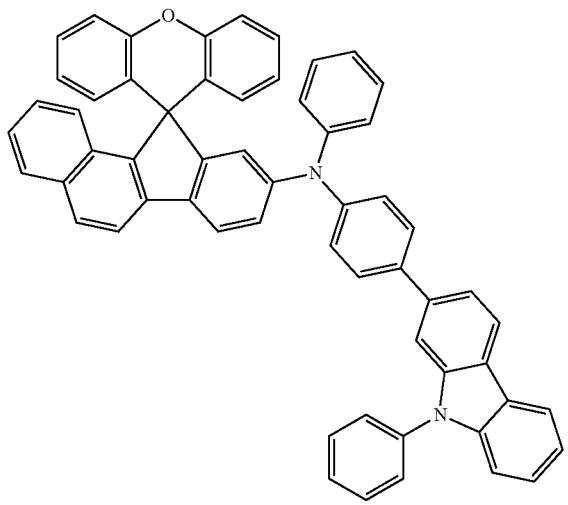
(91)
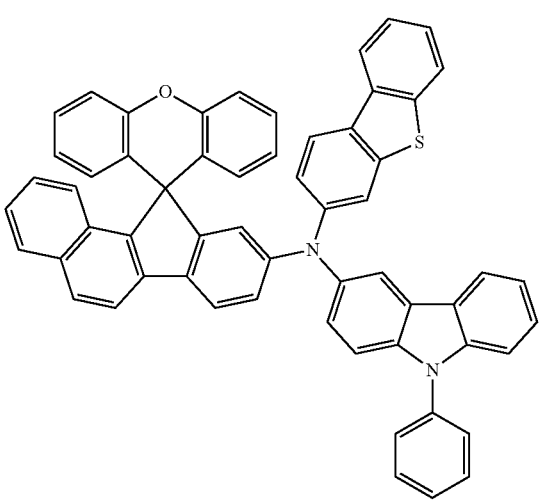
(94)

(95)
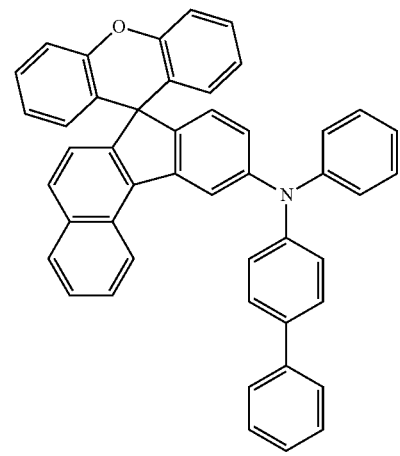
(96)
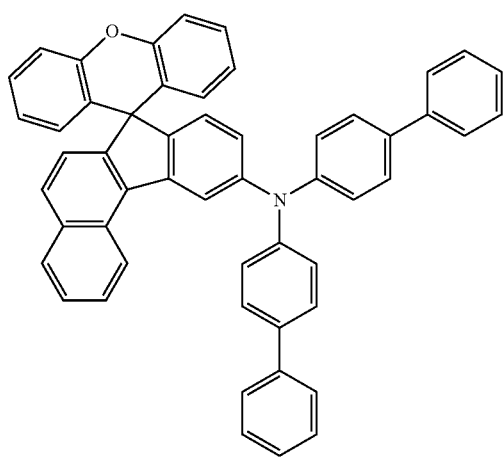
(97)
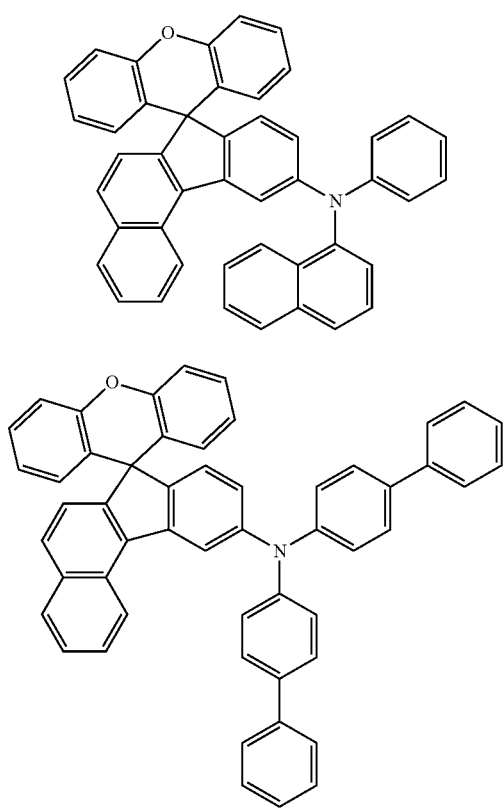
(98)
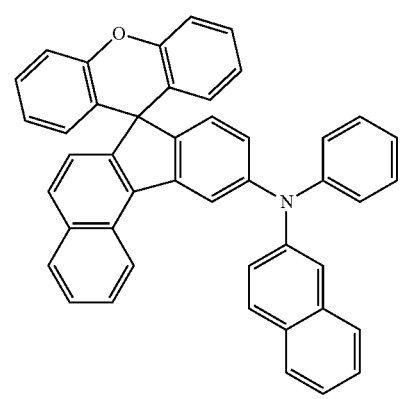
(99)
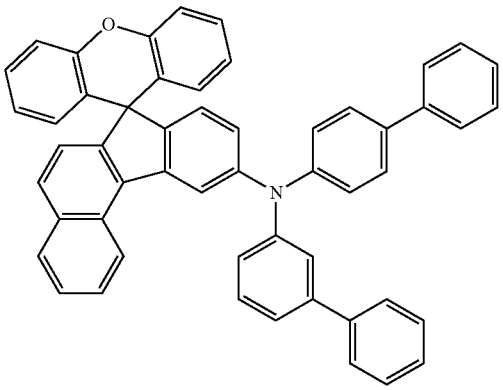
(100)
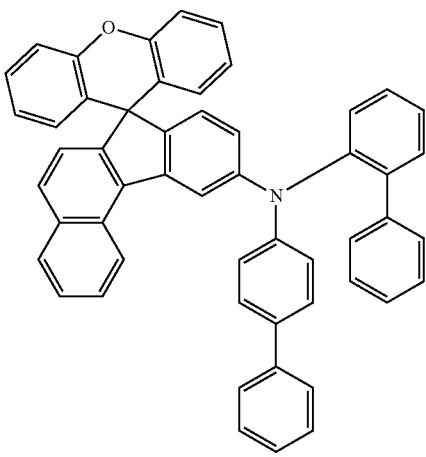
(101)
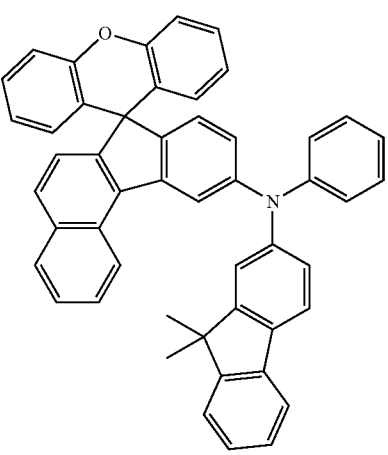

(102)
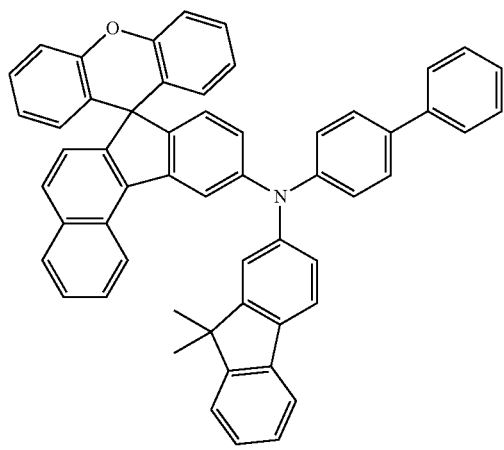
(103)
(104)
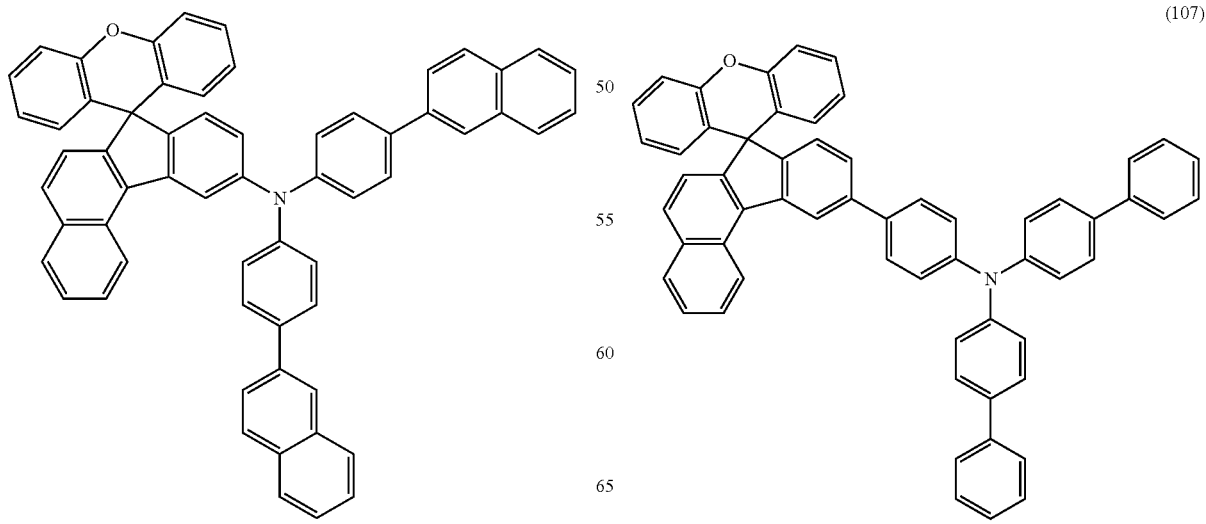
(105)
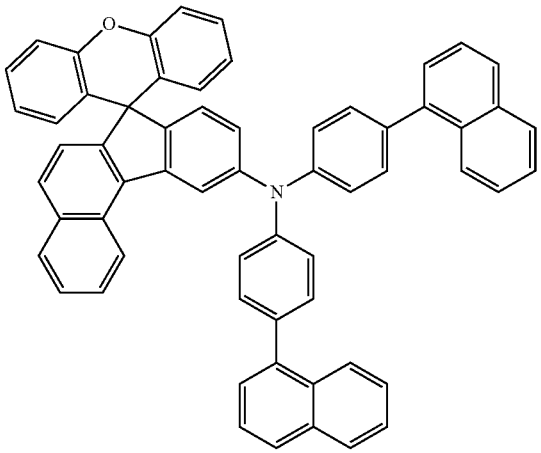
(106)
(107)
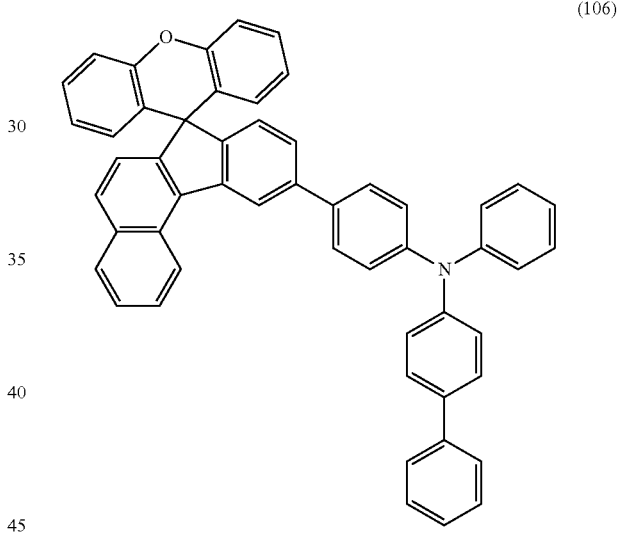

(108)
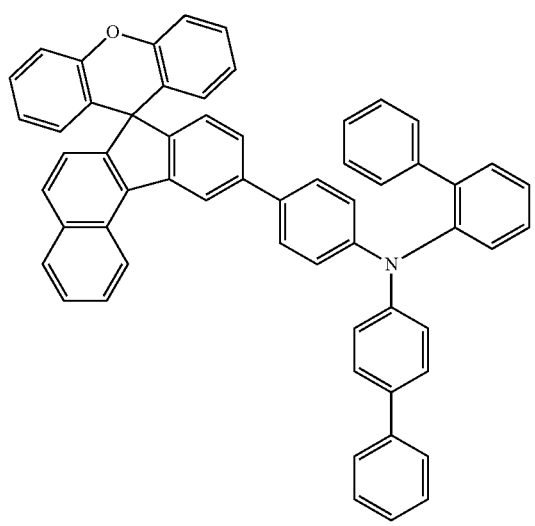
(109)
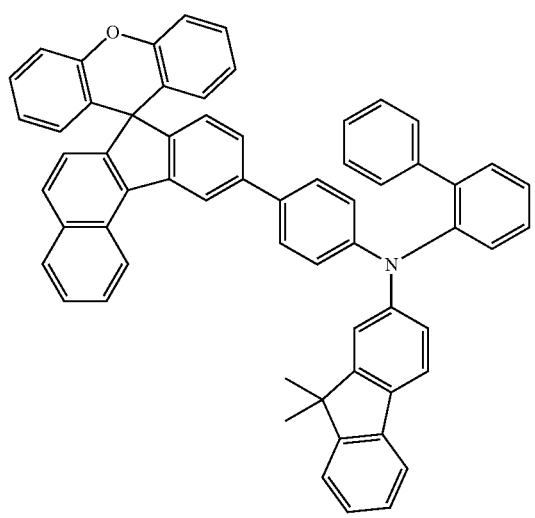
(110)
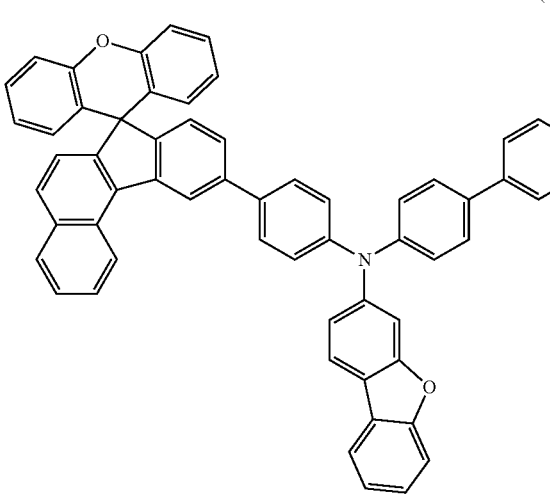
(111)
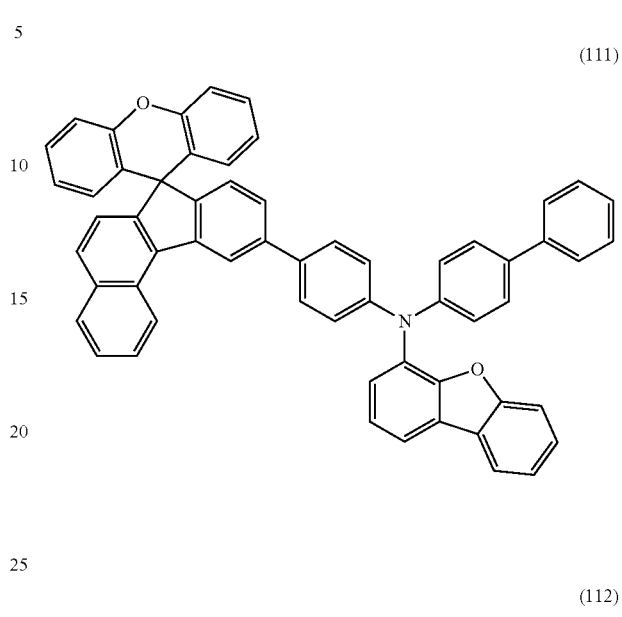
(112)
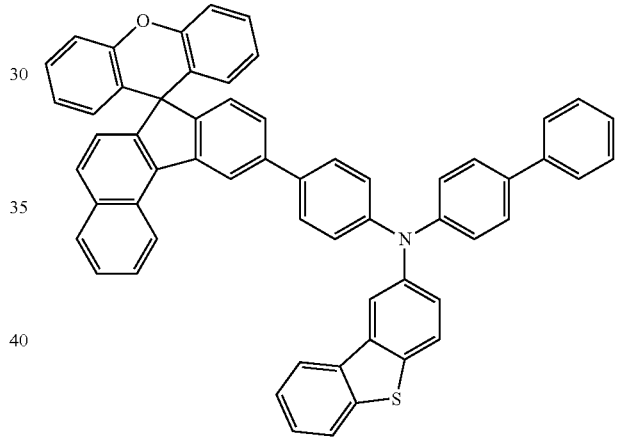
(113)
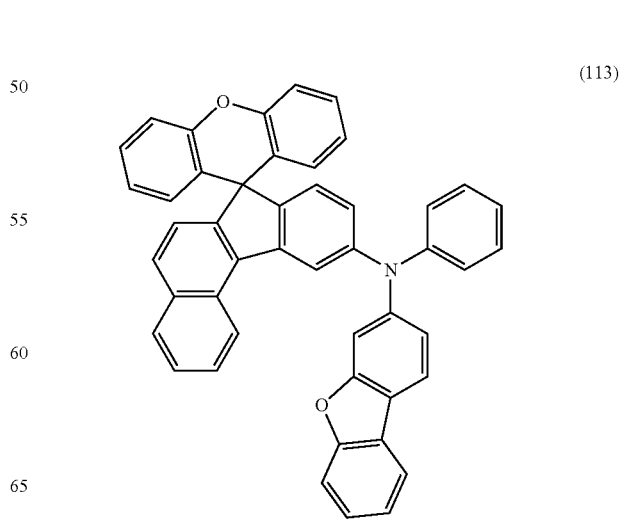

-continued
(114)
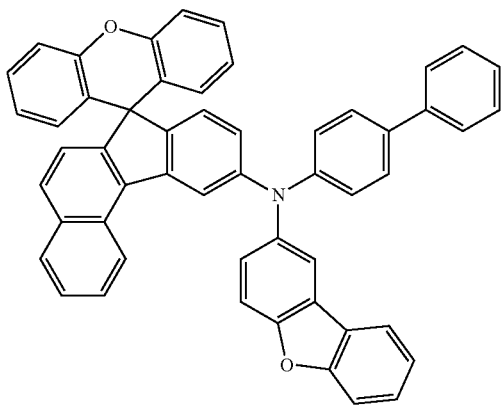
(115)
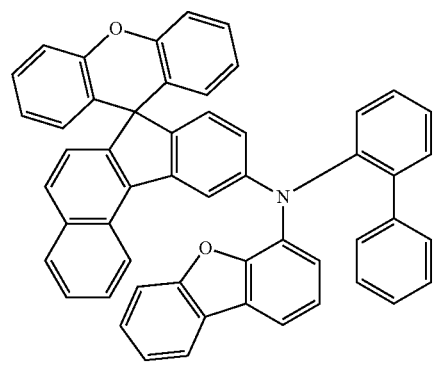
(116)
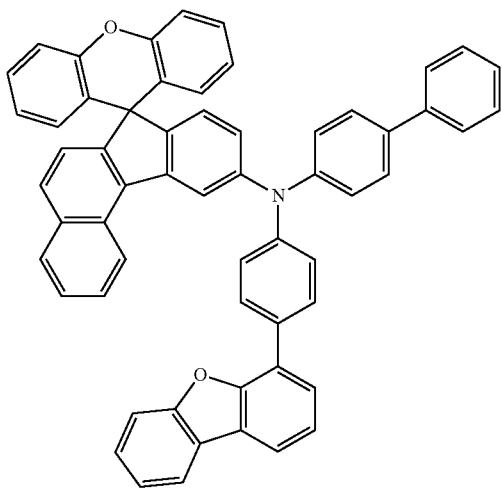
-continued
(117)
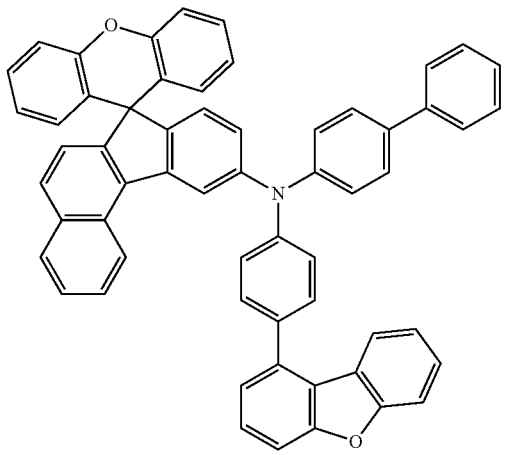
(118)
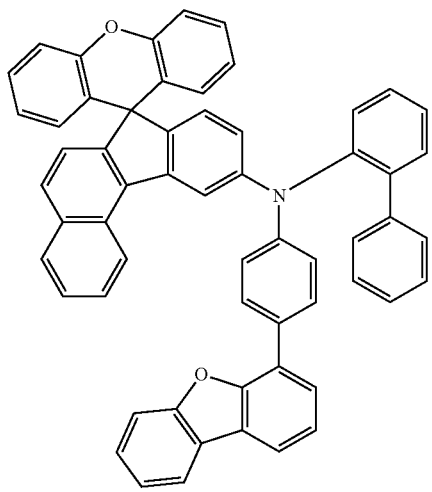
(119)
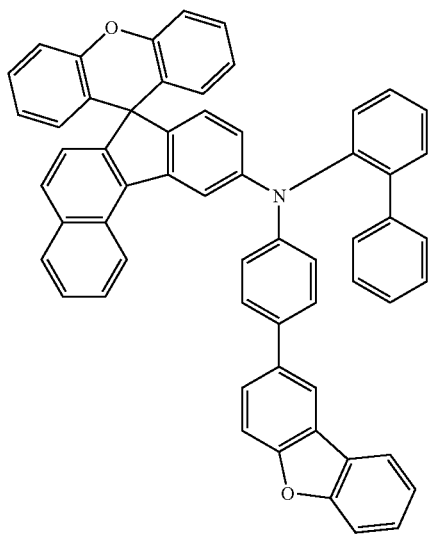

(120)
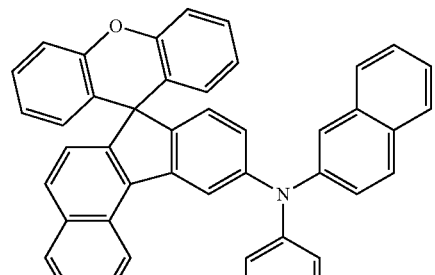
(121)
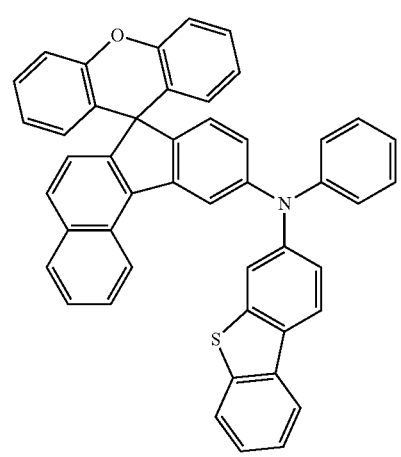
(122)
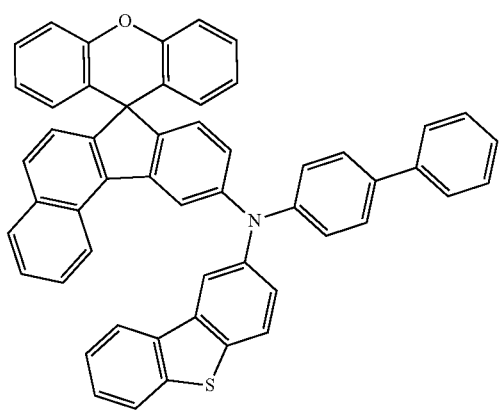
(123)
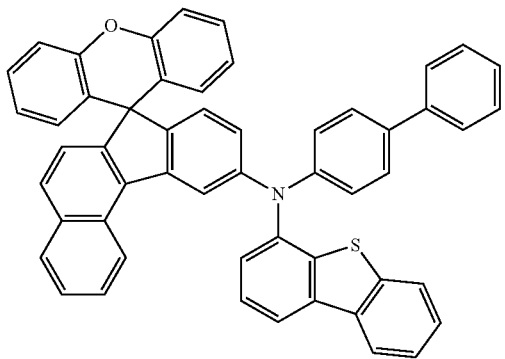
(124)
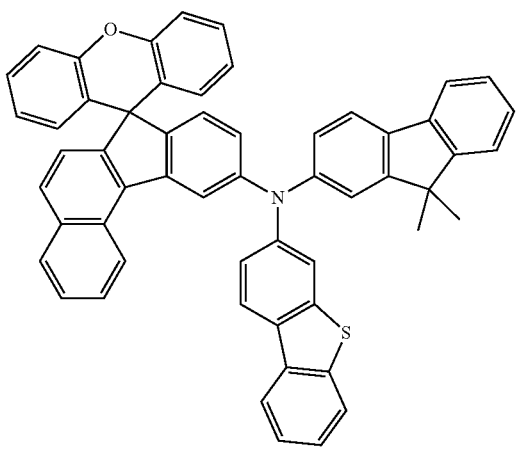
(125)
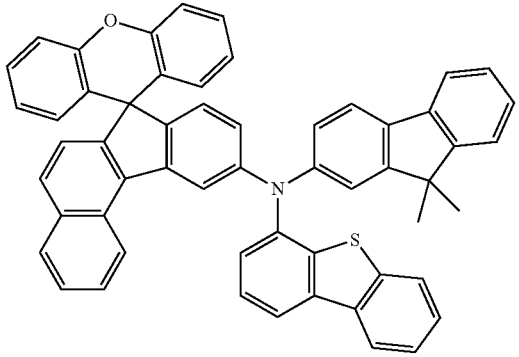
(126)
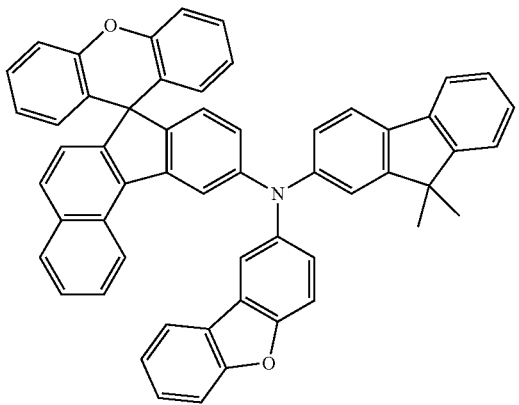

-continued
(127)
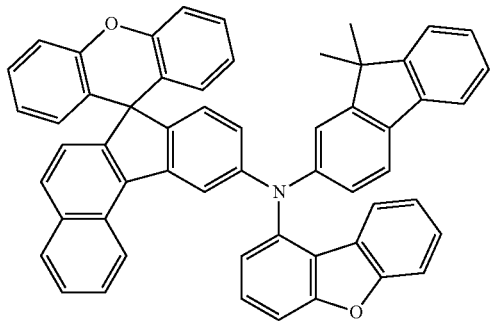
(128)
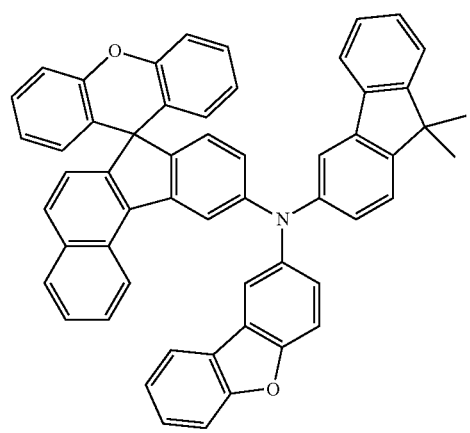
(129)
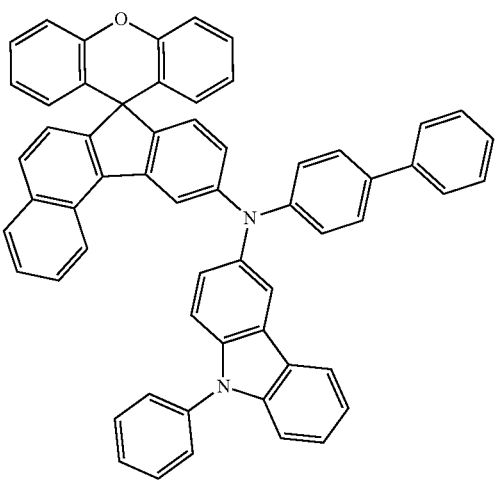
-continued
(130)
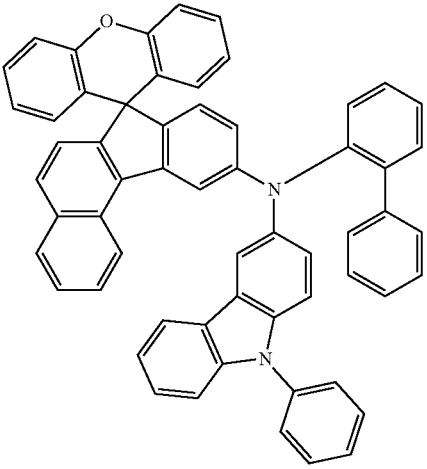
(131)
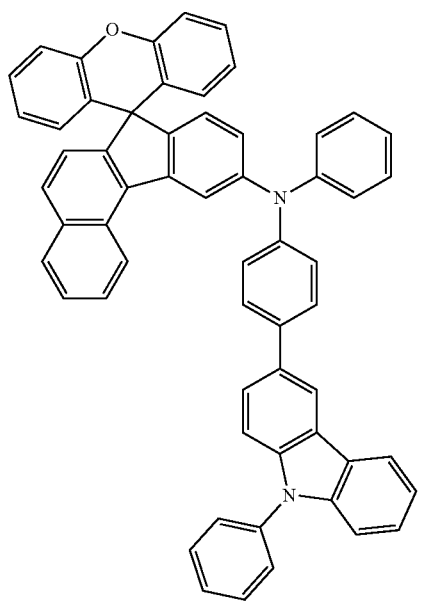
(132)
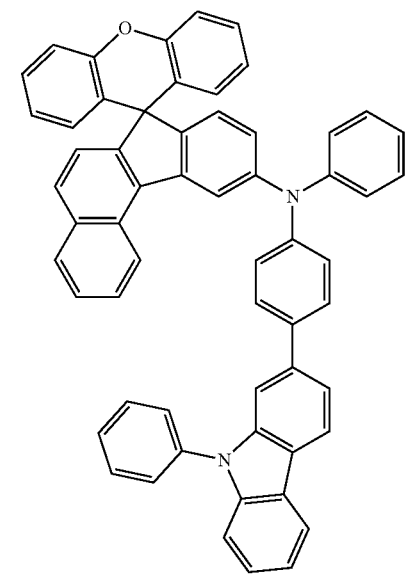

(133)
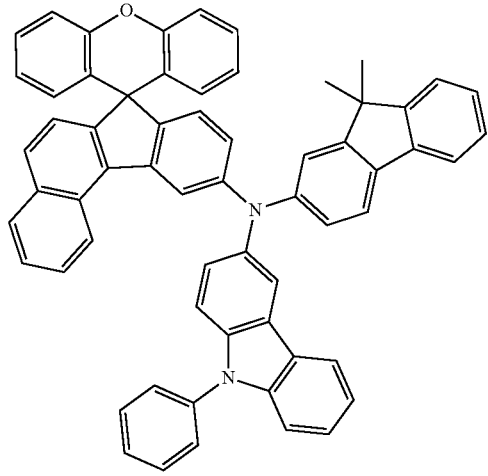
(134)
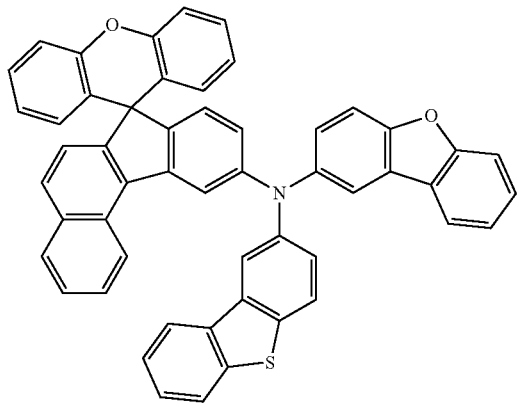
(135)
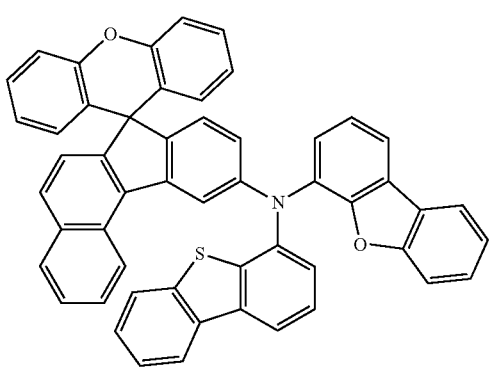
(136)
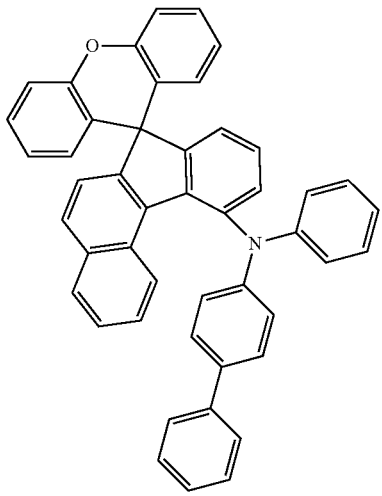
(137)
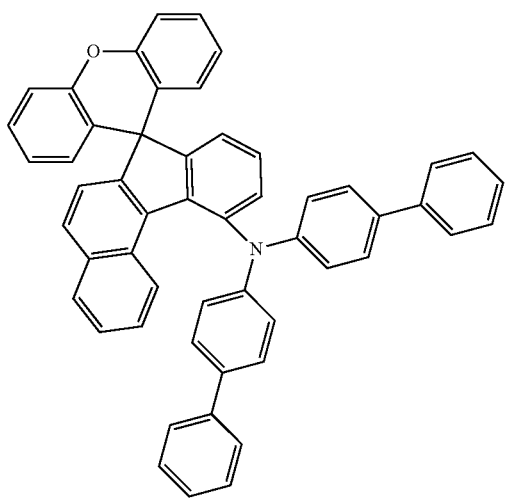
(138)
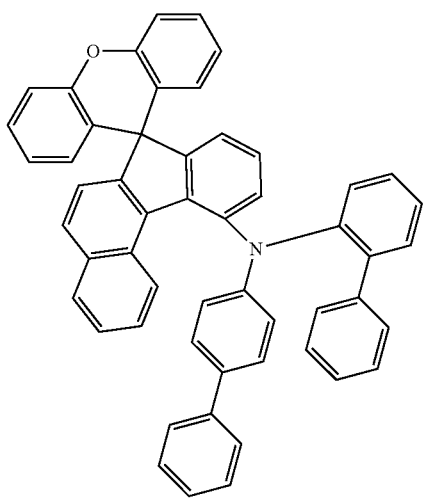

201
-continued
(139)
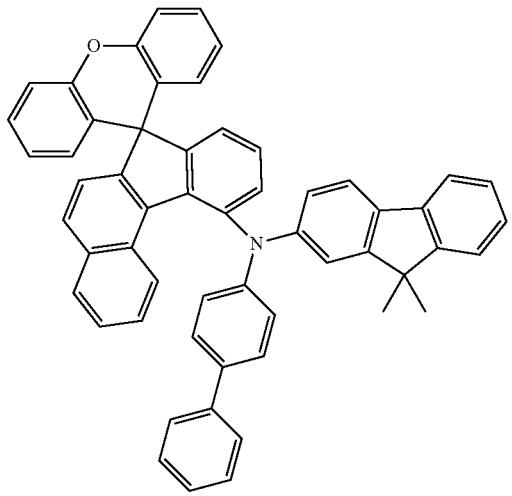
(140)
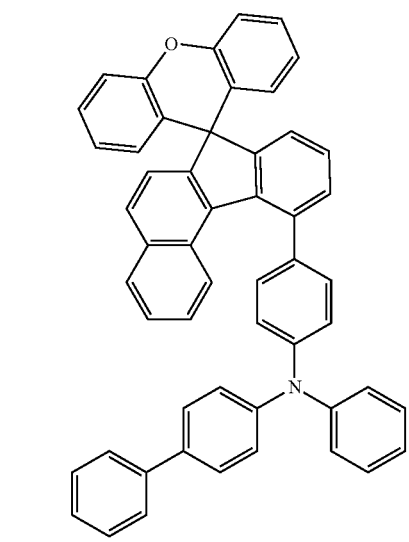
(141)
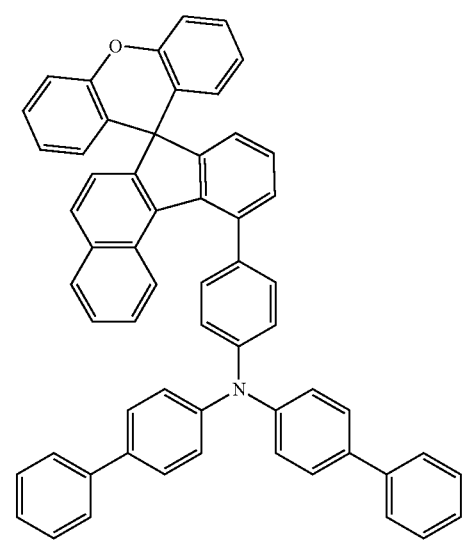
202
-continued
(142)
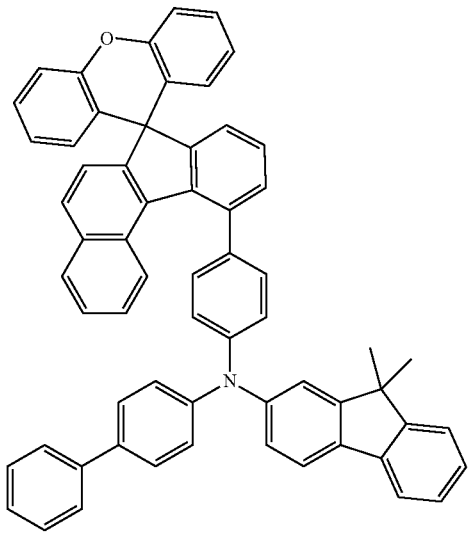
(143)
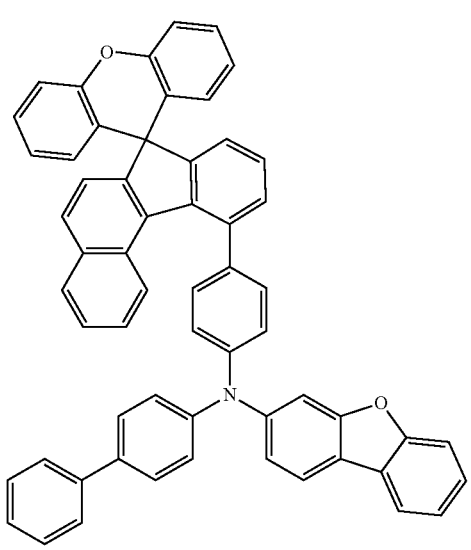
(144)
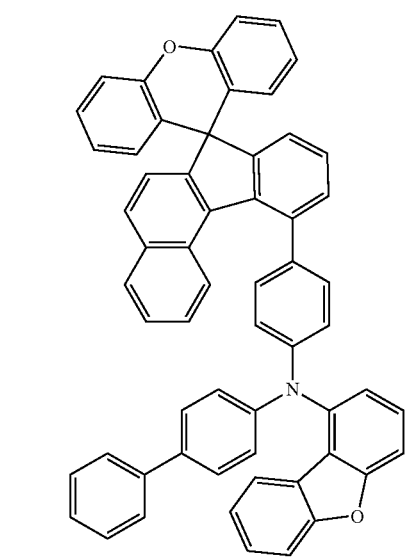

(145)
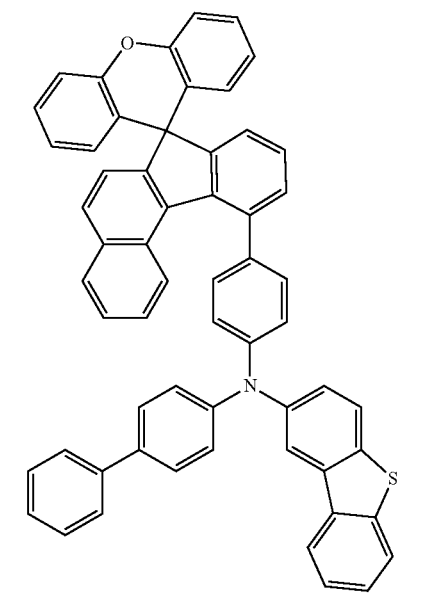
(146)
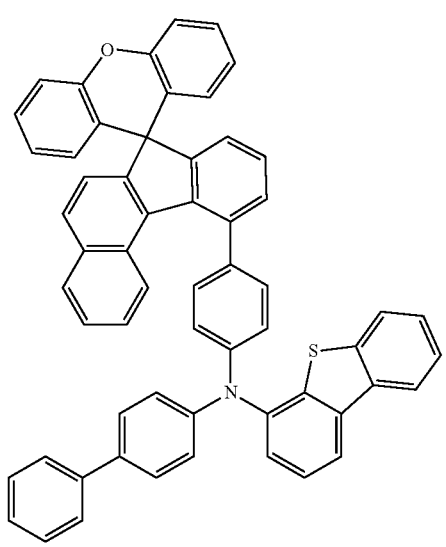
(147)
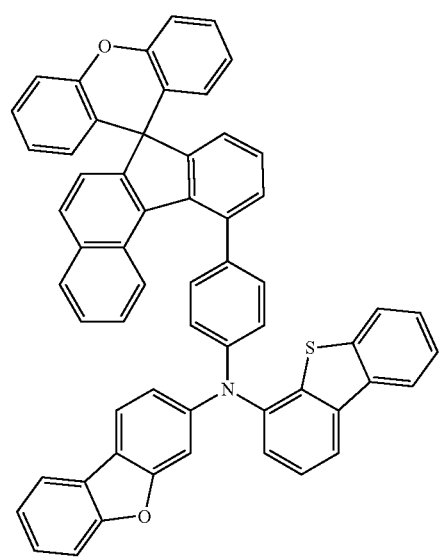
(148)
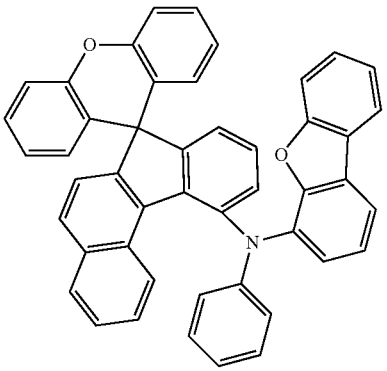
(149)
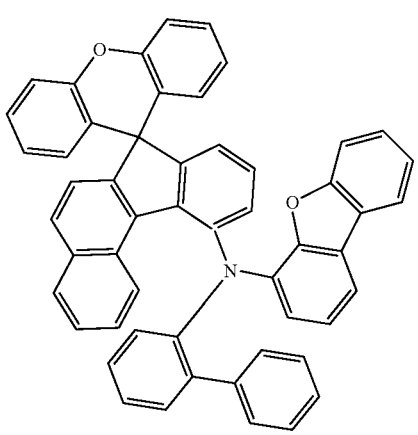
(150)
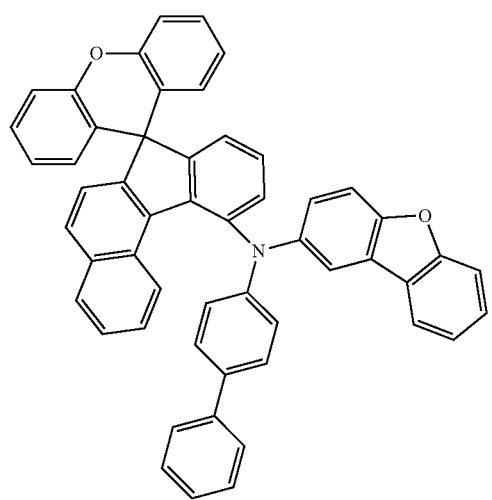

-continued
(151)
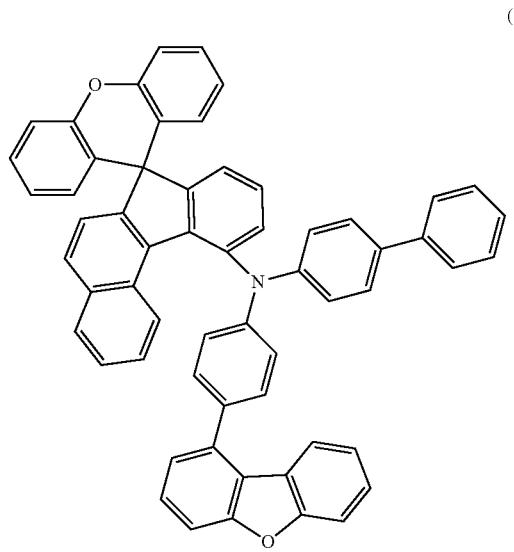
(152)
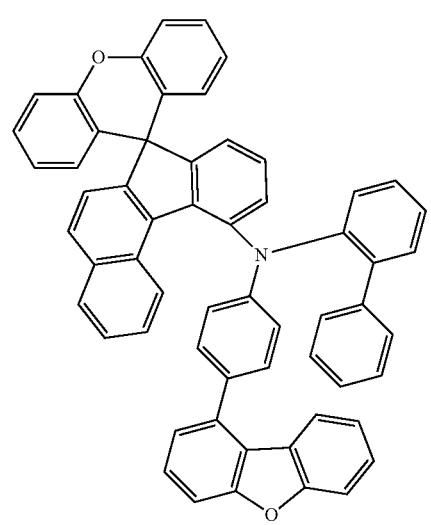
(153)
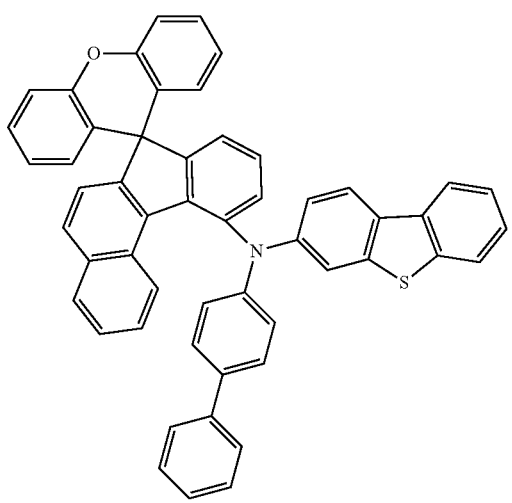
-continued
(154)
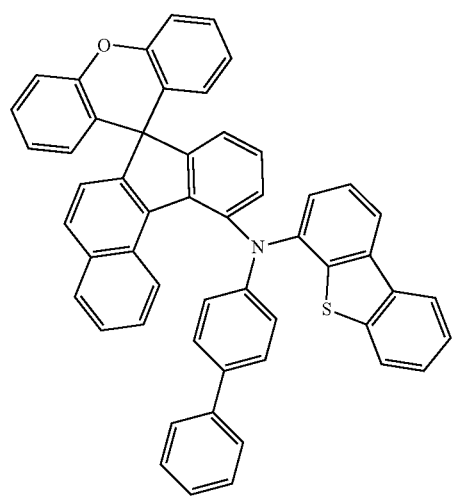
(155)
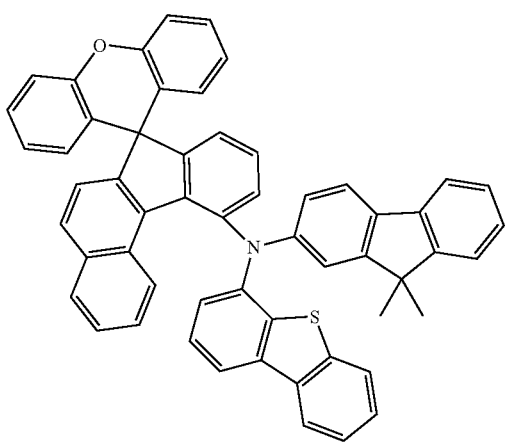
(156)
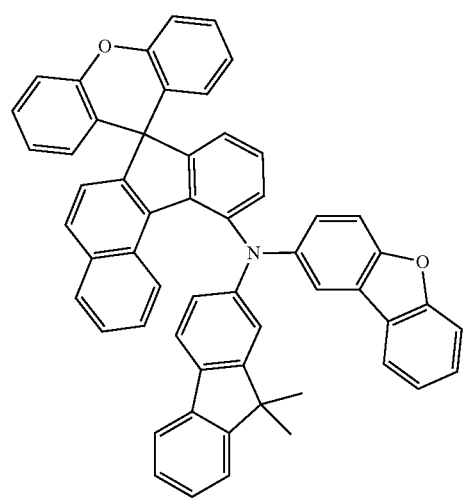

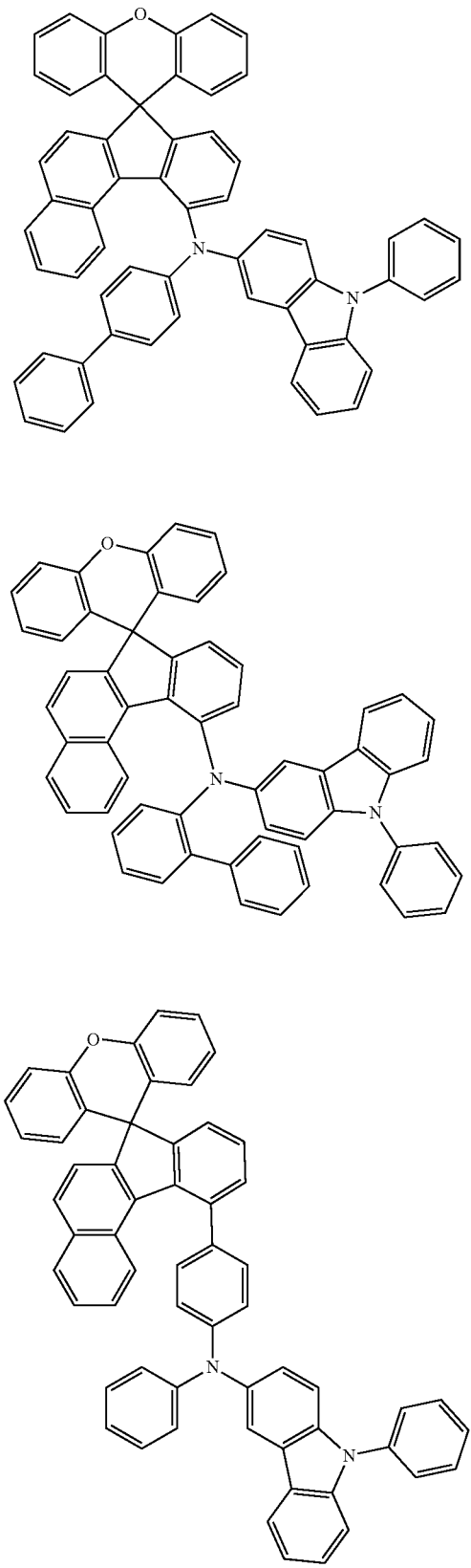
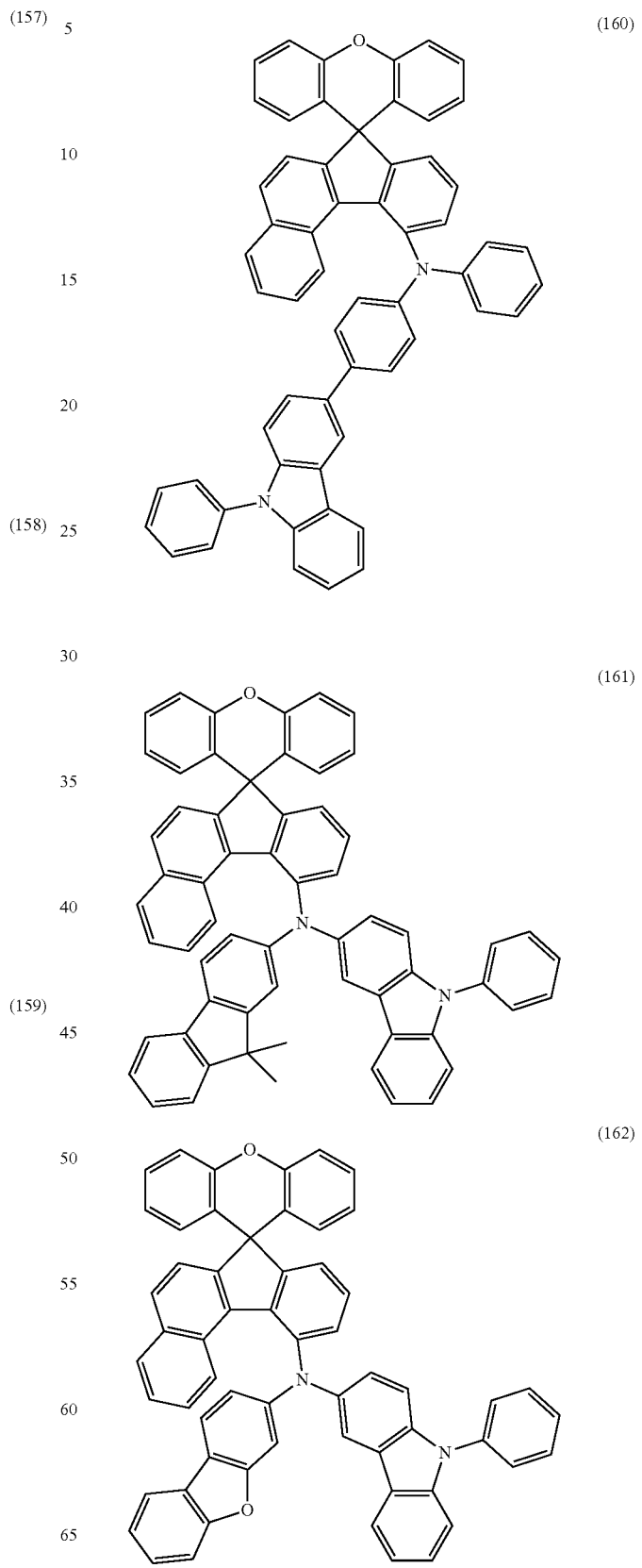

(163)
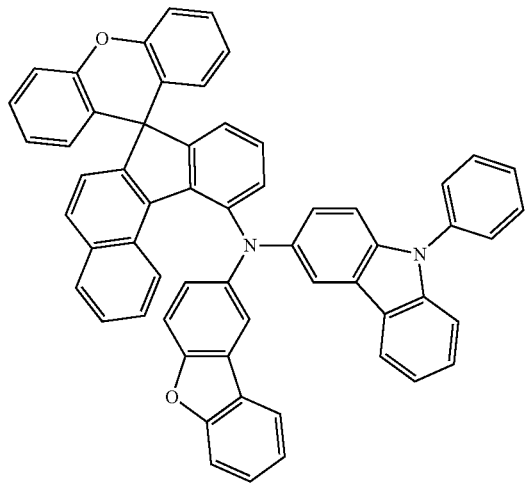
(164)
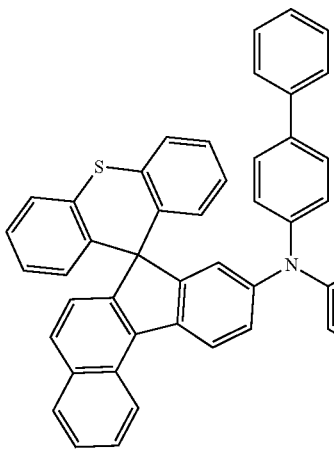
(165)
(166)
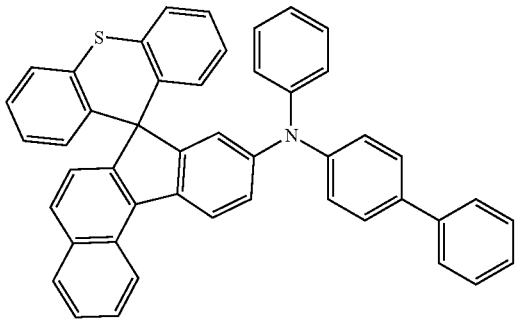
(167)
(168)
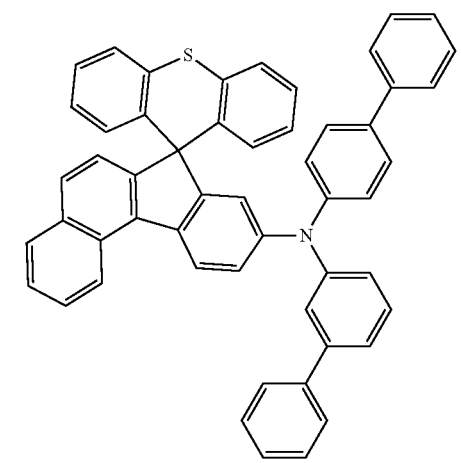
(169)
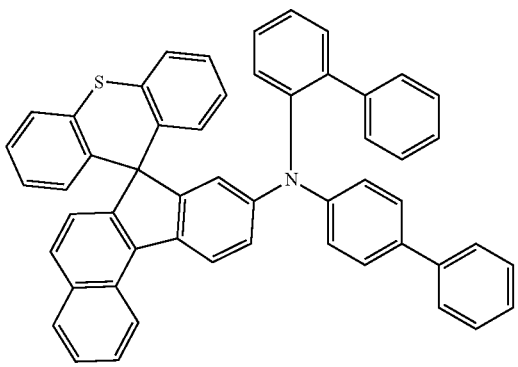

211
-continued
(170)
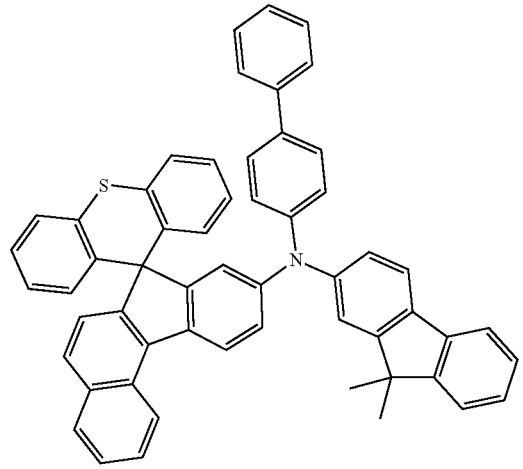
(171)
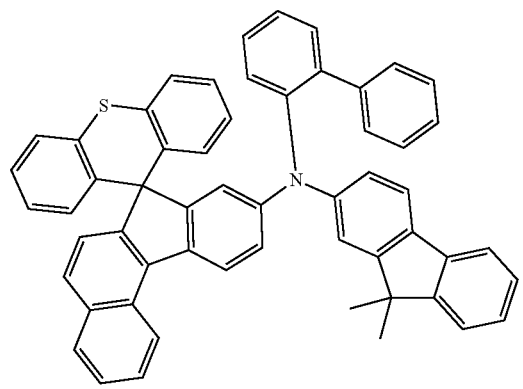
(172)
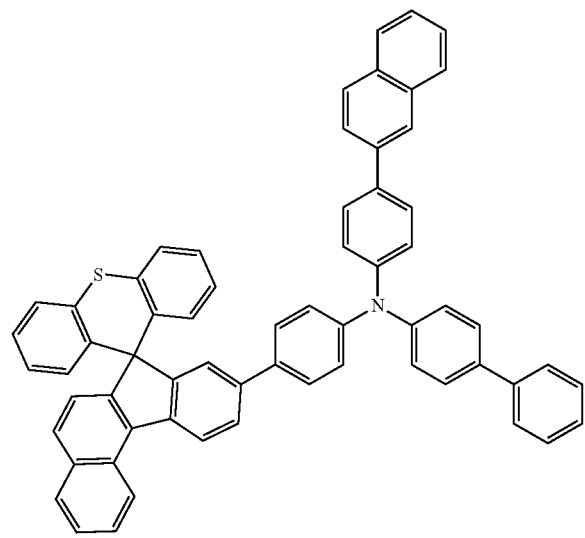
212
-continued
(173)
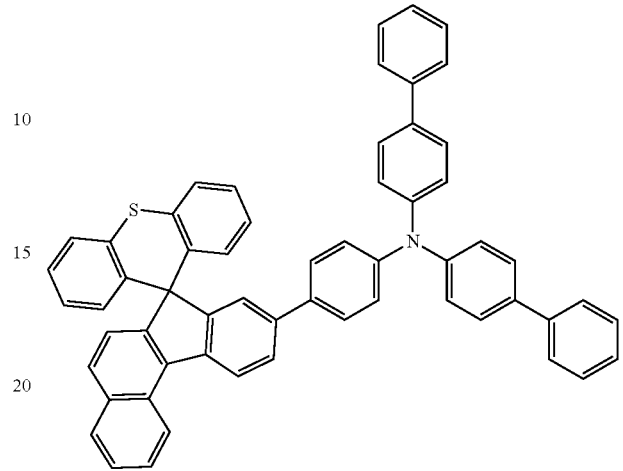
(174)
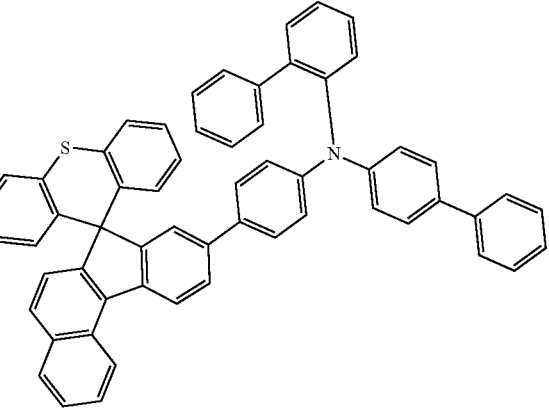
(175)
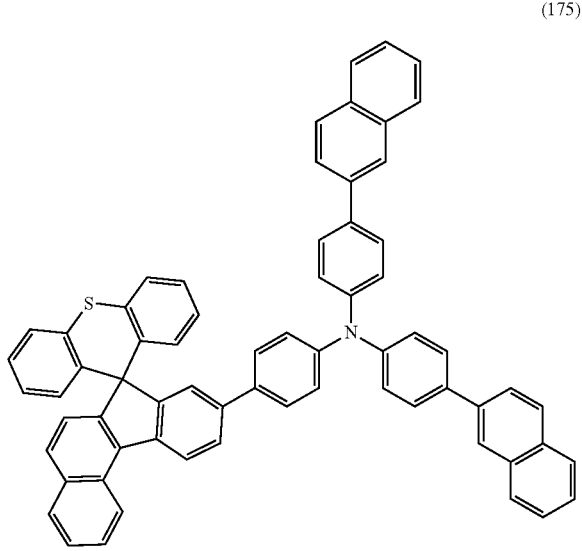

-continued
(176)
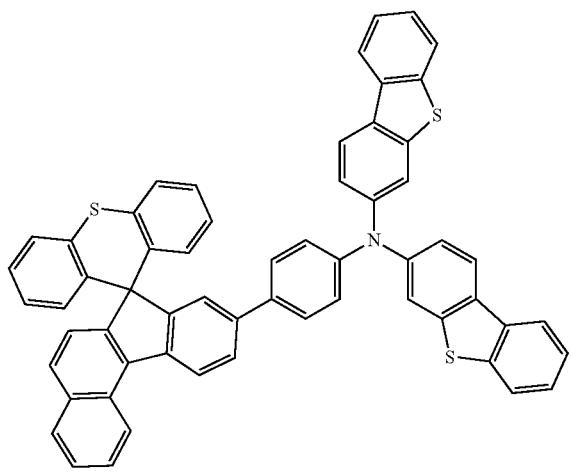
(177)
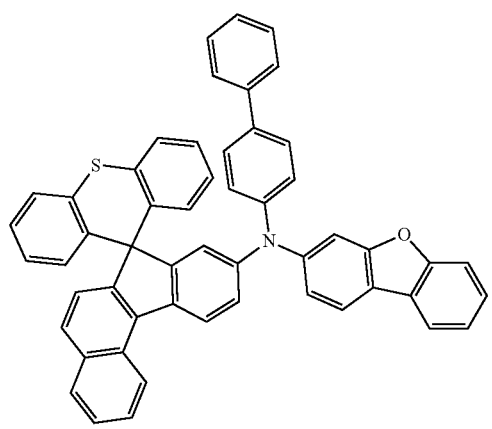
(178)
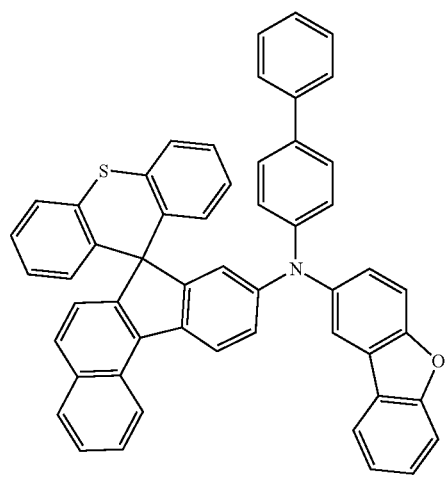
-continued
(179)
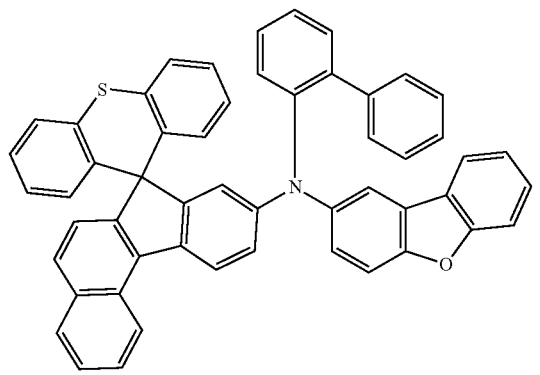
(180)
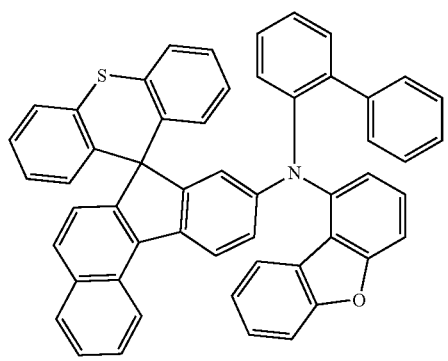
(181)
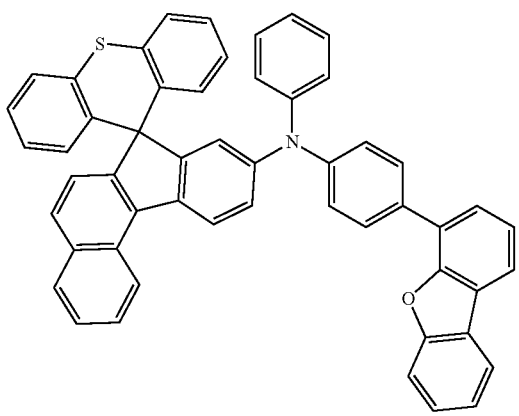

-continued
(182)
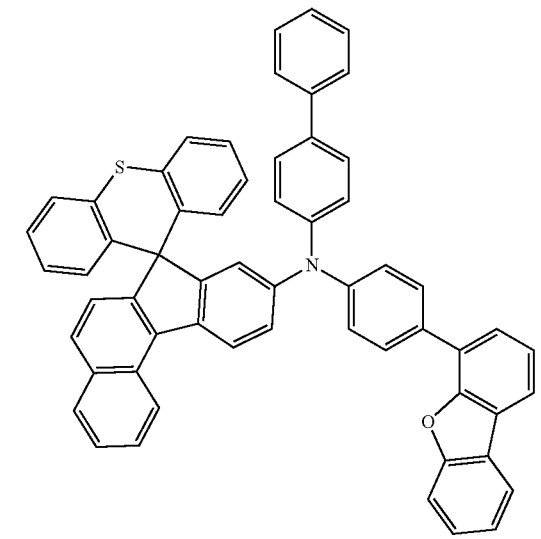
(183)
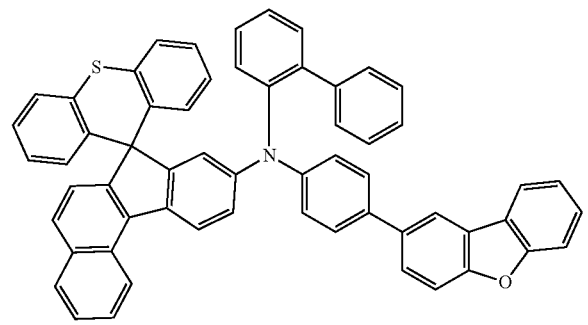
(184)
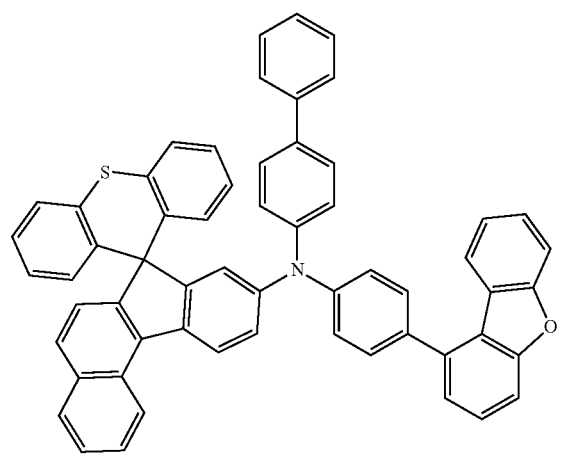
-continued
(185)
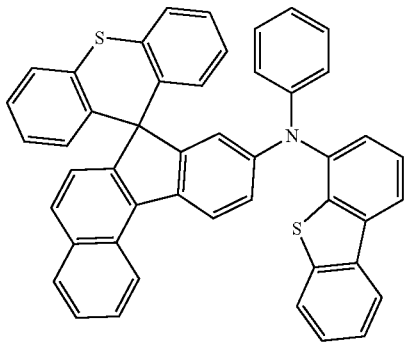
(186)
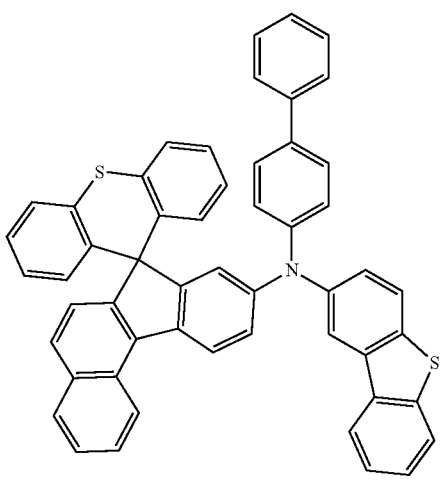
(187)
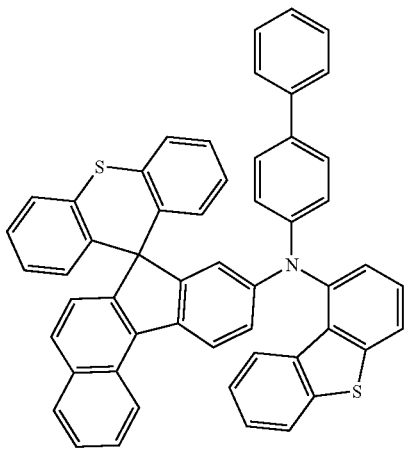
(188)
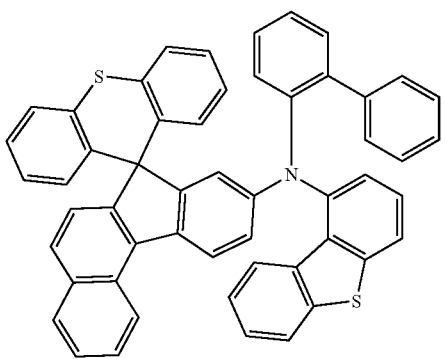

217
-continued
(189)
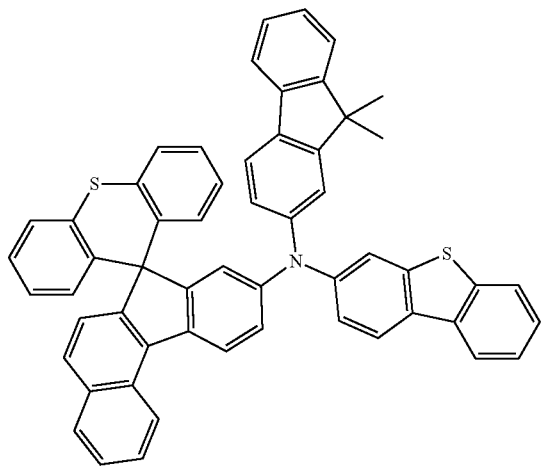
(190)
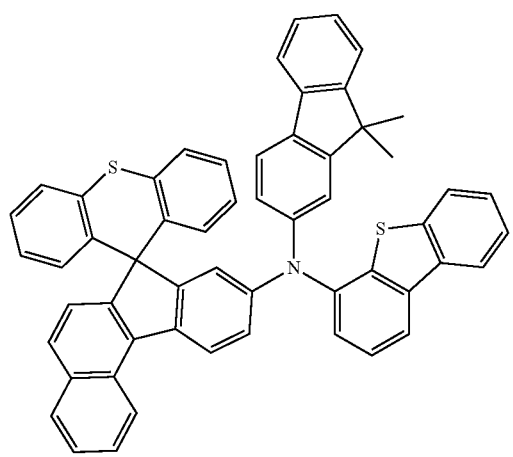
(191)
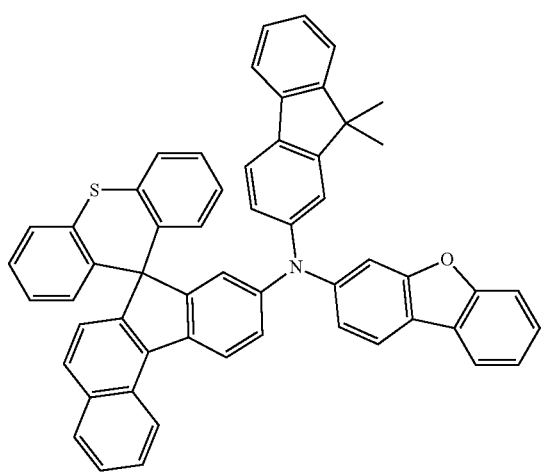
218
-continued
(192)
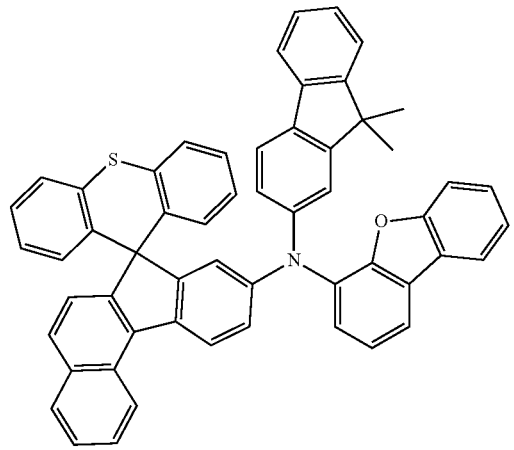
(193)
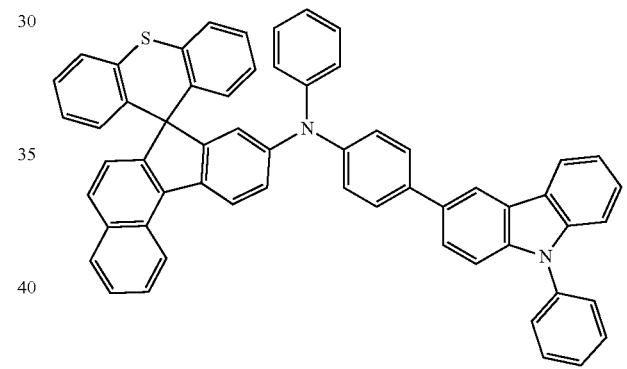
(194)
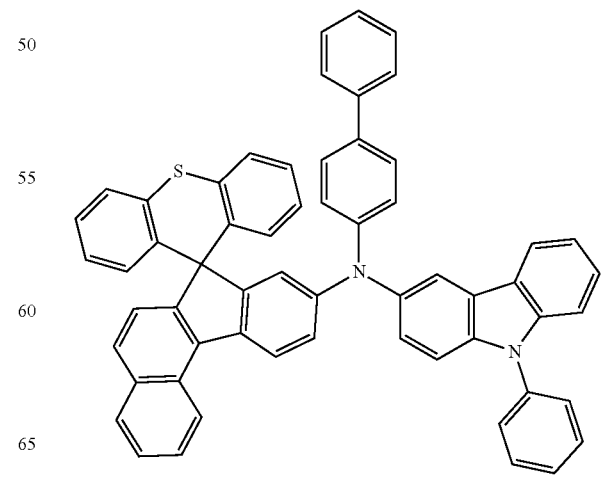

219
-continued
(195)
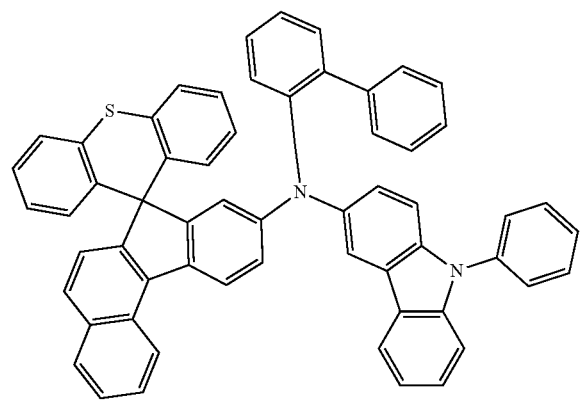
(196)
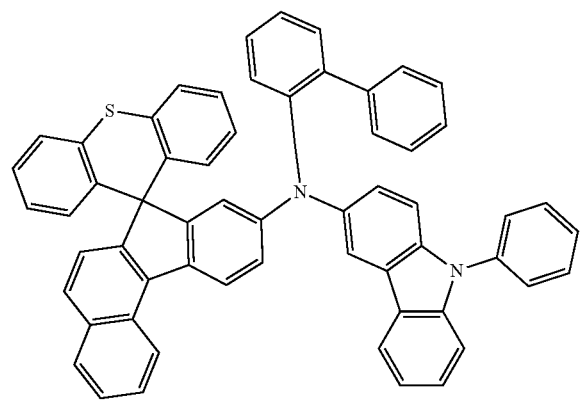
(197)
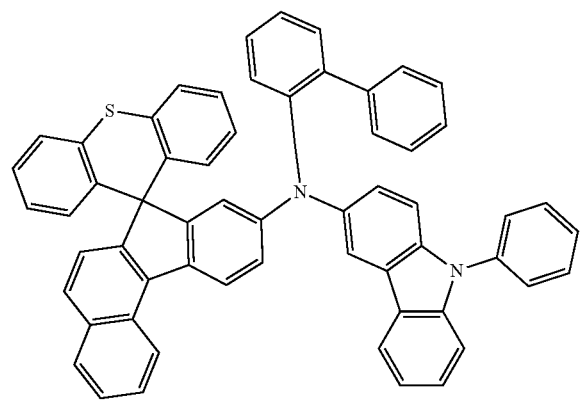
220
-continued
(198)
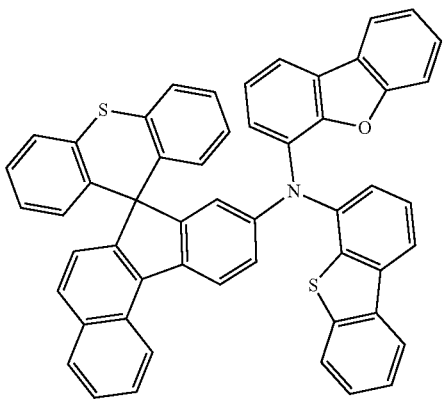
(199)
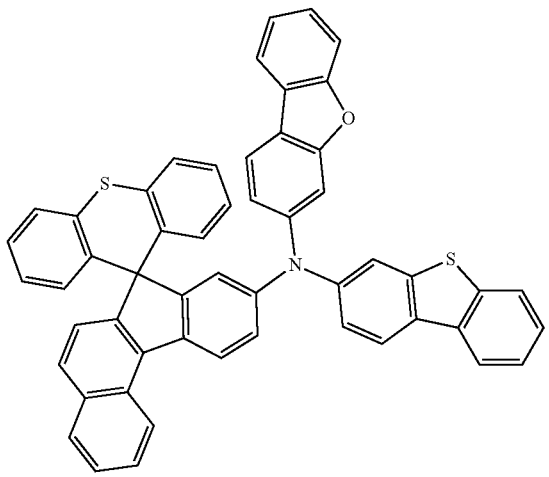
(200)
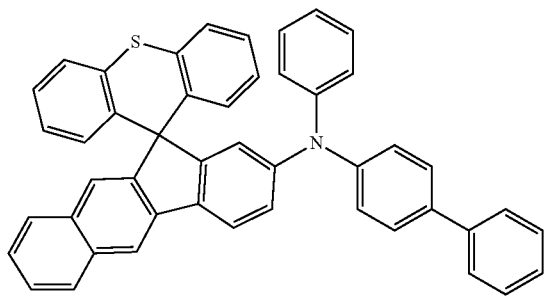
(201)
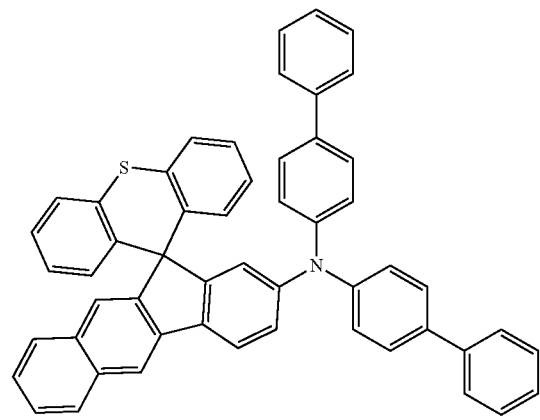

(202)
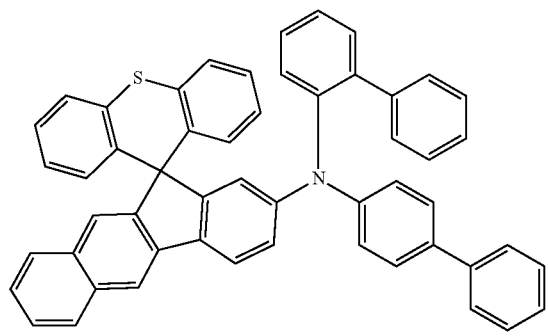
(203)
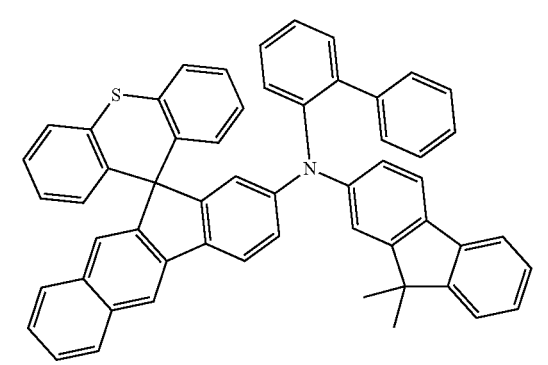
(204)
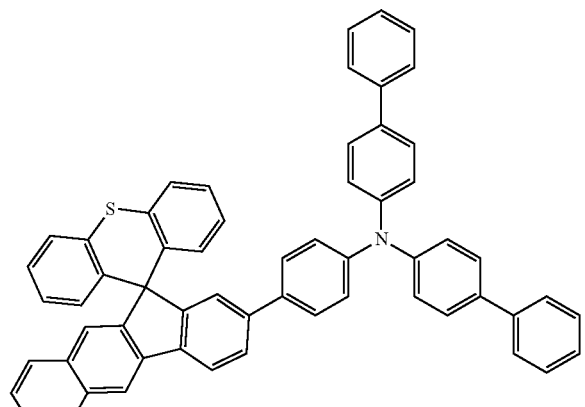
(205)
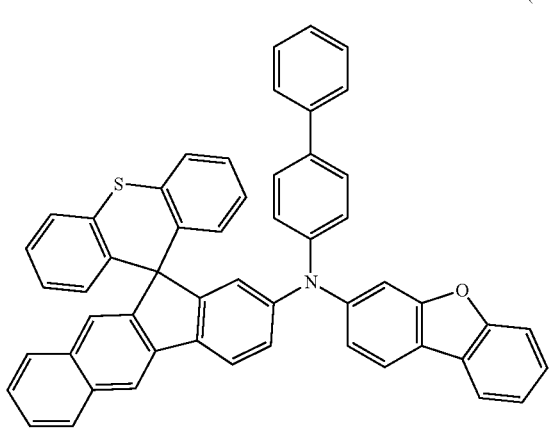
(206)
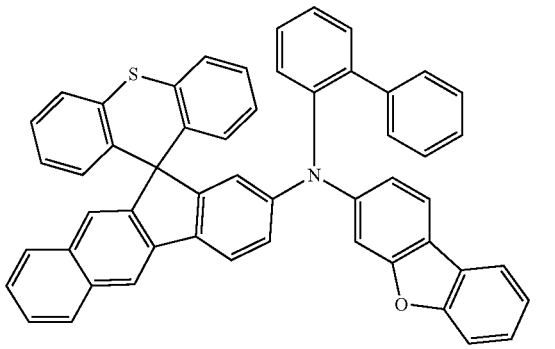
(207)
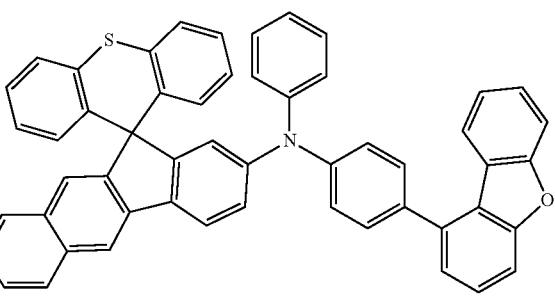
(208)
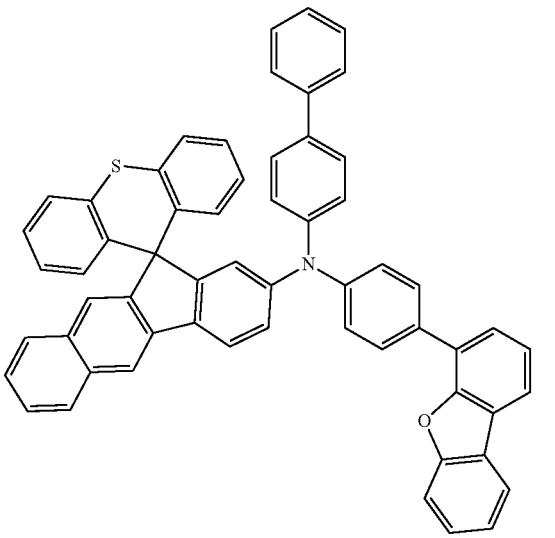

223
-continued
(209)
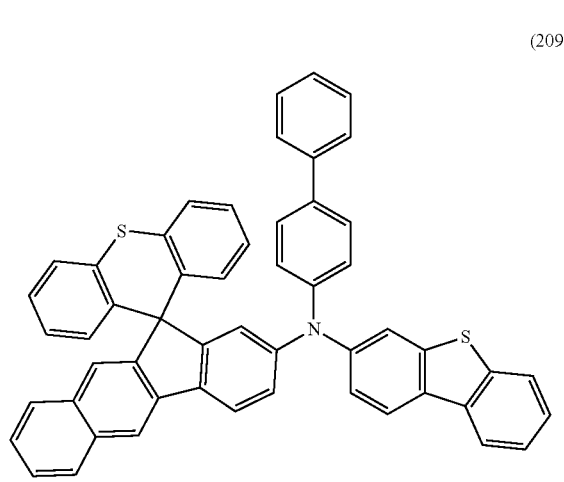
(210)
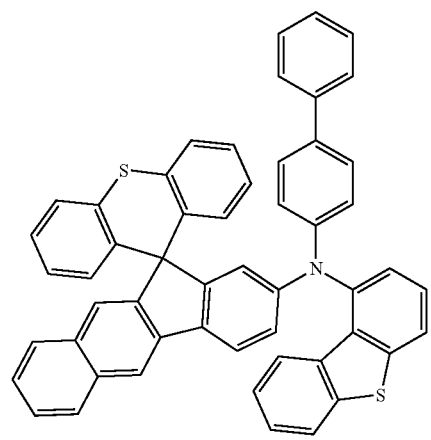
(211)
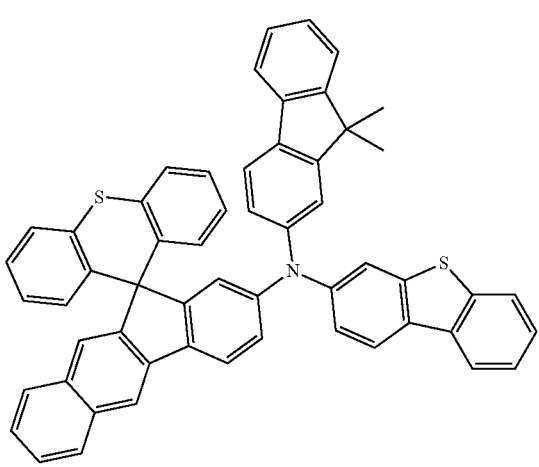
224
-continued
(212)
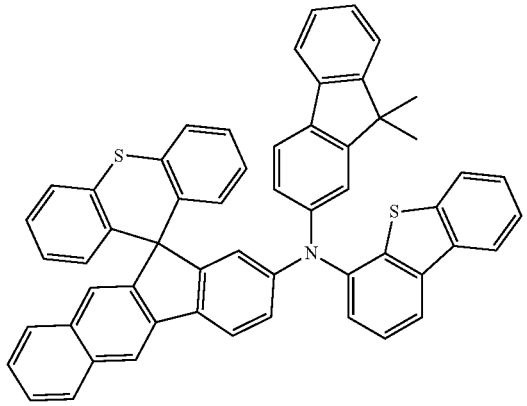
(213)
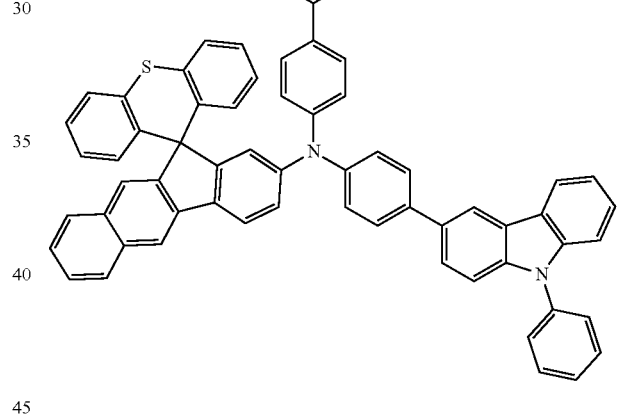
(214)
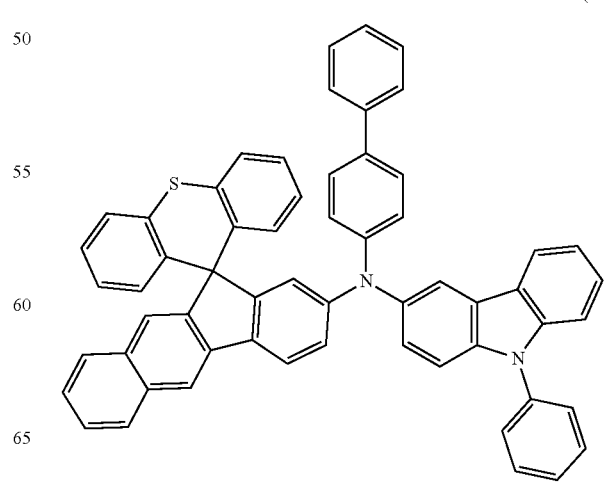

-continued
(215)
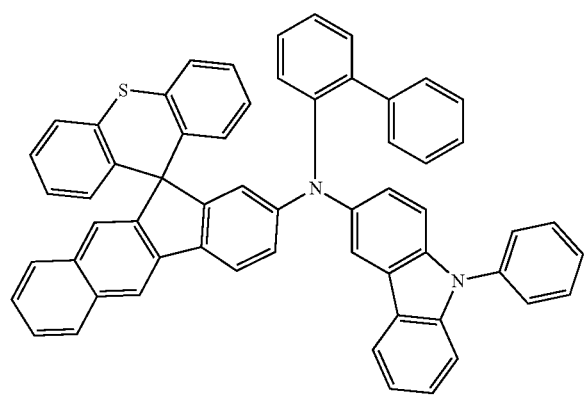
(216)
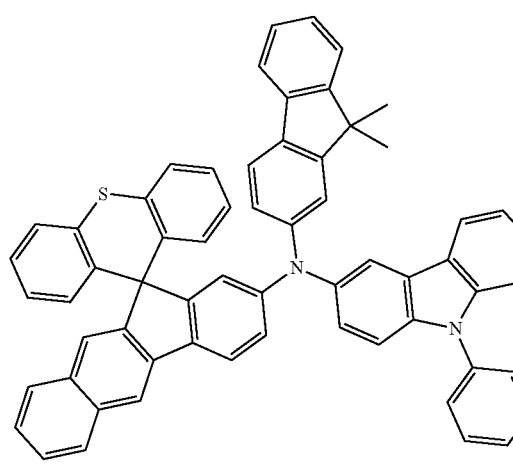
(217)
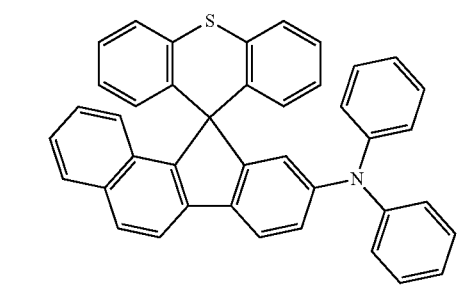
(218)
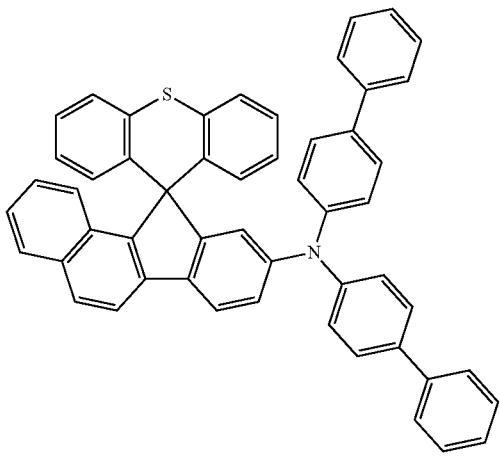
-continued
(219)
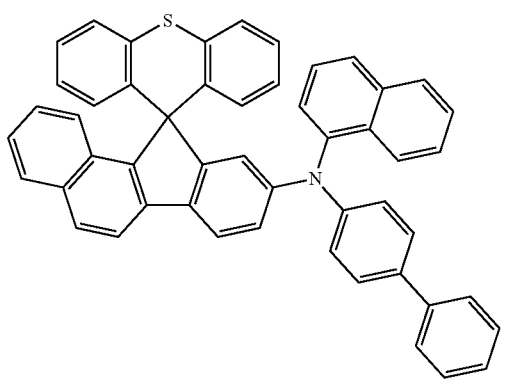
(220)
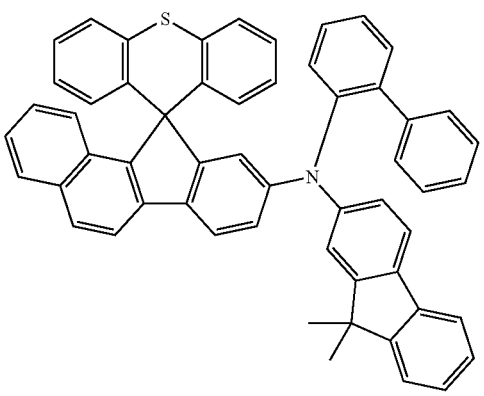
(221)
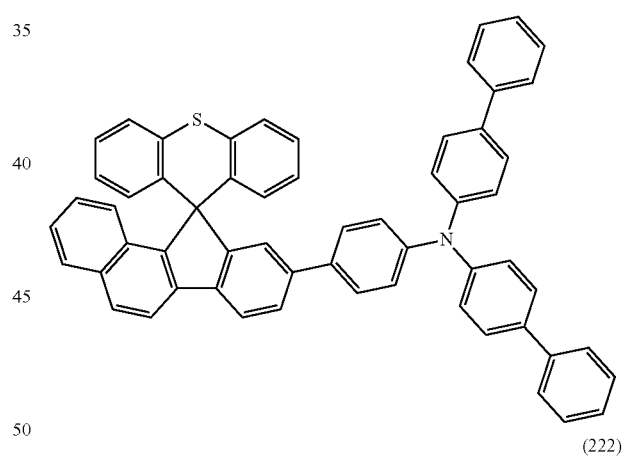
(222)
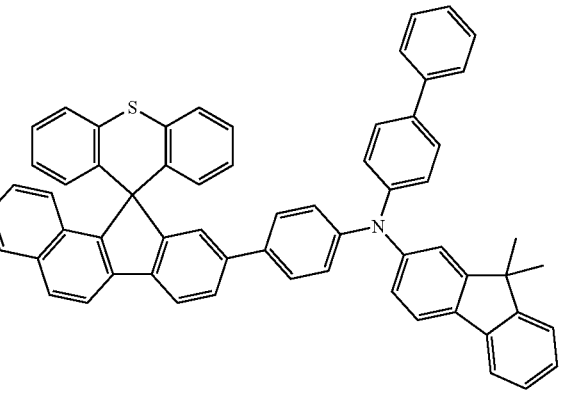

(223)
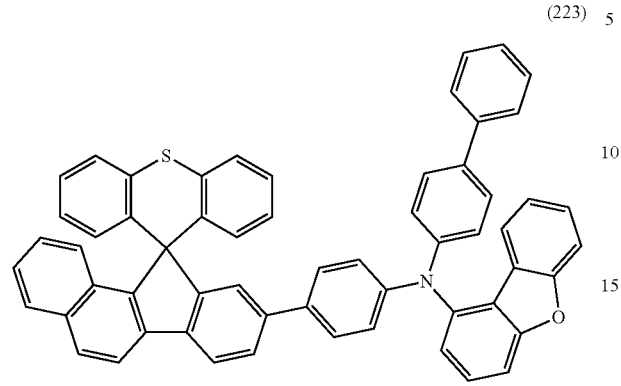
(224)
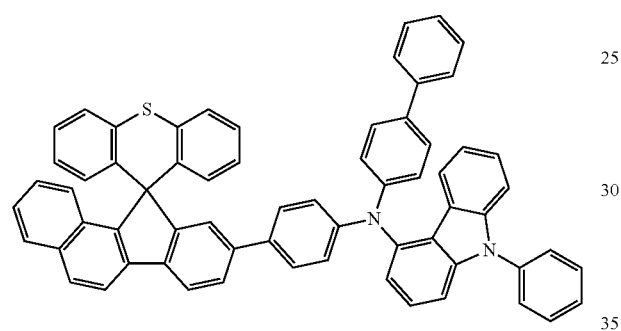
(225)
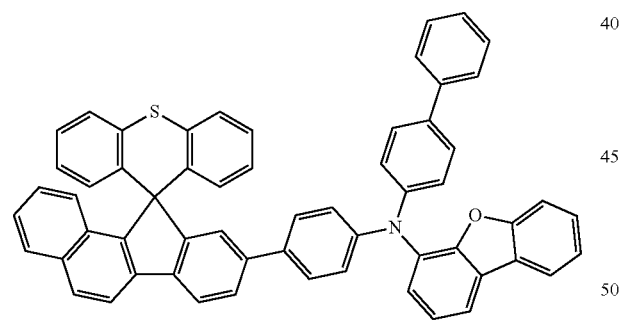
(226)
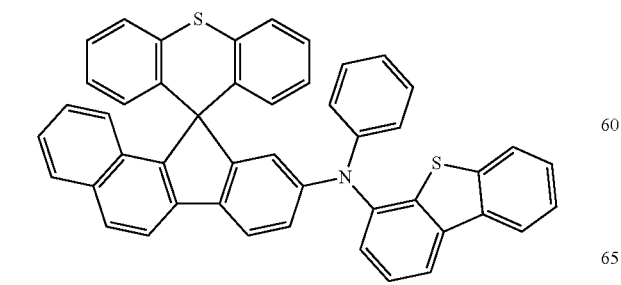
(227)
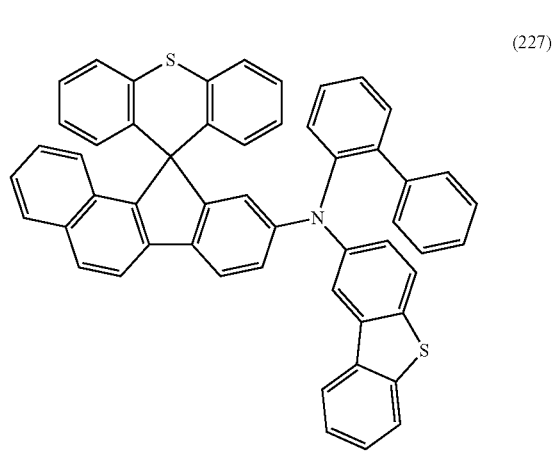
(228)
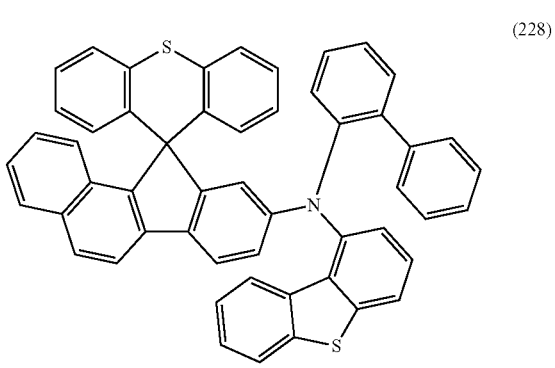
(229)
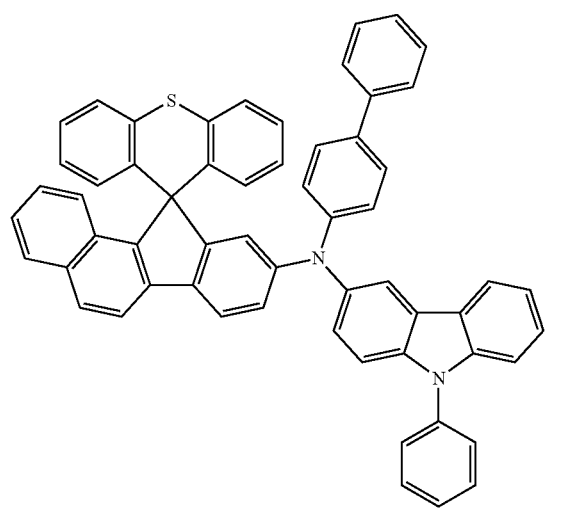

229
-continued
(230)
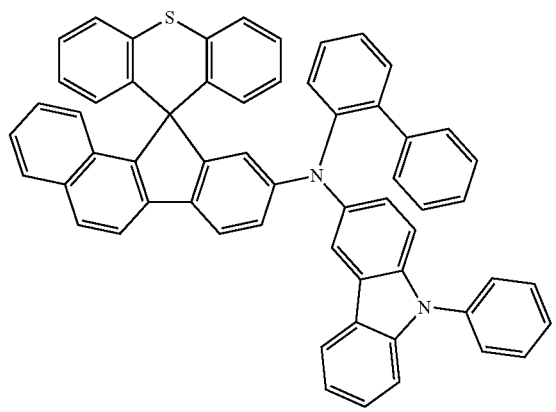
(231)
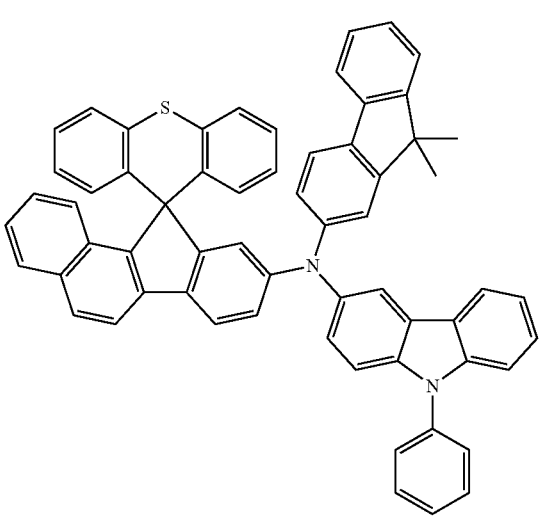
(232)
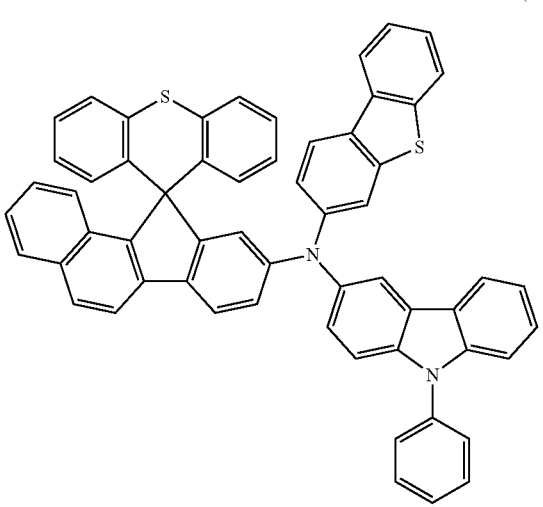
230
-continued
(233)
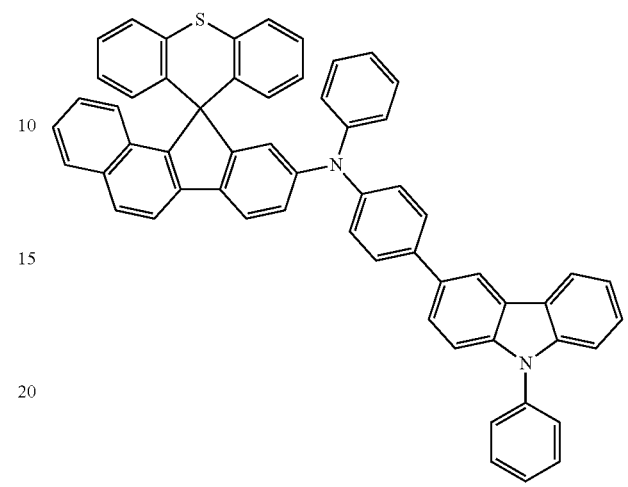
(234)
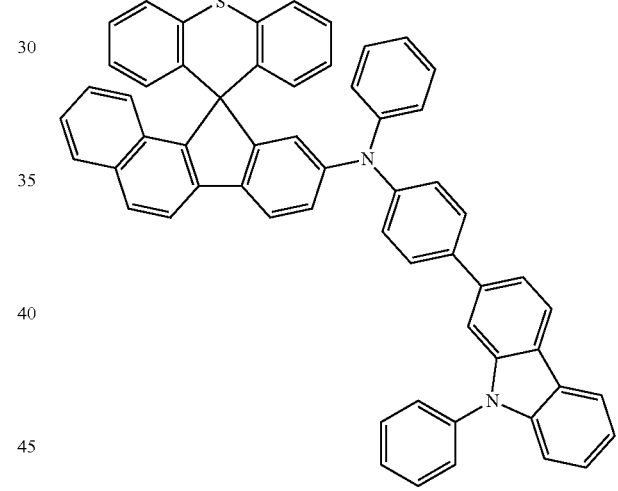
(235)
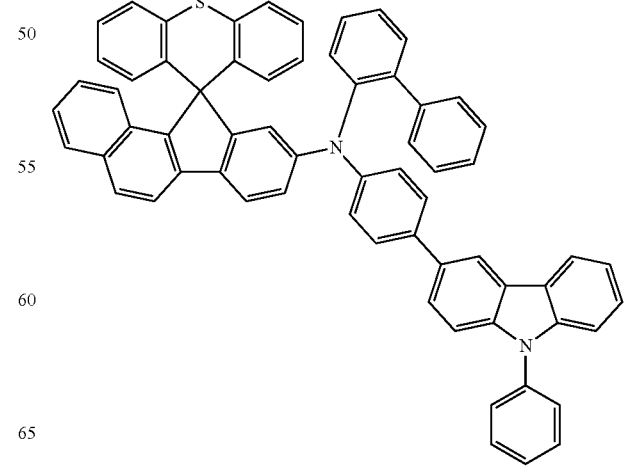

(236)
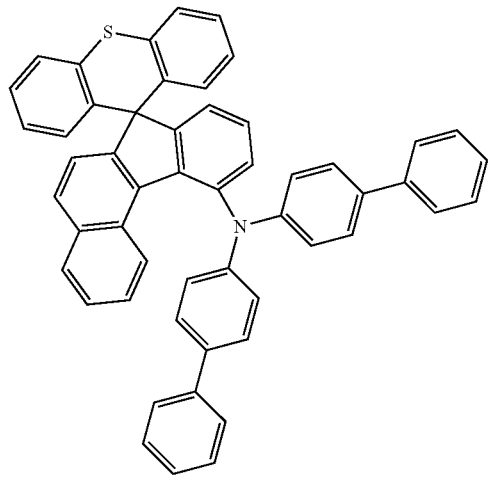
(237)
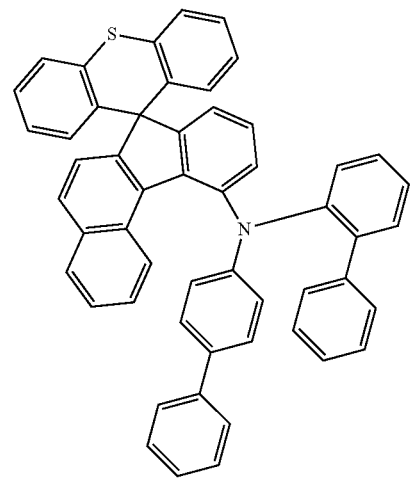
(238)
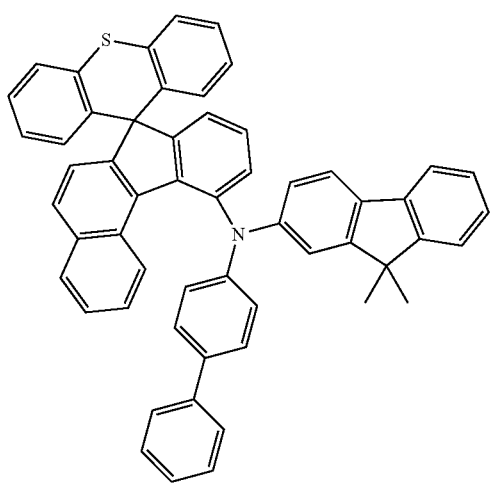
(239)
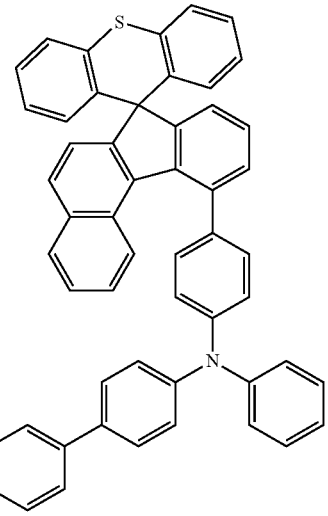
(240)
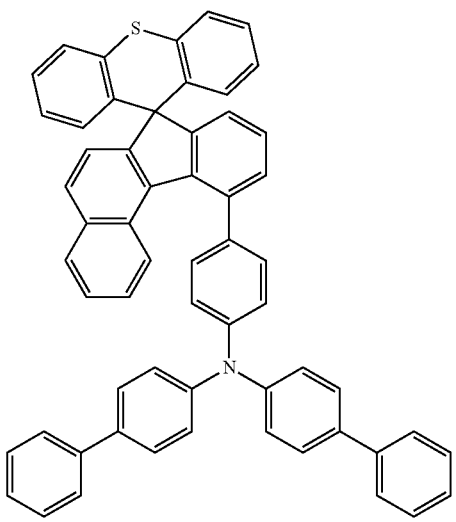
(241)
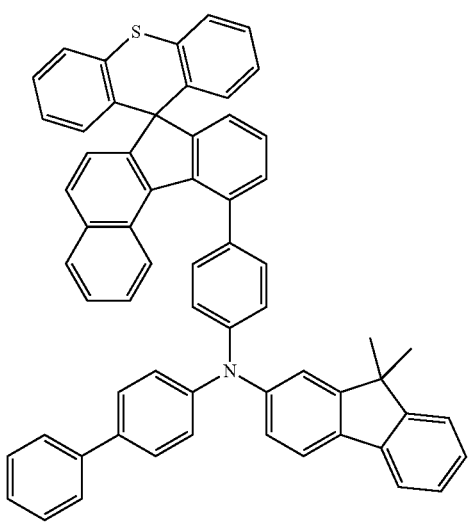

(242)
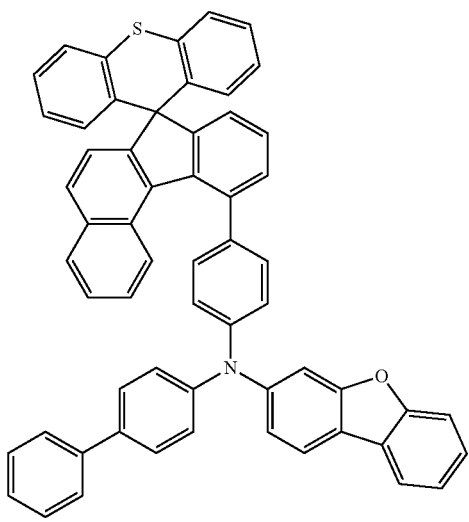
(243)
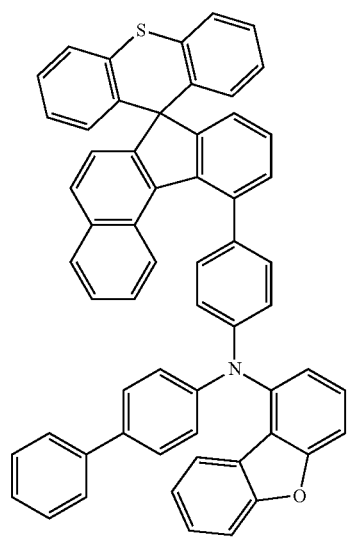
(244)
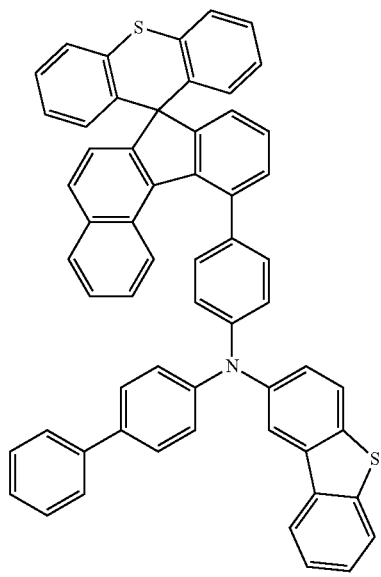
(245)
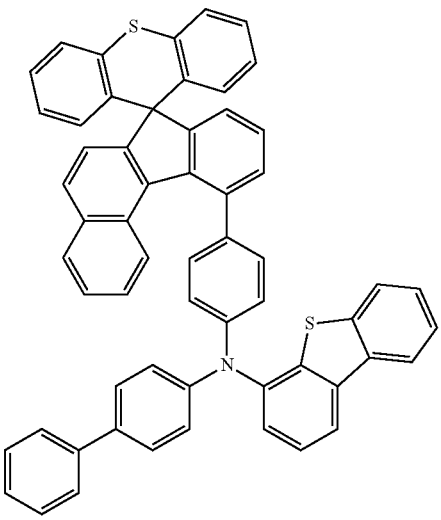
(246)
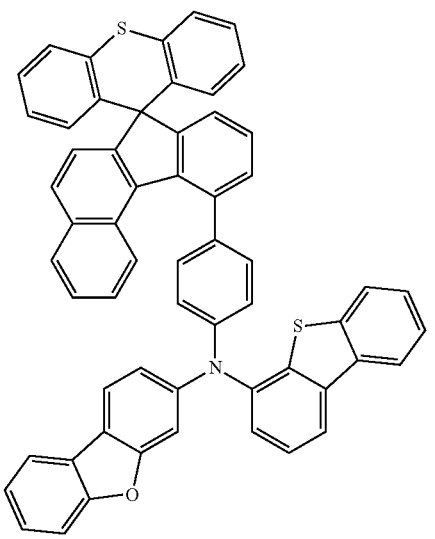
(247)
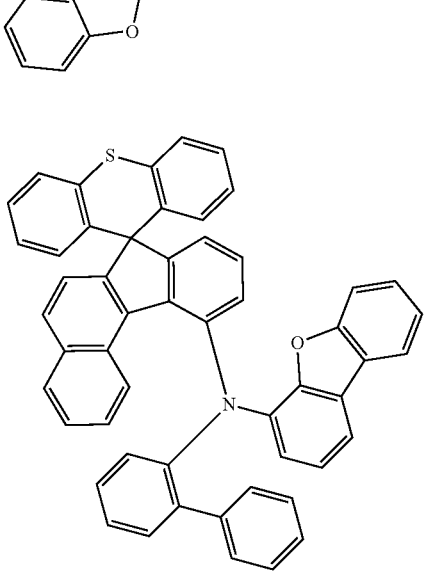

-continued
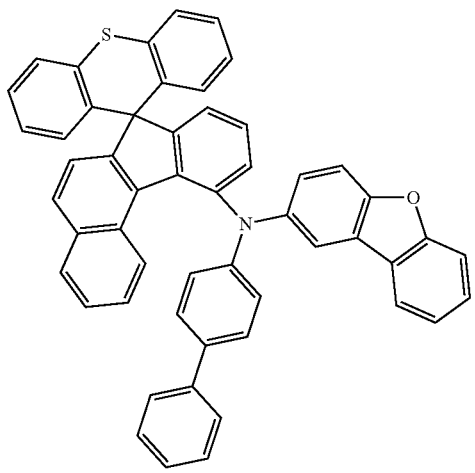
(248)
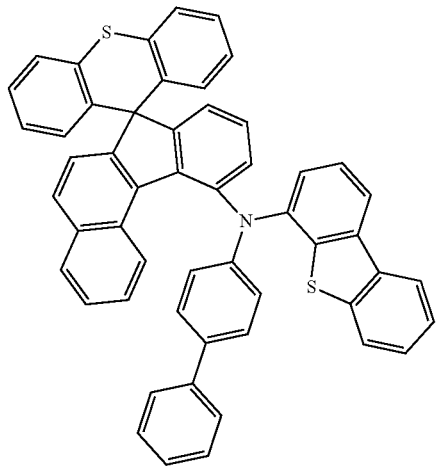
(251)
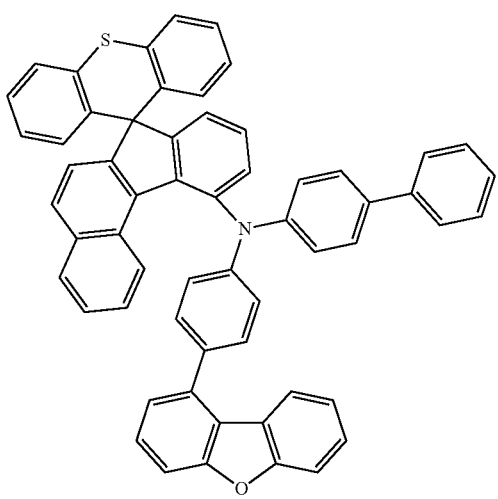
(249)
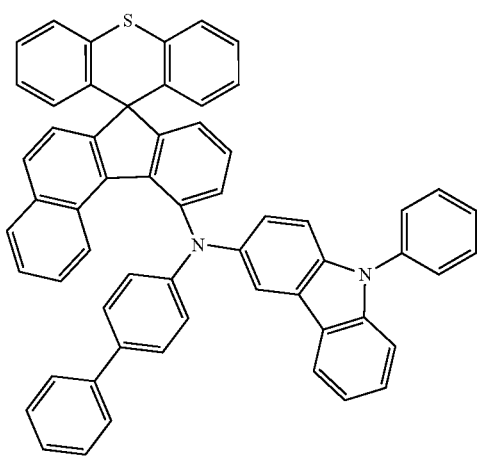
(252)
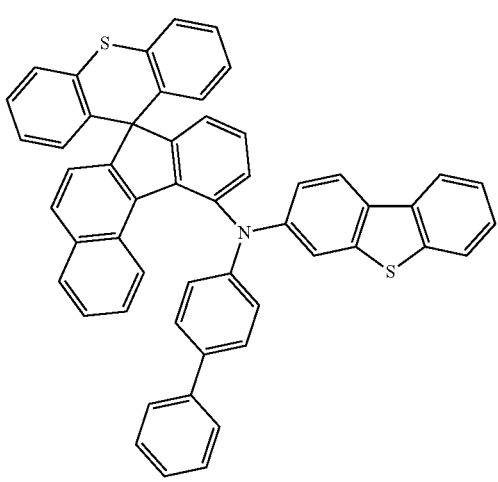
(250)
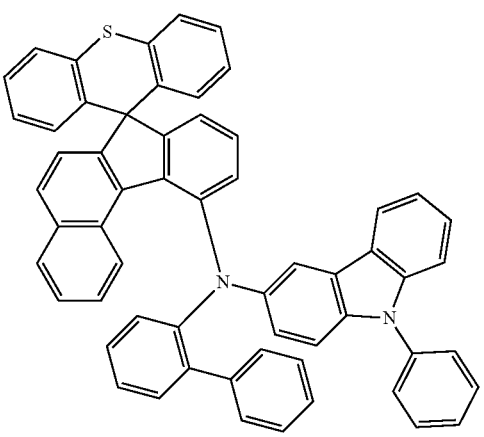
(253)

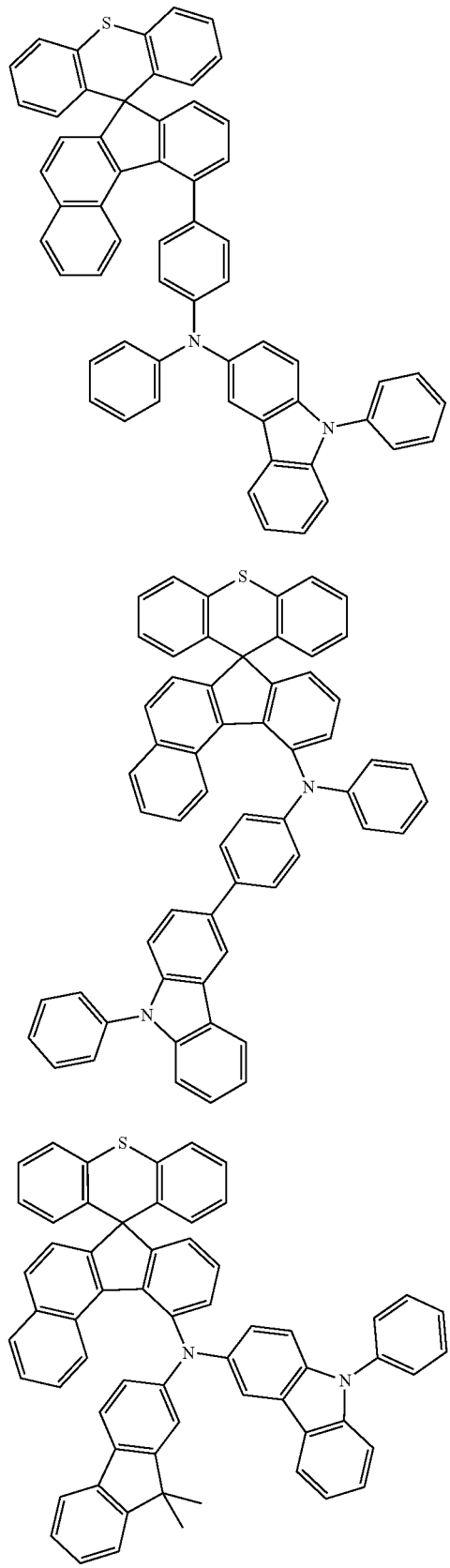
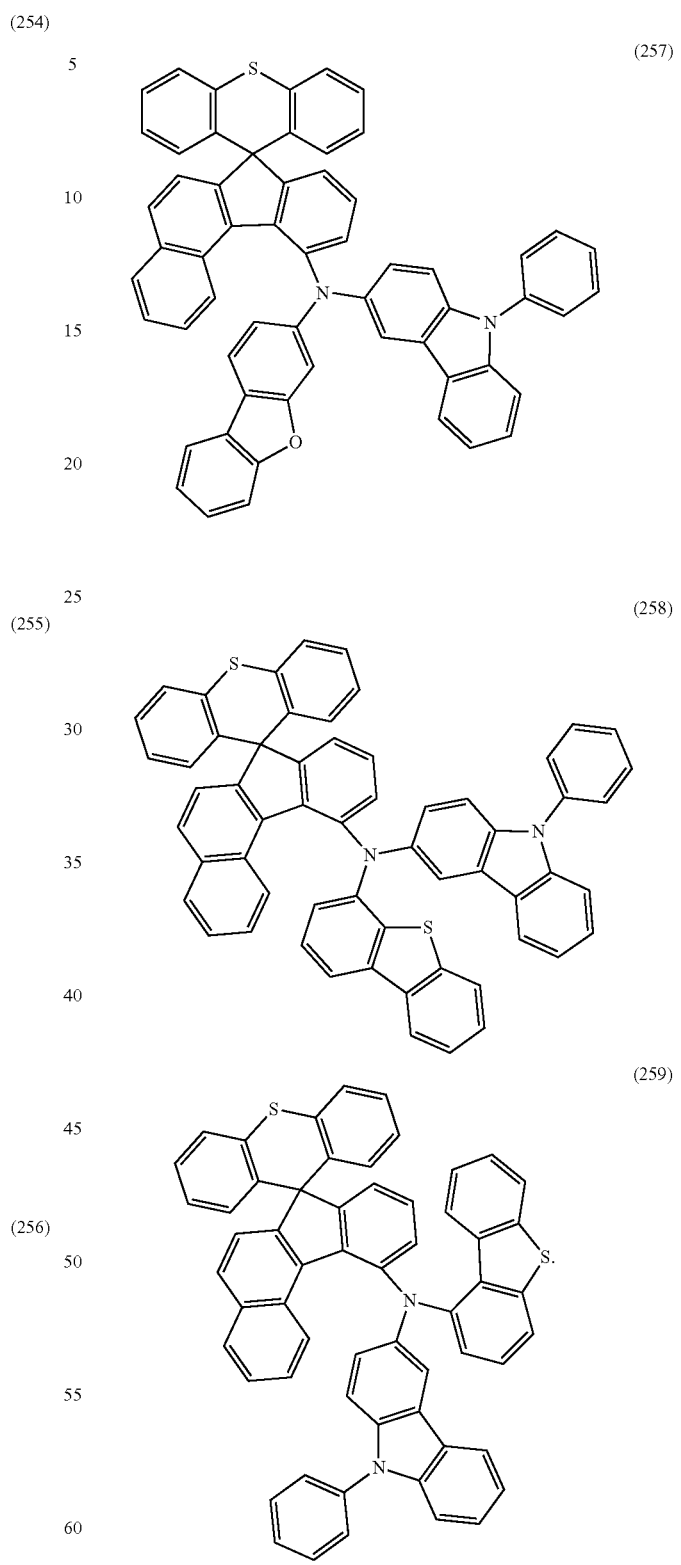
3. The organic compound of claim 1, wherein the compound represented by any one of the Chemical Formulas 3 to 5 is a compound represented by the following Chemical Formula 6 or 7:

[Chemical Formula 6]

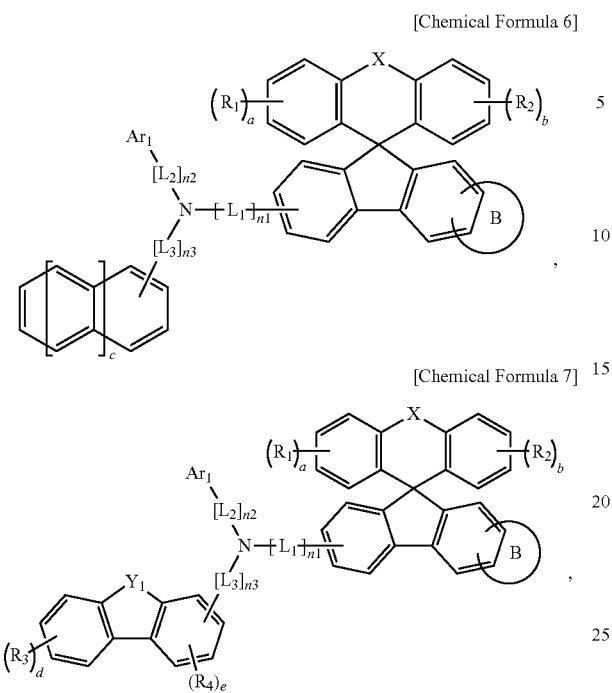

[Chemical Formula 7]

(wherein in Chemical Formulas 6 and 7,

X, $R_1$, $R_2$, a, b, $L_1$ to $L_3$, n1 to n3, and $Ar_1$ are as defined in claim 1, respectively, ring B is a $C_6$ monocyclic aromatic ring, c is 0 or 1, $Y_1$ is selected from the group consisting of O, S, C($Ar_3$)($Ar_4$) and N($Ar_5$), d is an integer ranging from 0 to 4, e is an integer ranging from 0 to 3, $R_3$, $R_4$, and $Ar_3$ to $Ar_5$ are the same as or different from each other, each independently being selected from the group consisting of hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and the monocyclic aromatic ring and the polycyclic aromatic ring of the ring B, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_3$, $R_4$, and $Ar_3$ to $Ar_5$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other).

4. The organic compound of claim 1, wherein the compound represented by any one of the Chemical Formulas 3 to 5 is a compound represented by any one of the following Chemical Formulas 8 to 13:

[Chemical Formula 8]

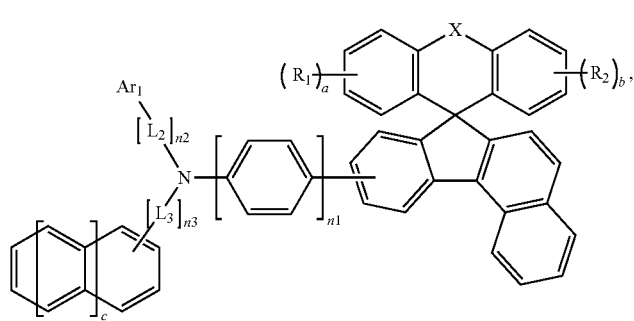

[Chemical Formula 9]

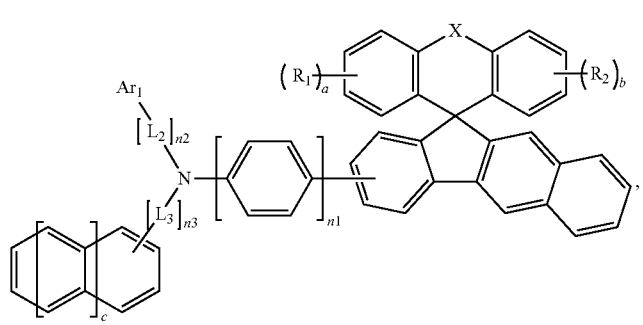

[Chemical Formula 10]

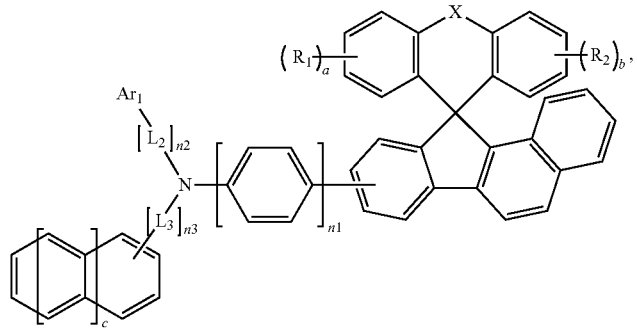

[Chemical Formula 11]

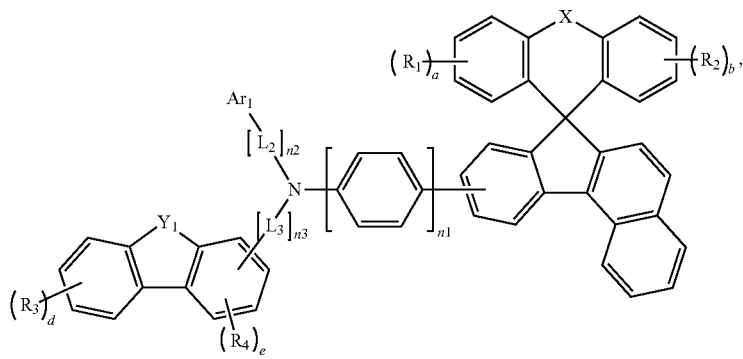

[Chemical Formula 12]

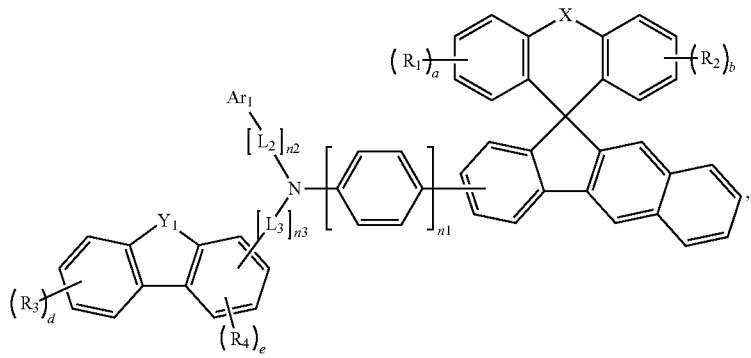

[Chemical Formula 13]

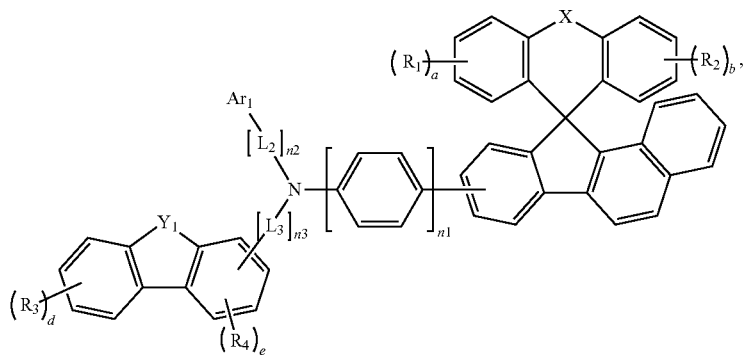

(wherein in Chemical Formulas 8 to 13,
X, $R_1$, $R_2$, a, b, $L_2$ to $L_3$, n1 to n3, and $Ar_1$ are as defined in claim 1, respectively,
c is 0 or 1,
$Y_1$ is selected from the group consisting of O, S, C($Ar_3$)($Ar_4$), and N($Ar_5$),
d is an integer ranging from 0 to 4,
e is an integer ranging from 0 to 3,
$R_3$, $R_4$, and $Ar_3$ to $Ar_5$ are the same as or different from each other, each independently being selected from the group consisting of hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_3$, $R_4$, and $Ar_3$ to $Ar_5$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other).

5. The organic compound of claim 1, wherein the compound represented by any one of the Chemical Formulas 3 to 5 is a compound represented by any one of the following Chemical Formulas 14 to 22:

[Chemical Formula 14]

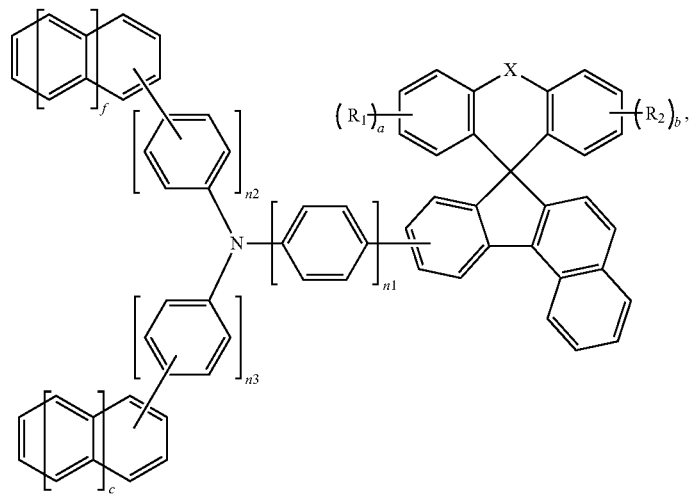

[Chemical Formula 15]

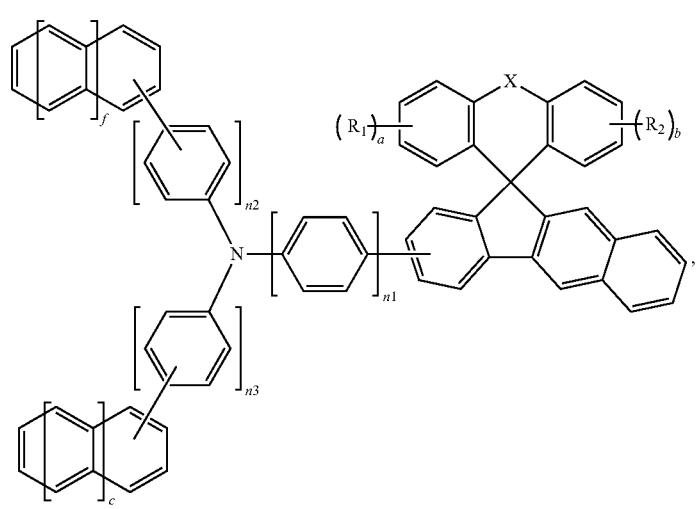

-continued
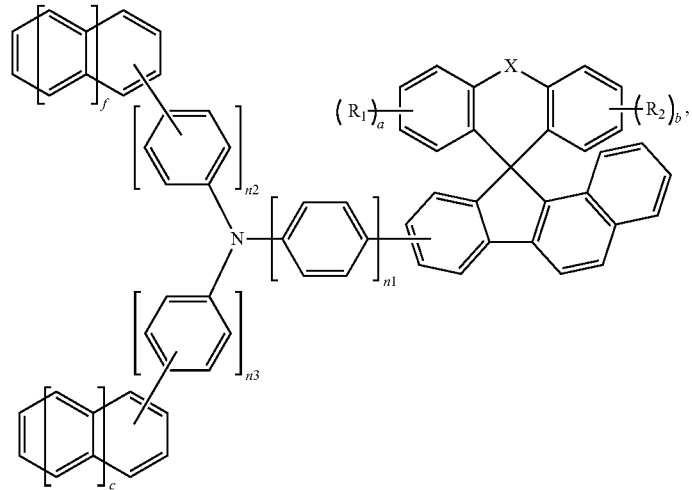
[Chemical Formula 16]
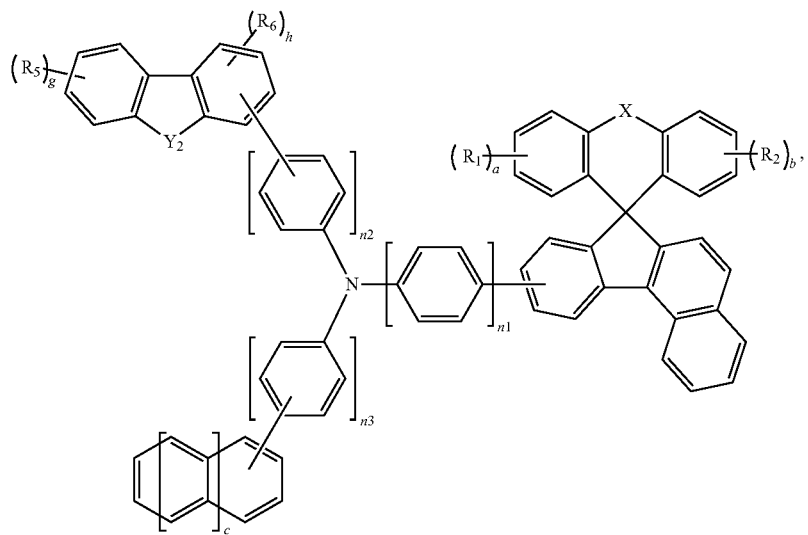
[Chemical Formula 17]
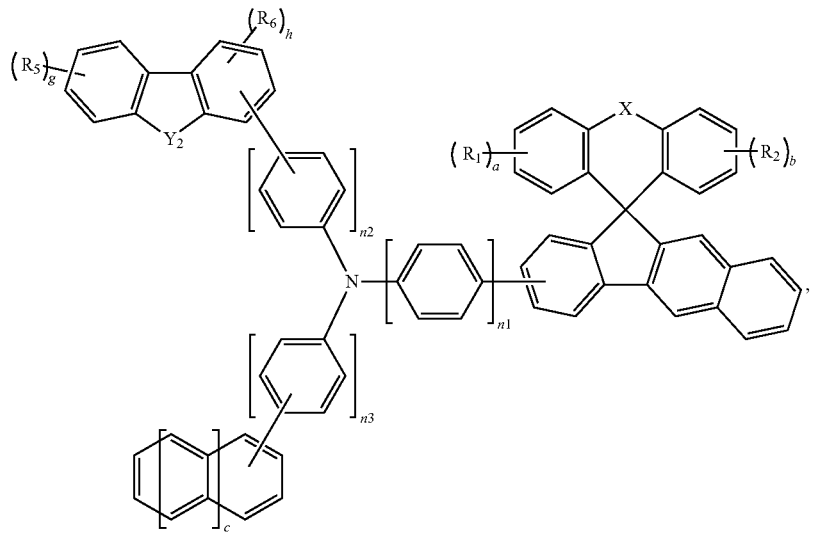
[Chemical Formula 18]

-continued
[Chemical Formula 19]
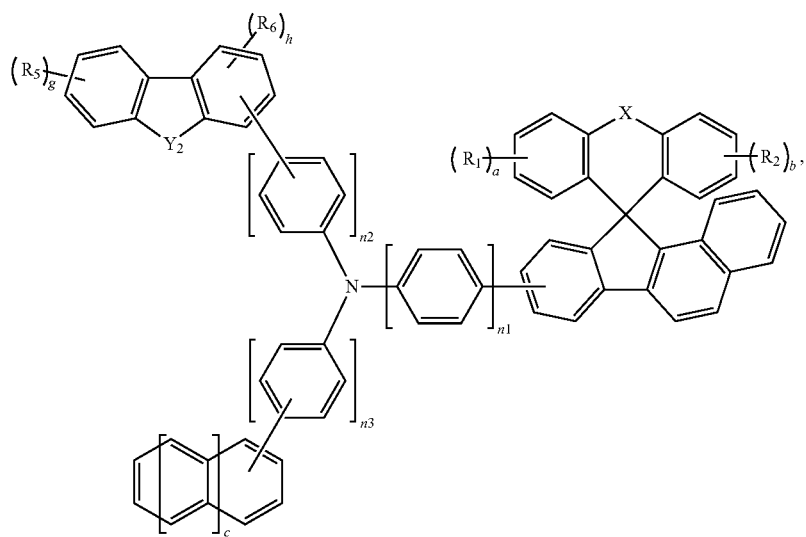
[Chemical Formula 20]
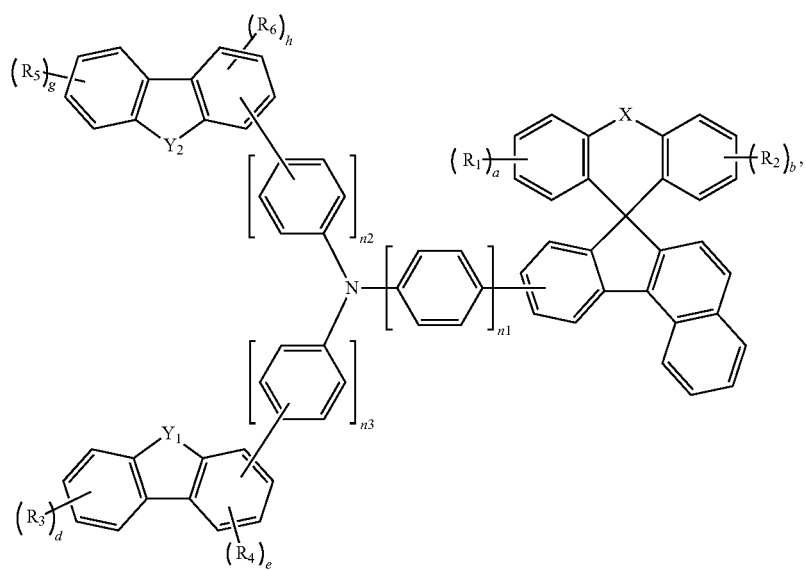
[Chemical Formula 21]
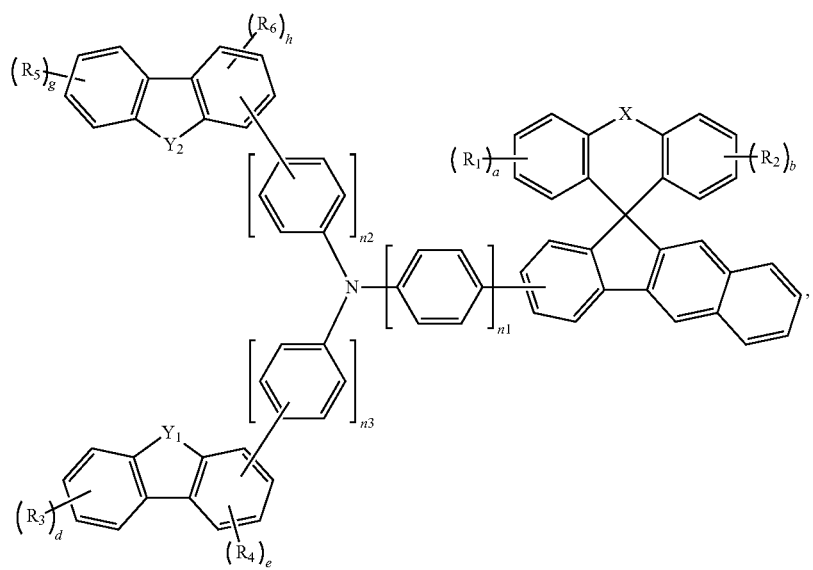

-continued

[Chemical Formula 22]

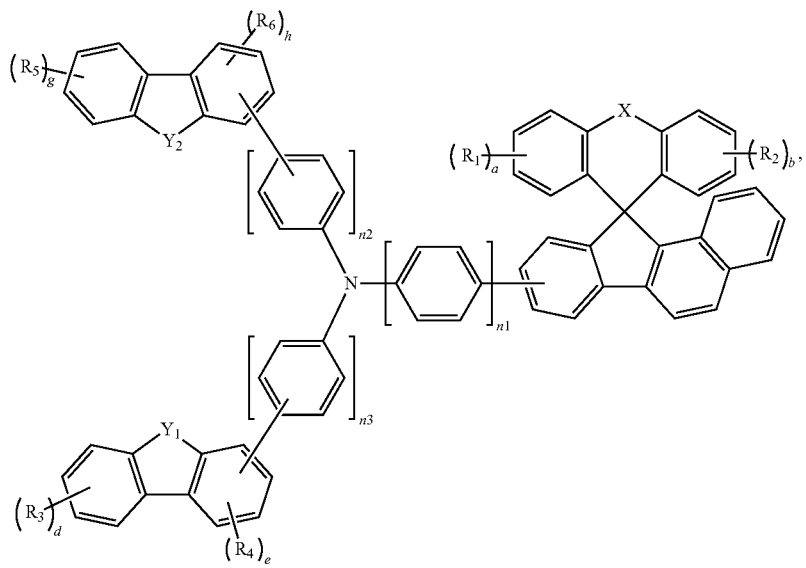

(wherein in Chemical Formulas 14 to 22,
X, $R_1$, $R_2$, a, b, and n1 to n3 are as defined in claim 1, respectively,
each of c and f is 0 or 1,
$Y_1$ is selected from the group consisting of O, S, $C(Ar_3)(Ar_4)$, and $N(Ar_5)$,
$Y_2$ is the same as or different from $Y_1$ and is selected from the group consisting of O, S, $C(Ar_6)(Ar_7)$, and $N(Ar_8)$,
each of d and g is an integer ranging from 0 to 4,
each of e and h is an integer ranging from 0 to 3,
$R_3$ to $R_6$ and $Ar_3$ to $Ar_8$ are the same as or different from each other, each independently being selected from the group consisting of hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and
the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_3$ to $R_6$ and $Ar_3$ to $Ar_8$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other).

6. An organic electroluminescence device comprising (i) an anode, (ii) a cathode, and (iii) one or more organic layers interposed between the anode and the cathode,
wherein at least one of the one or more organic layers comprises the organic compound represented by any one of the following Chemical Formulas 3 to 5:

[Chemical Formula 3]

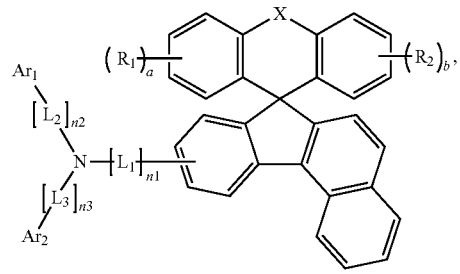

[Chemical Formula 4]

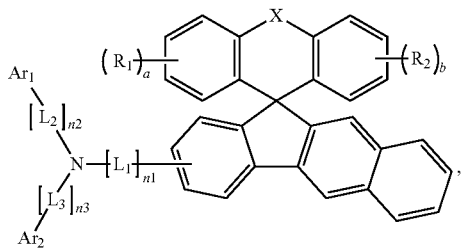

-continued

[Chemical Formula 5]

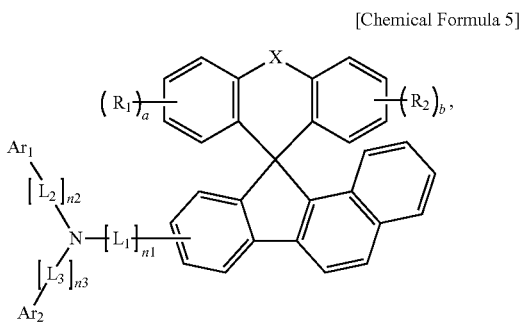

(wherein in Chemical Formulas 3 to 5,
X is O or S,
each of a and b is an integer ranging from 0 to 4,
$R_1$ and $R_2$ are the same as or different from each other, each independently being selected from the group consisting of hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group,
each of n1 to n3 is an integer ranging from 0 to 3,
$L_1$ to $L_3$ are the same as or different from each other, each independently selected from the group consisting of a single bond, a $C_6$ to $C_{18}$ arylene group and a heteroarylene group having 5 to 18 nuclear atoms,
$Ar_1$ and $Ar_2$ are the same as or different from each other, each independently being selected from the group consisting of a $C_6$ to $C_{60}$ aryl group and a heteroaryl group having 5 to 60 nuclear atoms, and
the arylene group and the heteroarylene group of $L_1$ to $L_3$, the aryl group and the heteroaryl group of $Ar_1$ and $Ar_2$, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ and $R_2$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other).

7. The organic electroluminescence device of claim 6, wherein the organic layer comprising the organic compound is a hole transporting layer.

8. The organic electroluminescence device of claim 6, wherein the organic compound represented by any one of e Chemical Formulas 3 to 5 is a compound embodied as a compound selected from a group consisting of:

(1)
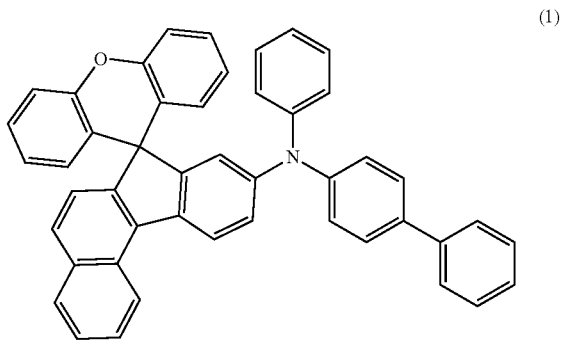

(2)
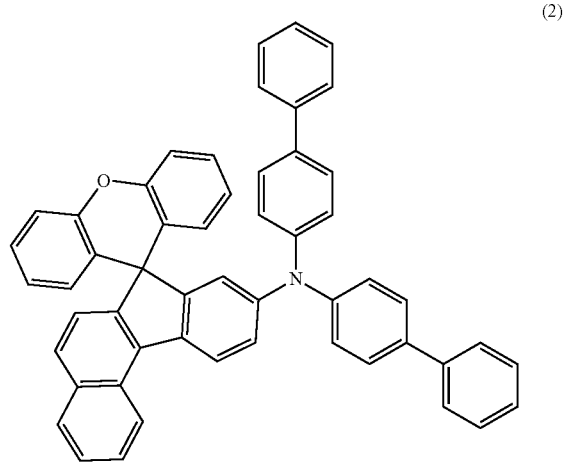

(3)
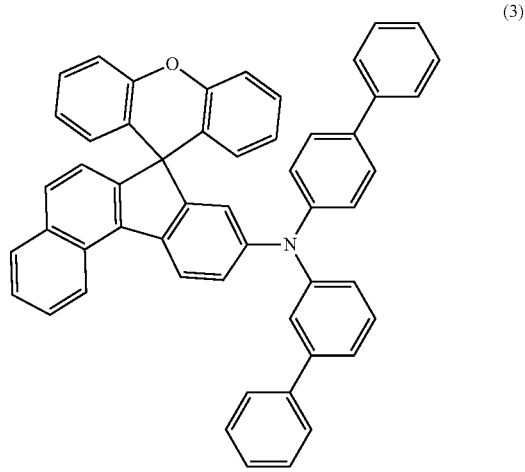

253
-continued
(4)
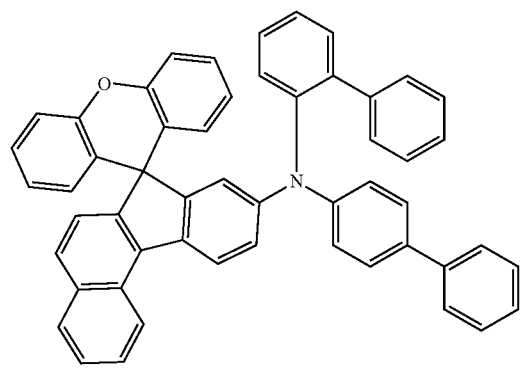
(5)
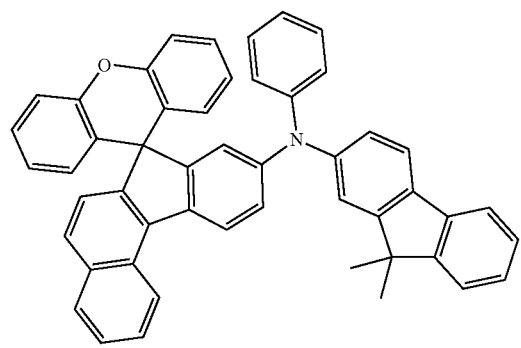
(6)
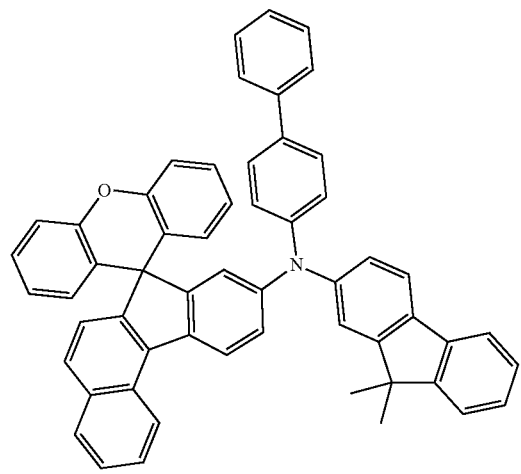
(7)
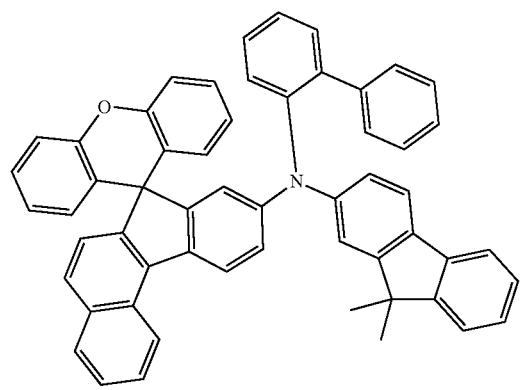
254
-continued
(8)
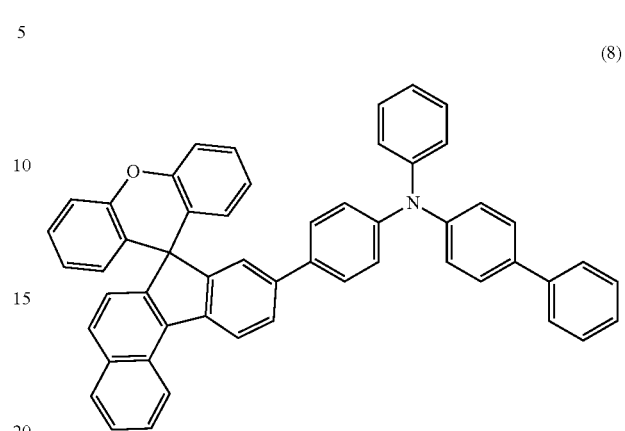
(9)
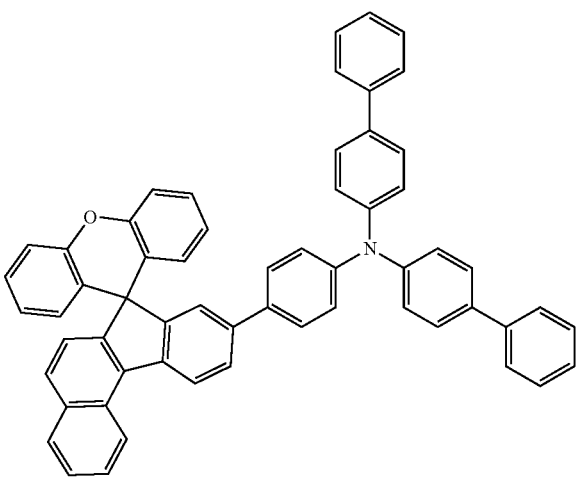
(10)
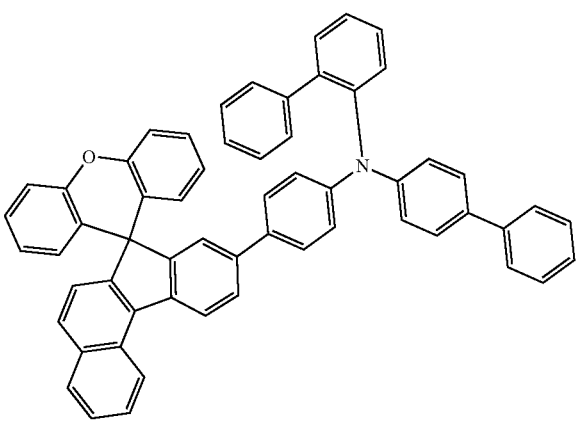

(11)
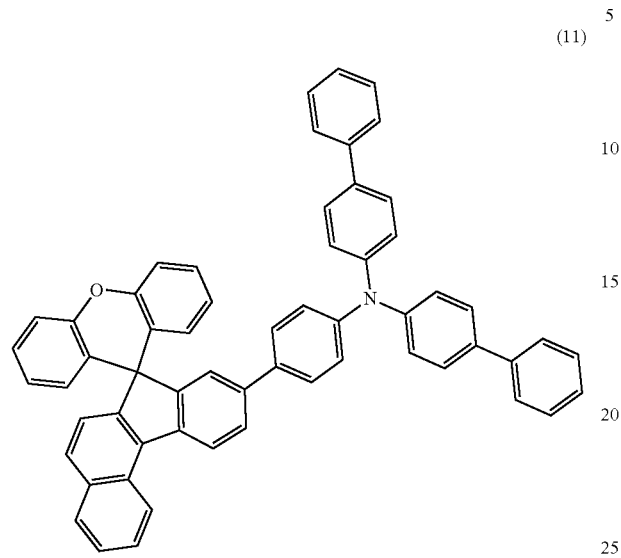
(14)
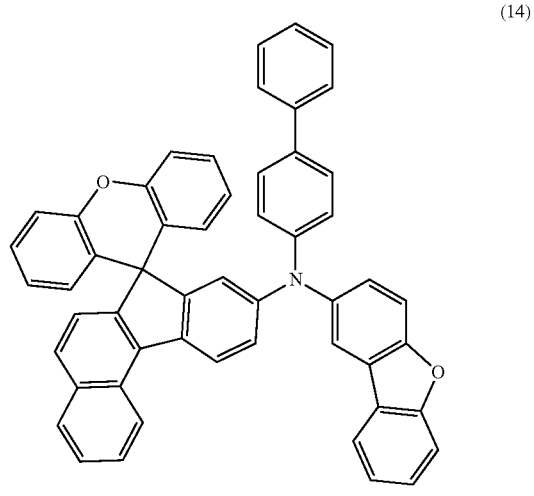
(12)
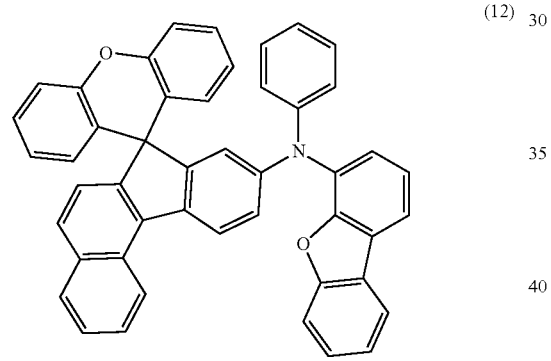
(15)
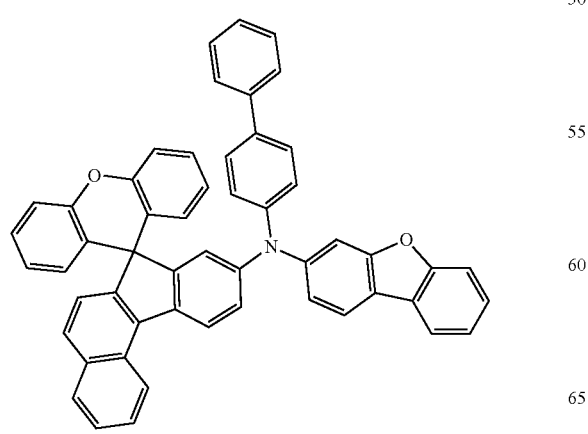
(13)
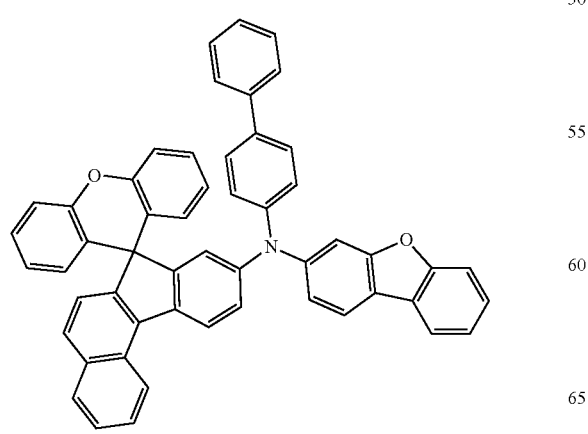
(16)
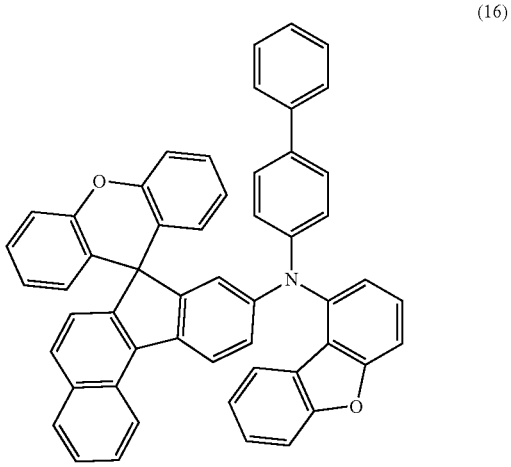

(17) 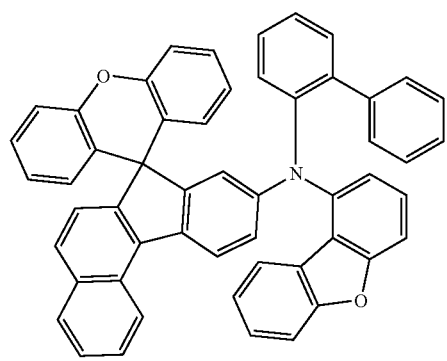
(18) 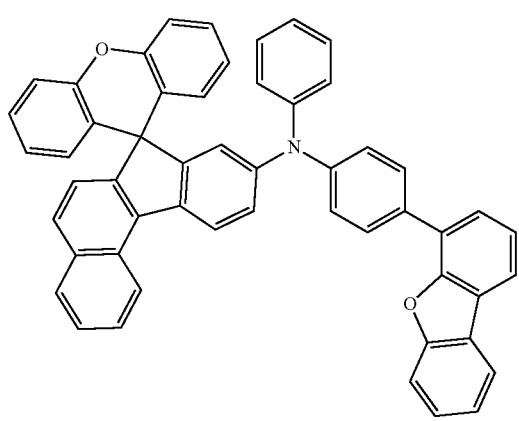
(19) 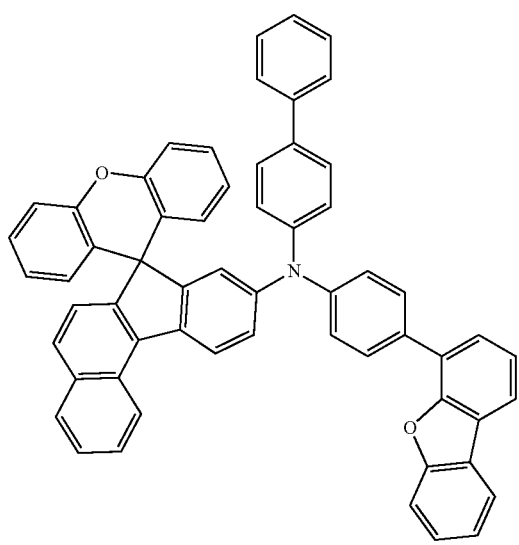
(20) 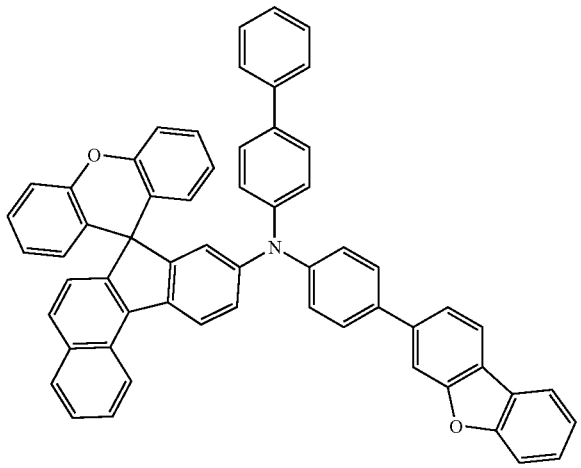
(21) 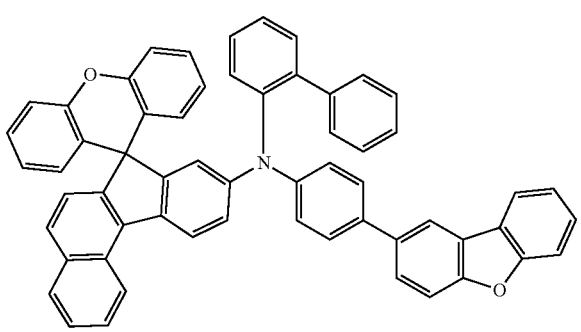
(22) 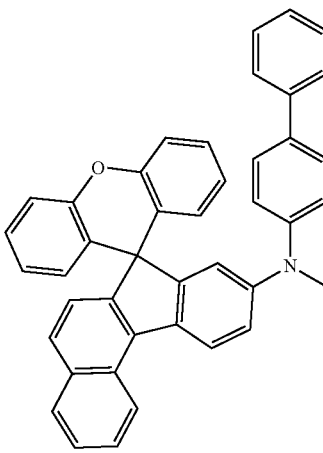
(23) 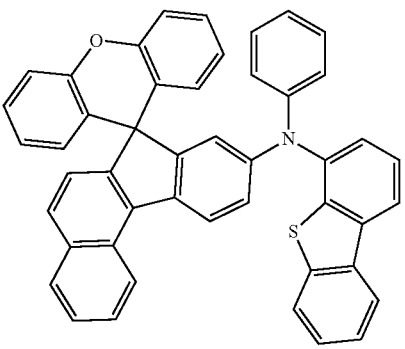

(24)
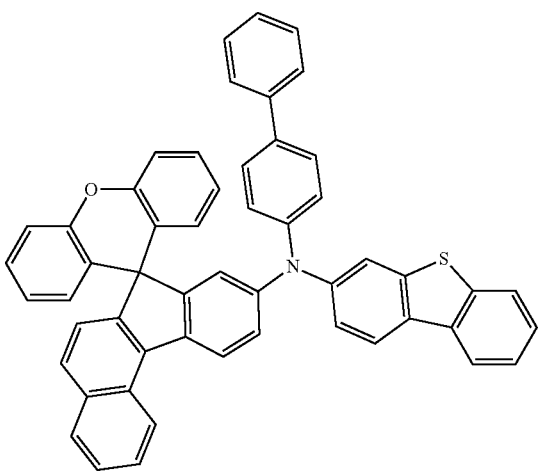
(25)
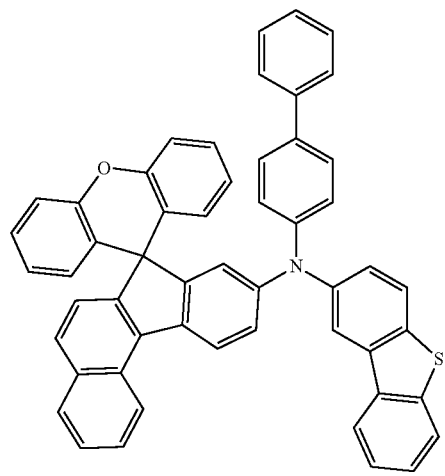
(26)
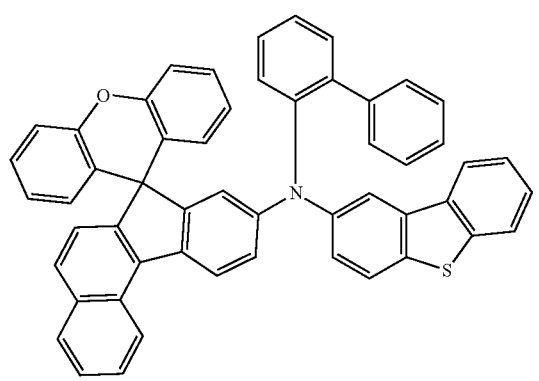
(27)
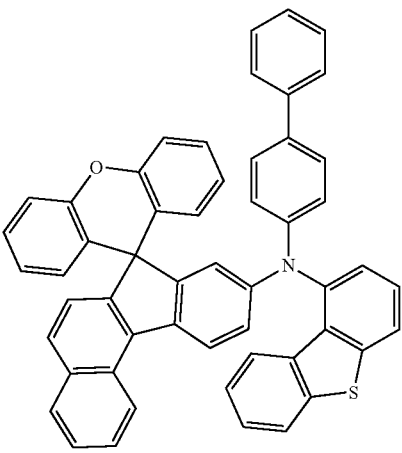
(28)
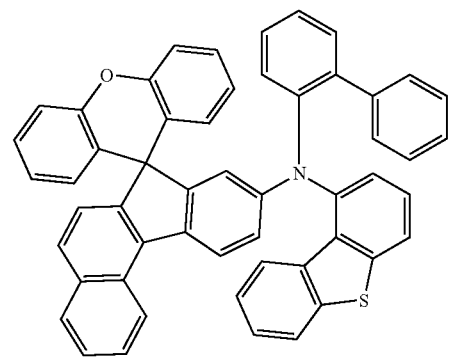
(29)
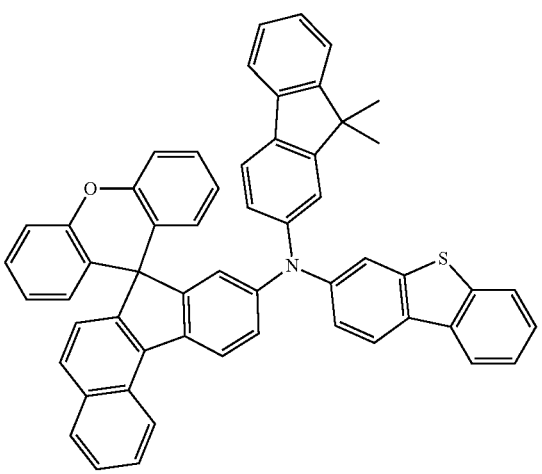

261
-continued
(30)
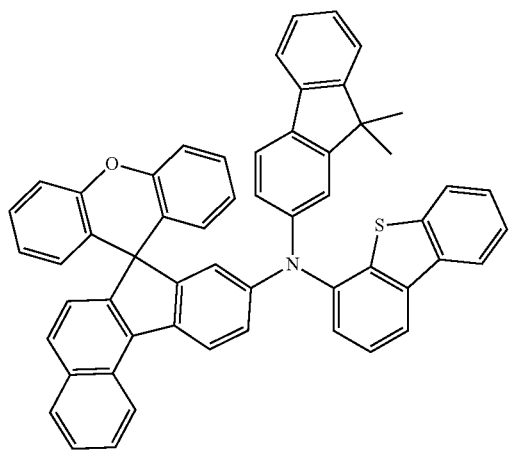
(31)
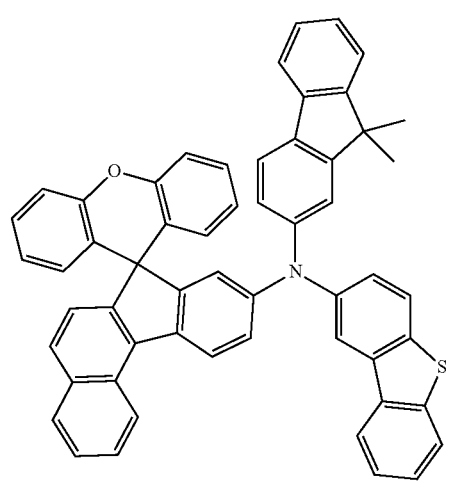
(32)
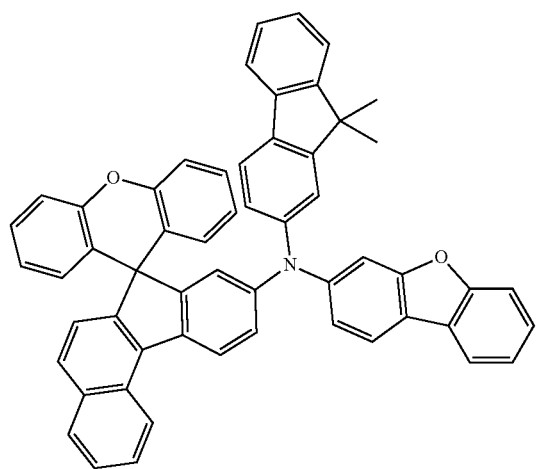
262
-continued
(33)
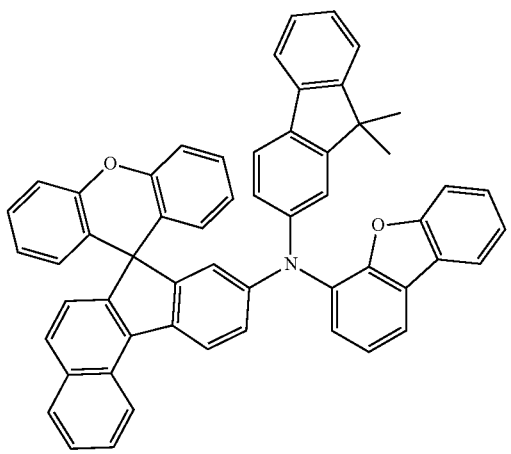
(34)
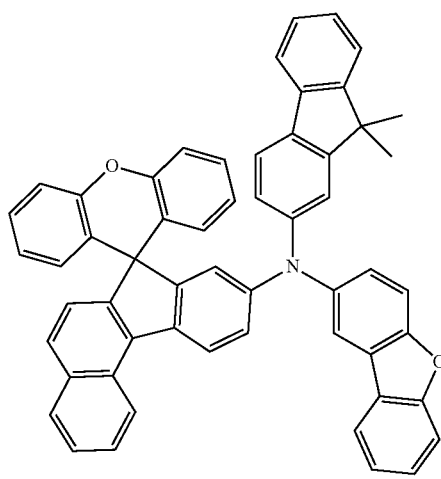
(35)
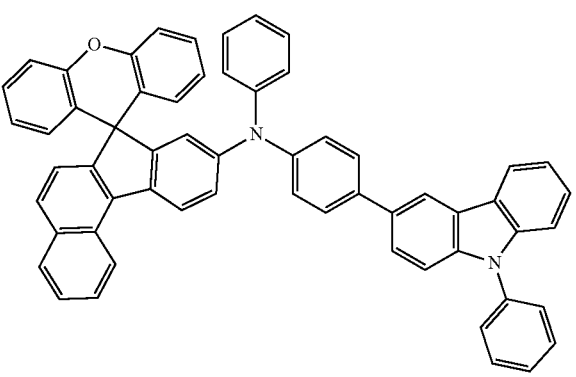

-continued
(36)
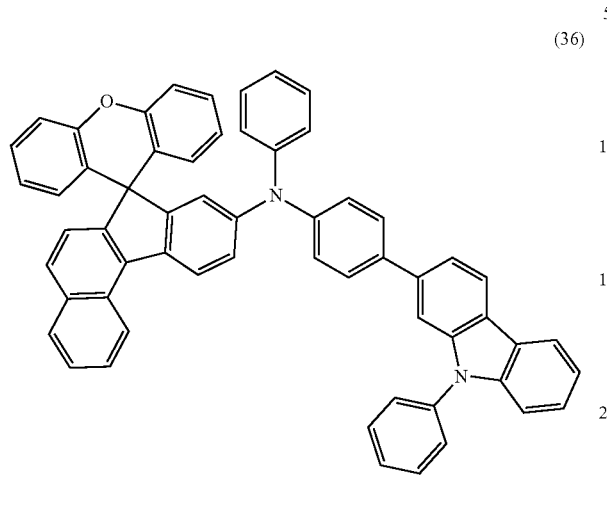
(37)
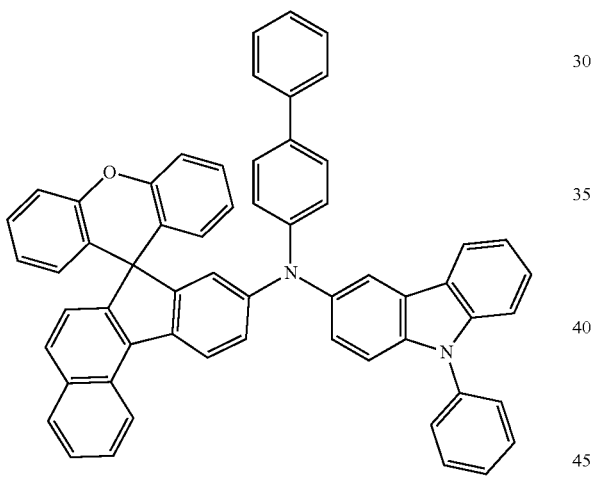
(38)
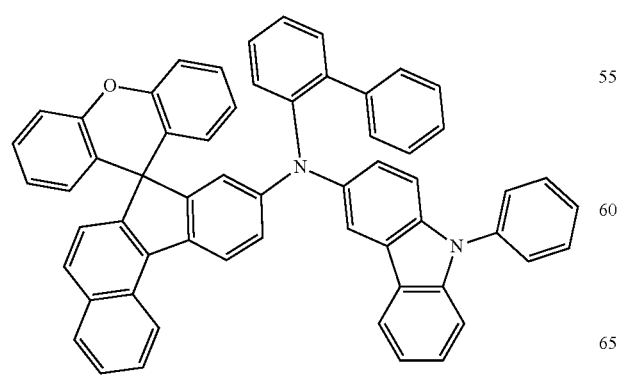
-continued
(39)
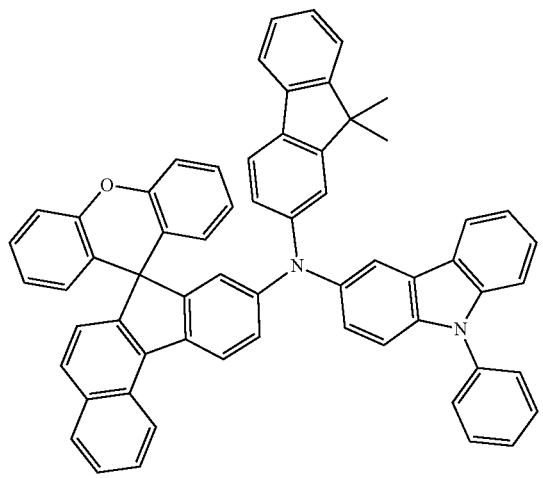
(40)
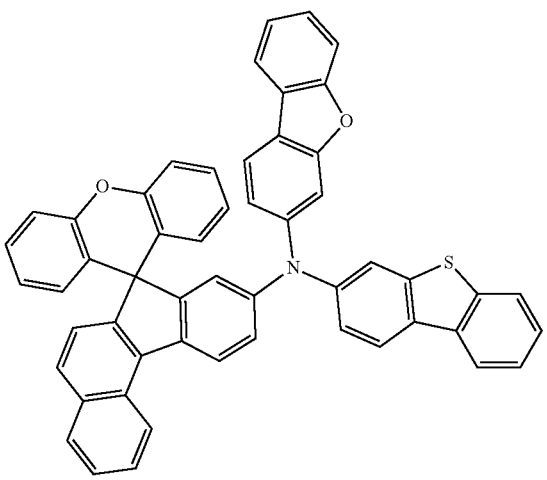
(41)
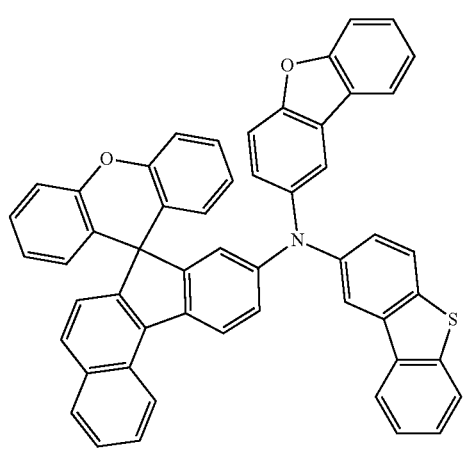

(42)
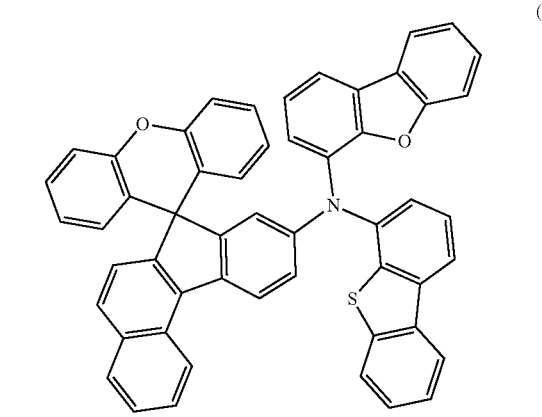
(43)
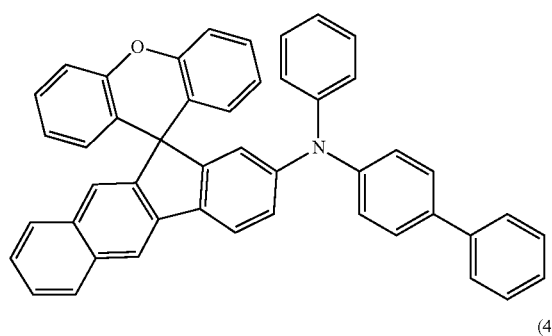
(44)
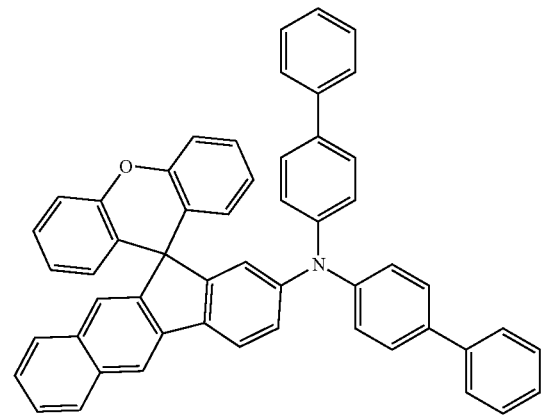
(45)
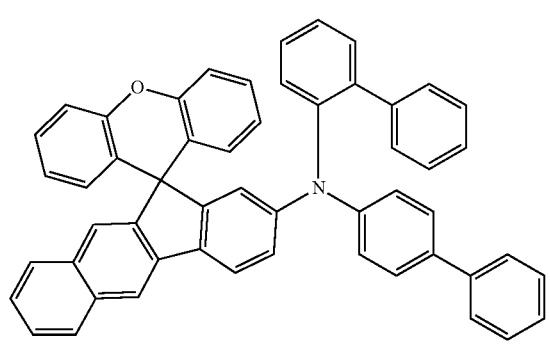
(46)
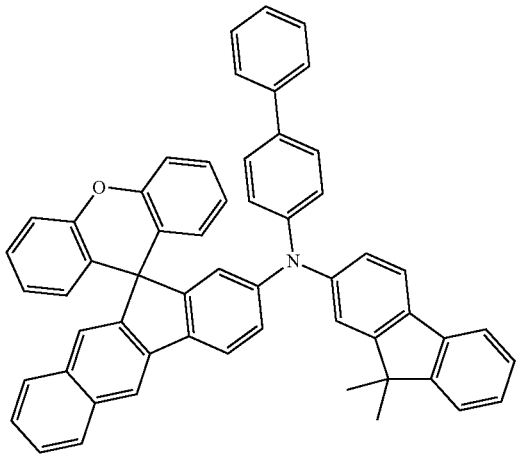
(47)
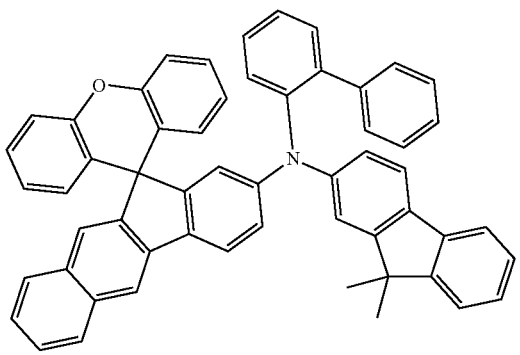
(48)
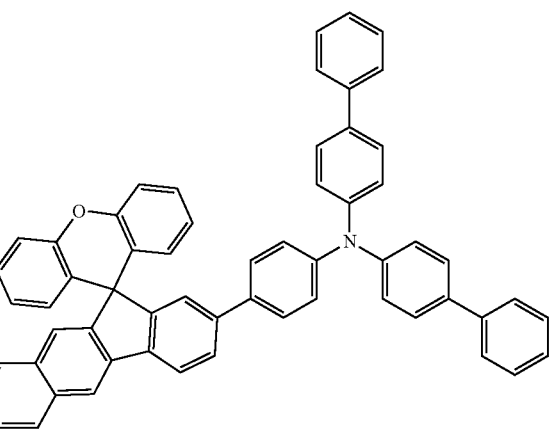

267
-continued
(49)
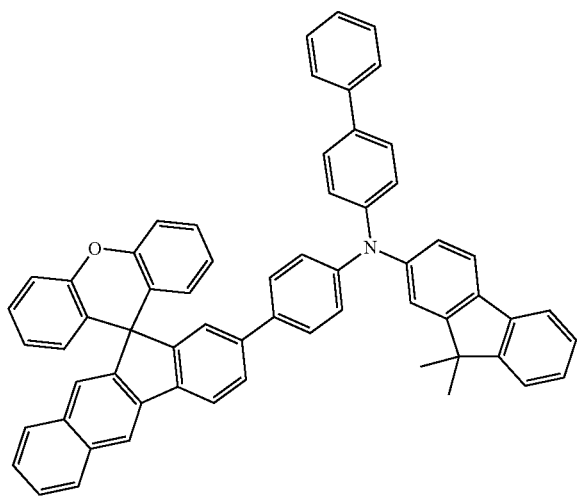
(50)
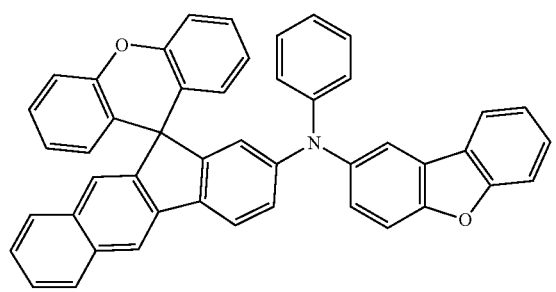
(51)
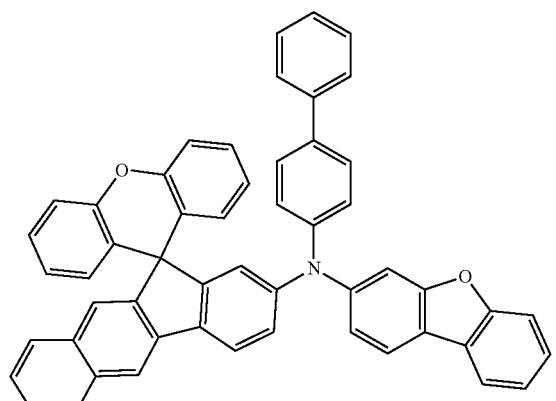
(52)
268
-continued
(53)
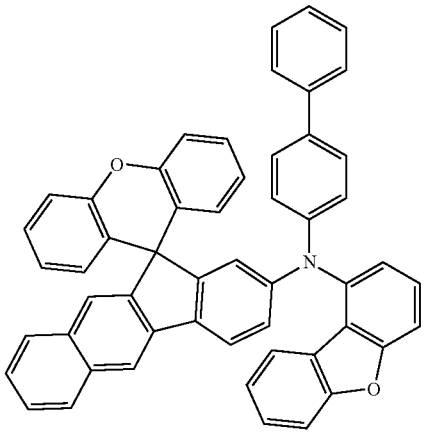
(54)
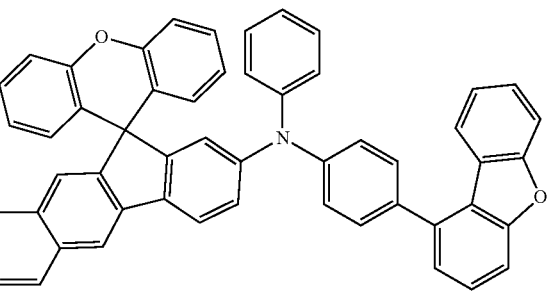
(55)
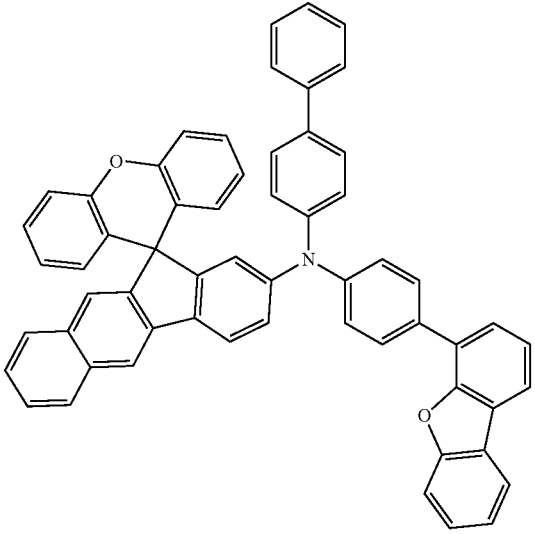
(56)
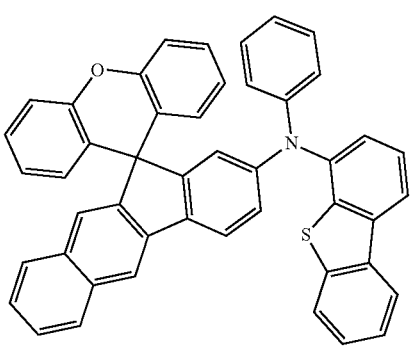

269
-continued
(57)
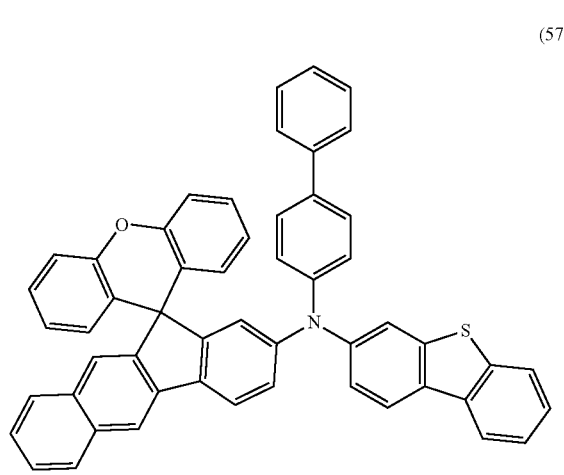
(58)
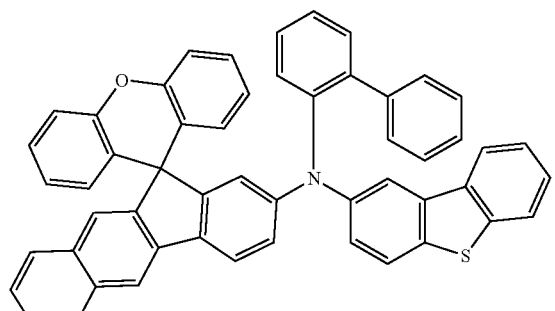
(59)
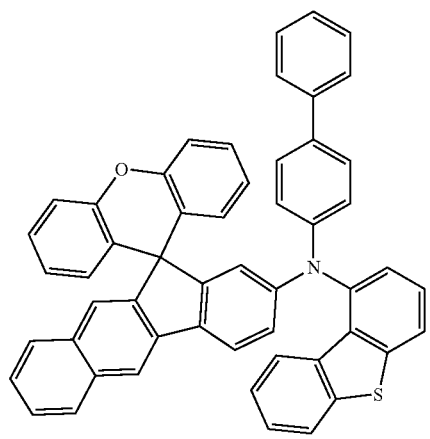
270
-continued
(60)
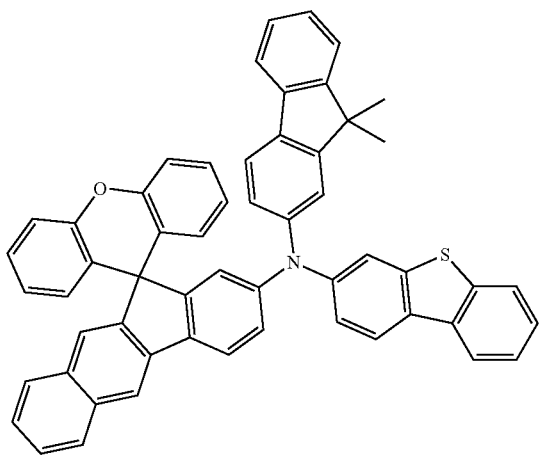
(61)
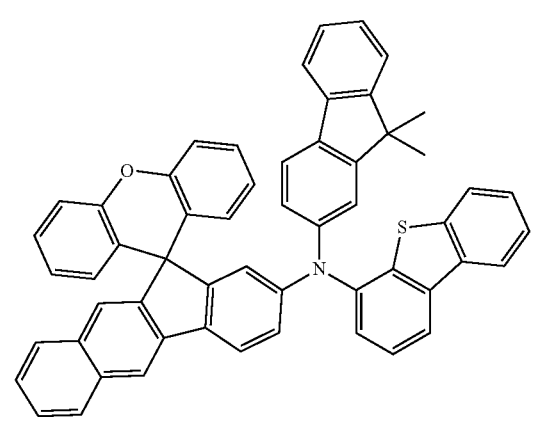
(62)
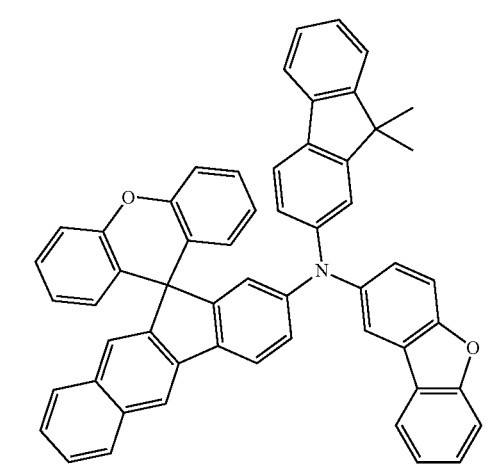

-continued
(63)
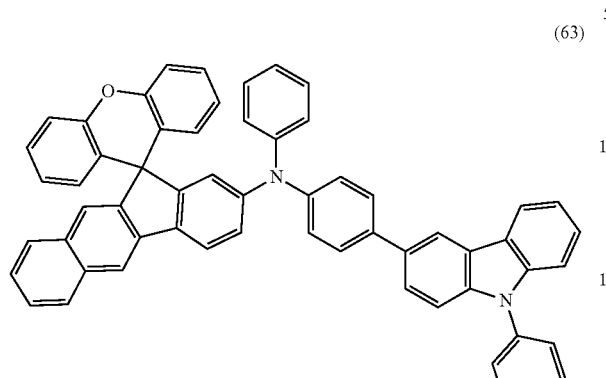
(64)
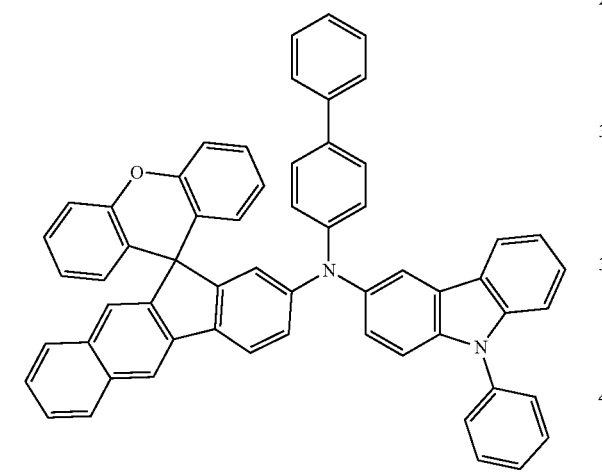
(65)
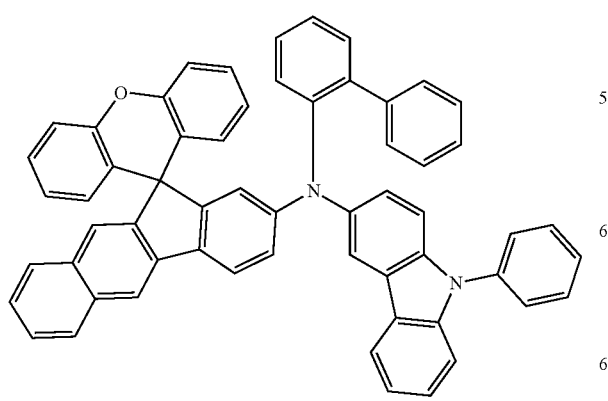
-continued
(66)
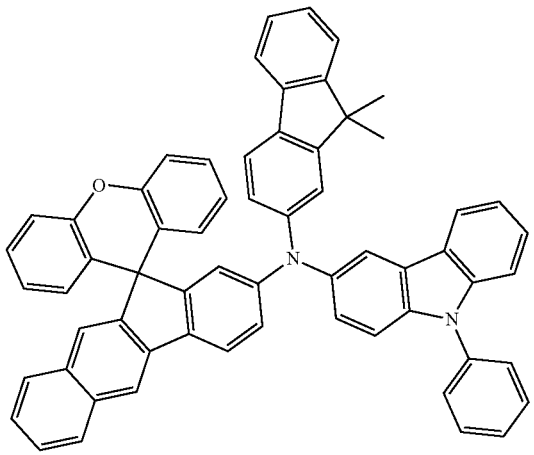
(67)
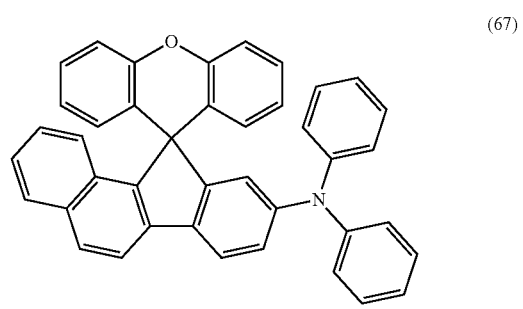
(68)
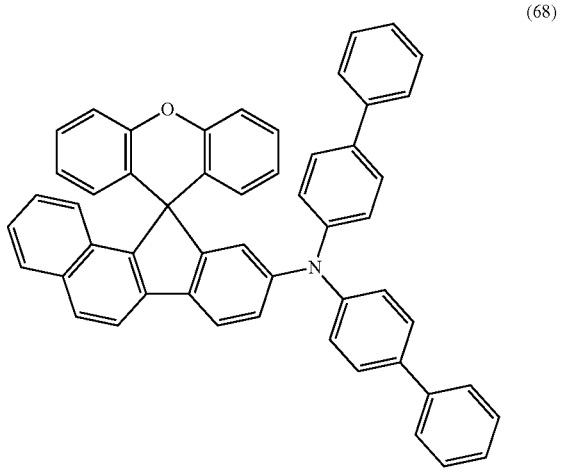

(69) 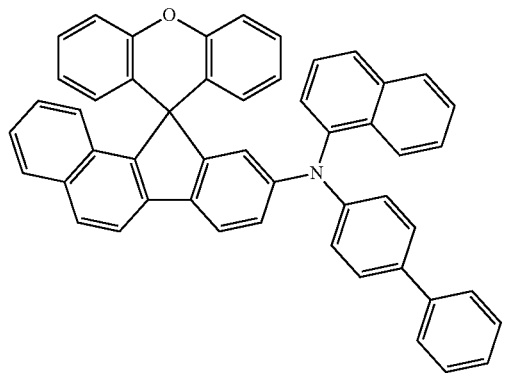
(70) 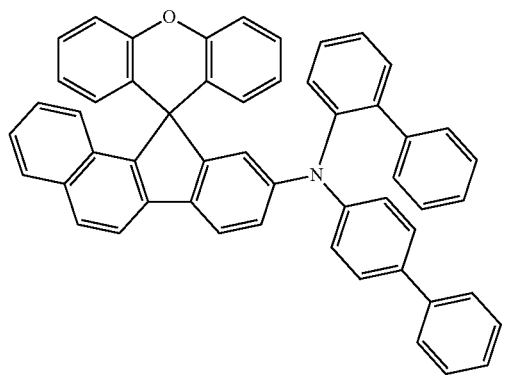
(71) 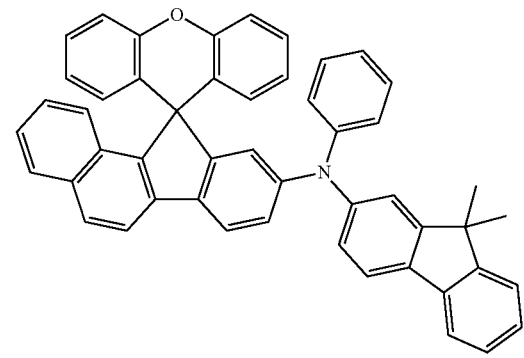
(72) 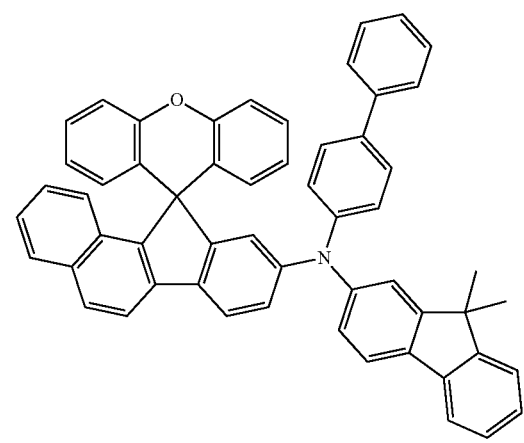
(73) 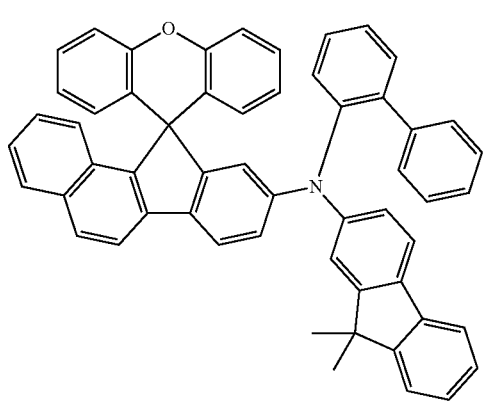
(74) 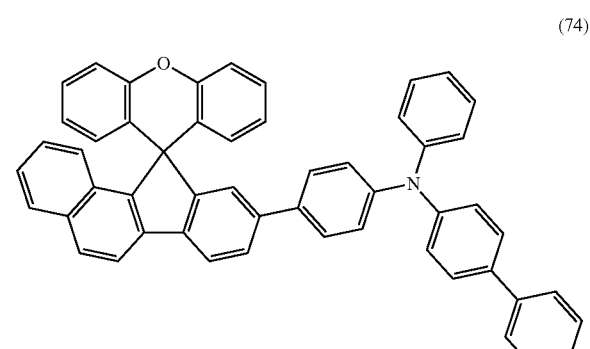
(75) 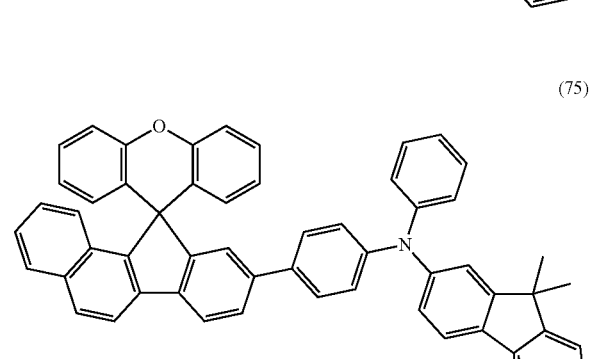
(76) 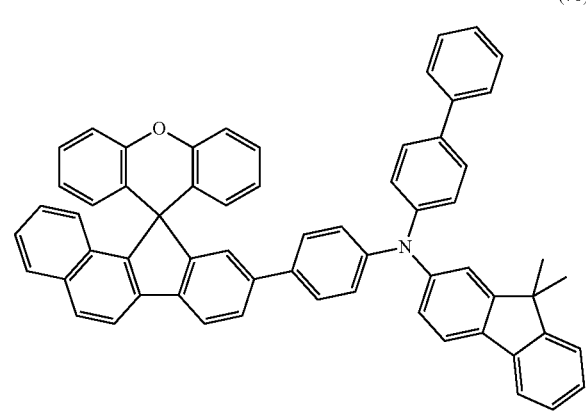

(77)
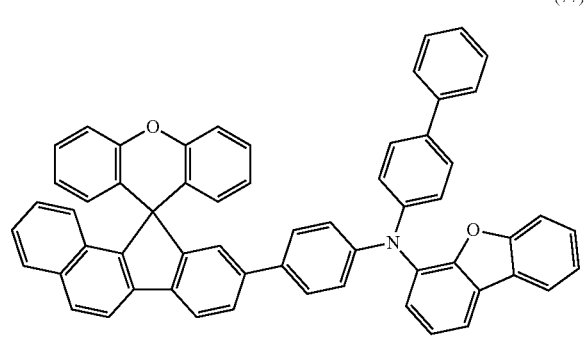
(78)
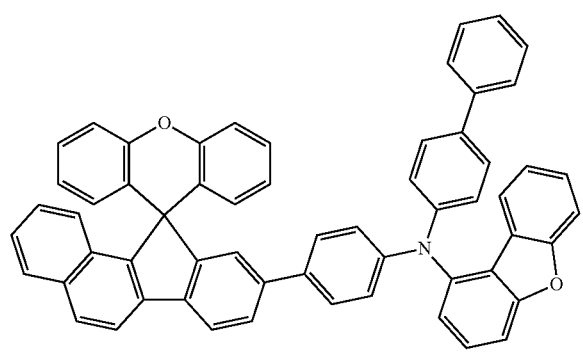
(79)
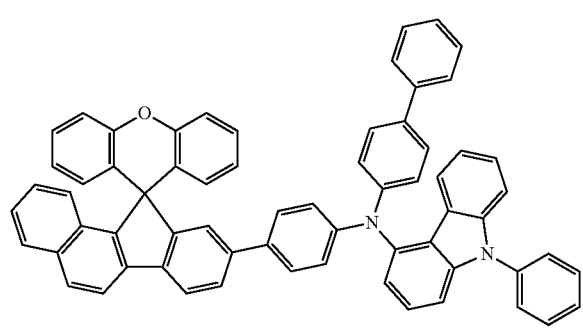
(80)
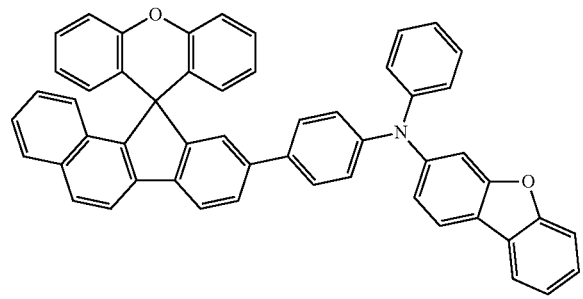
(81)
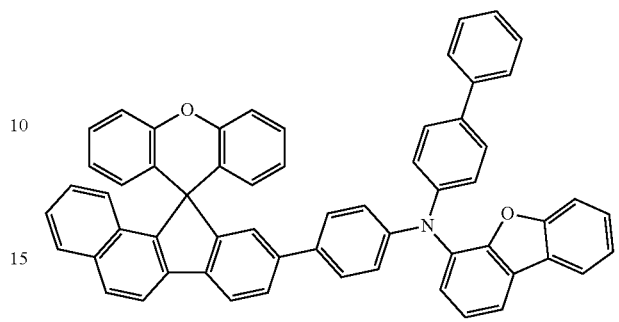
(82)
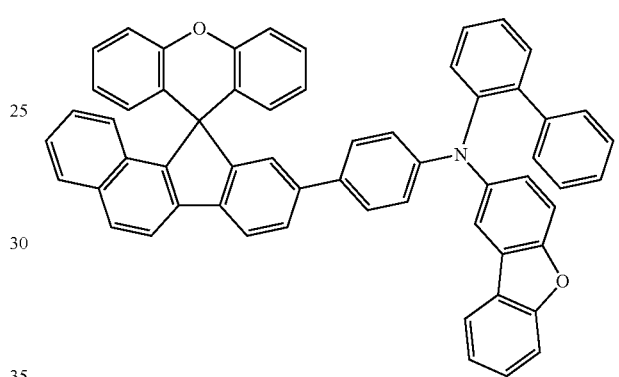
(83)
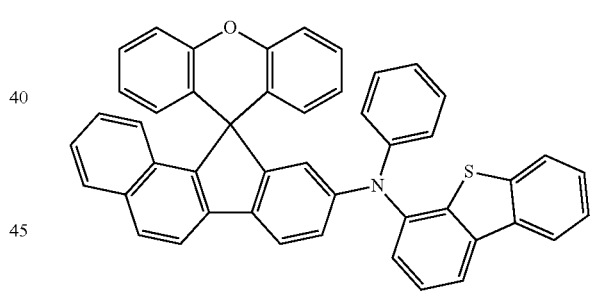
(84)
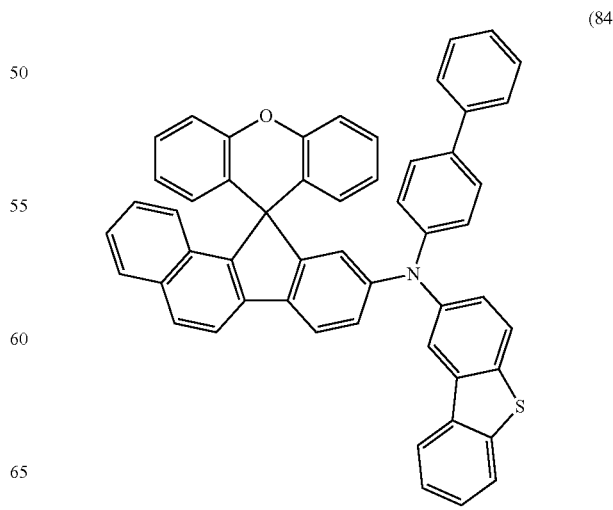

-continued
(85)
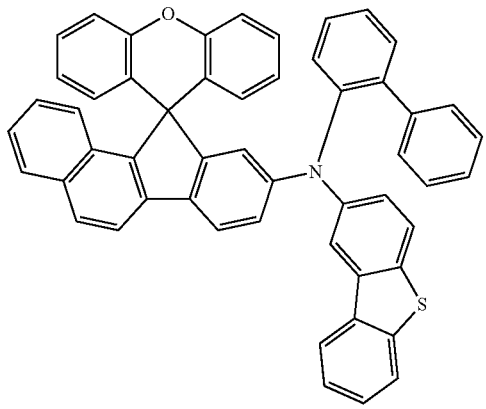
(86)
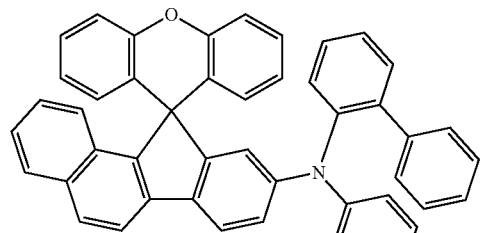
(87)
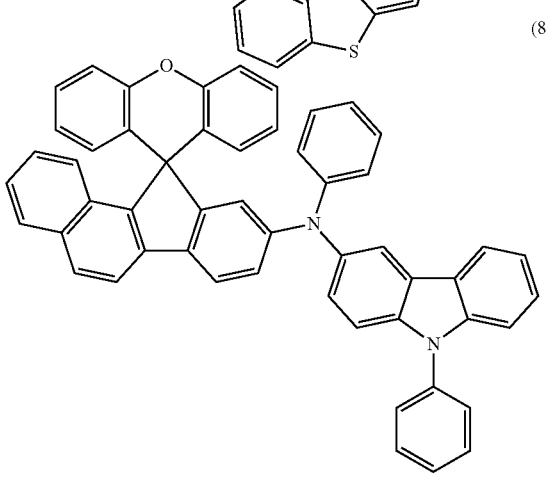
(88)
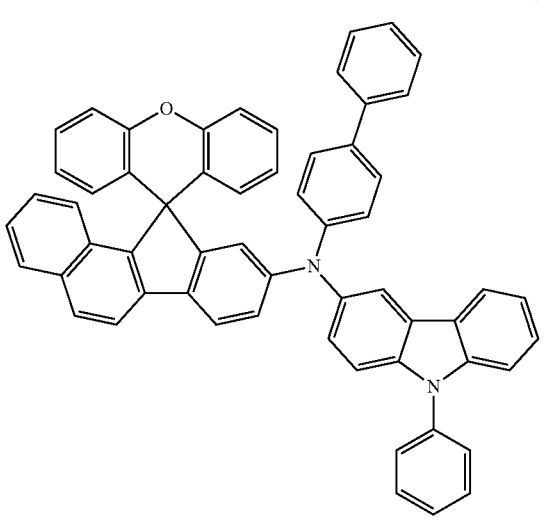
-continued
(89)
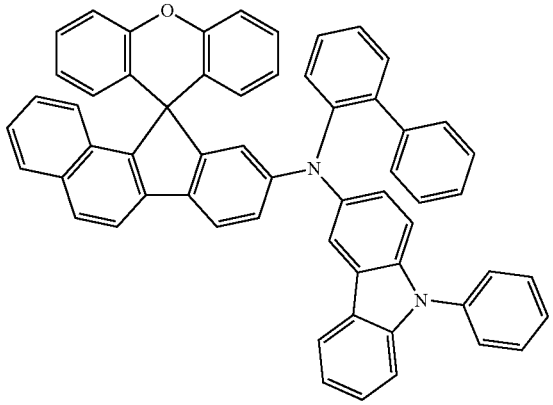
(90)
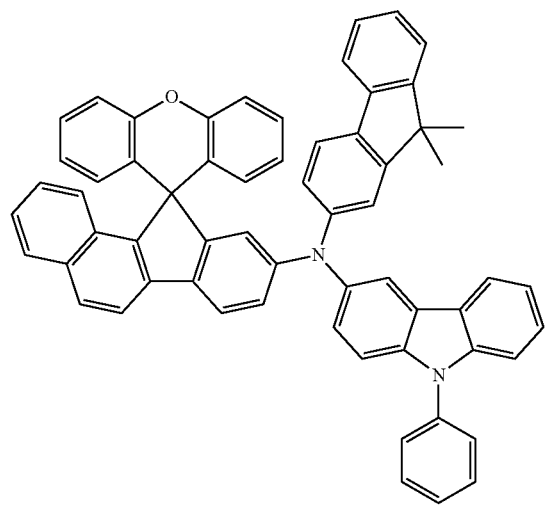
(91)
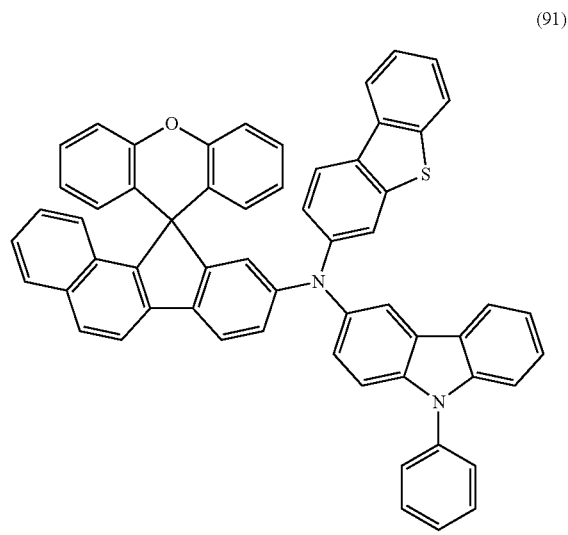

(92)
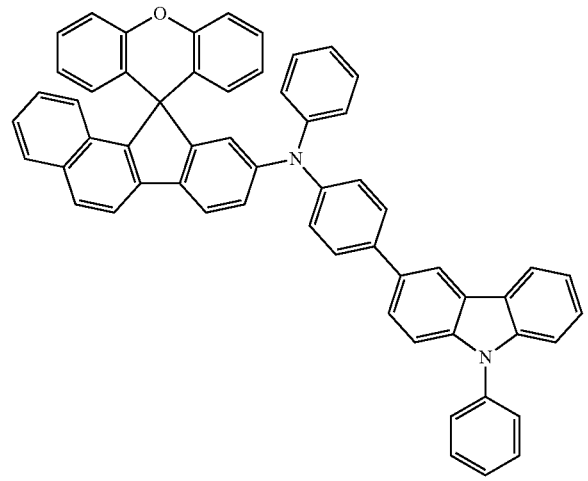
(93)
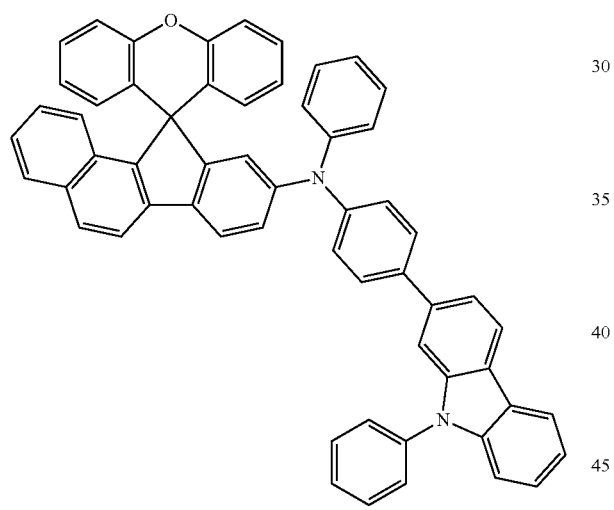
(94)
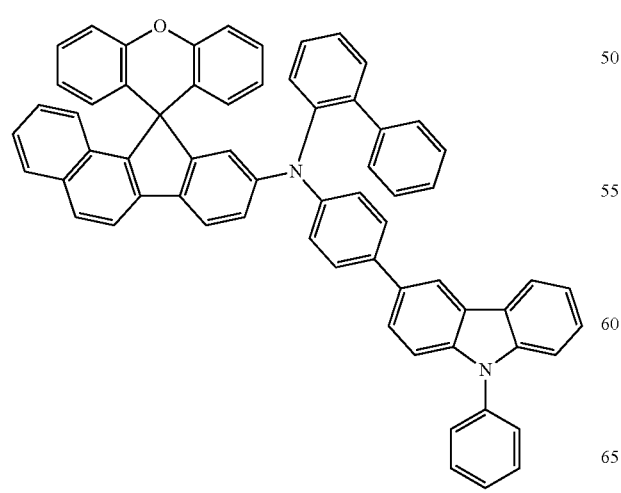
(95)
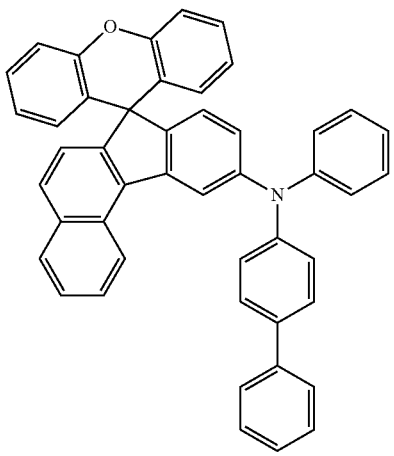
(96)
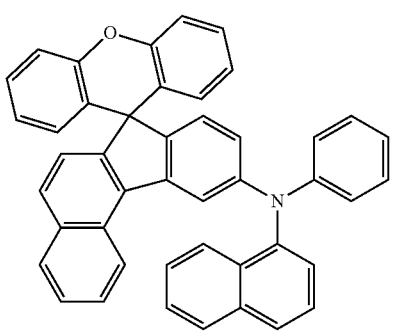
(97)
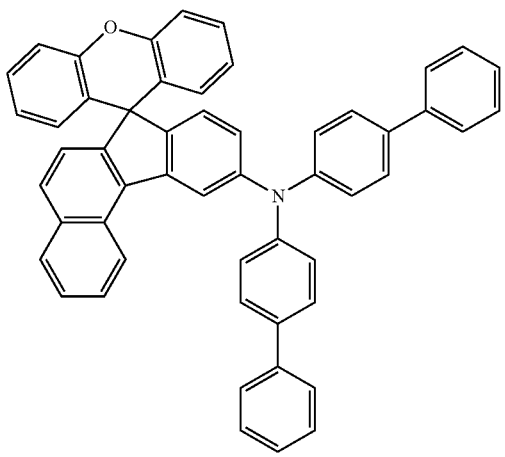
(98)
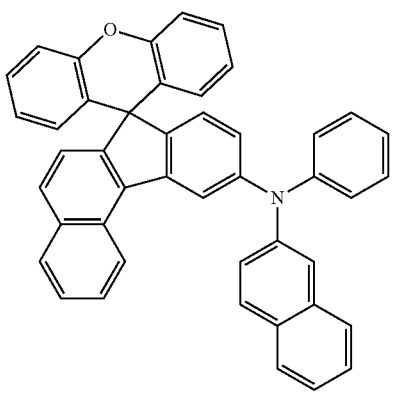

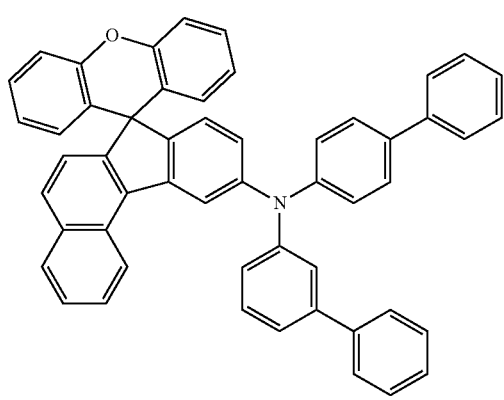
(99)
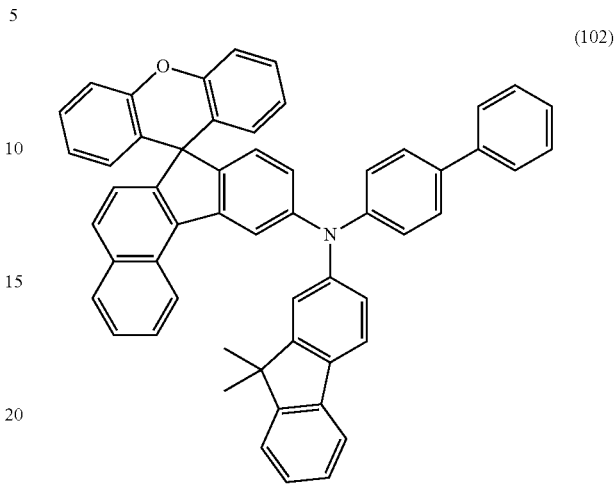
(102)
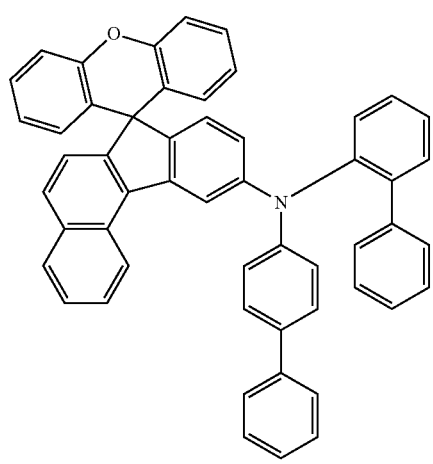
(100)
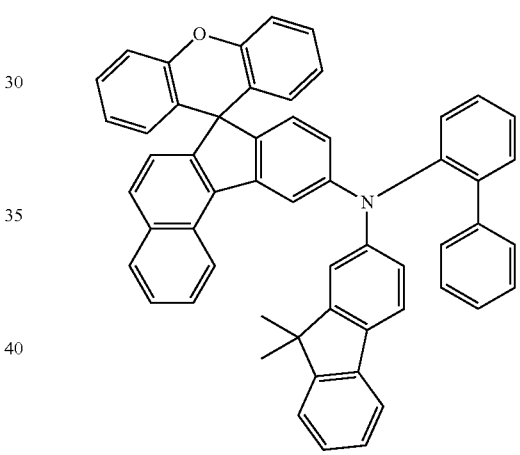
(103)
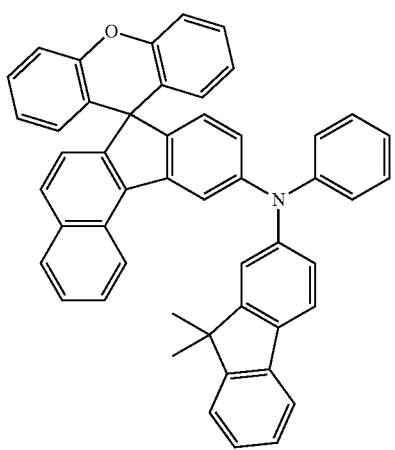
(101)
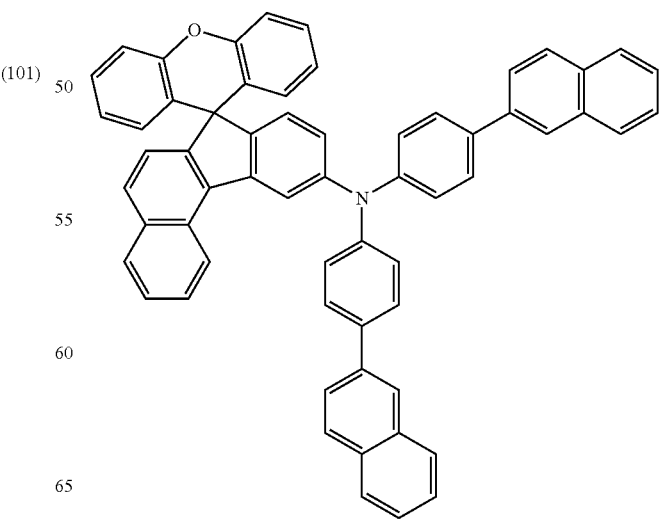
(104)

(105) 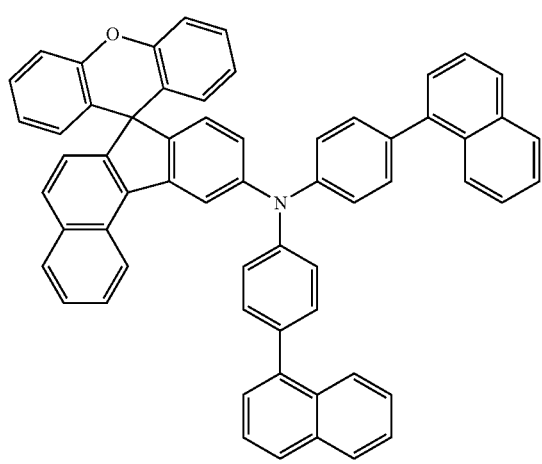
(106) 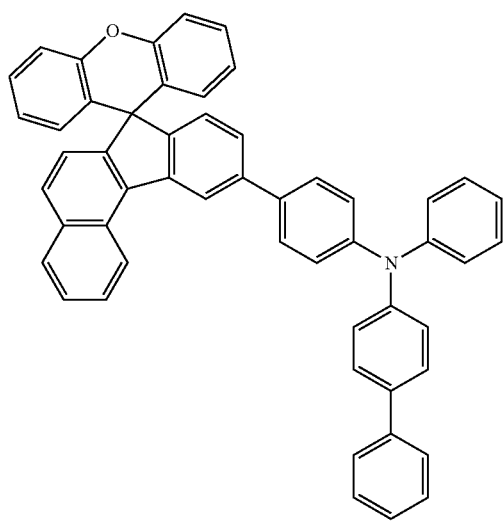
(107) 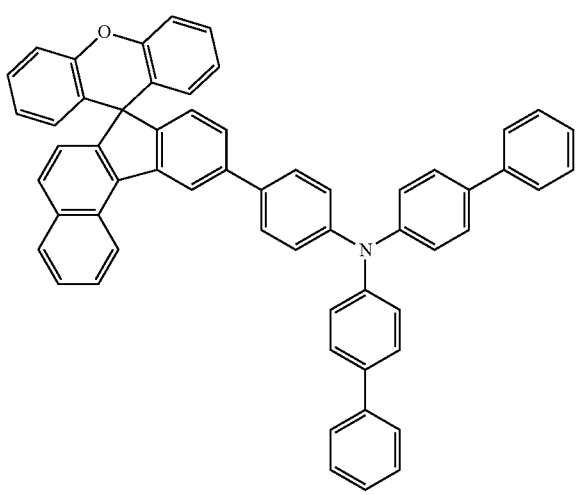
(108) 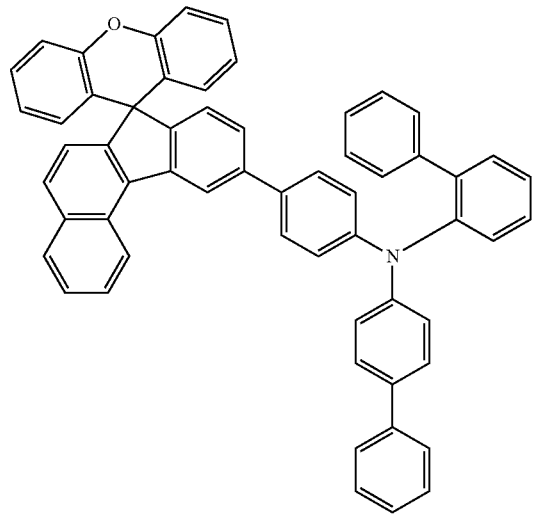
(109) 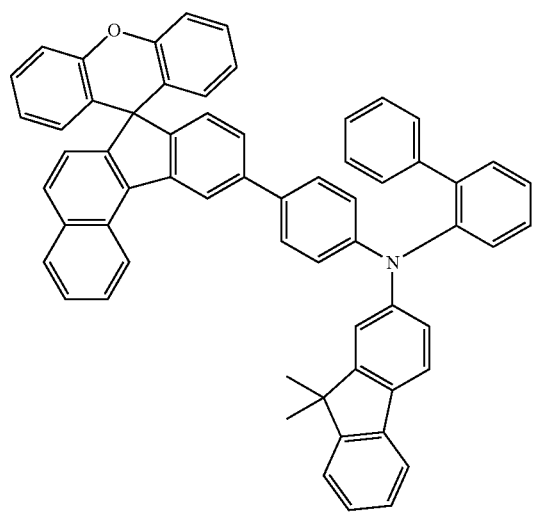
(110) 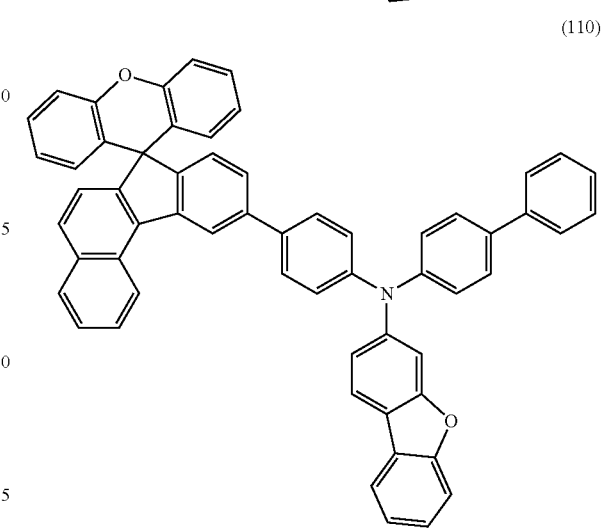

-continued
(111) 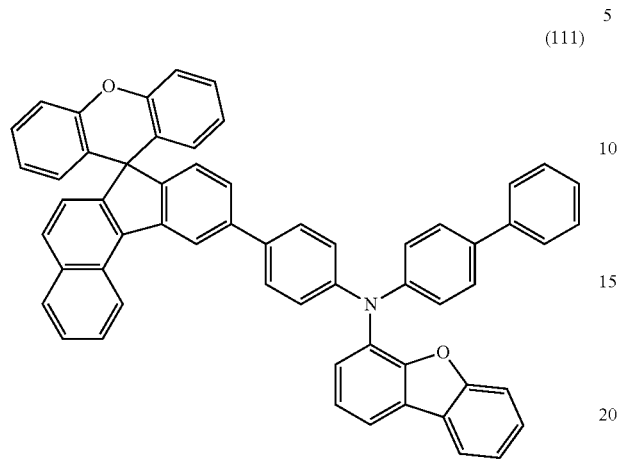
(112) 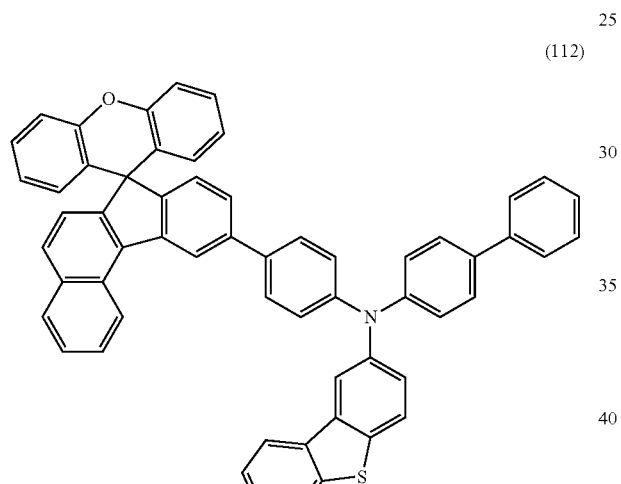
(113) 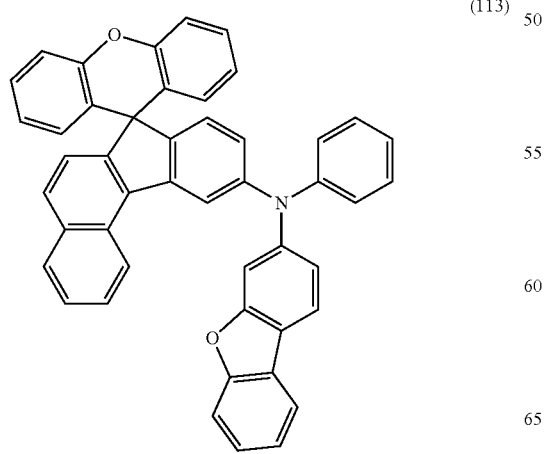
-continued
(114) 
(115) 
(116) 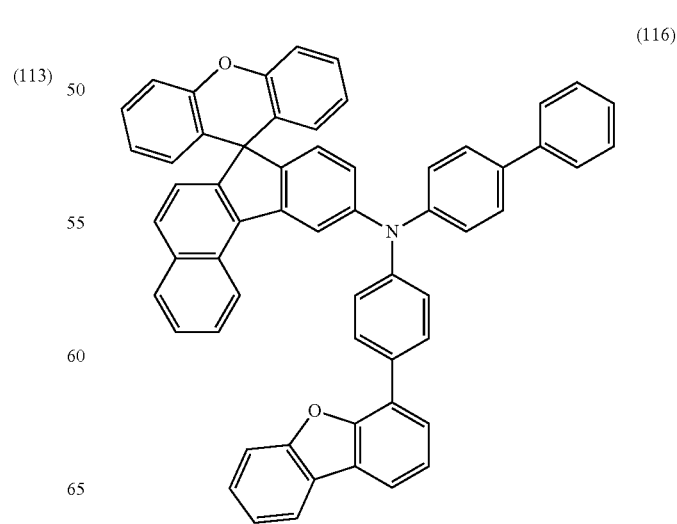

287
-continued
(117)
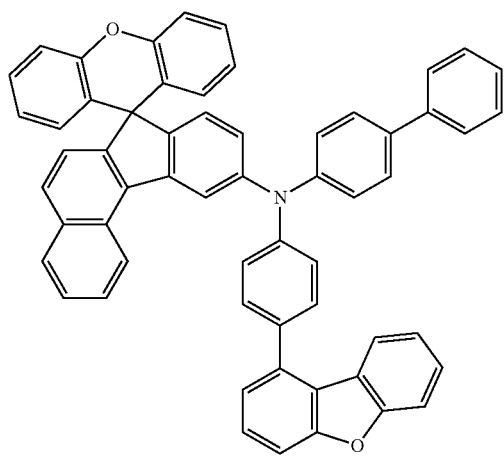
(118)
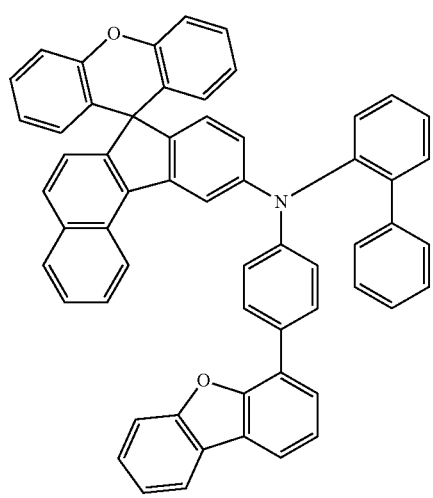
(119)
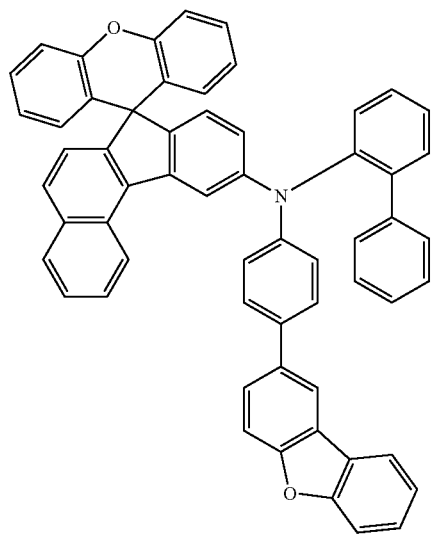
288
-continued
(120)
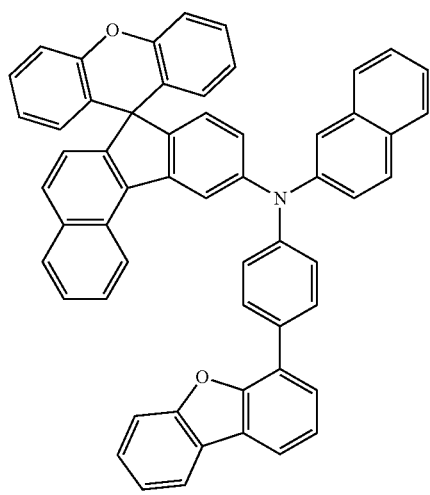
(121)
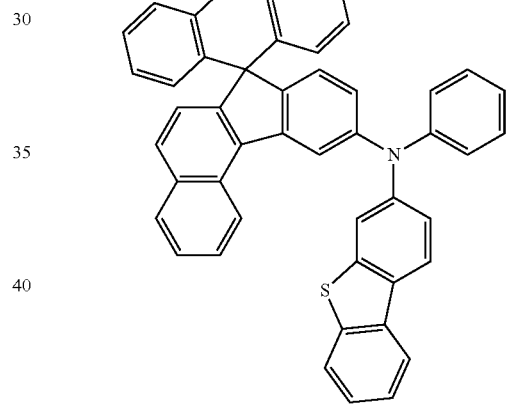
(122)
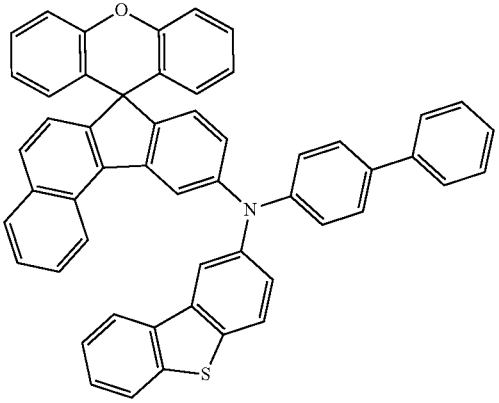

-continued
(123)
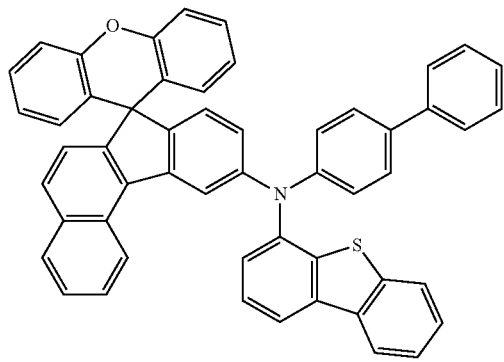
(124)
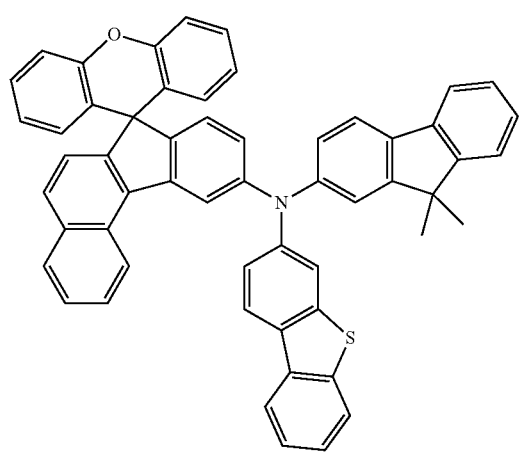
(125)
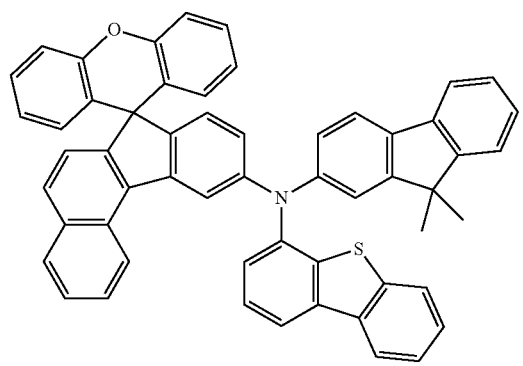
(126)
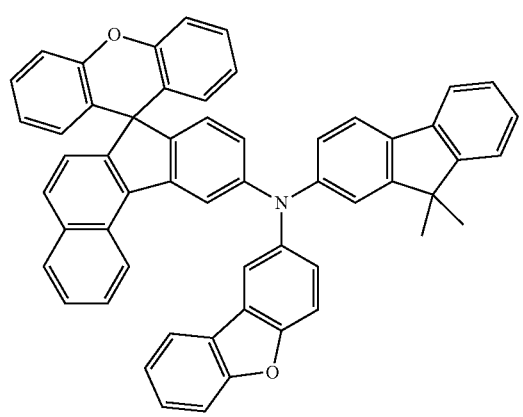
(127)
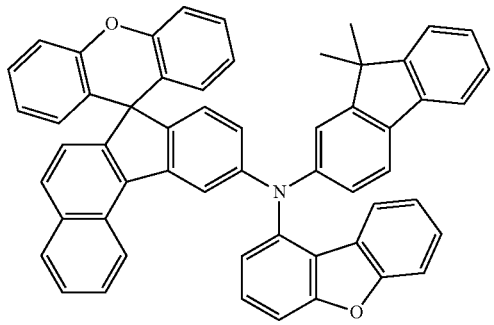
(128)
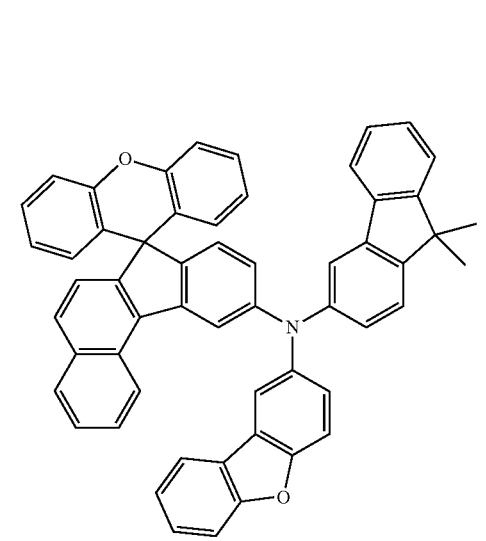
(129)
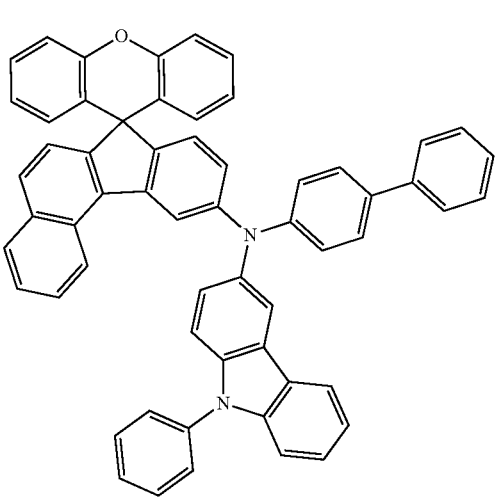

(130)
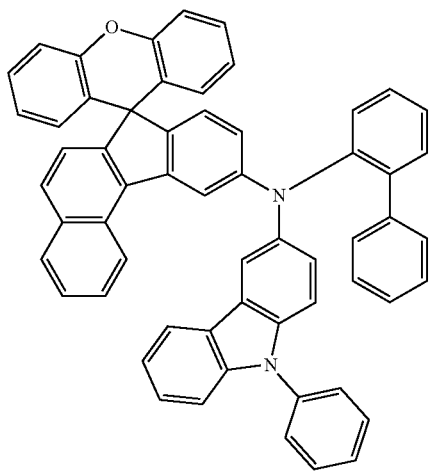
(131)
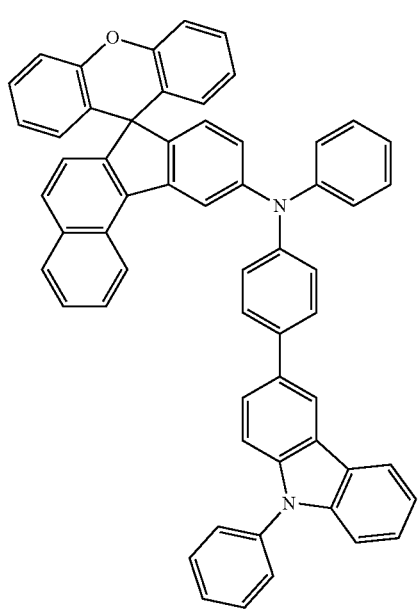
(132)
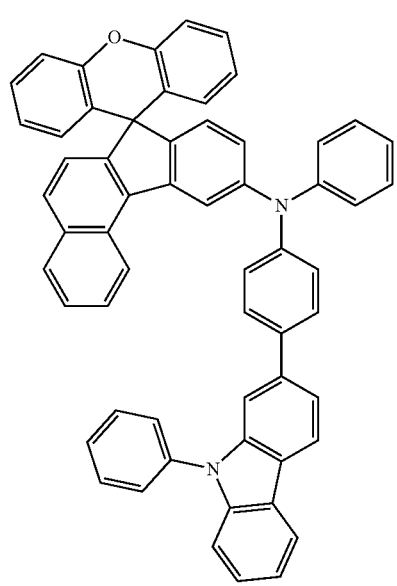
(133)
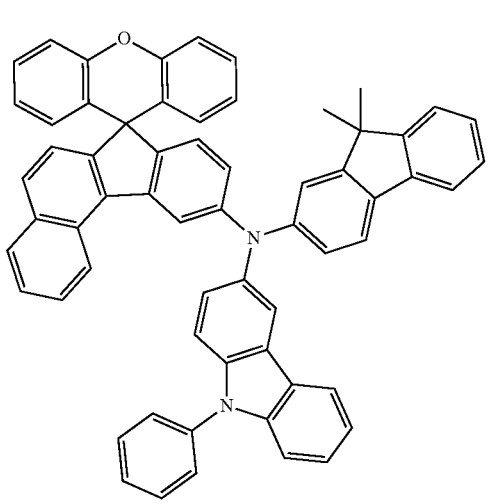
(134)
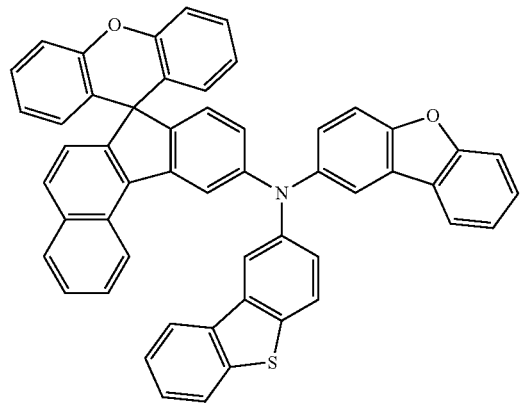
(135)
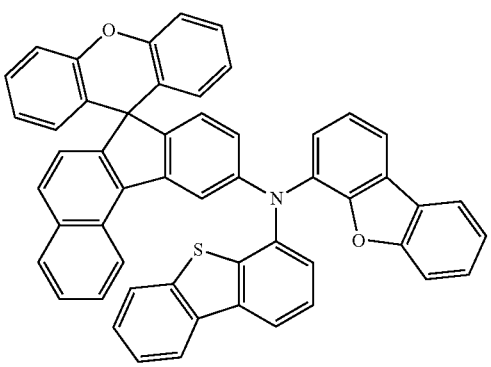

(136)
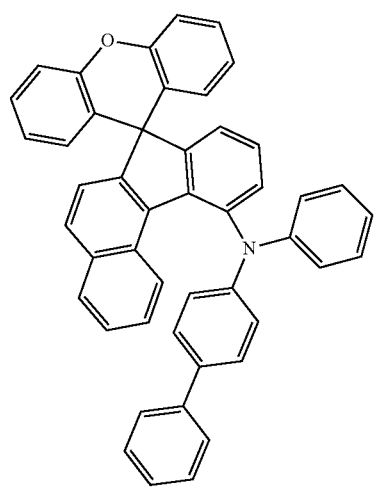
(137)
(138)
(139)
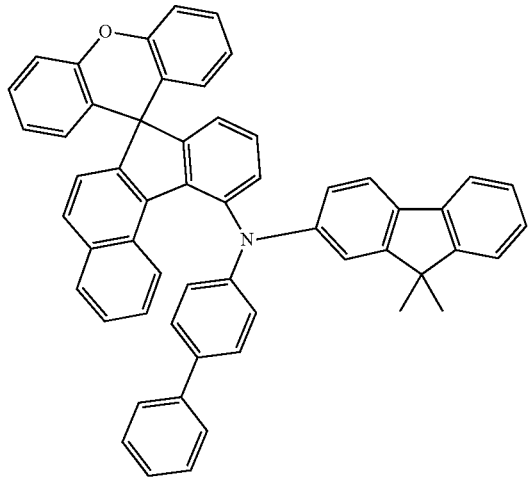
(140)
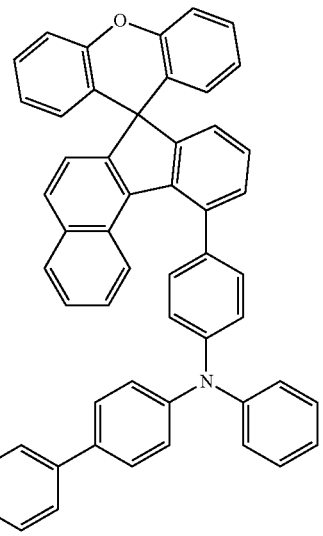
(141)
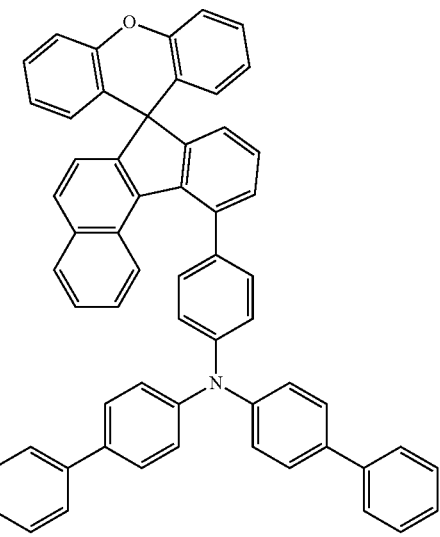

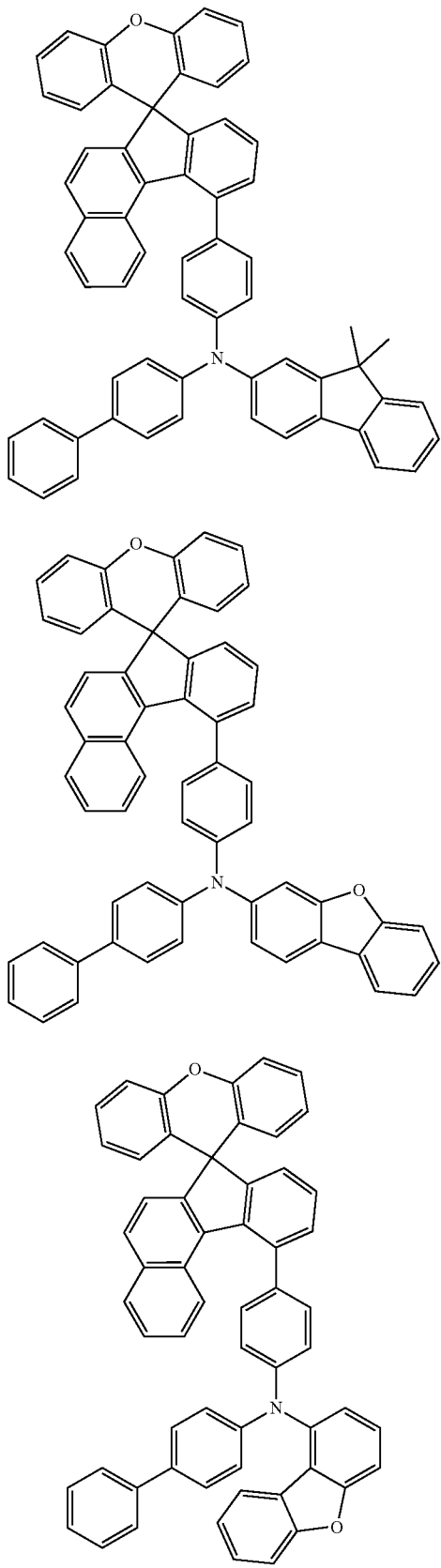
(142)
(143)
(144)
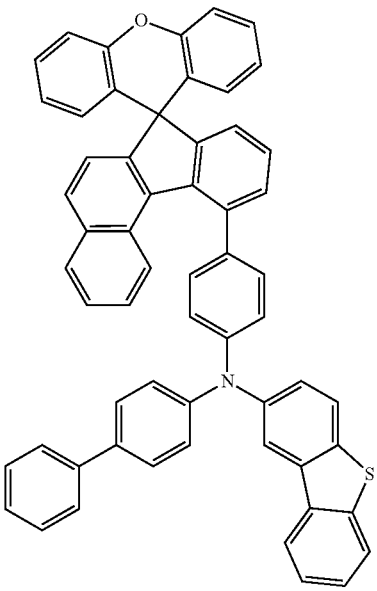
(145)
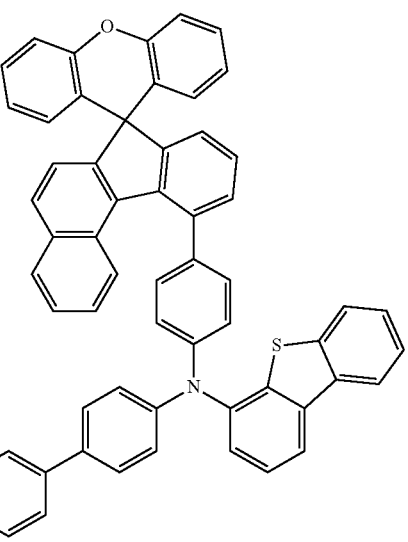
(146)
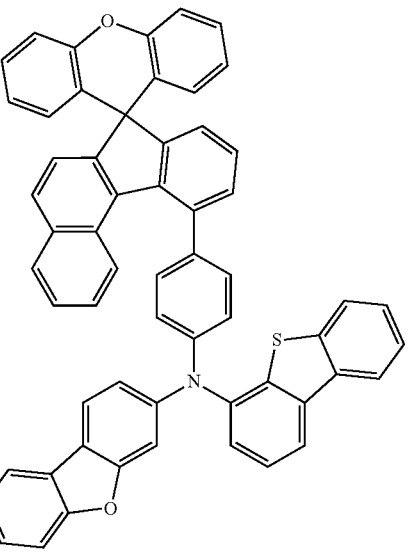
(147)

(148) 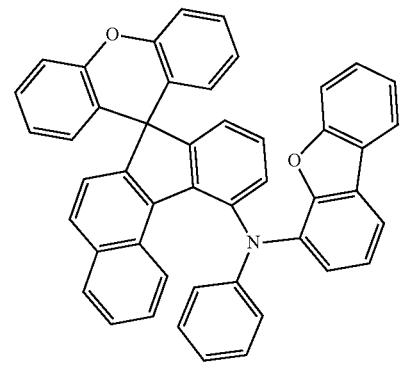
(149) 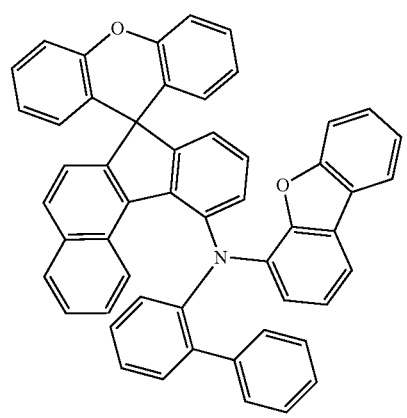
(150) 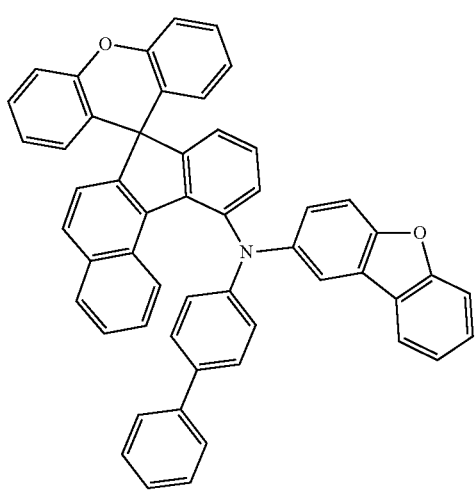
(151) 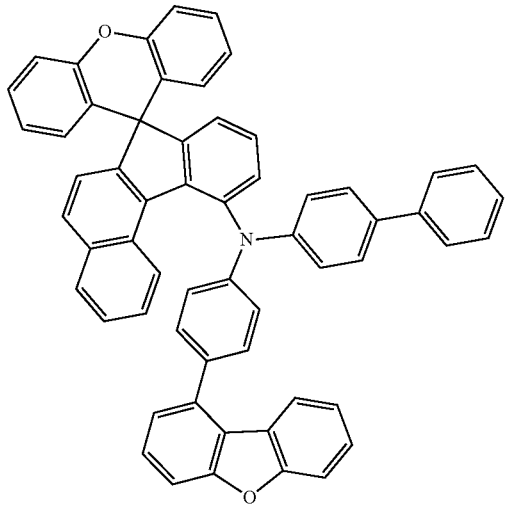
(152) 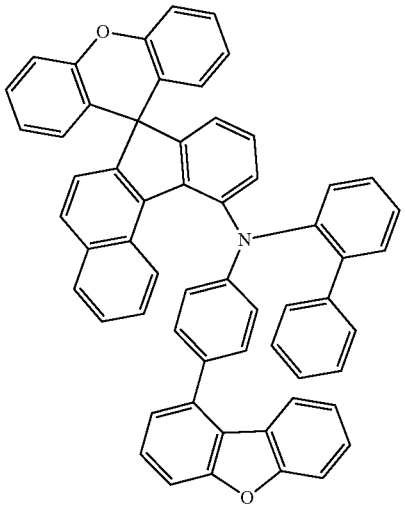
(153) 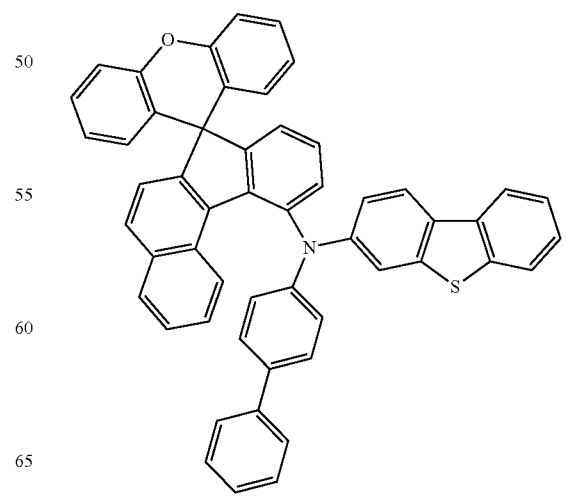

-continued
(154)
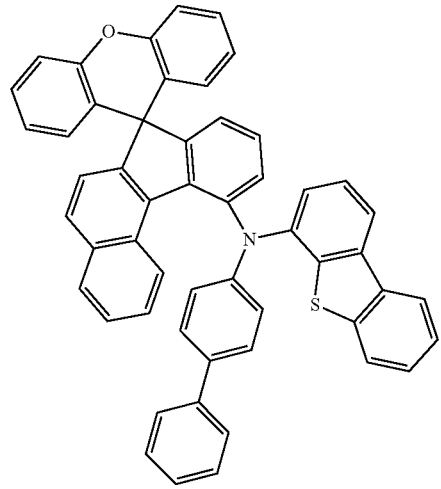
(155)
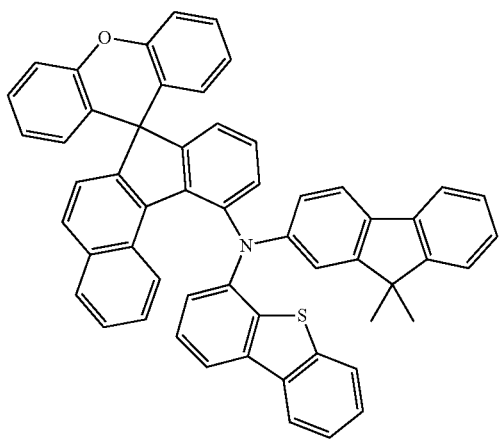
(156)
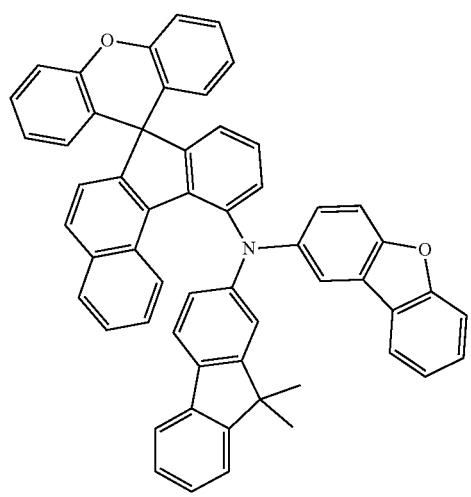
-continued
(157)
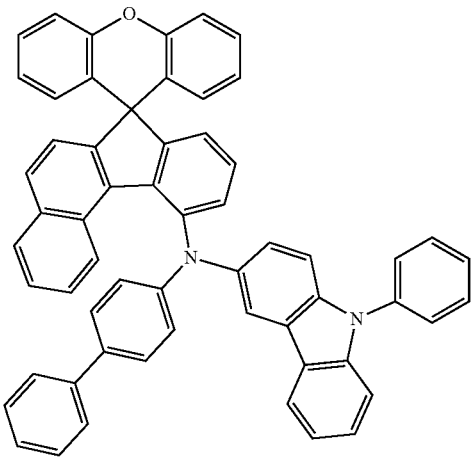
(158)
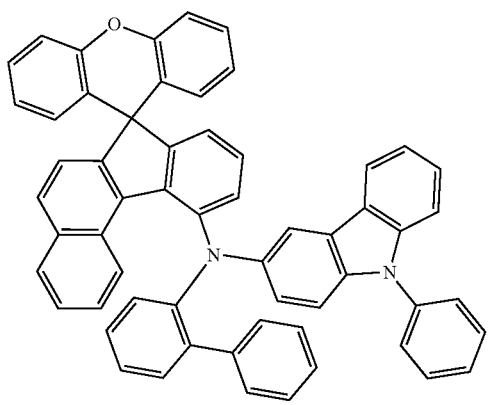
(159)
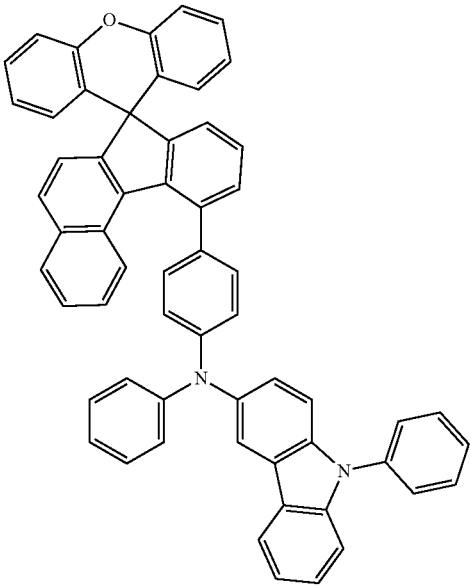

301
-continued
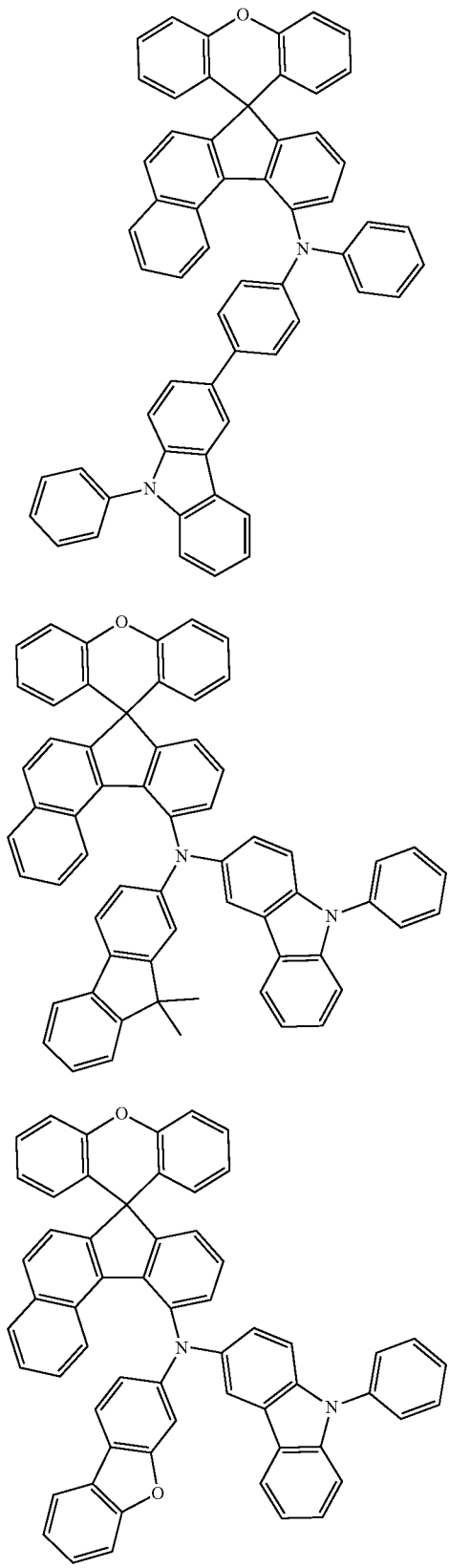
302
-continued
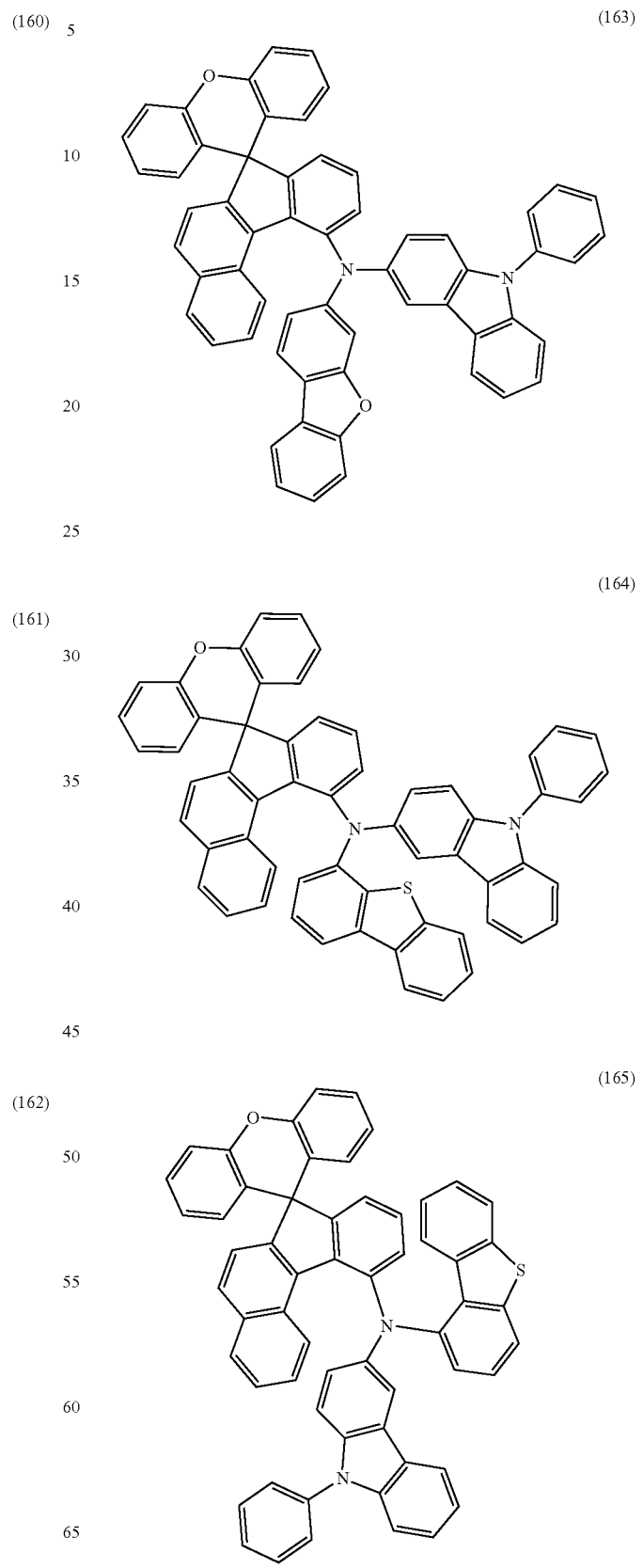

(166) 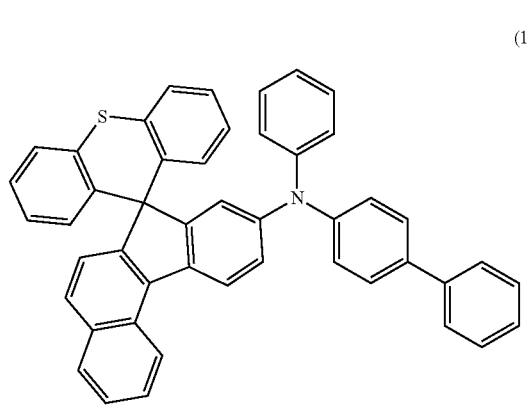
(167) 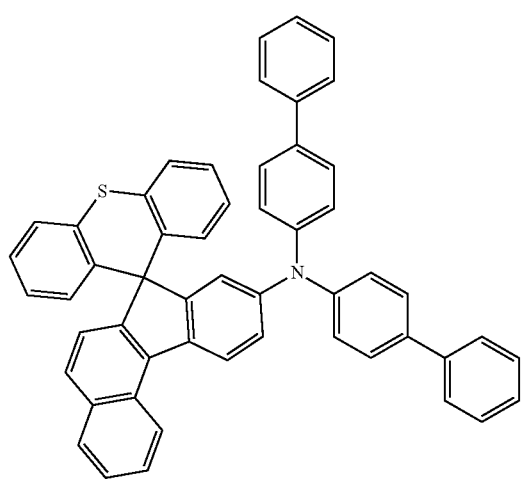
(168) 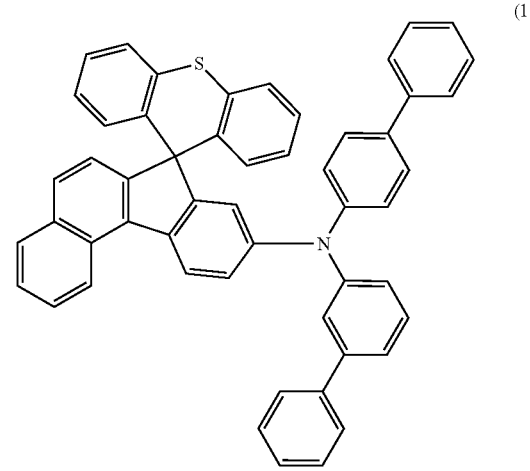
(169) 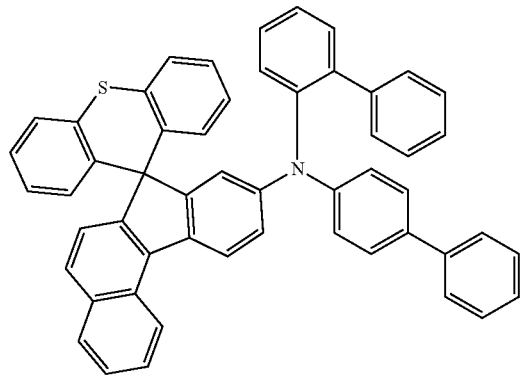
(170) 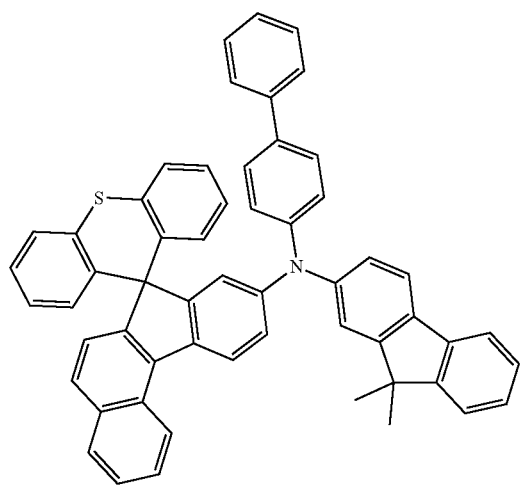
(171) 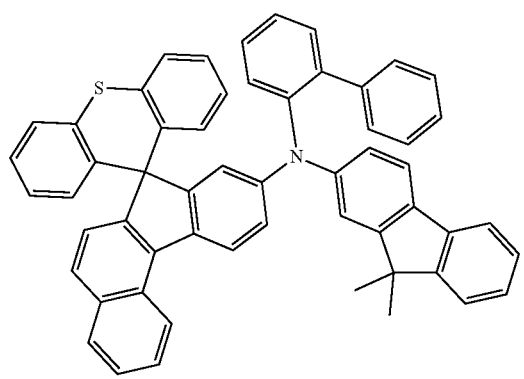

305
-continued
(172)
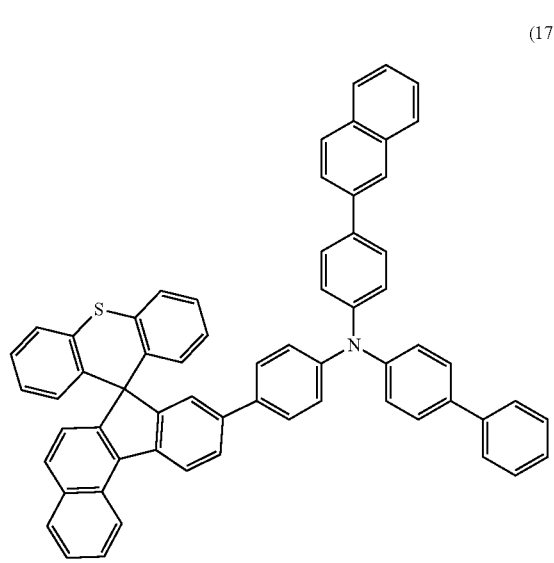
(173)
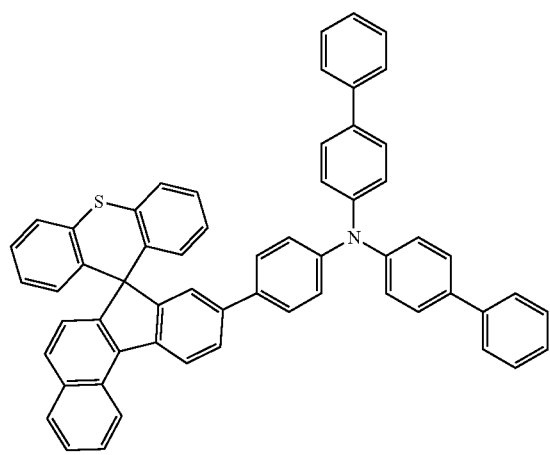
(174)
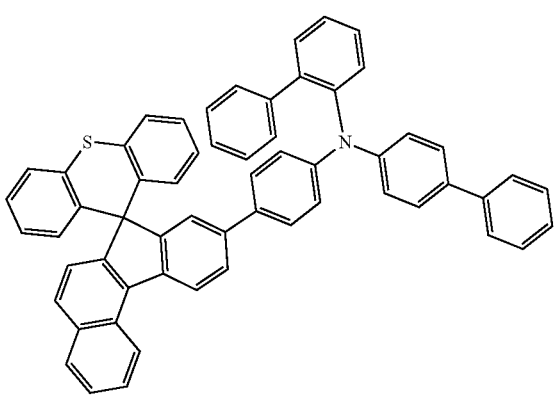
306
-continued
(175)
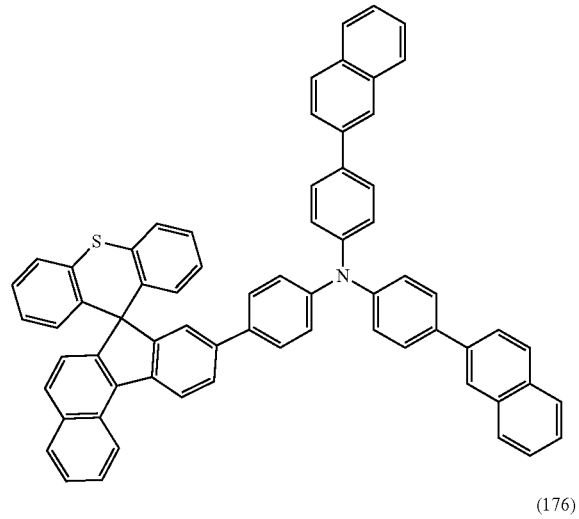
(176)
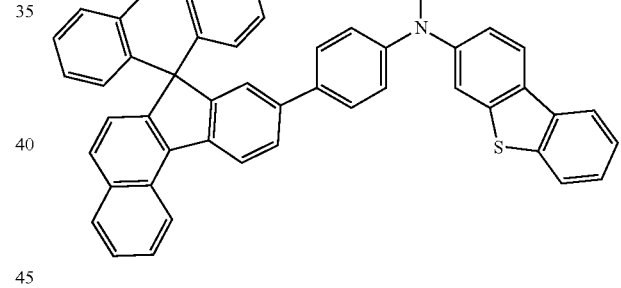
(177)
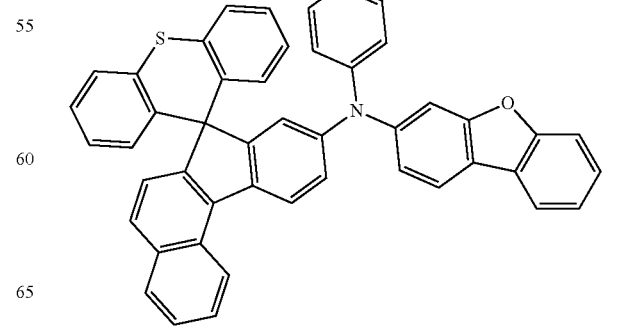

(178)
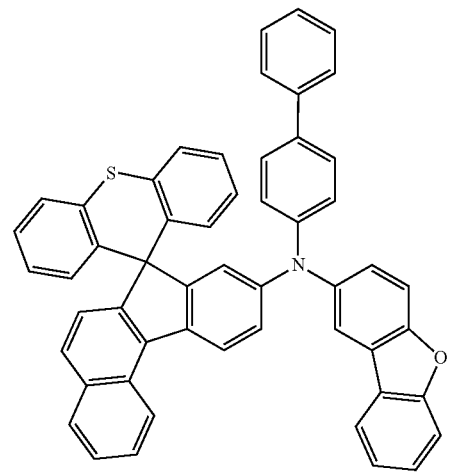
(179)
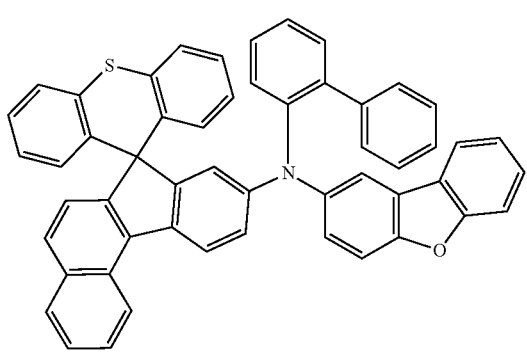
(180)
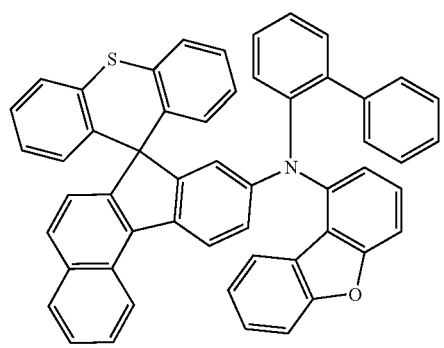
(181)
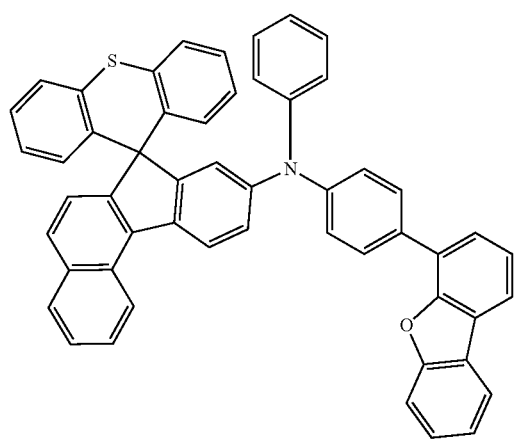
(182)
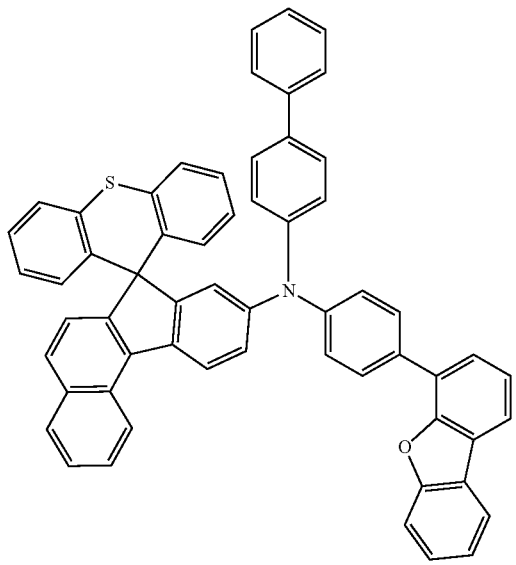
(183)
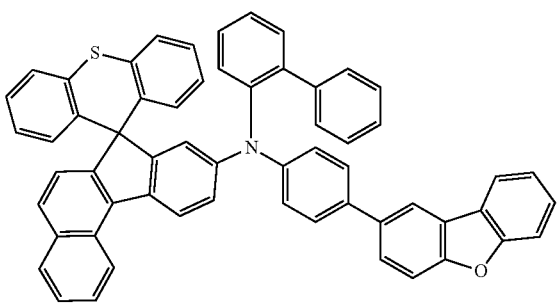
(184)
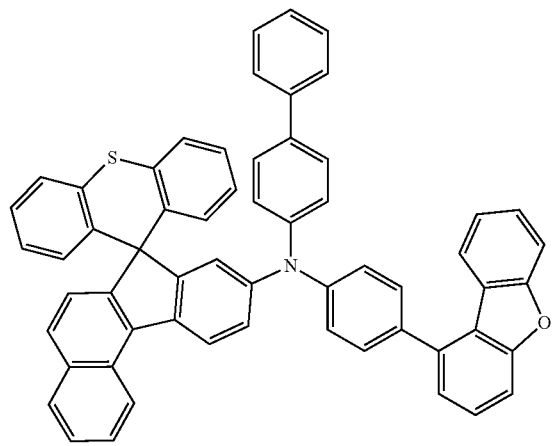

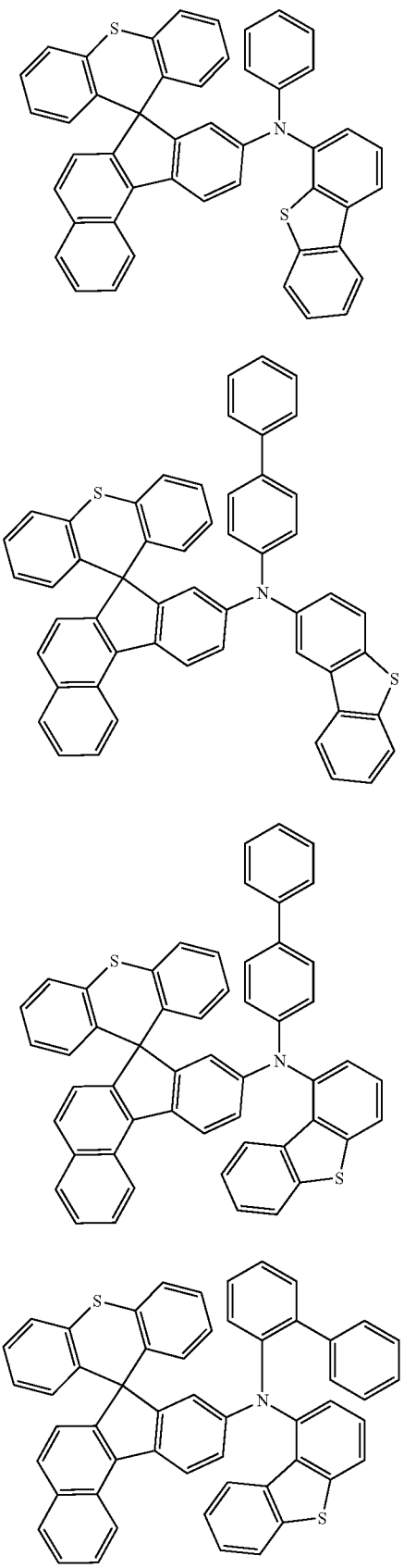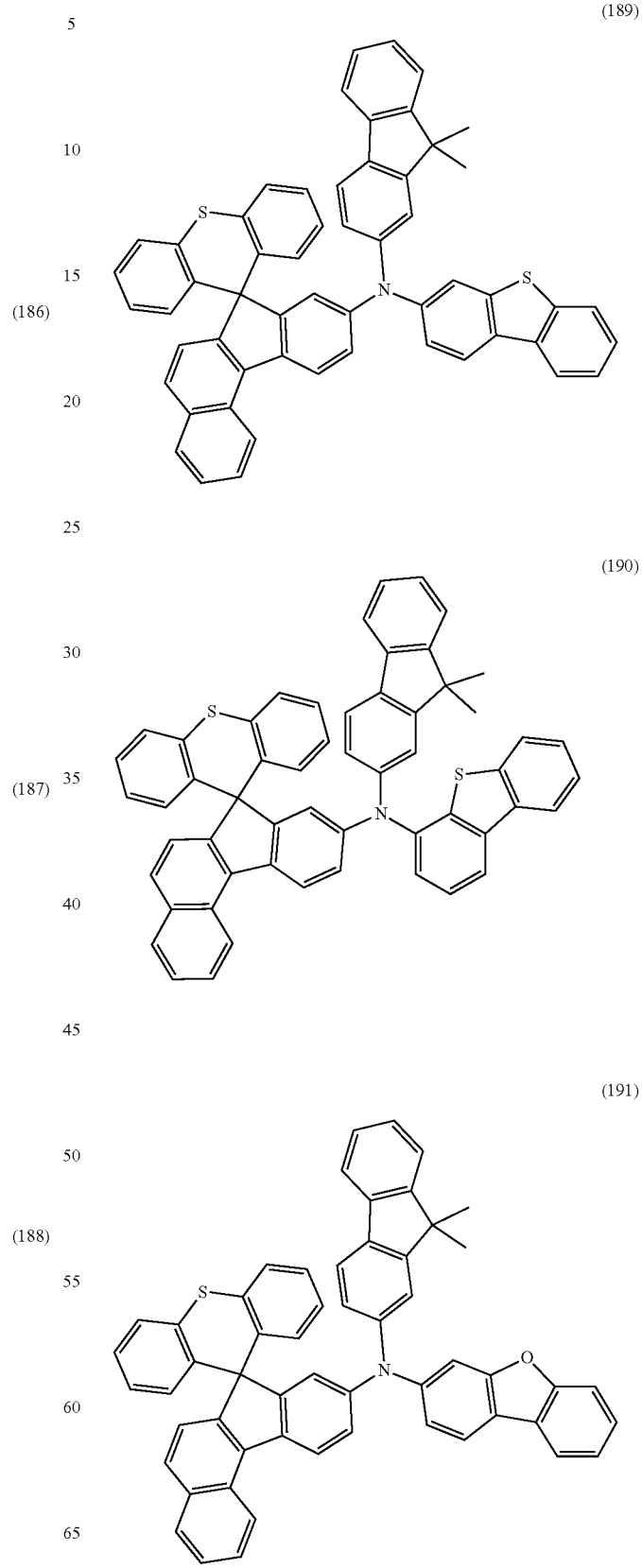

311
-continued
(192)
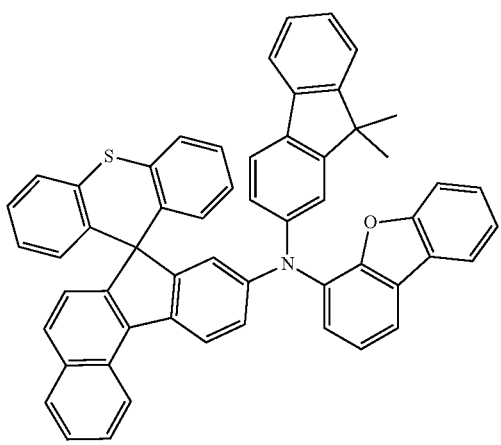
(193)
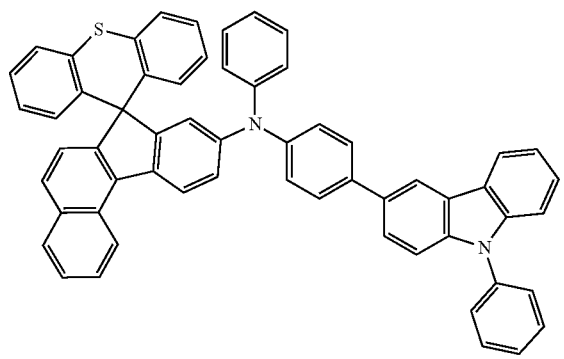
(194)
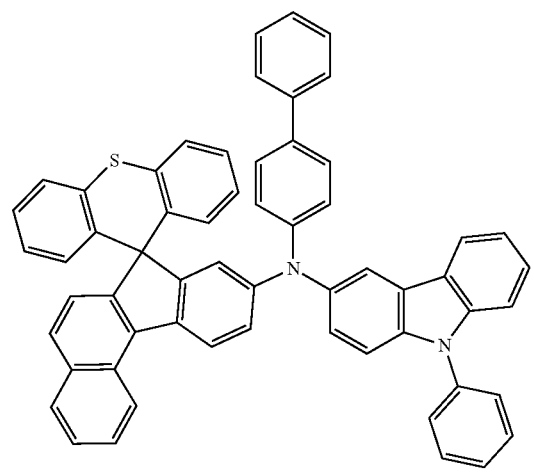
312
-continued
(195)
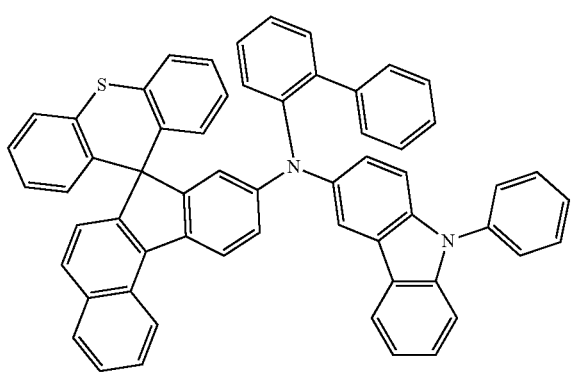
(196)
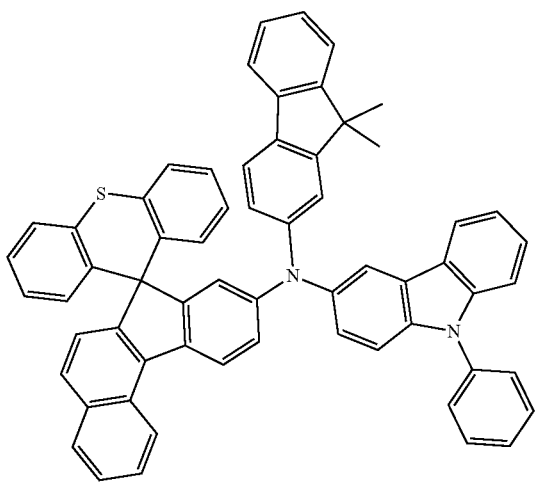
(197)
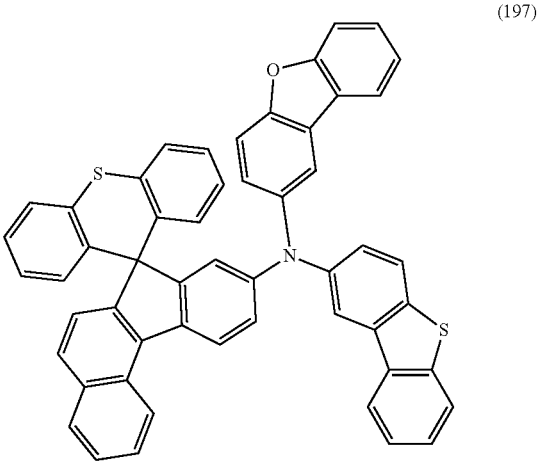

(198)
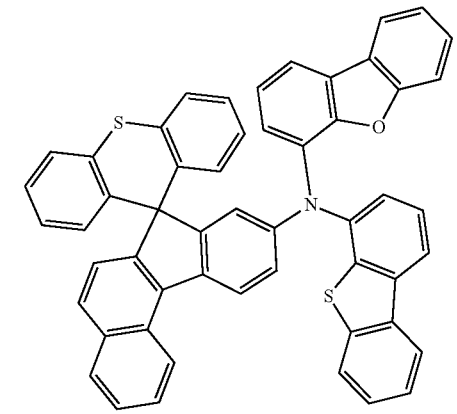
(199)
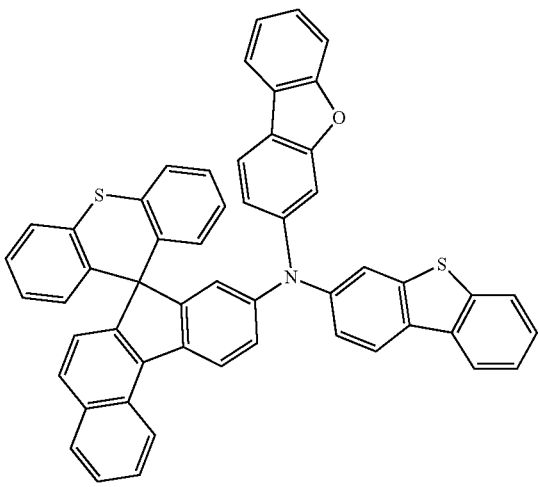
(200)
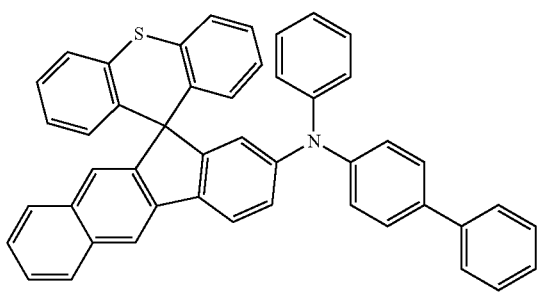
(201)
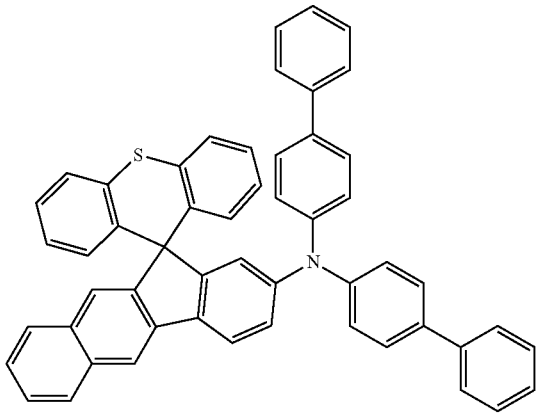
(202)
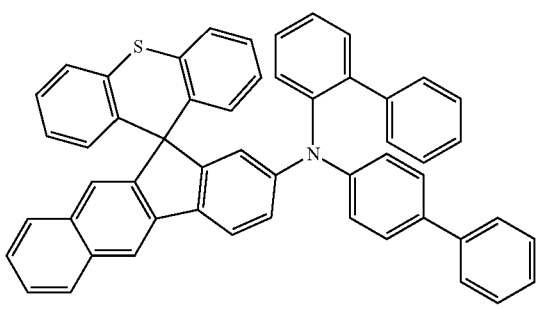
(203)
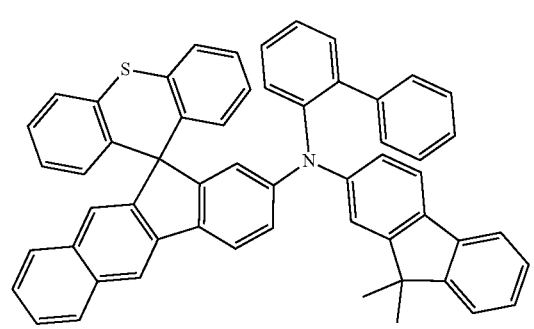
(204)
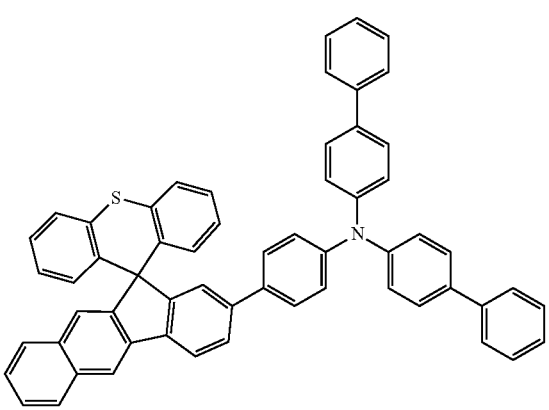

(205)
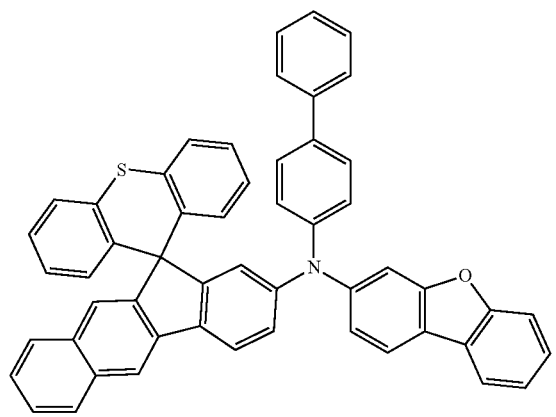
(206)
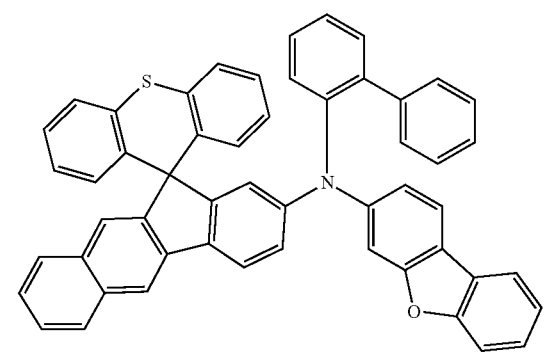
(207)
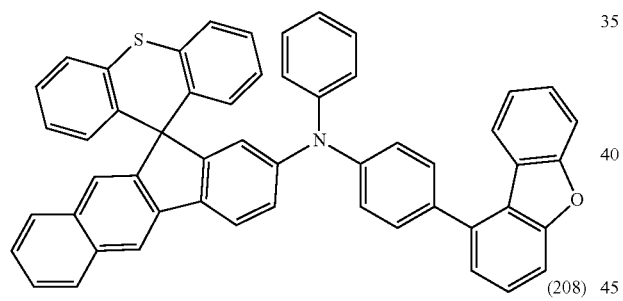
(208)
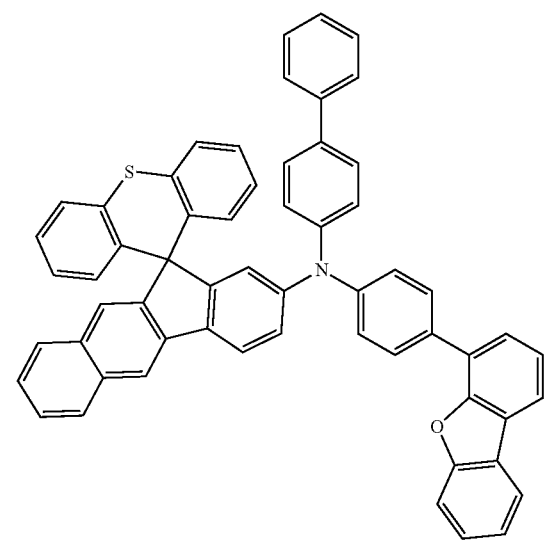
(209)
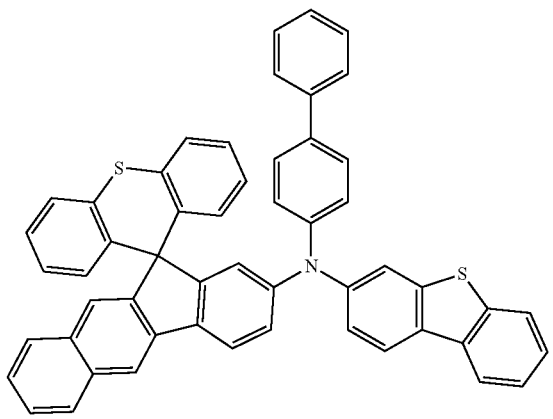
(210)
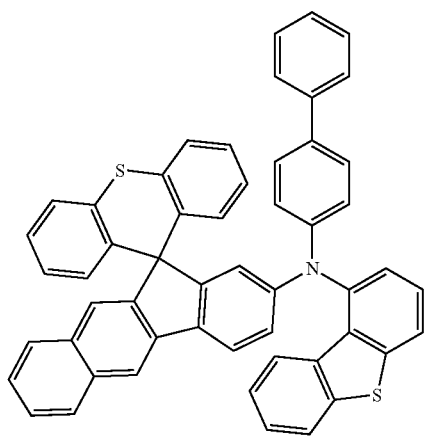
(211)
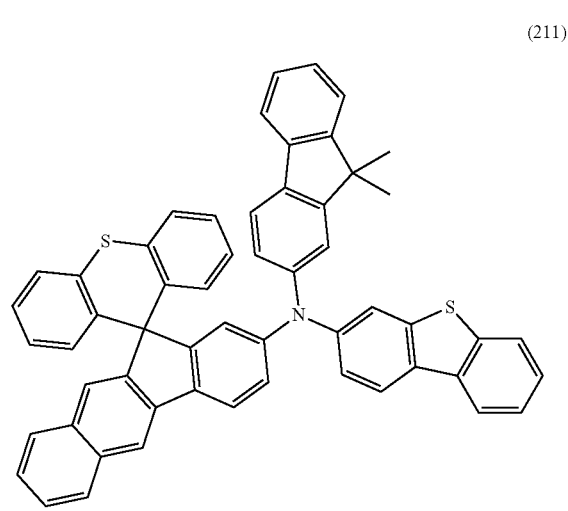

-continued
(212)
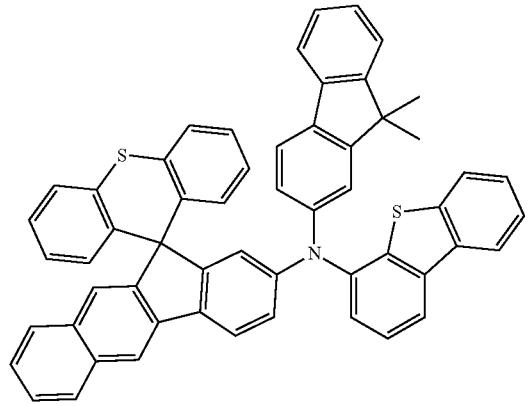
(213)
(214)
-continued
(215)
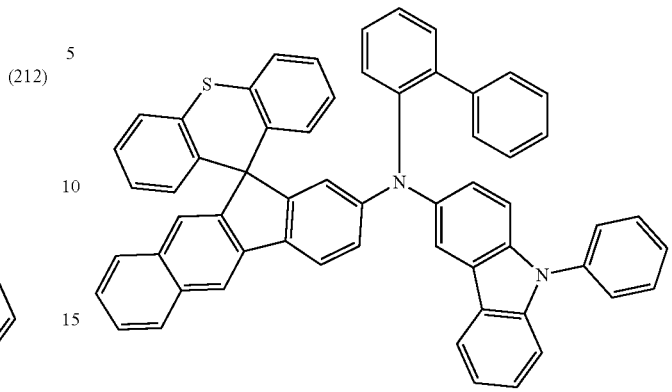
(216)
(217)
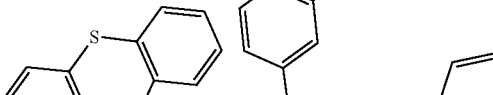
(218)

(219)
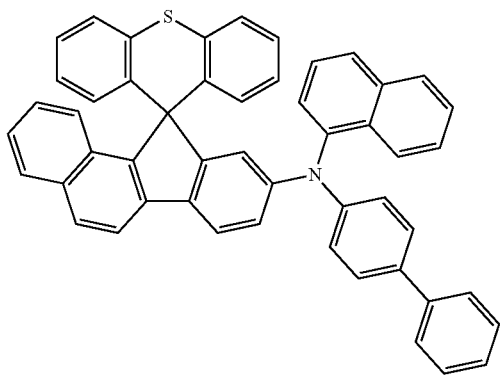
(220)
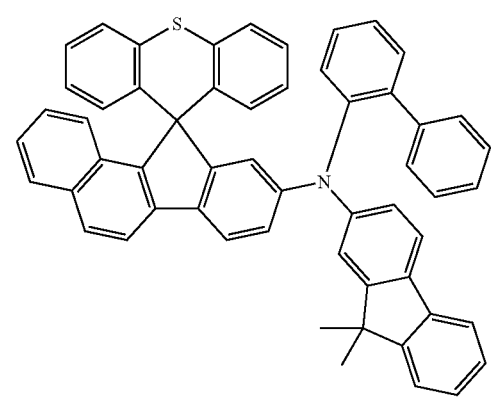
(221)
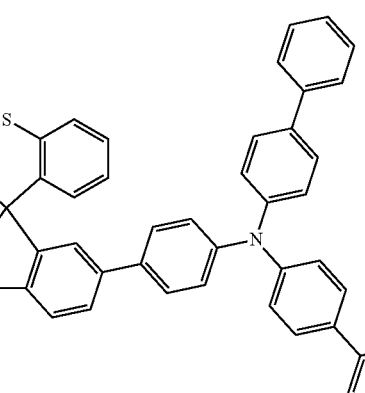
(222)
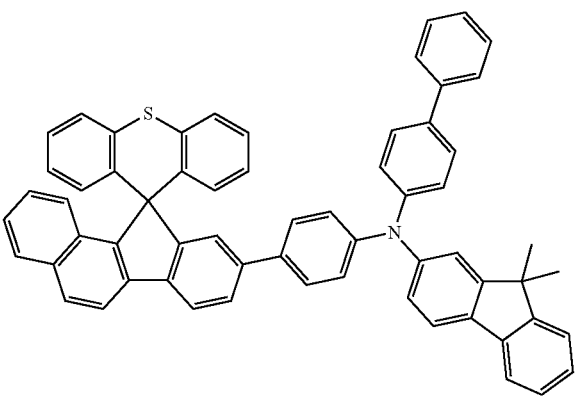
(223)
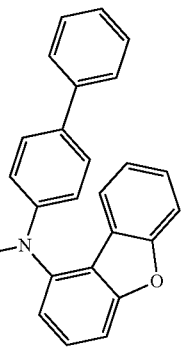
(224)
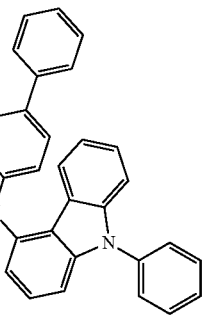
(225)
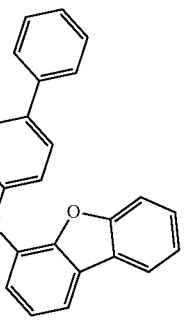
(226)
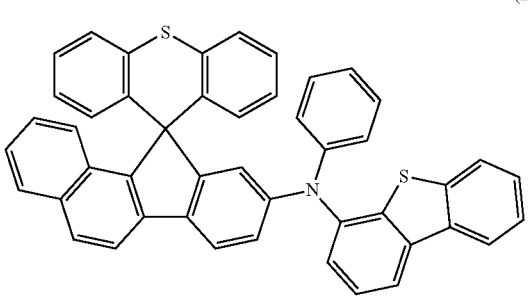

-continued
(227)
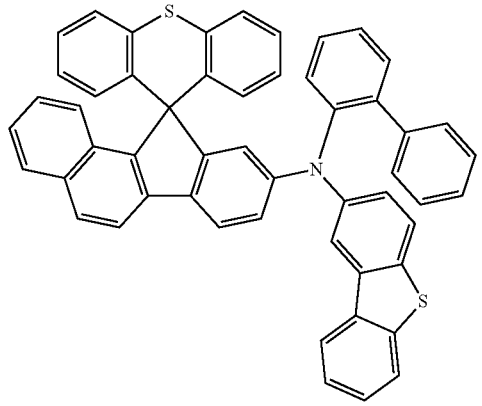
(228)
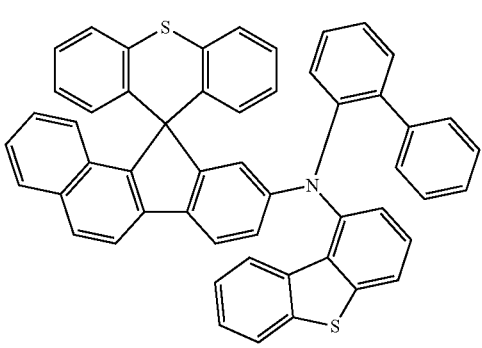
(229)
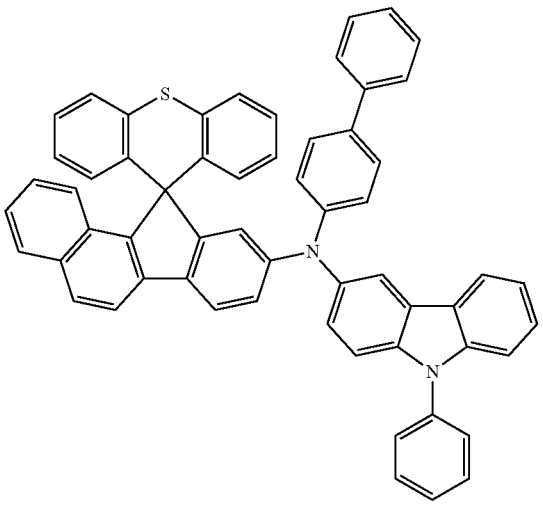
(230)
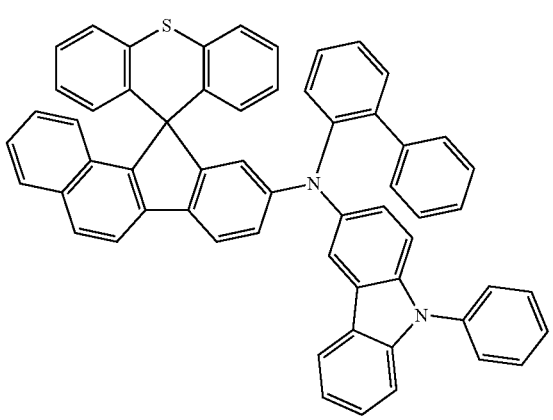
-continued
(231)
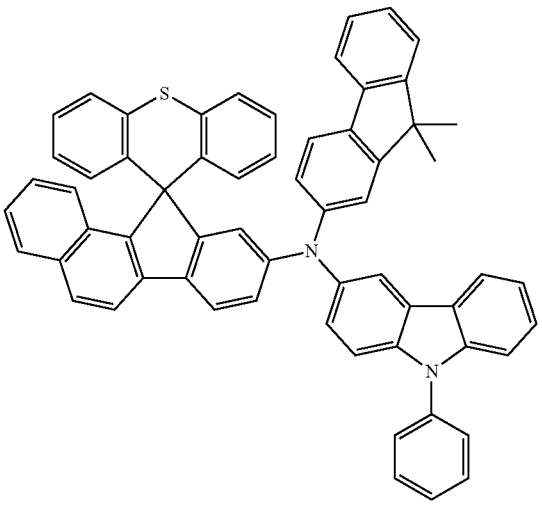
(232)
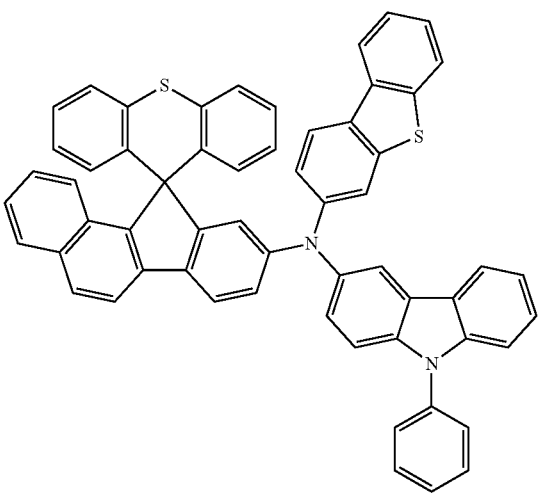
(233)
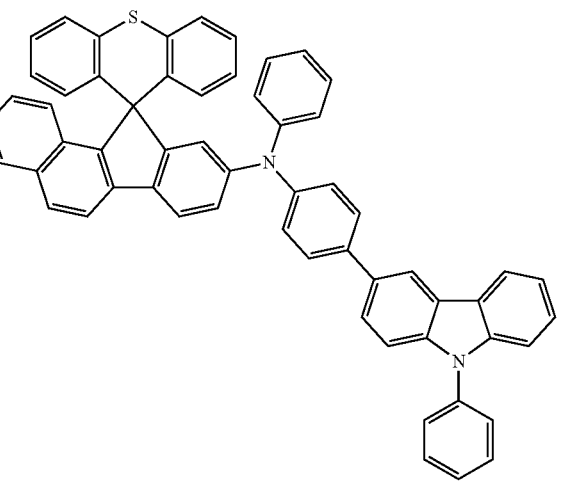

(234) 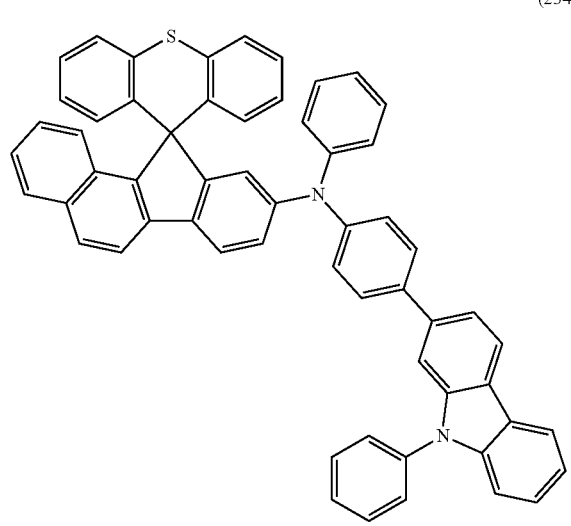
(235) 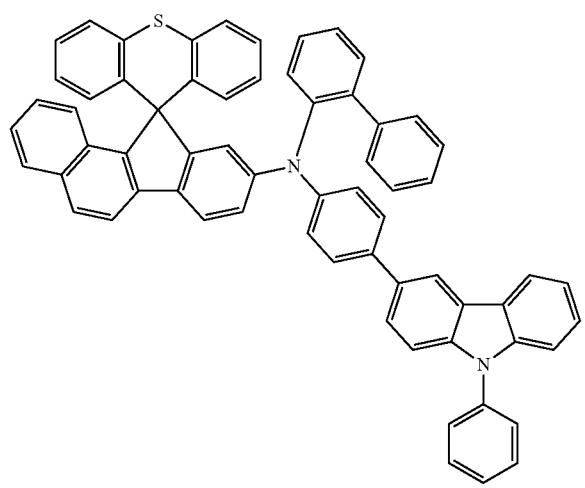
(236) 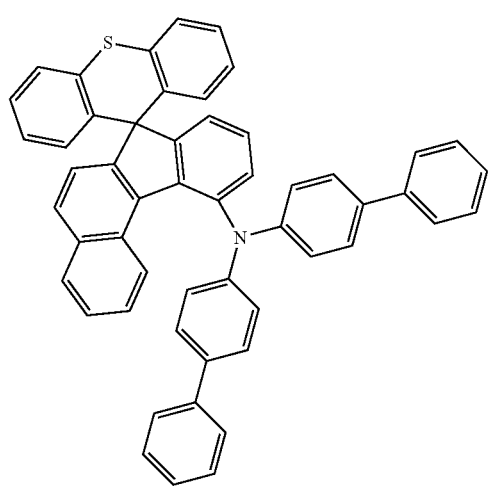
(237) 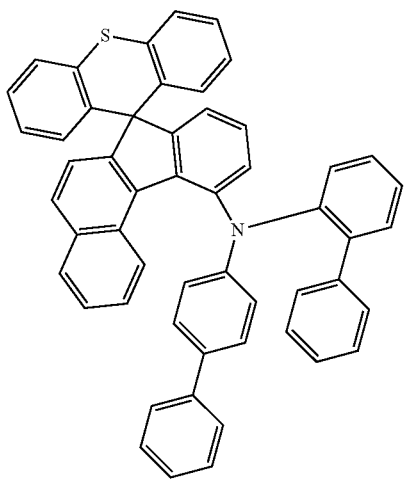
(238) 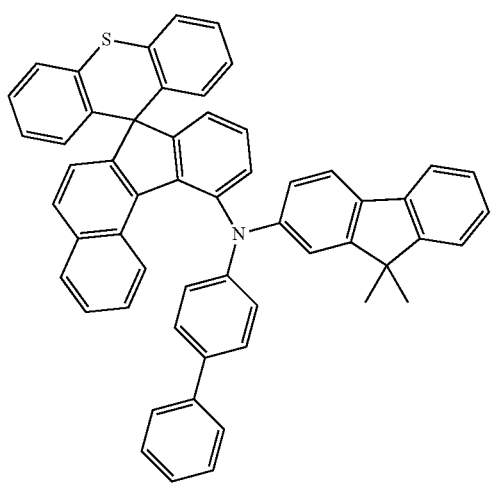
(239) 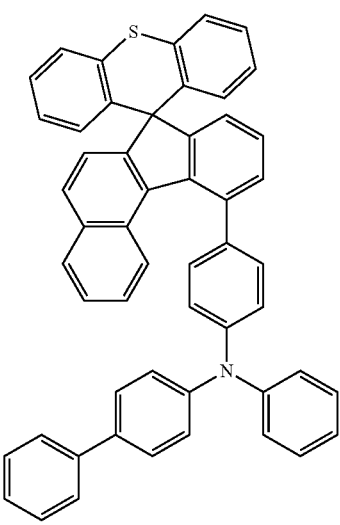

(240)
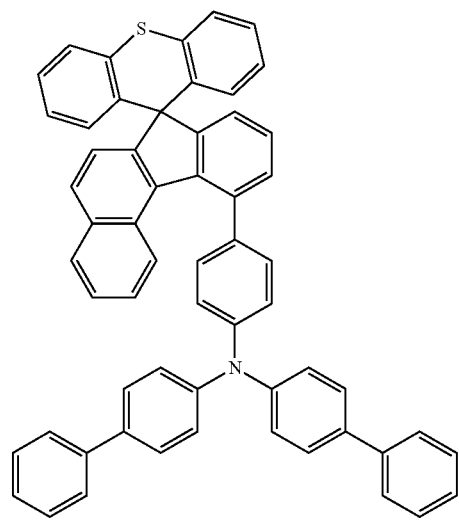
(241)
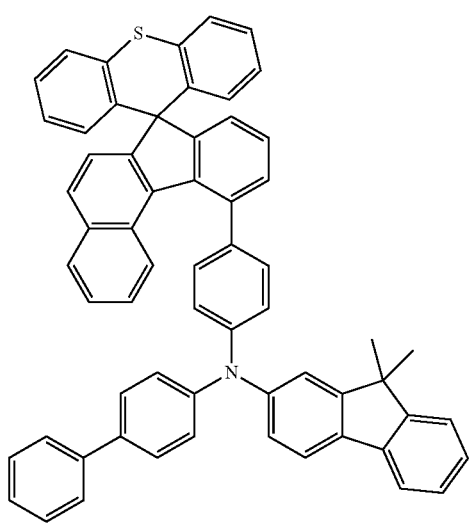
(242)
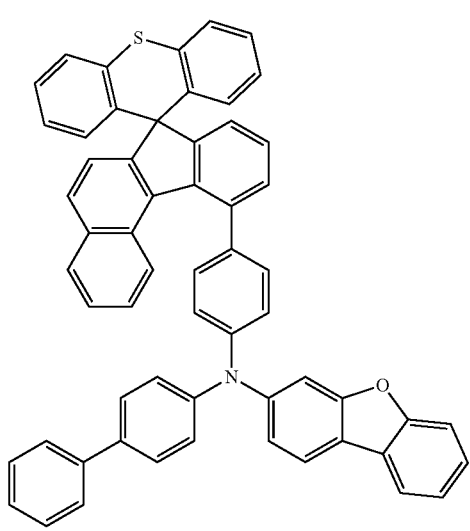
(243)
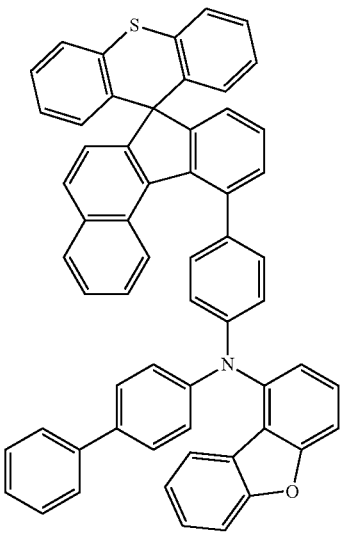
(244)
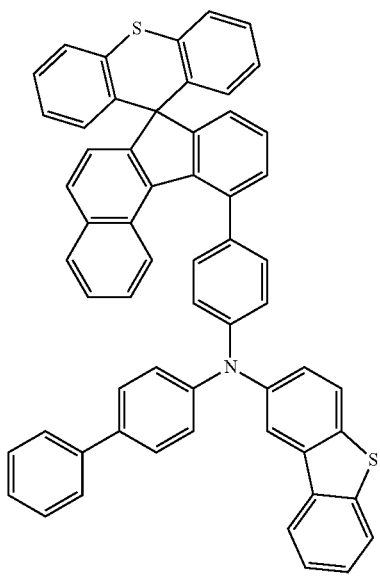
(245)
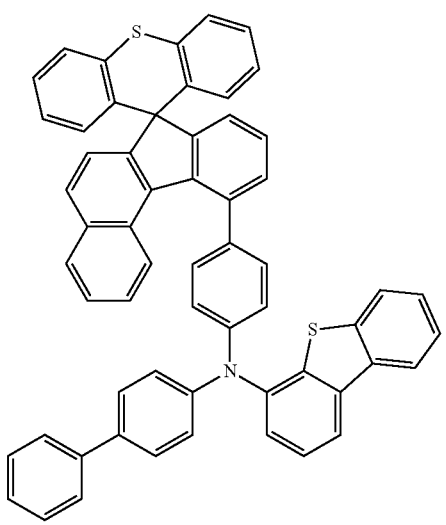

327
-continued
(246)
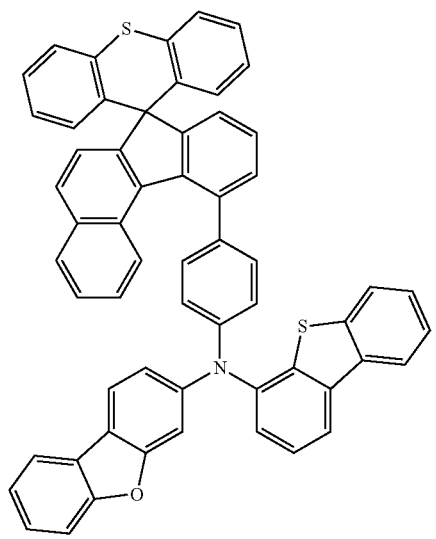
(247)
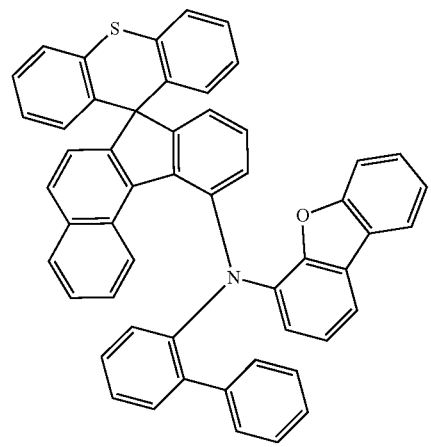
(248)
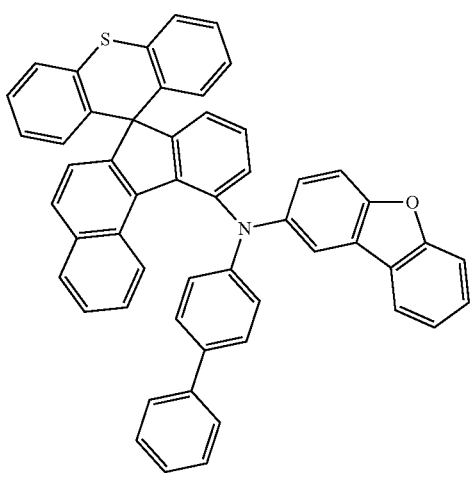
328
-continued
(249)
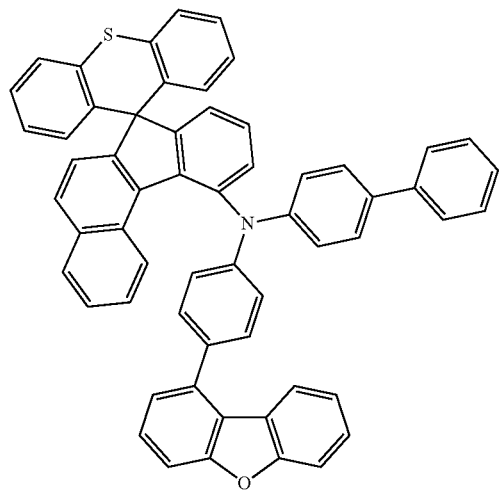
(250)
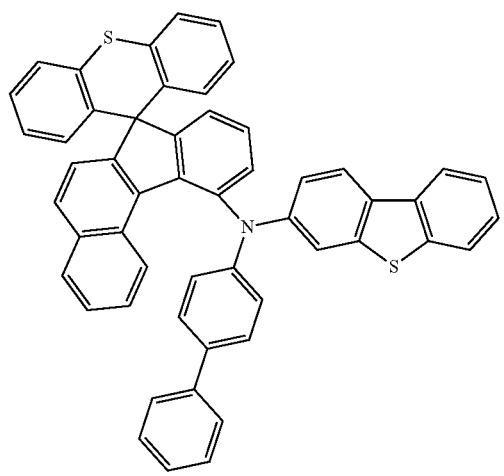
(251)
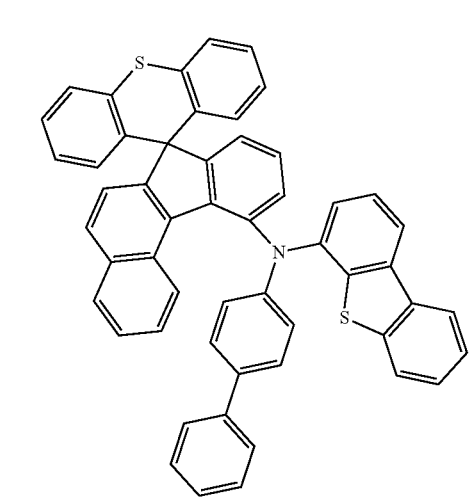

329
-continued
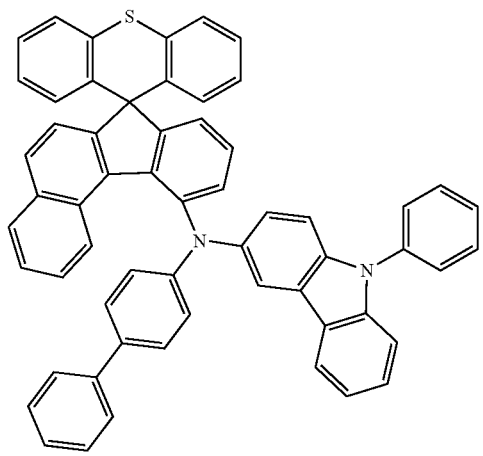
(252)
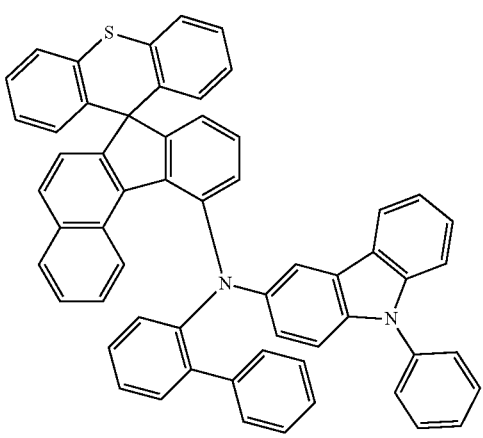
(253)
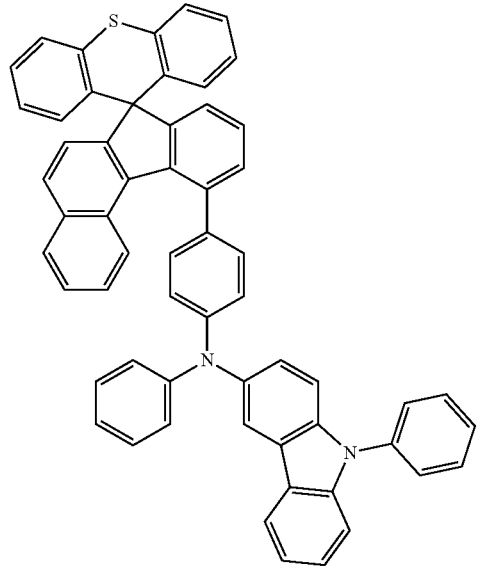
(254)
330
-continued
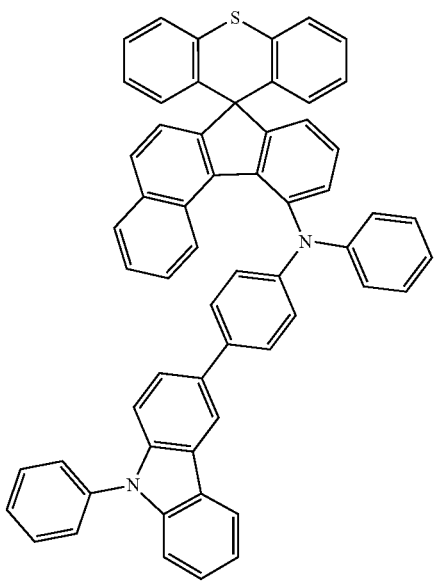
(255)
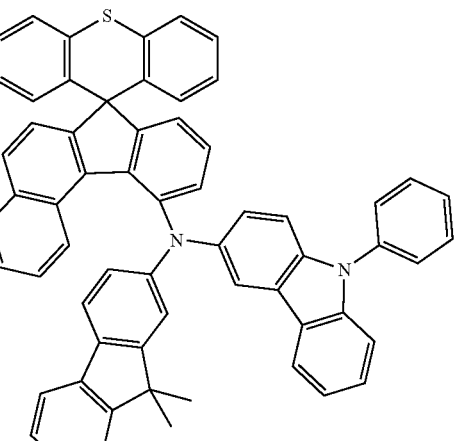
(256)
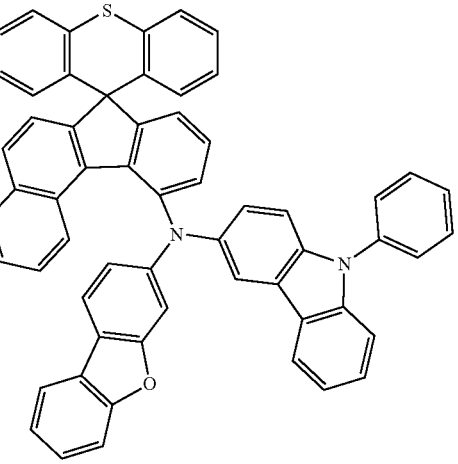
(257)

331
-continued

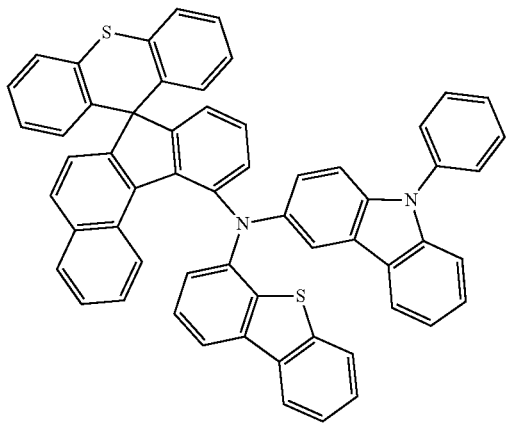
(258)

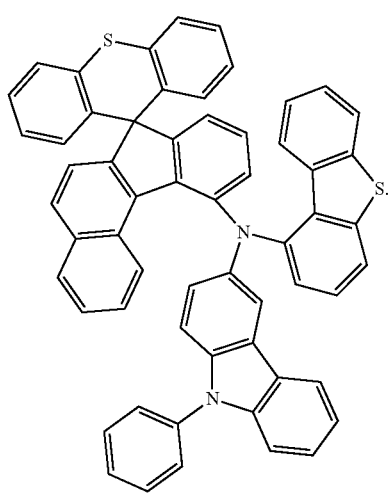
(259)

9. The organic electroluminescence device of claim 6, wherein the compound represented by any one of the Chemical Formulas 3 to 5 is a compound represented by the following Chemical Formula 6 or 7:

[Chemical Formula 6]

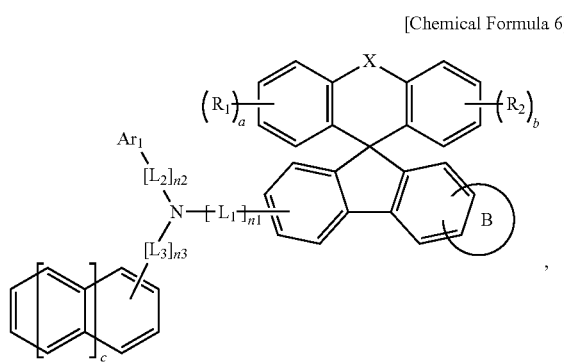

332
-continued

[Chemical Formula 7]

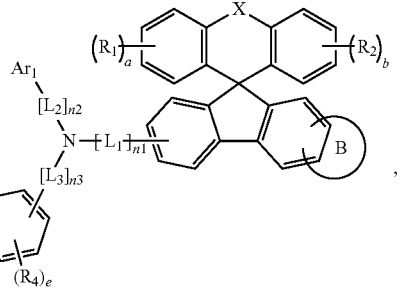

(wherein in Chemical Formulas 6 and 7,
X, $R_1$, $R_2$, a, b, $L_1$ to $L_3$, n1 to n3, and $Ar_1$ are as defined in claim 7, respectively,
ring B is a $C_6$ monocyclic aromatic ring,
c is 0 or 1,
$Y_1$ is selected from the group consisting of O, S, C($Ar_3$)($Ar_4$) and N($Ar_5$),
d is an integer ranging from 0 to 4,
e is an integer ranging from 0 to 3,
$R_3$, $R_4$, and $Ar_3$ to $Ar_5$ are the same as or different from each other, each independently being selected from the group consisting of hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and
the monocyclic aromatic ring and the polycyclic aromatic ring of the ring B, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_3$, $R_4$, and $Ar_3$ to $Ar_5$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other).

10. The organic electroluminescence device of claim 6, wherein the compound represented by any one of the Chemical Formulas 3 to 5 is a compound represented by any one of the following Chemical Formulas 8 to 13:

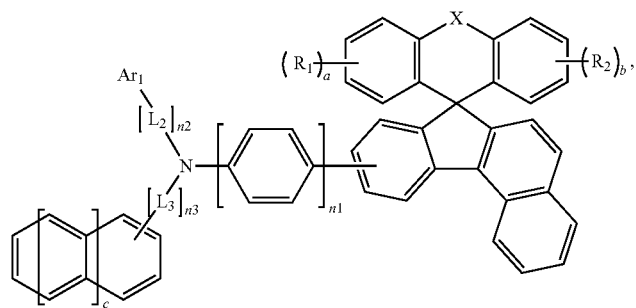
[Chemical Formula 8]
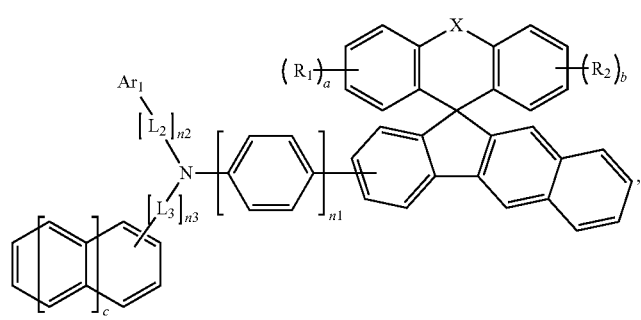
[Chemical Formula 9]
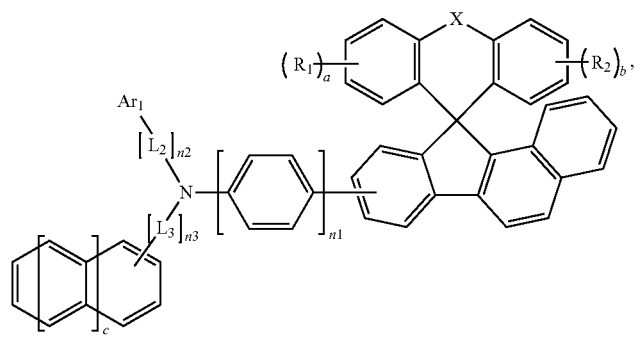
[Chemical Formula 10]
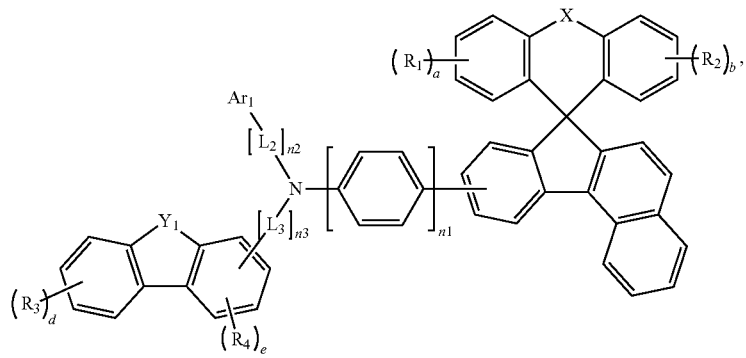
[Chemical Formula 11]

-continued

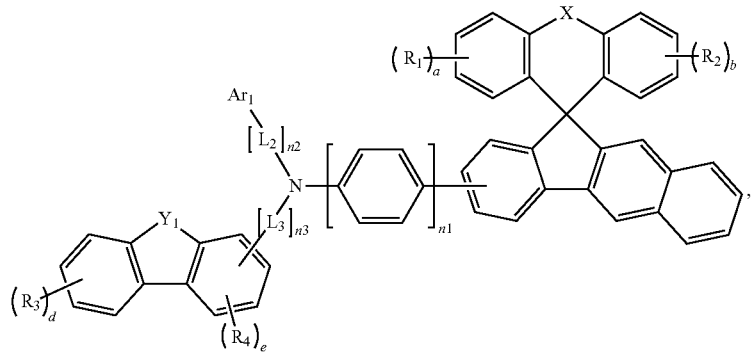

[Chemical Formula 12]

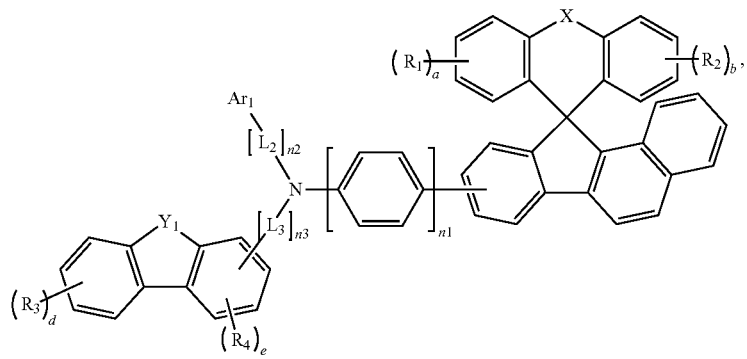

[Chemical Formula 13]

(wherein in Chemical Formulas 8 to 13,
X, $R_1$, $R_2$, a, b, $L_2$ to $L_3$, n1 to n3, and $Ar_1$ are as defined in claim 7, respectively,
c is 0 or 1,
$Y_1$ is selected from the group consisting of O, S, C($Ar_3$)($Ar_4$), and N($Ar_5$),
d is an integer ranging from 0 to 4,
e is an integer ranging from 0 to 3,
$R_3$, $R_4$, and $Ar_3$ to $Ar_5$ are the same as or different from each other, each independently being selected from the group consisting of hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and
the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_3$, $R_4$, and $Ar_3$ to $Ar_5$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other).

11. The organic electroluminescence device of claim 6, wherein the compound represented by any one of the Chemical Formulas 3 to 5 is a compound represented by any one of the following Chemical Formulas 14 to 22:

[Chemical Formula 14]
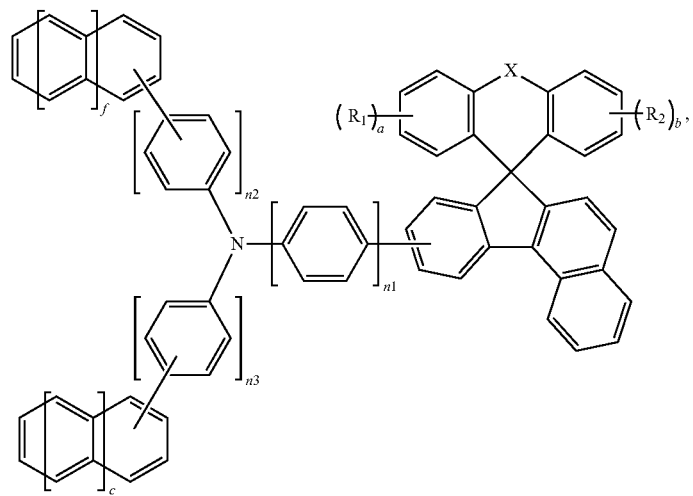
[Chemical Formula 15]
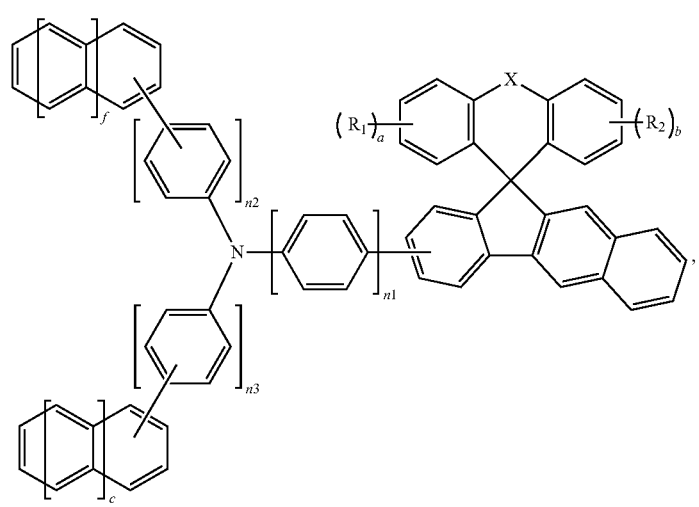
[Chemical Formula 16]
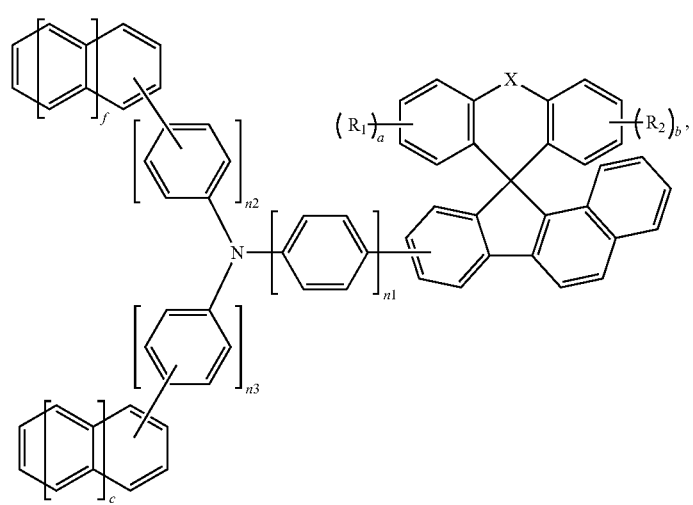

[Chemical Formula 17]
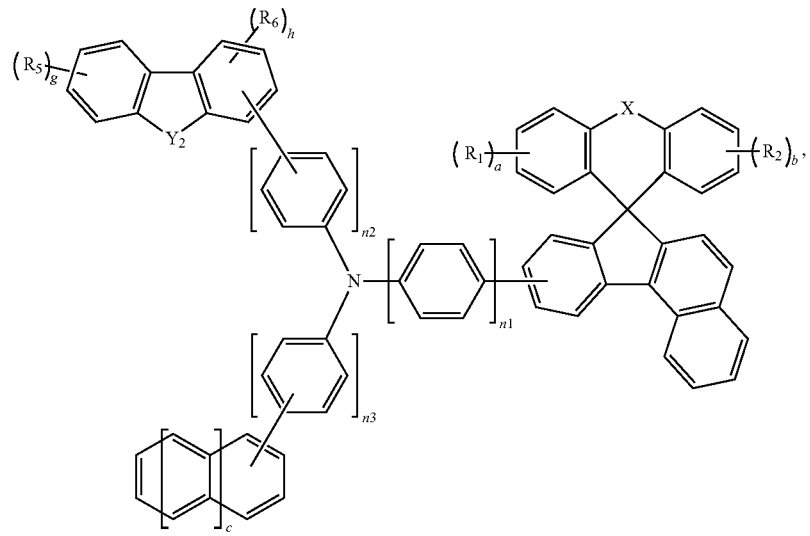
[Chemical Formula 18]
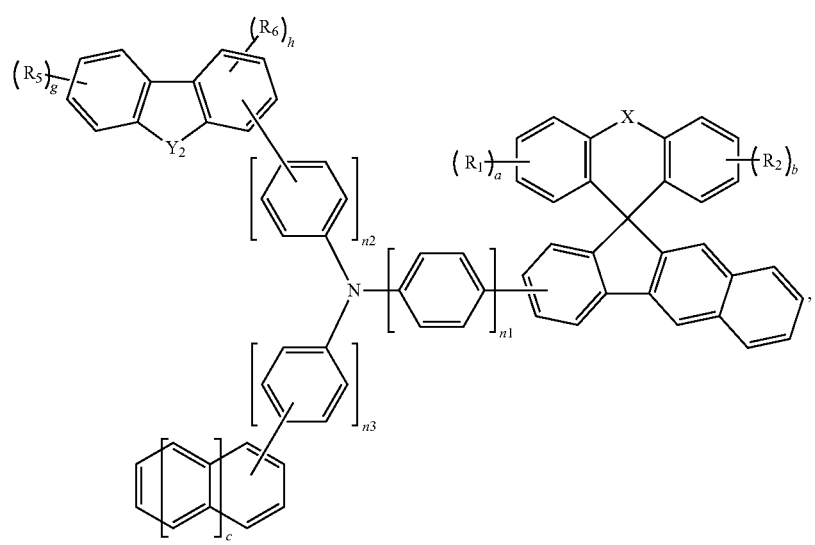
[Chemical Formula 19]
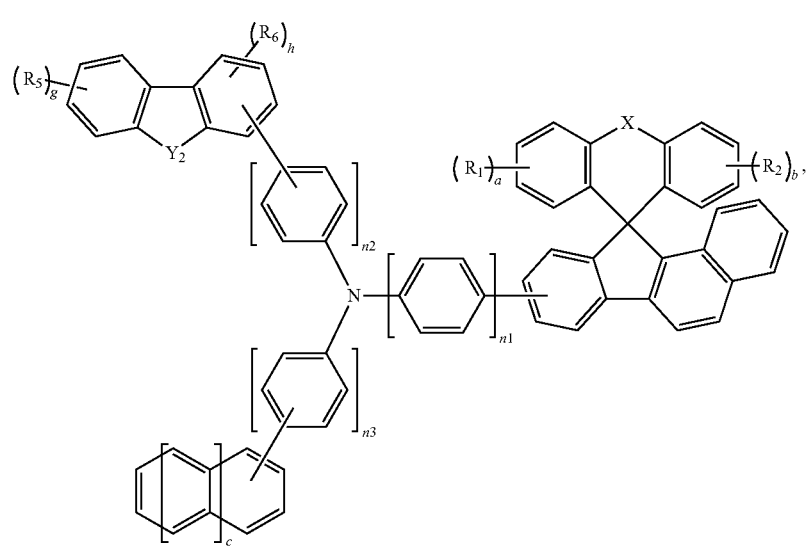

[Chemical Formula 20]
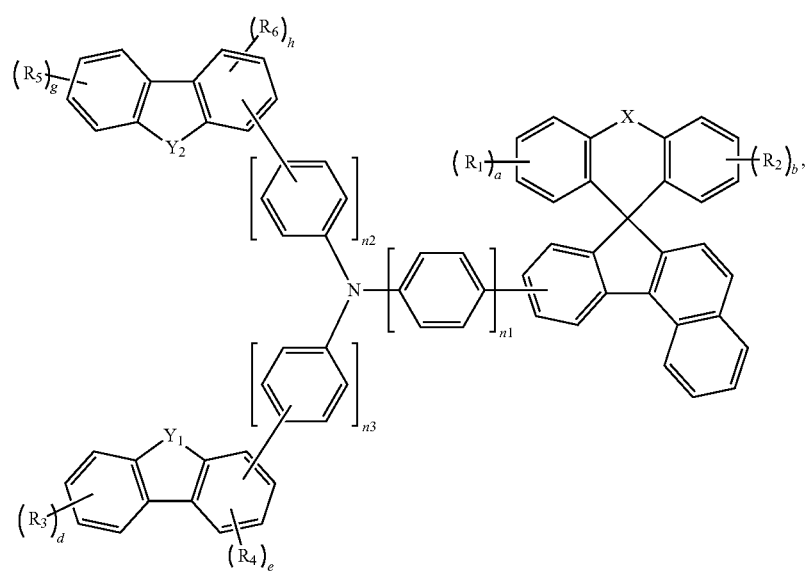
[Chemical Formula 21]
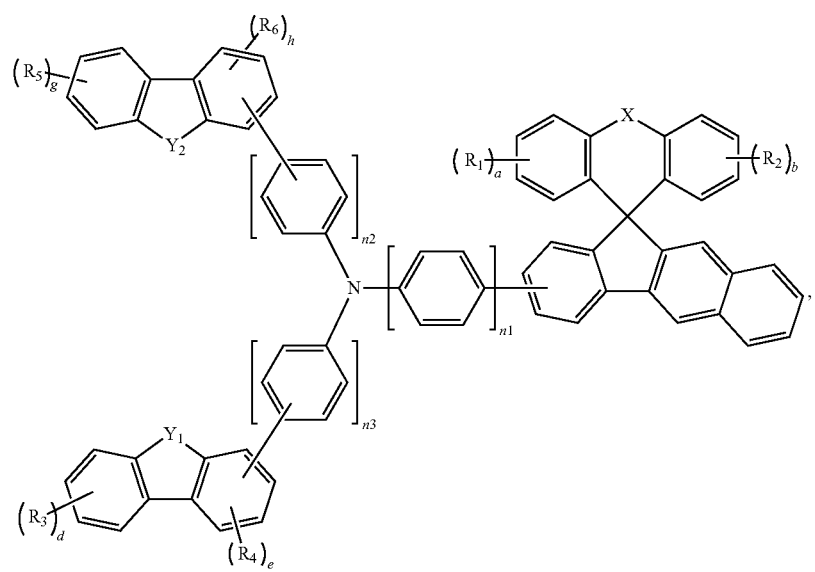

[Chemical Formula 22]

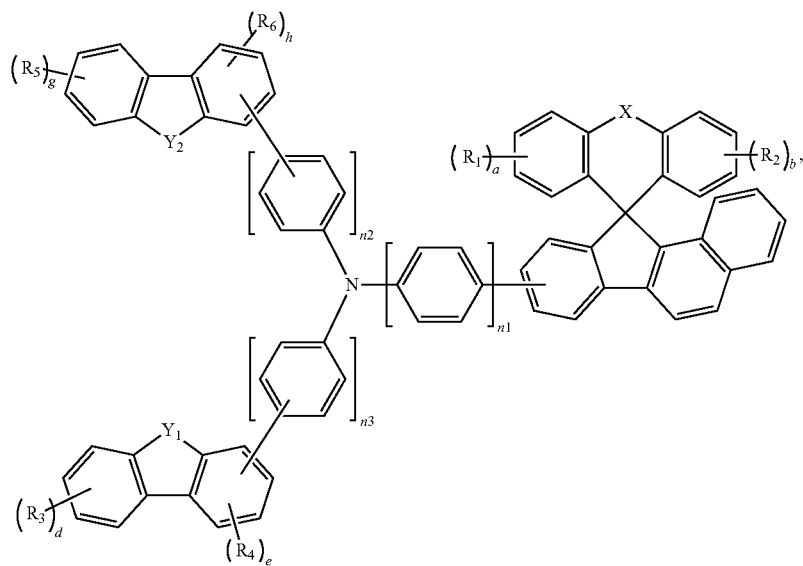

(wherein in Chemical Formulas 14 to 22,
X, $R_1$, $R_2$, a, b, and n1 to n3 are as defined in claim 7, respectively,
each of c and f is 0 or 1,
$Y_1$ is selected from the group consisting of O, S, $C(Ar_3)(Ar_4)$, and $N(Ar_5)$,
$Y_2$ is the same as or different from $Y_1$ and is selected from the group consisting of O, S, $C(Ar_6)(Ar_7)$, and $N(Ar_8)$,
each of d and g is an integer ranging from 0 to 4,
each of e and h is an integer ranging from 0 to 3,
$R_3$ to $R_6$ and $Ar_3$ to $Ar_8$ are the same as or different from each other, each independently being selected from the group consisting of hydrogen, deuterium, a halogen group, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_3$ to $R_6$ and $Ar_3$ to $Ar_8$ are each independently substituted or unsubstituted with one or more kinds of substituents selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and when the substituents are plural in number, the substituents are the same as or different from each other).

* * * * *